United States Patent [19]

Ladner et al.

[11] Patent Number: 5,096,815
[45] Date of Patent: Mar. 17, 1992

[54] GENERATION AND SELECTION OF NOVEL DNA-BINDING PROTEINS AND POLYPEPTIDES

[75] Inventors: Robert C. Ladner, Ijamsville, Md.; Sonia K. Guterman, Belmont, Mass.; Rachel B. Kent, Wilmington, Mass.; Arthur C. Ley, Newton, Mass.

[73] Assignee: Protein Engineering Corporation, Cambridge, Mass.

[21] Appl. No.: 293,980

[22] Filed: Jan. 6, 1989

[51] Int. Cl.$^5$ .................. C12N 15/63; C12N 15/09; C12P 21/00
[52] U.S. Cl. .................. 435/69.1; 435/172.3; 435/252.3; 435/320.1
[58] Field of Search ............. 435/69.1, 39, 320, 172.7, 435/252.3, 320.1

[56] References Cited

U.S. PATENT DOCUMENTS

| | | | |
|---|---|---|---|
| 4,436,815 | 3/1984 | Herschberger et al. | 435/172.3 |
| 4,506,013 | 3/1985 | Hershberger et al. | 435/172.3 |
| 4,556,643 | 12/1985 | Paau et al. | 436/501 |
| 4,568,640 | 2/1986 | Rubin | 435/70 |
| 4,631,257 | 12/1986 | Gelfand | 435/68 |
| 4,637,980 | 1/1987 | Auerbach et al. | 435/68 |
| 4,642,334 | 10/1987 | Moore et al. | 530/388 |
| 4,650,761 | 3/1987 | Hershberger et al. | 435/172.3 |
| 4,656,134 | 4/1987 | Ringold | 435/91 |
| 4,665,184 | 5/1987 | Dervan et al. | 546/109 |
| 4,704,692 | 11/1987 | Ladner | 364/496 |
| 4,732,847 | 3/1988 | Stuart et al. | 435/6 |
| 4,735,801 | 4/1988 | Stocker | 424/92 |
| 4,748,119 | 5/1988 | Rich et al. | 435/172.3 |
| 4,752,581 | 6/1988 | Robinson et al. | 435/217 |
| 4,777,129 | 10/1988 | Dattagupta et al. | 435/6 |

FOREIGN PATENT DOCUMENTS

| | | |
|---|---|---|
| 136907 | 12/1982 | European Pat. Off. . |
| 285123 | 7/1985 | European Pat. Off. . |
| 285220 | 7/1985 | European Pat. Off. . |
| WO88/06601 | 6/1988 | PCT Int'l Appl. . |
| WO88/06630 | 6/1988 | PCT Int'l Appl. . |
| 2166743 | 2/1980 | United Kingdom . |

OTHER PUBLICATIONS

Genetics 114:1 to 14, Sep. 1986, Benson et al., General Selection for Specific DNA Binding Activities.
Science 230:281 to 285, Oct. 18, 1985, Marvin Caruthers, Gene Synthesis Machines: DNA Chemistry and Its Uses.
Science 229:1193 to 1201, Sep. 20, 1985, Botstein and Shortle, Strategies and Applications of in Vitro Mutagenesis.
Science 219:666-671, Feb. 11, 1983, Kevin Ulmer, Protein Engineering.
Gene 44:177-183, 1986, Oliphant et al., Cloning of random-sequence oligodeoxynucleotides.
P.N.A.S. 83:5889-5893, Aug. 1986, Kadonaga and Tjian, Affinity purification of sequence-specific DNA binding proteins.
Science 242:240 to 245, Oct. 14, 1988, Bass et al., Mutant Trp Repressors with New DNA-Binding Specificities.
P.N.A.S. 82:1084 to 1088, Feb. 1985, Eisenbeis et al., Altered Cro Repressions from engineered mutagenesis of a synthetic Cro gene.
P.N.A.S. 83:8829 to 8833, Dec. 1986, Pakula et al., Bacterial λ Cro Mutations: Effects on activity and intracellular degradation.

(List continued on next page.)

Primary Examiner—Richard A. Schwartz
Assistant Examiner—John D. Ulm
Attorney, Agent, or Firm—Iver P. Cooper

[57] ABSTRACT

Novel DNA-binding proteins, especially repressors of gene expression, are obtained by variegation of genes encoding known binding protein and selection for proteins binding the desired target DNA sequence. A novel selection vector is used to reduce artifacts. Heterooligimeric proteins which bind to a target DNA sequence which need not be palindromic are obtained by a variety of methods, e.g., variegation to obtain proteins binding symmetrized forms of the half-targets and heterodimerization to obtain a protein binding the entire asymmetric target.

42 Claims, 12 Drawing Sheets

OTHER PUBLICATIONS

Science 241:53 to 57, Jul. 1, 1988, Reidhaar-Olson, Combinatorial Cassette Mutagenesis as a Probe of the Information Content of Protein Sequences.

Methods in Enzymology 155:568 to 583, 1987, Oliphant and Struhl. The Use of Random-Sequence Oligonucleotides for Determining Consensus Sequences.

Cell 54:191 to 197, Jul. 15, 1988, Bushman and Ptashne, Turning λ Cro into a transcriptional activator.

Isackson et al., Proc. Natl. Acad. Sci.; 82:6226-6230 (1985) Dominant negative mutations . . .

Wharton et al.; Cell 38:361-69 (1984); Substituting an α-helix Switches . . .

Wharton, et al.; Nature 316:601-605 (1985) Changing the binding specificity of a repressor . . .

Nelson, et al.; Cold Spring Harbor Symp Quant Biol 47:441-449 (1963) Mutations Defining the Operator . . .

Benson, et al.; Genetics 121:5-12 (1989) Phage Cro Protein and cI Repressor . . .

Bass, et al.; Genes & Development 1:565-572 (1987) DNA specificity determinants of $E.\ coli$ . . .

Youderian, et al.; Cell 35:777-783 (1983) Changing the DNA-Binding . . .

Hollis, et al.; Proc. Natl. Acad. Sci. 85:5834-5838 (1988); A repressor heterodimer binds . . .

Caruthers, et al.; Protein Structure 2:9-24 (1987) The Thymine 5-methyl Group.

Sauer, et al.; Biochemistry 25:5992-5998 (1986); An Engineered Intersubunit Disulfied . . .

Wharton, et al.; Nature 326:888-891 (1987); A new-specificity mutant of 434 repressor . . .

Hadi, et al.; J. Mol. Biol. 134:655-666 (1979) DNA Recognition and Cleavage . . .

Nash, et al.; Jour. of Bacteriology 169:4124-4127 (1987); Overproduction of $E.\ coli$ integration . . .

Porter, et al.; Nature 320:766-768 (1986); Homoeo-domain homology in yeast . . .

Bedouelle et al.; Nature 320:371-373 (1986); A mode of synthetase/transfer RNA . . .

Carter, et al.; Proc. Natl. Acad. Sci. 83:1189-1192 (1986); Construction of heterodimer tryosyl-tRNA . . .

Wetzel; Protein Engineering, 1:5-6 (1986); Comments on creation of novel heterodimers . . .

Kelly, et al.; Proc. Natl. Acad. Sci. 83:483-487 (1985); Mutational studies with the trp repressor . . .

Sheppard; Journal of Bacteriology 168:999-1001 (1986); Dominance relationships among mutant . . .

Matthews; Nature 335:294-295 (1988); No code for recognition.

Vershon, et al.; Academic Press 15:243-256 (1986) Mutagenesis for the Arc repressor . . .

Vershon, et al.; Proteins 1:302-311 (1986); Isolation and Analysis of Arc repressor . . .

Ward, et al.; J. Biol. Chem. 261(21)9576-78 (1986) Protein Engineering of Homodimeric . . .

Gutte, et al.; Nature 281:650-655 (1979).

Hecht, et al.; J. Mol. Biol. 186:53-63 (1985); Phage Lambda repressor revertants . . .

Ebright, et al.; Nature 311:232-245 (1984); Mutations that alter the DNA sequence . . .

Vershon, et al.; Journal of Biological Chemistry 260:12124-12129 (1985); The Bacteriophage P22 Arc and Mnt . . .

Nelson, et al., Cell; 42:549-558 (1985); Lambda Repressor Mutations . . . Operator Binding.

Nelson, et al.; Cold Spring Harbor Symp. Quant. Biol.; 47:441-449 (1983) Lambda Repressor . . . Operator Binding.

Lehming, et al.; EMBO Journal; 6(10)3145-3153 (1987); The Interaction of the Recognition helix . . . lac Operator.

Elledge, et al.; Proc. Natl. Acad. Sci. 86:3689-3693 (1989); Genetic Selection for Genes Encoding . . . proteins.

Elledge, et al.; Genes & Development 3:185-197 (1989) Position and Density Effects . . . DNA-binding proteins.

Georgopoulos, C. P.; Journal of Bacteriology; 97(3);1397-1402 (1969); Suppressor System . . . Subtilis 168.

Spiro, et al.; Molecular Microbiol. 1:53-58 (1987); Activation of the lac Operon of $E.\ coli$ . . . protein.

Hawthorne, et al.; Genetics 48:617-620 (Apr. 1963) Super-Suppressors in Yeast.

Wharton; The Binding Specificity Determinants of 434 Repressor; Ph.D. Thesis (1985); Chapter III and Appendices A, C and D.

DNA

DELTA 4 CELLS CONTAINING pKK175-6 ARE AmpR, TetS, FusR, AND GalR.

T2 IS rrnBt1; T3 IS rrnBt2; P2 IS Pamp

DELTA4 CELLS CONTAINING pAA3H are AmpR, TetS, FusR, AND GalS

T2 IS rrnBt1; T3 IS rrnBt2;
P1 IS pBR322 P1 PROMOTER;
P2 IS Pamp

DELTA 4 CELLS CONTAINING pEP1001 ARE
AmpR, TetS, FusR, GalS

P1 IS pBR322 P1 IS PROMOTER;
P2 IS Pamp

DELTA 4 CELLS CONTAINING pEP1002 ARE AmpR, TetS, FusR, AND GalS

P1 IS pBR322 P1 PROMOTER; P2 IS Pamp
T1 IS phage fd TERMINATOR; T2 IS rrnBt1;
T3 IS rrnBt2;

DELTA 4 CELLS CONTAINING pEP1003 ARE
AmpR, TetS, FusR, AND GalS
P2 IS Pamp
T1 IS phage fd TERMINATOR HB101 CELLS CONTAINING pEP1004 ARE
AmpR, TetS, FusR, AND Gal+

P2 IS Pamp
T1 IS phage fd TERMINATOR, T2 IS rrnBt1, T3 IS rrnBt2,

DELTA 4 CELLS CONTAINING pEP1005 ARE
AmpR, TetS, FusR, AND GalS
P2 IS Pamp, P3 IS Pneo
T1 IS phage fd TERMINATOR, T2 IS rrnBt1 T3 IS rrnBt2

DELTA 4 CELLS CONTAINING pEPI007 ARE
AmpR, TetR, FusS, AND GalS

P2 IS Pamp, P3 IS Pneo, P4 IS PlacUV5
T1 IS phage fd TERMINATOR, T2 IS rrnBt1, T3 IS rrnBt2
T4 IS trp A TERMINATOR DELTA 4 CELLS CONTAINING pEPI009 ARE
AmpR, TetS, FusR, AND GalR IN PRESENCE OF IPTG
AmpR, TetR, FusS, AND GalS IN ABSENCE OF IPTG P2 IS Pamp, P3 IS Pneo, P4 IS P lacUV5
T1 IS phage fd TERMINATOR, T3 IS rrnBt1, T3 IS rrnBt2
T3 IS trpA TERMINATOR

GENERATION AND SELECTION OF NOVEL DNA-BINDING PROTEINS AND POLYPEPTIDES

CROSS-REFERENCE TO RELATED APPLICATION

The commonly owned application of Ladner and Guterman, Ser. No. 07/240,160, "Generation and Selection of Novel Binding Proteins," is directed to related subject matter, and is hereby incorporated by reference.

BACKGROUND OF THE INVENTION

1. Field of the Invention

This invention relates to development of novel DNA-binding proteins and polypeptides by an iterative process of mutation, expression, selection, and amplification.

2. Information Disclosure Statement

Proteins that bind sequence-specifically to DNA determine which genetic messages will be expressed and in what quantity. The present application deals only with sequence-specific DNA-binding proteins, abbreviated DBP. Numerous proteins are known that bind to specific DNA sequences and much has been written on the nature of the interactions between DNA and proteins. In a few cases, x-ray crystal structures have been determined for segments of DNA bound to protein; Matthews has recently reviewed structures of such complexes (MATT88). In only a handful of cases have researchers been able to construct or isolate new proteins that recognize different DNA sequences, and they did not demonstrate the ability to prepare a suitable DBP specific for an arbitrary predetermined DNA sequence.

The ability to create novel DNA-binding proteins will have far-reaching applications, including, but not limited to, use in: a) treating viral diseases, b) treating genetic diseases, c) preparation of novel biochemical reagents, and d) biotechnology to regulate gene expression in cell cultures.

In both prokaryotes and eukaryotes, proteins having affinity for specific sites on DNA modulate transcriptional expression of genes. Through direct interaction with DNA at specific sites in genes, certain proteins called repressors hinder transcription by making the DNA inaccessible to RNA polymerase. Other DNA-binding proteins and some multi-functional repressors are activators which allow RNA polymerase to initiate transcription with increased efficiency.

DNA-binding proteins have been studied to determine in atomic detail how these proteins actually contact the DNA molecule and interact with it to influence gene expression. The best known are a group of proteins primarily studied in prokaryotes that contain the structural motif alpha-helix-turn-alpha-helix (H-T-H) (PAB084). These proteins bind as dimers or tetramers to DNA at specific operator sequences that have approximately palindromic sequences. Contacts made by two adjacent alpha helices of each monomer in and around two sites in the major groove of B-form DNA are a major feature in the interface between DNA and these proteins. Proteins that bind in this manner share sequence similarity in the H-T-H region but vary in the extent of similarity in other regions. This group of proteins includes the temperate bacteriophage repressor proteins and Cro proteins, bacterial metabolic repressor proteins such as GalR, LacI, LexA, and TrpR, bacterial activator protein CAP and dual activator/repressor protein AraC, bacterial transposon and plasmid TetR proteins (PABO84), the yeast mating type regulator proteins MATa1 and MATalpha2 (MILL85) and eukaryotic homeo box proteins (EVAN88).

Interactions between dimeric repressors and approximately palindromic operators have usually been discussed in the literature with attention focused on one half of the operator with the tacit or explicit assumption that identical interactions occur in each half of the complex. Departures from palindromic symmetry allow proteins to distinguish among multiple related operators (SADL83, SIMO84). One must view the DNA-protein interface as a whole. The emphasis in the literature on dyad symmetry is a barrier to determining the requirements for general novel recognition of DNA by proteins.

While single crystals of short segments of DNA, of DBPs, and of DNA-DBP complexes have all been studied by X-ray diffraction and other analytical techniques, it is not yet possible to design a protein to bind strongly and specifically to an arbitrary DNA sequence. As taught by the present invention, however, it is possible to use theoretical considerations to postulate a family of potential DBP mutants and identify one having the desired specificity by other means.

The simple antiparallel double helical idealization of B-DNA having 10.5 regularly spaced base pairs per turn, a rise of 3.4 Angstroms (A) per base pair, and a helical diameter of 19.0 A, though still an invaluable generalization, does not fit the details of 3D structures of specific DNA sequences. It has been observed that AT base pairs are wound more tightly than GC pairs (DICK83). An AT base pair may advance the helix by as little as 29° (ANDE87) while a GC pair may advance it by as much as 45°; the average for random DNA is about 36°/base pair (SAEG83).

Physical and theoretical methods indicate that the flexibility of DNA as well as the equilibrium geometry are a function of the sequence. Hogan and Austin have suggested that AT-rich segments of DNA are more flexible than GC-rich regions and they have resolved the flexibility into bending and torsion (HOGA87). Gartenberg and Crothers (GART88) have shown that certain aspects of DNA flexibility a) are best stated in terms of sections comprising two base pairs, and b) are directional in nature: A or T favors bending toward the minor groove while G or C favors bending toward the major groove. Ulanovsky and Trifonov (ULAN87) have reviewed the significant static effect that AA dinucleotides can induce on the curvature of the DNA axis.

DNA is strongly negatively charged due to the ionization of the phosphate groups. In solution at or near physiological pH, cations become localized between phosphate groups in the minor groove (OHLE85). Ulanovsky and Trifonov (ULAN87) suggest that electrostatic interactions between DNA and proteins will significantly affect the twist, tilt and roll of bases. Entrapped water molecules and ions may also mediate the interaction between the protein and the DNA, as in the case of the binding of Trp repressor (TrpR) to its operator (OTWI88).

Matthews (MATT88), commenting on the current collection of protein-DNA structures, concludes that: a) different H-T-H DBPs use their recognition helices differently, b) there is no simple code that relates particular base pairs to particular amino acids at specific locations in the DBP, and c) "full appreciation of the complexity and individuality of each complex will be discouraging to anyone hoping to find simple answers to the recognition problem."

Other prokaryotic repressors exist that have little or no sequence homology to H-T-H binding proteins and have no H-T-H binding motif. Binding of operators with approximate palindromic sequence symmetry is observed among some proteins of this group, such as *Salmonella typhimurium* bacteriophage P22 Mnt protein (VERS87a) and *E. coli* TyrR repressor protein (DEFE86). Others of this group bind to operator sequences that are partially symmetric (*S. typhimurium* phage P22 Arc protein, VERS87b; *E. coli* Fur protein, DEL087; plasmid R6K pi protein, FILU85) or non-symmetric (phage Mu repressor, KRAU86).

Several eukaryotic transcriptional activation proteins of eukaryotes have been identified which bind to specific DNA sequences; however, there is only limited information on the DNA-binding motif of these proteins.

The ease and rapidity of genetic analysis in prokaryotes has enabled extensive mutational analysis of prokaryotic DNA-binding proteins and their specific nucleic acid sequences, producing a wealth of information on the relationships between structure and function in the molecular complexes. Altered protein or nucleic acid sequences have been obtained via a variety of mutagenesis techniques. Mutant proteins and operators produced by these techniques have been used alone or in combination with native or mutant sequences and proteins to determine relationships among sequence, structure, and binding in protein-DNA complexes.

Mutations that alter the amino acid sequence of a protein show an enormous variety of effects ranging from no observable changes in structure or function to complete loss of function, protein destabilization, and degradation. A general conclusion from the mutational studies of the DNA-binding proteins is that mutations in protein sequence that result in the decrease or loss of protein function fall into two large (and overlapping) classes: 1) those mutations which have destabilizing effects on global protein structure or folding and 2) those which affect protein function by specifically altering protein-protein (in the case of dimerization or activation) or protein-DNA (in the case of DNA-binding) interactions. Analysis of the first class of mutations provides information on the general problem of what factors determine protein folding and stability, while analysis of the second class serves to define the surfaces and interactions involved in the formation and stabilization of the protein-DNA complex. A third class of mutations that yields information concerning protein-DNA interactions is that of mutant operator sequences.

Reidhaar-Olson and Sauer (REID88) have extensively studied amino acid substitutions at positions 84 to 91 in alpha helix 5 of lambda repressor. The authors used cassette mutagenesis to vary residues at two or three positions through all twenty amino acids simultaneously and selected for those combinations that resulted in normal functional N-terminal domains. The authors neither discuss optimization of the number or positions of residues to vary to obtain any particular functionality, nor do they attempt to obtain proteins having alternate dimerization or recognition functions.

Pakula et al. (PAKU86) have used random mutagenesis to generate a large number of altered lambda Cro proteins containing single missense mutations (see Table 1). Twenty mutations were recovered in residues proposed to interact in dimer formation (L7, L23, A34, I40, E54, V55, K56, F58). (We use the single-letter code for amino acids, shown in Table 9. Mutants are indicated by: a) the amino acid of the parent, b) the new amino acid, and c) the position in the protein. Thus FV58 indicates a change from phenylalanine (F) to valine (V) at position 58.) Proteins with substitutions at K56 (which may interact with DNA directly (PAKU86, TAKE86)) do not bind DNA and are present in the cell. All other mutations recovered in these residues drastically decrease both the in vivo levels of the altered proteins and the binding.

DNA-binding proteins bind DNA with sequence-specific and sequence-independent interactions. Sequence-independent interactions are thought to occur via electrostatic interactions between the sugar phosphate backbone of the DNA and peptide NH groups or the side groups of appropriately charged or H-bonding residues (viz. N, Q, K, R, T, Y, H, E, D, and S) on the surface of the protein (ANDE87, LEWI83, and TAKE85). Sequence-specific interactions involve H-bonding, nonpolar, or van der Waals contacts between surface exposed residue side groups or peptide NH groups of the polypeptide main chain and base pair edges exposed in the major and minor grooves of the DNA at the binding site. Both non-specific and specific interactions contribute to the binding energy at the binding site. In addition, the long range electrostatic interactions involved in some sequence-independent bonds can kinetically facilitate site-specific binding by allowing the protein to rapidly bind weakly to DNA and then to diffuse long distances along the DNA strand (KIMJ87, TAKE86). This mechanism greatly accelerates the process of protein diffusion to binding sites by reducing the protein search from three dimensions to one dimension (KIMJ87). In the non-specific protein—DNA complex, the protein is thought to be displaced less than 4 A outward from the DNA axis and to lack the major groove contacts (TAKE85, TAKE86). Thus, many sequence-independent interactions (e.g. phosphate-to-peptide NH H-bonds) are possible only in the specific configuration achieved at the binding site. In addition, some interactions change from sequence-independent to sequence-specific in the transition from the non-specific complex to the specific complex at the binding site (e.g. R41 and R43 in 434 Repressor (ANDE87)).

Mutations that alter residues involved in specific binding interactions with DNA have been identified in a number of prokaryotic DNA-binding proteins including lambda, 434, and P22 repressor and Cro proteins, P22 Arc and Mnt, and *E. coli* trp and lac repressors and CAP. In general, these mutations occur in residues that are exposed to solvent in the free protein but buried in the protein-DNA complex and result in relatively stable expressed proteins.

A few cases have been reported (BASS88, YOUD83, VERS85a, CARU87, WHAR87, and EBRI84) in which a change in a single residue in a DNA-binding protein not only abolishes binding by the protein to the wild-type operator but also confers strong binding to a different operator.

Youderian et al. (YOUD83) and Vershon et al. (VERS85a) have described the isolation and binding characteristics of an altered P22 Mnt repressor (Mnt-bs) which recognizes an altered operator. Mnt-bs binds tightly to a symmetrically altered operator (mA/mA operator) in which the base pairs at the positions 3 and 15 are changed from G:C pairs to A:T pairs. The host cells produce dam methylase so that the adenines at operator positions are methylated. In vitro, Mnt-bs binds as tightly to the mA/mA operator as the wild-type protein binds to the G/G operator. In addition, wild-type repressor binds to the mA/mA operator 1000-fold less well than to the wild-type operator while Mnt-bs shows an identical 1000-fold decrease in binding to the G/G operator relative to the mA/mA operator. Mnt-bs does not bind to the unmethylated A/A operator isolated from dam⁻ cells (VERS85a). Thus, the altered recognition of Mnt-bs involves the major groove N6-methyl groups of the adenines at positions 3 and 15 of the mA/mA operator.

At pH lower than 8.5, wild-type P22 Mnt shows a strong pH dependence for binding to the G/G operator while Mnt-bs binding to the mA/mA operator shows relatively little pH dependence (VERS85a). These observations are consistent with the proposal (VERS85a) that H6 acts as a hydrogen donor to O6 or N7 of the guanines at positions 3 and 15 of the wild-type operator. Thus, the change in specificity shown by Mnt-bs relative to wild-type Mnt results from the replacement of one set of contacts (H-bonds between H6 of P22 Mnt and guanine 3 or 15) with an energetically equivalent set (hydrophobic interactions between P6 of Mnt-bs and the N6 methyl groups of methylated adenines at operator positions 3 or 15).

A similar example of a single residue change producing an altered protein which recognizes a different operator has been described using lambda Cro binding to lambda $O_R1$ (CARU87). In the wild-type Cro-wild-type $O_R1$ complex, Q27 is believed to form H-bonds with N6 and N7 of adenines at positions 2 or 16 in $O_R1$. Based on computer modeling predictions, Caruthers et al. (CARU87) replaced the adenines at positions 2 and 16 in $O_R1$ with thymine (to make $O_R1^*$) and constructed altered Cro repressors having C, L, V, I, and G in place of Q at position 27. The $O_R1$-to-$O_R1^*$ change results in a more than 40-fold decrease in wild-type Cro binding. The QC27, QL27, QV27, and QI27 changes all produce proteins that bind to $O_R1^*$ as well as wild-type Cro binds to $O_R1$. QG27 Cro does not bind well to either operator. The QC27 mutation reduces binding of the altered Cro to $O_R1$ 8-fold relative to wild-type binding, while the QI27, QL27, and QV27 substitutions produced proteins that bind to $O_R1$ almost as well as the wild-type Cro. Thus, the larger hydrophobic amino acid substitutions (I, L, V) result in proteins with a loss of specificity in operator binding (A or T at positions 2 and 16 are acceptable) perhaps due to an interaction between the large side groups and thymine methyl groups across the major groove. The QC27 substitution produces an altered Cro which distinguishes between $O_R1$ and $O_R1^*$ and binds to $O_R1^*$ with the same affinity as the wild-type Cro repressor binds to $O_R1$.

Wharton and Ptashne (WHAR85b) have described the construction of an altered 434 repressor with altered operator binding properties. These authors show that any single base pair change in the outer 8 positions (1-4, 11-14) of a synthetic 434 operator reduces operator binding by wild-type 434 repressor more than 150-fold. The single QA28 change in 434 repressor produces an altered repressor which cannot bind to the wild-type operator. QA28 repressor binds to an altered operator, 1T, in which thymidine has been substituted for adenine at the symmetrically located 1 and 14 positions. Binding of QA28 repressor to operator 1T is almost as strong as binding of wild-type repressor to wild-type operator.

QA28 repressor does not bind to operators 1C, 1G, or 1U and binds with 50-fold lower affinity to an operator in which 5-methylcytosine replaces adenine at positions 1 and 14. Molecular modeling suggests that the change in specificity results from the substitution of a single hydrophobic interaction (van der Waals contact between the A28 side group methyl and the 5 methyl group of thymidine) in the QA28-repressor-operator-1T complex for the two hydrogen bonds (between N and O of Q28 and N7 and N6 of adenine) in the wild-type repressor-wild-type operator complex. The reduced binding of QA28 repressor to the 5-methyl-C operator may result from a slight misalignment of the protein and DNA methyl groups (WHAR87).

Ebright et al. (EBRI84) have described the isolation of three mutations that alter sequence-specificity in cAMP receptor protein (CRP) of *Escherichia coli*, also known as catabolite activator protein (CAP). The altered proteins show specificity for A:T base pairs at the symmetrically located positions 7 and 16 in the operator rather than for the G:C pairs required for binding by wild-type CRP. Model building suggests that the three missense mutations, each of which changes residue 181 (EK181, EL181, EV181), produce changes in major groove contacts between protein side groups and DNA base pairs in the operator. The H-bond between N4 of cytosine and an oxygen of Q181 present in the wild-type complex is replaced in the altered complexes by hydrophobic interactions between K181, L181 or V181 methyl groups and the thymine methyl group. In addition, K181 can form a H-bond with the thymidine O4 atom.

Spiro and Guest (SPIR88) have changed the DNA-binding properties of *E. coli* FNR protein to be very similar to those of *E. coli* CRP by changing three residues in the recognition helix. FNR is a protein of known sequence but unknown 3D structure that has significant sequence similarity to CRP and is involved in turning on genes needed in anaerobic conditions. Shaw et al. (SHAW83) suggest that FNR is similar to CRP in that it can bind its cognate operator only when an effector molecule, as yet unknown, is bound to FNR. The sequence similarity between FNR and CRP suggests that the 3D structure of FNR may be similar to CRP. The residues of FNR that correspond to the cAMP-contacting residues of CRP are different from those of CRP.

In all of the examples cited above, alteration of binding specificity has been accomplished by using symmetrically-located pairs of alterations in the operator sites and repressor DNA-binding regions. Single, asymmetric changes or multiple changes asymmetrically located in either the binding protein or its operator were not considered.

The class of DNA-binding mutations that change protein recognition includes the "helix swap" constructions (WHAR84, WHAR85b, WHAR85a, SPIR88). In these altered proteins, multiple mutations are introduced into the DNA-binding recognition helix of H-T-H proteins with the goal of changing the operator specificity of one protein to that of another.

Wharton et al. (WHAR84) have described an experiment in which they introduced five site specific changes (EQ32, QL33, LI34, NA36, and KV38) in alpha 3 (recognition helix) of 434 repressor. The resulting alpha 3 was identical in sequence to the alpha 3 of 434 Cro. In DMS methylation protection experiments, the altered repressor and wild-type Cro have effects on operator purine methylation which are identical to each other and different from wild-type repressor. The relative affinities of the altered repressor for 434 operator sites $O_R1$, $O_R2$ and $O_R3$ are intermediate between those of wild-type 434 repressor and 434 Cro, although the overall affinity of the hybrid molecule for operator DNA is reduced. Wharton et al. (WHAR84) also reported that the converse helix swap experiment in which the recognition helix of 434 Cro was replaced with that of 434 repressor (except for I34) produces a hybrid protein which protects host cells against infection by 434 phage.

In a second set of helix swap experiments, Wharton and Ptashne (WHAR85b) introduced changes in the solvent-exposed residues of 434 repressor alpha 3 (TR27, QN28, QV29, ES32, NR36) to produce a hybrid repressor protein having the solvent exposed alpha 3 surface of P22 repressor while the remainder of the protein (including the buried alpha 3 surface) was identical to 434 repressor. When overexpressed, the hybrid repressor protects host cells from lambda immP22 phages but not from lambda imm434 phages. In addition, the overexpressed hybrid is trans-dominant, suggesting that heterodimers of altered and wild-type 434 repressor monomers form but are non-functional.

Wild-type P22 and 434 repressors do not bind to each other's operators in vitro and the hybrid 434(P22 recognition) repressor protein does not bind to 434 operator sequences in vitro (WHAR85b). DNase I protection experiments show that the hybrid protein binds to and protects P22 $O_R1$, $O_R2$, and $O_R3$ with the same relative affinities as wild-type P22 repressor, although the absolute affinities are reduced about 10-fold relative to the wild-type protein.

Wharton and Ptashne (WHAR85b) have reported that P22/434 hybrid repressor proteins in which substitutions with P22 residues are limited to the six to seven N-terminal residues of alpha 3 can protect host cells against infection with lambda immP22 phages but not against lambda imm434 phages. In contrast, hybrid repressors with substitutions of P22 residues in the C-terminal 5 to 6 residues of alpha 3 protect host cells from infection with lambda imm434 phages but not from infection with lambda immP22 phages. Thus, sequence-specific recognition by 434 repressor appears to be confined to the N-terminal half of alpha 3.

Wharton (WHAR85a) has reported that recognition helix swap experiments between 434 repressor and lambda repressor, lambda Cro, and CAP produce hybrid proteins which are non-functional in vivo and in vitro. Lambda repressor, Cro and CAP recognize larger operators than 434 repressor and, in addition, may employ different binding orientations (CAP) (PAB084, WHAR85a), or additional binding interactions (e.g. lambda repressor and Cro N- and C-terminal arms) to stabilize the bound structure. The greater than 40-fold decrease in operator affinity due to alpha 2 substitutions in Cro67 (BUSH88) further emphasizes the importance of regions outside the recognition helix to repressor specificity and binding.

An extension of the "helix swap" experiments uses a mixture of 434 repressor and 434R[alpha3(P22R)] (HOLL88). This mixture recognizes and binds in vitro with high affinity to a 16 bp chimeric operator consisting of a 434 half-site and a P22 half-site, indicating that active heterodimers are formed. The authors did not extend the results to in vivo cellular repression, nor did they perform mutagenesis of the repressors and selection of cells to create novel recognition patterns.

Comparison of the results of the helix swap experiments with the results of the single residue change experiments described previously highlights the importance of protein structure outside the recognition helix to binding affinity. While the altered proteins produced from single residue changes recognize the altered operators with high affinities, the hybrid proteins produced in helix swap experiments recognize their operators with reduced affinities relative to the wild-type "helix donors". In the case of a single site-specific alteration in alpha 3, the altered protein recognizes the new operator in the context of a complex in which wild-type protein structure is conserved. In helix swap experiments in which both monomers contain altered recognition helices, the recognition helix of one protein interacts with its operator in the context of a framework provided by a different protein. The less than ideal three dimensional conformation imposed by the host protein can reduce the affinity of the hybrid for the operator or, as is the case for lambda repressor, lambda Cro or CAP recognition helices in 434 repressor, abolish binding altogether. In contrast, the heterodimeric repressor described by Hollis et al. (HOLL88) recognizes the chimeric operator nearly as well as the wild type 434 repressor protein recognizes its operator. This requires that the heterodimer is sufficiently flexible to allow the adjustments needed for optimal interactions at both half-sites.

Hollis et al. (HOLL88) have shown that heterodimers of two highly similar DBPs bind in vitro to a chimeric operator having no sequence symmetry. Hollis et al. mixed equal quantities of 434 repressor and "helix-swapped" 434 repressor bearing the alpha 3 helix of P22 repressor, to form the mixed dimer.

With the exception of Hollis et al. (HOLL88), all of the helix swap experiments described involve the creation, through direct substitutions of known binding sequences, of symmetrical homodimers of hybrid repressor monomers which interact with known operators having some degree of symmetry. None of these studies, including that of Hollis et al., discuss binding to completely novel non-symmetric operator sites via proteins containing two different recognition sites, nor construction of novel DNA binding regions by simultaneous variations of sets of residues on the protein surface.

The recently developed techniques of "reverse genetics" have been used to produce single specific mutations at precise base pair loci (OLIP86, OLIP87, and AUSU87). Mutations are generally detected by sequencing and in some cases by loss of wild-type function. These procedures allow researchers to analyze the function of each residue in a protein (MILL88) or of each base pair in a regulatory DNA sequence (CHEN88). In these analyses, the norm has been to strive for the classical goal of obtaining mutants carrying a single alteration (AUSU87).

Reverse genetics is frequently applied to coding regions to determine which residues are most important to the protein structure and function. In such studies, isolation of a single mutant at each residue of the protein and determination of the phenotype conferred gives an initial estimate of which residues play crucial roles.

Prior to the invention of Ladner and Guterman (Ser. No. 07/240,160), two general approaches have been developed to create novel mutant proteins through reverse genetics. Both methods start with a clone of the gene of interest. In one approach, dubbed "protein surgery" (reviewed by Dill, (DILL87)), a specific substitution is introduced at a single protein residue by a synthetic method using the corresponding natural or synthetic cloned gene. Craik et al. (CRAI85), Roa et al. (RAOS87), and Bash et al. (BASH87) have used this approach to determine the effects on structure and function of specific substitutions in trypsin.

The other approach has been to generate a variety of mutants at many loci within the cloned gene, the "gene-directed random mutagenesis" method. The specific location and nature of the change or changes are determined by DNA sequencing. It may be possible to screen for mutations if loss of a wild-type function confers a cellular phenotype. Using immunoprecipitation, one can then differentiate among mutant proteins that: a) fold but fail to function, b) fail to fold but persist, and c) are degraded, perhaps due to failure to fold. This approach is exemplified by the work of Pakula et al. (PAKU86) on the effect of point mutations on the structure and function of the Cro protein from bacteriophage lambda. This approach is limited by the number of colonies that can be examined. An additional important limitation is that many desirable protein alterations require multiple amino acid substitutions and thus are not accessible through single base changes or even through all possible amino acid substitutions at any one residue.

The objective in both the surgical and gene-directed random mutagenesis approaches has been, however, to analyze the effects of a variety of single substitution mutations, so that rules governing such substitutions could be developed (ULME83). Progress has been greatly hampered by the extensive efforts involved in using either method and the practical limitations on the number of colonies that can be inspected (ROBE86).

The term "saturation mutagenesis" with reference to synthetic DNA is generally taken to mean generation of a population in which: a) every possible single-base change within a fragment of a DNA coding or regulatory region is represented, and b) most mutant genes contain only one mutation. Thus a set of all possible single mutations for a 6 base-pair length of DNA comprises a population of 18 mutants. Oliphant et al. (OLIP86) and Oliphant and Struhl (OLIP87) have demonstrated ligation and cloning of highly degenerate oligonucleotides and have applied saturation mutagenesis to the study of promoter sequence and function. They have suggested that similar methods could be used to study genetic expression of protein coding regions of genes, but they do not say how one should: a) choose protein residues to vary, or b) select or screen mutants with desirable properties.

Ward et al. (WARD86) have engineered heterodimers from homodimers of tyrosyl-tRNA synthetase. Methods of converting homodimeric DBPs into heterodimeric DBPs are disclosed in the present invention. Creighton (CREI84, p263-264) has reviewed cases in which gene duplication and evolution have produced single-polypeptide proteins with approximate dyad symmetry despite very low internal sequence homology. Methods of deriving single-polypeptide pseudo-dimeric DBPs from homodimeric DBPs are disclosed in the examples of the present invention. An example of naturally occurring heterodimer binding to a nonpalindromic site consisting of two naturally occurring half-sites is found in the yeast MATalpha2 protein. The DNA site that it recognizes consists of two unlike half-sites, and each of these are found in full palindromes at other yeast loci.

Benson et al. (BENS86) have developed a scheme to detect genes for sequence-specific DNA-binding proteins that utilizes the immI region of phage P22. They have demonstrated that five different operators can function at the same site to repress transcription when the appropriate DNA-binding protein is present. They do not consider non-symmetric target DNA sequences nor do they suggest mutagenesis to generate novel DNA-binding properties. Their method is presented as a method to detect genes for naturally occurring DNA-binding proteins. Because the selective system is lytic growth of phage, low levels of repression can not be detected. Selective chemicals, as disclosed in the present application, on the other hand, can be finely modulated so that low level repression is detectable.

Ladner and Bird, WO88/06601, published 7 September 1988 and claiming priority from a U.S. application filed Mar. 2, 1987, suggest strategies for the preparation of asymmetric repressors. In one embodiment, a gene is constructed that encodes, as a single polypeptide chain, the two DNA-binding domains of a naturally-occurring dimeric repressor, joined by a polypeptide linker that holds the two binding domains in the necessary spatial relationship for binding to an operator. While they prefer to design the linker based on protein structural data (cf. Ladner, U.S. Pat. No. 4,704,692) they state that uncertainties in the design of the linker may be resolved by generating a family of synthetic genes, differing in the linker-encoding subsequence, and selecting in vivo for a gene encoding the desired pseudo-dimer. Ladner and Bird do not consider the background of false positives that would arise if the two-domain polypeptides dimerize to form pseudo-tetramers.

The binding of lambdoid repressors, Cro and CI repressor, is taken, in WO88/06601, as canonical even though other DBPs were known having operators of different lengths. WO88/06601 maintains that the 17 bp lambdoid operators can be divided into three regions: a) a left arm of five bases, b) a central region of seven bases, and c) a right arm of five bases. Several other DBPs are known for which this division is inappropriate. Further, WO88/06601 states that the sequence and composition of the central region, in which edges of bases are not contacted by the DBP, are immaterial. There is direct evidence for 434 repressor (KOUD87) that the sequence and composition of the central region strongly influences binding of 434 repressor.

Once a pseudo-dimer is obtained, they then obtain an asymmetric pseudo-dimer by the following technique. First, the user of WO88/06601 is directed to construct a family of hybrid operators in which the sequence of the left and right arms are specified; no specification is given for the central seven bases. In each member of the family, the left arm contains the same sequence as the wild-type operator left arm while the right arm 5-mer is systematically varied through all 1024 possibilities. Similarly, in the gene encoding the pseudodimer, the codons for one recognition helix have the wild-type sequence while the codons coding for the other recognition helix are highly varied. The variegated pseudo-dimer genes are expressed in bacterial cells, wherein the hybrid operators are positioned to repress a single highly deleterious gene. Thus, it is supposed that one can identify a recognition helix for each possible 5-mer right arm of the operator by in vivo selection; the correspondences between 5-mer right arms and sequences of recognition helices are compiled into a dictionary. The consequences of mutations or deletions in the deleterious genes are not considered. WO88/06601 suggests that successful constructions may be very rare, e.g. one in $10^6$, but ignore other genetic events of similar or greater frequency.

To obtain a repressor for an arbitrary 17-mer operator, the user of WO88/06601:
a) finds the 5-mer sequence of the left arm in the dictionary and uses the corresponding recognition helix sequence in the first DNA-binding domain of the pseudodimer,
b) ignores the sequence and composition of the next seven bases, and
c) finds the 5-mer sequence of the right arm in the dictionary and uses the corresponding recognition helix sequence in the second DNA-binding domain of the pseudodimer.

WO88/06601 also envisions means for producing a heterodimeric repressor. A plasmid is provided that carries genes encoding two different repressors. A population of such plasmids is generated in which some codons are varied in each gene. WO88/06601 instructs the user to introduce very high levels of variegation without regard to the number of independent transformants that can be produced. WO88/06601 also instructs the user to introduce variegation at widely separated sites in the gene, though there is no teaching concerning ways to simultaneously introduce high levels of variegation at widely separated sites in the gene or concerning maintenance of diversity without selective pressure, as would be needed if the variegation were introduced stepwise. WO88/06601 teaches that codons thought to be involved in the protein-protein interface should be preferentially mutated to generate heterodimers. Cells transformed with this population of plasmids will produce both the desired heterodimer and the two "wild-type" homodimers. WO88/06601 advises that one select for production of the heterodimer by providing a highly deleterious gene controlled by a hybrid operator, and beneficial genes controlled by the wild-type operators. The fastest growing cells, it is taught, will be those that produce a great deal of the heterodimer (which blocks expression of the deleterious gene) and little of the homodimers (so that the beneficial genes are more fully expressed). There is no consideration of mutations or deletions in the deleterious gene or in the wild-type operators; such mutations will produce a background of fast-growing cells that do not contain the desired heterodimers.

Ladner, U.S. Pat. No. 4,704,692, "Computer Based System and Method for Determining and Displaying Possible Chemical Structures for Converting Double- or Multiple-Chain Polypeptides to Single-Chain Polypeptides" (Ladner ,692), assigned to Genex Corporation. Ladner '692 describes a design method for converting proteins composed of two or more chains into proteins of fewer polypeptide chains, but with essentially the same 3D structure. There is no mention of variegated DNA and no genetic selection.

Ladner, Glick and Bird, WO88/06630, published 7 September 1988, and claiming priority from a U.S. application filed Mar. 2, 1987, relates to the preparation of "single chain antibodies." The present invention, on the other hand, is directed to the preparation of non-immunoglobulin proteins which bind to DNA, and particularly those which affect gene expression. A cell containing a gene encoding a "single chain antibody" expresses that gene and displays the antibody on the cell surface as a domain of a fusion protein. It is suggested that a diverse population of antibody domains may be obtained by varying the sequene of the DNA encoding the domain by mutation techniques. Cells displaying antibody domains which bind the antigen of interest are selected. There is no teaching as to where to mutate the gene, and selection is by extracellular binding of a surface-displayed domain to an immobilized extracellular antigen.

Robert Charles Ladner is a joint inventor on five other patent applications pending before the USPTO and assigned to Genex Corporation:
07/92,110, 07/21,047, 07/34,964, 07/34,965, and 07/34,966

Sonia K. Guterman is a joint inventor on U.S. Pat. No. 4,745,056 ("Streptomyces Secretion Vector") and on U.S. patent application Ser. No. 07/21,465, pending before the USPTO, both assigned to BioTechnica International, Inc.

Rachel B. Kent is a joint inventor on U.S. patent application Ser. No. 07/229,644 pending before the USPTO and assigned to Massachusetts Institute of Technology and Yale University.

None of the foregoing is to be construed as an admission of the scope and content of the prior art or of the pertinency of that art. Where the referenced work is by another, the discussion is based solely on the published description and no admission is made that the work was performed as described. The dates given for the references are the nominal dates given in the cited work and may not correspond to the true publication dates under applicable law.

SUMMARY OF THE INVENTION

This invention relates to the development of novel proteins or polypeptides that preferentially bind to a specific subsequence of double-stranded DNA (the "target") which need not be symmetric, using a novel scheme for in vivo selection of mutant proteins exhibiting the desired binding specificities.

The novel binding proteins or polypeptides may be obtained by mutating a gene encoding on expression: 1) a known DNA-binding protein within the subsequence encoding a known DNA-binding domain, 2) a protein that, while not possessing a known DNA-binding activity, possesses a secondary or higher order structure that lends itself to binding activity (clefts, grooves, helices, etc.), 3) a known DNA-binding protein but not in the subsequence known to cause the binding, or 4) a polypeptide having no known 3D structure of its own.

This application uses the term "variegated DNA" to refer to a population of molecules that have the same base sequence through most of their length, but that vary at a number of defined loci. Using standard genetic engineering techniques, variegated DNA can be introduced into a plasmid so that it constitutes part of a gene (OLIP86, OLIP87, AUSU87, REID88). When plasmids containing variegated DNA are used to transform bacteria, each cell makes a version of the original protein. Each colony of bacteria produces a different version from most other colonies. If the variegations of the DNA are concentrated at loci that code on expression for residues known to be on the surface of the protein or in loops, a population of genes will be generated that code on expression for a population of proteins, many members of which will fold into roughly the same 3D structure as the parental protein. Most often we generate mutations that are concentrated within codons for residues thought to make contact with the DNA. Secondarily, we introduce mutations into codons specifying residues that are not directly involved in DNA contact but that affect the position or dynamics of residues that do contact the DNA.

In general, a variegated population of DNA molecules, each of which encodes one of a large (e.g. $10^7$) number of distinct potential target-binding proteins, is used to transform a cell culture. The cells of this cell culture are engineered with binding marker genes so that, under selective conditions, the cell thrives only if the expressed potential target-binding protein in fact binds to the target subsequence preventing expression of these binding marker genes. (Typically, binding of a successful target-binding protein to the target subsequence blocks expression of a gene product that is deleterious under selective conditions.) The mutant cells are directed to express the potential target-binding proteins and the selective conditions are applied. Cells expressing proteins binding successfully to the target are thus identified by in vivo selection. If the binding characteristics are not fully satisfactory, the amino acid sequences of the best binding proteins are determined (usually by sequencing the corresponding genes), a new population of DNA molecules is synthesized that encode variegated forms of the best binding proteins of the last cull, mutant cells are prepared, the new population of potential DNA-binding proteins is expressed, and the best proteins are once again identified by the superior growth of the corresponding transformants under selective conditions. The process is repeated until a protein or polypeptide with the desired binding characteristics is obtained. Its corresponding gene may then be identified and moved to a suitable expression system for large-scale production.

In the simplest form of this invention, the mutant cells are provided with a selectable gene coding on expression for a product deleterious to the survival or growth of the cell, operably linked to a promoter regulating the expression of the gene. The promoter, or other non-coding region of the gene itself (for example, an intron), has been modified to include the desired target subsequence in a position where it will not interfere with expression of the selectable gene unless a protein binds to that target subsequence. Each mutant cell is also provided with a gene encoding on expression a potential DNA-binding protein, operably linked to a promoter that is preferably regulated by a chemical inducer. When this gene is expressed, the potential DNA-binding protein has the opportunity to bind to the target and thereby protect the cell from the selective conditions under which the product of the binding marker gene would otherwise harm the cell.

In addition to the desired outcome of these in vivo selections, there exist a number of possible genetic events that allow the cells to escape the selection, producing artifacts and inefficiency by allowing the growth of colonies that do not express the desired sequence-specific DNA-binding proteins. Examples of mechanisms, other than the desired outcome, that lead to cell survival under the selective conditions include: a) a point mutation or a deletion in the selectable gene eliminates expression or function of the selectable gene product; b) a host chromosomal mutation compensates for or suppresses function of the selectable gene product; c) the introduced potential DNA-binding protein binds to a DNA subsequence other than the chosen target subsequence and blocks expression of the selectable gene; d) the introduced potential DNA-binding protein binds to and inactivates the gene product of the selective gene; and e) a DNA-binding protein endogenous to the host mutates so that it binds to the selectable gene and blocks expression of the selectable gene.

This invention relates, in particular, to the design of a vector that confers upon the host cells the desired conditional sensitivity to the selection conditions in such a manner as to greatly reduce the likelihood of false positives and artifactual colonies.

First, at least two selectable genes that are functionally unrelated are used to reduce the risk that a single point mutation in the vector (or in the host chromosome) will destroy the sensitivity of the cell to the selective conditions, since it will eliminate only one of the two (or more) deleterious phenotypes. Similarly, a single introduced gene for a potential DNA-binding protein that binds to and inactivates the gene product of one selectable gene will not bind and inactivate the gene product of the other selectable gene. The likelihood that point mutations will occur in both selectable genes or that two host chromosomal mutations will spontaneously arise that suppress the effects of two genes is the product of each single individual probabilities of the necessary event, and thus is extremely low.

The DNA sequences of the two or more selectable genes preferably should not have long segments of identity: a) to avoid isolation of a DBP that binds these identical regions instead of the intended target sequence, and b) to reduce the likelihood of genetic recombination. The degeneracy of the genetic code allows us to avoid exact identity of more than a few, e.g. 10, bases.

Second, the selectable genes are placed on the vector in alternation with genetic elements that are essential to plasmid maintenance. Thus, a single deletion event, even of thousands of bases, cannot eliminate both selectable genes without also eliminating vital genetic elements.

Third, different promoters are associated with each of the selectable genes. This ensures that the selection does not isolate cells harboring genes encoding on expression novel DNA-binding proteins that bind specifically to subsequences that are part of the promoter but not the chosen target subsequence. Each cell expresses only one or a few introduced potential DNA-binding proteins (multiple potential DNA-binding proteins could arise if one cell is transformed by two or more variegated plasmids). The probability that two such proteins will occur in one cell and that one will bind to the promoter of the first selectable gene and that the second will bind to the different promoter of the second selectable gene is the product of all of the individual probabilities of transformation of the cells by DNA and successful mutation to binding. Because the individual probabilities are very small, the product is negligibly small.

Finally, the same promoter is used to initiate transcription of two genes: a) one of the deleterious selectable binding marker genes, and b) a beneficial or essential gene also borne on the plasmid and used to select for uptake and maintenance of the plasmid (e.g. an antibiotic resistance gene, such as amp). In the case of the beneficial or essential gene, however, there is no instance of the predetermined target DNA subsequence associated with the promoter. Thus, if a DNA-binding protein binds to a subsequence of the promoter other than the predetermined target DNA subsequence, it will frustrate expression not only of the deleterious gene, but also of the beneficial or essential one. If desired, more than one such beneficial or essential gene may be provided. In that event, copies of promoter A may be operably linked to both deleterious gene A' (with an instance of the target) and beneficial gene A" (without an instance of the target), while copies of promoter B are operably linked to both deleterious gene B' (with target) and beneficial gene B" (without target).

The selection system described above is a powerful tool that eliminates most of the artifacts associated with selections based on cloning vectors that use a single selectable gene or that have all selectable genes in a contiguous region of the plasmid. While this invention embraces using the aforementioned elements of a selection system singly or in partial combination, most preferably all are employed.

In one embodiment, the invention relates to a cell culture comprising a plurality of cells, each cell bearing:
i) a gene coding on expression for a potential DNA-binding protein or polypeptide, where such protein or polypeptide is not the same for all such cells, but rather varies at a limited number of amino acid positions; and
ii) at least two independent operons, each comprising at least one binding marker gene coding on expression for a product conditionally deleterious to the survival or reproduction of such cells, the promoter of each said binding marker gene containing a predetermined target DNA subsequence so positioned that, if said target DNA subsequence is bound by a DNA-binding protein or polypeptide, said conditionally deleterious product is not expressed in functional form.

Most known DNA-binding proteins bind to palindromic or nearly palindromic operators. It is desirable to be able to obtain a protein or polypeptide that binds to a target DNA subsequence having no particular sequence symmetry. In another embodiment of the present invention, such a binding protein is obtained by creating a hybrid of two dimeric DNA-binding proteins, one of which ($DBP_L$) recognizes a symmetrized form of the left subsequence of the target subsequence, and the other of which ($DBP_R$) recognizes a symmetrized form of the right subsequence of the target subsequence.

Cells producing equimolar mixtures of $DBP_L$ and $DBP_R$ contain approximately 1 part $(DBP_L)_2$, 2 parts $DBP_L:DBP_R$, and 1 part $(DBP_R)_2$. The $DBP_L:DBP_R$ heterodimers, which bind to the non-symmetric target subsequence, may be isolated from a cell lysate by affinity chromatography using the target sequence as the ligand. If desired, the heterodimers may be stabilized by chemically crosslinking the two binding domains.

It is also possible to modify both $DBP_L$ and $DBP_R$, by a process of variegation and selection, so that they have (without disturbing their affinity for the predetermined DNA target subsequence) complementary but not dyad-symmetric protein-protein binding surfaces. When such polypeptides are mixed, in vivo or in vitro, the primary species will be $DBP_L:DBP_R$ heterodimers. Alternatively, reversing the steps, a dimeric binding protein may be modified so that its two binding domains have complementary but not dyad-symmetric protein-protein binding surfaces, and then the DNA-contacting surfaces are modified to bind to the right and left halves of the target DNA subsequence. In either case, the resulting cooperative domains can be crosslinked for increased stability.

When a binding protein is engineered so that its two binding domains have complementary, but not dyad-symmetric protein-protein binding surfaces, then in the preferred embodiment one of the steps will be a "reverse selection", i.e. a selection for a protein that does not bind to the symmetrized half-target sequence. To facilitate such reverse selection, it is desirable that the binding marker genes be capable of "two-way" selection (VINO87). For a two-way selectable gene there exist both a first selection condition in which the gene products are deleterious (preferably lethal) to the cell and a second selection condition in which the gene product is beneficial (preferably essential) to the cell. The first selection condition is used for forward selection in which we select for cells expressing proteins that bind to the target so that gene expression is repressed. The second selection condition is used for reverse selection in which we select for cells that do not express a protein that binds to the target, thereby allowing expression of the gene product.

It is to be understood that abolition of function is much easier than engineering of novel function. Reverse selection can isolate cells that: a) express no DBP, b) express unstable proteins descendant from a parental DBP, c) express a protein descendant from a parental DBP having very nearly the same 3D structure as the parental DBP, but lacking the functionality of the parent. We are interested in this third class. It is difficult, however, to distinguish among these classes genetically. Therefore, when using reverse selection, we carefully choose sites to mutate the protein (so as to minimize the chances of destroying tertiary structure) and we introduce a lower level of variegation than in forward selection. We must verify biochemically that a stable, folded protein is produced by the isolated cells.

Another concept of the present invention is the use of a polypeptide, rather than a protein, to preferentially bind DNA. This polypeptide, instead of binding the DNA molecule as a preformed molecule having shape complementary to DNA, will wind about the DNA molecule in the major or minor groove. Such a polypeptide has the advantage that it is smaller than a protein having equivalent recognizing ability and may be easier to introduce into cells.

In a preferred embodiment, the DNA inserts that code on expression for potential-DNA-binding proteins or polypeptides are incorporated into a gene that is regulated by addition of chemical inducer to the cell culture, such as isopropylthiogalactoside (IPTG). Other regulatable promoters having different inducers or other means of regulation are also appropriate.

The invention encompasses the design and synthesis of variegated DNA encoding on expression a collection of closely related potential DNA-binding proteins or polypeptides characterized by constant and variable regions, said proteins or polypeptides being designed with a view toward obtaining a protein or polypeptide that binds a predetermined target DNA subsequence.

For the purposes of this invention, the term "potential DNA-binding polypeptide" refers to a polypeptide encoded by one species of DNA molecule in a population of variegated DNA wherein the region of variation appears in one or more subsequences encoding one or more segments of the polypeptide having the potential of serving as a DNA-binding domain for the target DNA sequence or having the potential to alter the position or dynamics of protein residues that contact the DNA. A "potential DNA-binding protein" (potential- DBP) may comprise one or more potential DNA-binding polypeptides. Potential-DBPs comprising two or more polypeptide chains may be homologous aggregates (e.g. $A_2$) or heterologous aggregates (e.g. AB).

From time to time, it may be helpful to speak of the "parental sequence" of the variegated DNA. When the novel DNA-binding domain sought is a homolog of a known DNA-binding domain, the parental sequence is the sequence that encodes the known DNA-binding domain. The variegated DNA is identical with this parental sequence at most loci, but will diverge from it at chosen loci. When a potential DNA-binding domain is designed from first principles, the parental sequence is a sequence that encodes the amino acid sequence that has been predicted to form the desired DNA-binding domain, and the variegated DNA is a population of "daughter DNAs" that are related to that parent by a high degree of sequence similarity.

The fundamental principle of the invention is one of forced evolution. The efficiency of the forced evolution is greatly enhanced by careful choice of which residues are to be varied. The 3D structure of the potential DNA-binding domain and the 3D structure of the target DNA sequence are key determinants in this choice. First a set of residues that can either simultaneously contact the target DNA sequence or that can affect the orientation or flexibility of residues that can touch the target is identified. Then all or some of the codons encoding these residues are varied simultaneously to produce a variegated population of DNA. The variegated population of DNA is introduced into cells so that a variegated population of cells producing various potential-DBPs is obtained.

The highly variegated population of cells containing genes encoding potential-DBPs is selected for cells containing genes that express proteins that bind to the target DNA sequence ("successful DNA-binding proteins"). After one or more rounds of such selection, one or more of the chosen genes are examined and sequenced. If desired, new loci of variation are chosen. The selected daughter genes of one generation then become the parental sequences for the next generation of variegated DNA (vgDNA).

DNA-binding proteins (DBPs) that bind specifically to viral DNA so that transcription is blocked will be useful in treating viral diseases, either by introducing DBPs into cells or by introducing the gene coding on expression for the DBP into cells and causing the gene to be expressed. In order to develop such DBPs, we need use only the nucleotide sequence of the viral genes to be repressed. Once a DBP is developed, it is tested against virus in vivo. Use of several independently-acting DBPs that all bind to one gene allow us to: a) repress the gene despite possible variation in the sequence, and b) to focus repression on the target gene while distributing side effects over the entire genome of the host cell. Animals, plants, fungi, and microbes can be genetically made intracellularly immune to viruses by introducing, into the germ line, genes that code on expression for DBPs that bind DNA sequences found in viruses that infect the animal (including human), plant, fungus, or microbe to be protected.

Sequence-specific DBPs may also be used to treat autoimmune and genetic disease either by repressing noxious genes or by causing expression of beneficial genes. For example, in sickle-cell anemia, it may be beneficial to cause expression of epsilon-globin and repress the expression of the mutant beta-globin. As with the treatment of viral disease, treatment may be effected by delivery of protein into cells or by delivery of a gene that codes on expression for the protein.

In multiple sclerosis (MS), it has been shown that astrocytes are activated by gamma interferon. In the activated state, astrocytes can present the major histocompatibility complex (MHC) and antigens, such as myelin basic protein, to T-cells. The ability to repress expression of MHC genes in astrocytes may be therapeutic in MS patients. In addition, it has been shown that suppressor T-cells of MS patients have abnormally high levels of norepinephrine-receptors; down-regulation of the T-cell norepinephrine-receptor gene may be therapeutic in MS patients.

Some naturally-occurring DBPs bind sequence-specifically to DNA only in the presence or absence of specific effector molecules. For example, Lac repressor does not bind the lac operator in the presence of lactose or isopropylthiogalactoside (IPTG); Trp repressor binds DNA only in the presence of tryptophan or certain analogues of tryptophan. The method of the present invention can be used to select mutants of such DBPs that a) recognize a different cognate DNA sequence, or b) recognize a different effector molecule. These alterations would be useful in biotechnology because: a) known inducible or derepressible DBPs allows us to use the novel DBP without affecting existing metabolic pathways. Having novel effectors allows us to induce or derepress the regulated gene without altering the state of genes that are controlled by the natural effectors. In addition, temperature-sensitive DBPs could be made which would allow us to control gene expression in the same way that lambda cI857 and $P_R$ and $P_L$ are used.

Conferring novel DNA-recognition properties on proteins will allow development of novel restriction enzymes that recognize more base pairs and therefore cut DNA less frequently. For example, the methods of the present invention will be useful in developing a derivative of EcoRi (recognition GAATTC) that recognizes and cleaves a longer recognition site, such as TGAATTCA, GGAATTCC or AGAATTCT.

Proteins that recognize specific DNA sequences may also be used to block the action of known restriction enzymes at some subset of the recognition sites of the known enzyme, thereby conferring greater specificity on that enzyme. For example, a protein that binds to wGAGCTCw (where w stands for A or T) would protect one quarter of SacI sites (recognition GAGCTC). In the presence of such a blocking protein, SacI would cut wGAGCTCs, sGAGCTCw, and sGAGCTCs (where s stands for C or G).

Other DNA-binding enzymes may also be obtained by the methods described herein.

The methods of the present invention are primarily designed to select from a highly variegated population those cells that contain genes that code on expression for proteins that bind sequence-specifically to predetermined DNA sequences. The genetic constructions employed can also be used as an assay for putative DBPs that are obtained in other ways. 999

The appended claims are hereby incorporated by reference into this specification as a further enumeration of the preferred embodiments.

DETAILED DESCRIPTION OF THE INVENTION AND ITS PREFERRED EMBODIMENTS

Abbreviations

Figure 1:
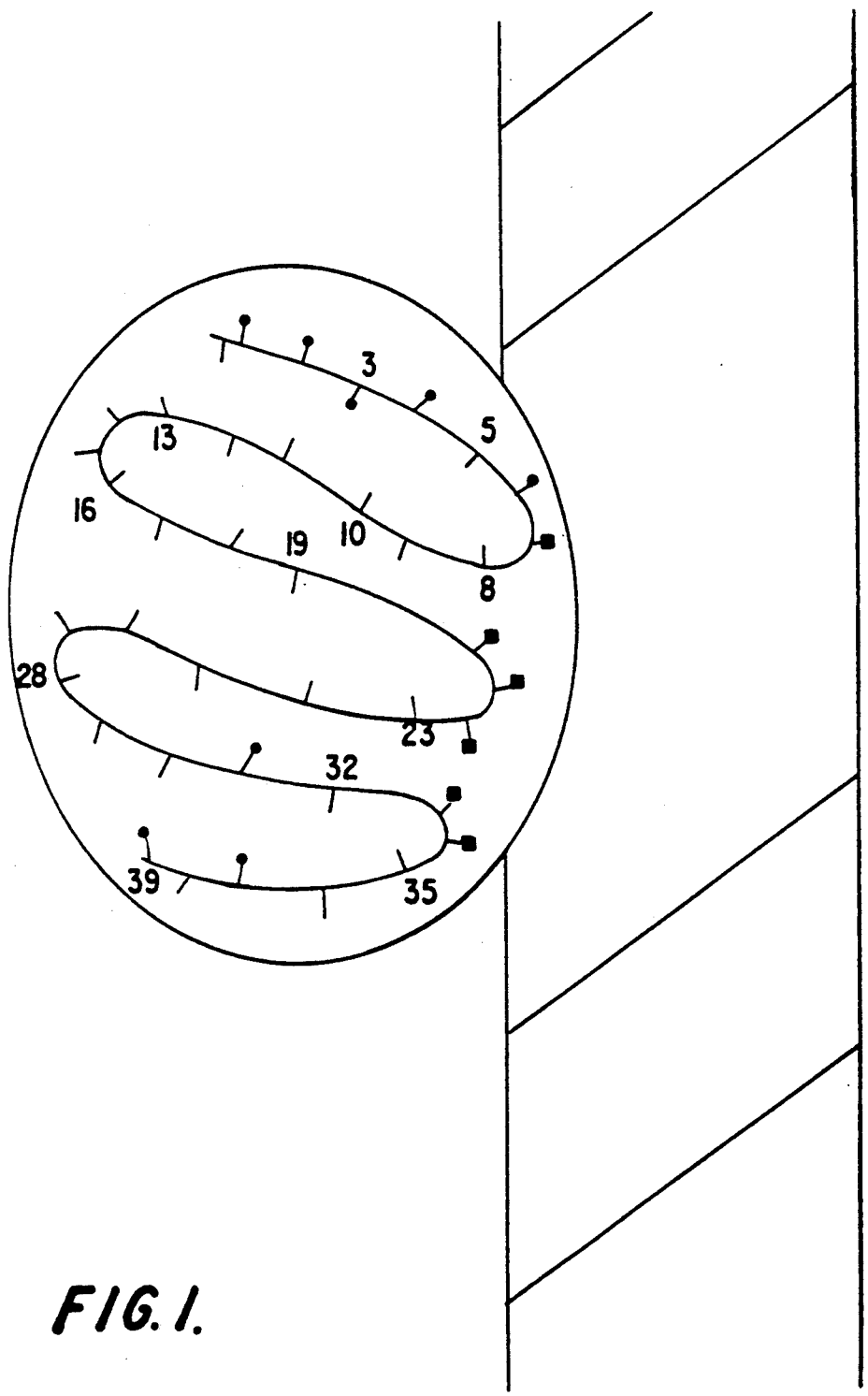
FIG. 1 Schematic of Hypothetical DBP binding a DNA target.

The following abbreviations will be used throughout the present invention:

| Abbreviation | Meaning |
| --- | --- |
| DBP | DNA-binding protein |
| idbp | A gene encoding the initial DBP |
| pdbp | A gene encoding a potential-DBP |
| vgDNA | variegated DNA |
| dsDNA | double-stranded DNA |
| ssDNA | single-stranded DNA |
| $Tet^R$, $Tet^S$ | Tetracycline resistance or sensitivity |
| $Gal^R$, $Gal^S$ | Galactose resistance or sensitivity |
| $Gal^+$, $Gal^-$ | Ability or inability to utilize galactose |
| $Fus^R$, $Fus^S$ | Fusaric acid resistance or sensitivity |
| $Kan^R$, $Kan^S$ | Kanamycin resistance or sensitivity |

Terminology

A domain of a protein that is required for the protein to specifically bind a chosen DNA target subsequence, is referred to herein as a "DNA-binding domain". A protein may comprise one or more domains, each composed of one or more polypeptide chains. A protein that binds a DNA sequence specifically is denoted as a "DNA-binding protein". In one embodiment of the present invention, a preliminary operation is performed to obtain a stable protein, denoted as an "initial DBP", that binds one specific DNA sequence. The present invention is concerned with the expression of numerous, diverse, variant "potential-DBPs", all related to a "parental potential-DBP" such as a known DNA-binding protein, and with selection and amplification of the genes encoding the most successful mutant potential-DBPs. An initial DBP is chosen as parental potential-DBP for the first round of variegation. Selection isolates one or more "successful DBPs". A successful DBP from one round of variegation and selection is chosen to be the parental DBP to the next round. The invention is not, however, limited to proteins with a single DNA binding domain since the method may be applied to any or all of the DNA binding domains of the protein, sequentially or simultaneously.

Conventionally, DNA sequences are written from 5' to 3', left-to-right.

```
protein:      M—L—F—
anti-sense DNA: 5' ATG CTT TTC ... 3'
    sense DNA: 3' TAC GAA AAG ... 5'
        mRNA: 5' AUG CUU UUC ... 3'
```

We will use the convention that the "sense" strand is the strand used as template for mRNA synthesis. Although this convention is widely used in the literature, the opposite convention is also found.

In the present invention, the words "grow", "growth", "culture", and "amplification" mean increase in number, not increase in size of individual cells. In the present invention, the words "select" and "selection" are used in the genetic sense; i.e. a biological process whereby a phenotypic characteristic is used to enrich a population for those organisms displaying the desired phenotype, or to enable growth only of those organisms displaying the desired phenotype. Choices or elections to be made by users are indicated by "choose", "pick", "take", etc.

One selection is called a "selection step"; one pass of variegation followed by as many selection steps as are needed to isolate a successful DBP, is called a "variegation step". The amino acid sequence of one successful DBP from one round becomes the parental potential-DBP to the next variegation step. We perform variegation steps iteratively until the desired affinity and specificity of DNA-binding between a successful DBP and chosen target DNA sequence are achieved.

In a "forward selection" step, we select for the binding of the PDBP to a target DNA sequence; in a "reverse selection" step, for failure to bind. The target DNA sequence may be the final target sequence of interest, or the immediate target may be a related sequence of DNA (e.g., a "left symmetrized target" or "right symmetrized target"). There is an important distinction between screening and selection. Screening merely reveals which cells express or contain the desired gene. Selection allows desired cells to grow under conditions in which there is little or no growth of undesired cells (and preferably eliminates undesired cells).

The term "operon" is used to mean a collection of one or more genes that are transcribed together. Although operon is usually limited to prokaryotic cells, we will use operon to refer also to one or more genes that are transcribed together in eukaryotic cells independent of post-transcriptional processing.

The term "binding marker gene" is used to mean those genes engineered to detect sequence-specific DNA binding, as by association of a target DNA with a structural gene and expression control sequences. A single operon may include more than one binding marker gene (e.g., galT,K). A "control marker gene" is one whose expression is not affected by the specific binding of a protein to the target DNA sequence. The "control promoter" is the promoter operably linked to the control marker gene.

Palindrome, palindromic, and palindromically are used to refer to DNA sequences that are the same when read along either strand, e.g.

Palindromic DNA

-continued

Rotational axis

5'CTAGCCT AGGCTAG 3'
3'GATCGGA TCCGATC 5'.

The arrow indicates the center of the palindrome; if the sequence is rotated 180° about the central dot, it appears unchanged. In the present application, "Palindromic" does not apply to sequences that have mirror symmetry within one strand, such as Mirror Plane

5'CTAGCCT|TCCGATC 3'
3'GATCGGA|AGGCTAG 5'.

DNA sequences can be partially palindromic about some point (that can be either between two base pairs or at one base pair) in which case some bases appear unchanged by a 180° rotation while other bases are changed.

A special case of partially palindromic sequence is a "gapped palindrome" in which palindromically related bases are separated by one or more bases that lack such symmetry:

Gapped Palindrome 1 2 3 4 5 6 7 8 9 10 11 12 13 14 15 16

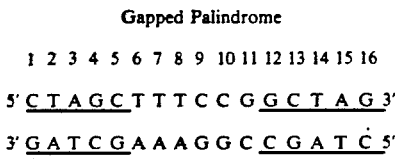

5' CTAGC TTTCC GGCTAG 3'

3' GATCG AAAGGC CGATC 5' has CTAGC (bases 1-5) palindromically related to GCTAG (bases 12-16) while the sequence TTTCCG (bases 6-11) in the center has no symmetry.

For the purposes of this invention, a "nondeleterious cloning site" is a region on a plasmid or phage that can be cut with one restriction enzyme or with a combination of restriction enzymes so that a large linear molecule can be recovered, and that site is positioned to that the large linear molecule comprises undisrupted copies of all the essential and desired genetic elements of the plasmid or phage. The essential elements are those needed for replication and maintenance of the phage or plasmid; the desired elements are those needed to accomplish the purposes of the user. A phage or plasmid could have several nondeleterious cloning sites. A nondeleterious cloning site could be the unique restriction site of an enzyme, so that the molecule is merely the linearized plasmid. It could also be one or segments of DNA which are cut away by one or more restriction enzymes, but leaving a large linear fragment having the characteristics stated above. If, for example, there are neither KpnI nor HindIII sites and does not bear those elements in the essential or desired elements of the phage or plasmid, then a segment that is bounded by KpnI and HindIII sites is a unique cloning site; it is preferred that digestion with KpnI and HindIII does not disrupt or remove essential or desired elements. The KpnI-to-HindIII segment could be of any length and could contain any number of restriction sites of any type.

It is to be understood that all plasmids bear a conventional marker gene, such as an antibiotic resistance gene or a nutritional gene, by which one can select for uptake and maintenance of the plasmid. This selection is always maintained for a plasmid-bearing strain and will not be described repeatedly.

Overview: The Selection System

The present invention separates mutated genes that specify novel proteins with desirable sequence-specific DNA-binding properties from closely related genes that specify proteins with no or undesirable DNA-binding properties, by: 1) arranging that the product of each mutated gene be expressed in the cytoplasm of a cell carrying a chosen DNA target subsequence, and 2) using genetic selections incorporating this chosen DNA target subsequence to enrich the population of cells for those cells containing genes specifying proteins with improved binding to the chosen target DNA sequence.

A selectably deleterious gene is positioned relative to, usually downstream from, the target sequence so that the gene is not expressed if a successful DNA-binding protein specific to this target is expressed in the cell and binds the target sequence. The cell will survive exposure to the selective conditions of the growth medium if the selectably deleterious gene is not expressed.

The preferred cell line or strain is easily cultured, has a short doubling time, has a large collection of well characterized selectable genes, includes variants that are deficient in genetic recombination, and has a well developed transformation system that can easily produce at least $10^7$ independent transformants/ug of DNA. A transformation system that can produce even more independent transformants is preferred. Bacterial cells are preferred over yeasts, fungi, plant, or animal cells because they are superior on every count. Among bacteria, E. coli is the premier candidate because of the wealth of knowledge of genetics and cellular processes. Other bacterial strains, such as S. typhimurium, Pseudomonas aeruginosa, Klebsiella aerogenes, Bacillus subtilis, or Streptomyces coelicolor could be used. Use of these organisms and yeasts and mammalian systems are described further below. DBPs that bind to host regulatory sequences, such as promoters, will be toxic. Thus, development of a DBP that specifically binds to E. coli promoters is preferably done in a cell line or strain, such as S. coelicolor, having significantly different promoter sequences.

Because the intended use of the novel DBPs will often be in eukaryotic cells, some final development and testing may be done in eukaryotic cells such as Saccharomyces cerevisiae or Chinese hamster ovary cells. Genes that code on expression for DBPs that have been shown to work in bacterial cells will be introduced into eukaryotic cells to demonstrate that each DBP functions. Only limited variegation, however, can be used because, to date, the transformation systems for eukaryotic cells are, at best, 1000-fold less efficient than those used in E. coli K-12.

In the most preferred embodiment, all novel DBPs are developed in E. coli recA⁻ strains. Host strains that are Rec⁻ are preferred so that recombinations between the vector and the host genome and within the vector are minimized. The recA⁻ genotype is preferred over other rec⁻ mutations because recA⁻ mutation reduces the frequency of recombination more than other known rec⁻ mutations and the recA⁻ mutation has fewer undesirable side effects.

We obtain DBPs that bind to targets in vivo. Some targets will be methylated or altered in other ways by the host as determined by the sequence. In some cases, changing from one host to another or from in vivo to in vitro will lead to changes in methylation of the target that could cause a change in DNA-protein binding affinity.

Most strains of *E. coli* contain the dam and dcm DNA-methylating systems. The Dam methylase transfers a methyl from S-adenosylmethionine (SAM) to the $N_6$ of adenine residues in the subsequence GATC. The Dcm methylase transfers a methyl from SAM to the internal cytosine in the sequences CCAGG and CCTGG. If a DBP is desired that will bind to unmethylated DNA, and if the target sequence contains either the Dam or Dcm recognition sequence, then a Dam− or Dcm− strain should be used.

The bacterial chromosome or viral chromosomes could be used as the vector. Phage, such as M13, have the advantage of a high infectivity rate. Organisms or phage having a phase in their life cycle in which the genome is single-stranded DNA have a higher mutation rate than organisms or phage that have no phase in which the genome is single-stranded DNA. Plasmids are, however, preferred because genes on plasmids are much more easily constructed and altered than are genes in the bacterial chromosome and are more stable than genes borne on phage, such as M13.

The cloning vector will carry: a) the selectable genes for successful DBP isolation, b) the pdbp gene, c) a plasmid origin of replication, and d) an antibiotic resistance gene not present in the recipient cell to allow selection for uptake of plasmid. Preferably the operative vector is of minimum size.

Standard selections for plasmid uptake and maintenance in E. coli include use of the antibiotics ampicillin, kanamycin, tetracycline and chloramphenicol, as shown in Table 2. Colicin immunity has been used, however, these proteins are not commercially available. Titration of colicin is critical since immunity breaks down at high stoichiometric quantities of colicin. Selection of cells with antibiotics is preferred to nutritional selections, for example of the TrpA+ phenotype, for several reasons. Nutritional selection may be overcome by large volumes of cells or growth medium; host chromosomal auxotrophy is rarely total due to turnover of macromolecules; crossfeeding of the non-growing cells by prototrophic recipients obscures the outlines of the colonies; and late mutations to prototrophy may arise on the plate due to spontaneous mutation of nongrowing cells. Nonetheless, nutritional selection may be employed.

Similarly, plasmids for use in *B. subtilis* are engineered for selection of uptake and maintenance using antibiotics, for example, kanamycin, tetracycline, chloramphenicol and erythromycin. Plasmids used in streptomycete species bear genes for resistance to antibiotics such as thiostrepton, neomycin, viomycin, and methylenomycin. These markers are more efficient than auxotrophic markers or sporulation and pigment screens such as spo in bacilli and mel in streptomycetes, which require manipulation of individual colonies.

Extensive recombinant DNA manipulations in yeasts have been achieved using complementation of auxotrophic markers, some of which are shown in Table 3. High backgrounds are surmounted by use of two unrelated binding marker genes carried on the same vector, e.g., Leu2+ and Ura3+· Selection for G418 resistance conferred by the bacterial aphII gene expressed in yeast offers the advantages of reduced background and a wider range of appropriate recipient strains. The current upper range of efficiency of DNA uptake into yeast cells indicates that this organism is not now preferred for the process described in this patent, although results could be achieved by large scale practice.

The potential-DBP is required to bind to the target DNA sequence in the DNA constructs described, for cell survival under selective conditions. The selection systems must be so structured that other mechanisms for loss of gene expression are much less likely than the desired result, repression at the target DNA subsequence. Other mechanisms that could yield the desired phenotype include: point mutations that inactivate the deleterious gene or genes, deletion of the deleterious gene or genes, host mutations that suppress the deleterious genes, and repression at a site other than the target DNA sequence.

We apply a double selection so that two point mutations (frequency $<10^{-12}$ per cell) would be needed for cells to survive selection. Among $10^7$ to $10^8$ independent transformants, resistant colonies arising from two independent point mutations are extremely unlikely.

Selectable phenotypes are a basic tool of genetics and molecular biology in all cell culture and microbiological systems, and a wide range of examples for *E. coli* and *S. typhimurium* have recently been described (VINO87). Two broad classes of selections are useful in this invention: nutritional, in which an essential component is omitted from the medium and, in some cases, an alternative nutrient provided; and chemical resistance, in which a toxic or inhibitory component is added to the medium.

Such selections are inherently conditional in that they employ addition of a growth-inhibitory chemical to the selective medium, or manipulation of the nutrient components of the selective medium. Deleterious effects on growth or maintenance of the strain are not usually observed on non-selective media.

Further conditionality of the preferred method is imposed by transcriptional regulation (e.g. by IPTG in combination with the lacUV5 promoter and the LacI$^q$ repressor) of the variegated pdbp gene. In those members of the population that express DBPs that bind to the target, IPTG indirectly controls the selectable genes; in these cells, increased IPTG leads to reduced expression of the selectable genes. Therefore the correct phenotypes for selection are distinguished only in the presence of an inducing chemical, and potential deleterious effects of these phenotypes are avoided during storage and routine handling of the strains by growth in the absence of the inducer and on nonselective medium.

Selection of mutant strains capable of producing proteins that can bind to the target DNA subsequence is enabled by engineering conditional lethal genes or growth-inhibiting genes located downstream from the promoter that contains the target DNA subsequence. In the preferred embodiment, at least two independent conditional lethal or inhibitory selections are performed simultaneously. It is possible to use a single selection to achieve the same purpose, but this is not preferred. Two selections are strongly preferred since a simple mutation in the selected gene, occurring at a frequency of $10^{-6}$ to $10^{-8}$/cell, would occur in two selected genes simultaneously at the product of the individual frequencies, $10^{-12}$ to $10^{-16}$. Thus use of two selections substantially reduces the probability of isolation of artifactual revertant or suppressor strains.

Selectable genes for which both forward and reverse selections exist are preferred because, by changing host or media, we can use these genes to select for binding by a DBP to a target DNA sequence such that expression of one of these genes is repressed, or we can select phenotypes characteristic of cells in which there is no binding of the DBP. For example, expression of the tet gene is essential in the presence of tetracycline. On the other hand, expression of the tet gene is lethal in the presence of fusaric acid. Expression of the galT and galK genes in a GalE$^-$ host in the presence of galactose is lethal. On the other hand, expression of galT and galK in a host that is GalE$^+$ and either GalT$^-$ or GalK$^-$ renders the cells GAl$^+$ and allows them to grow on galactose as sole carbon source.

When the selective agent is a potential cell metabolite, the selective medium may contain a precursor of the selective agent in place of the agent itself, which the cell will convert into the agent, or substance catalyzing the cellular production of the agent, from an available procursor. The term "source of a selective agent" includes the selective agent itself and any media components which cause the cell to manufacture the selective agent.

The Detailed Examples describe selection of strains with successful DBP binding to novel target subsequences due to turn off of two genes, each of which, if expressed, confers sensitivity to a toxic substance. It is also possible to use selection of strains in which successful DBP binding to novel target operators turns off repressors of genes encoding required gene products. For example, using the binding marker gene P22 arc, we place an Arc operator site so that binding of Arc represses expression of a beneficial or conditionally essential gene, such as amp. Another alternative is selection of expression of required gene products due to successful binding of DBP proteins derived from positive effectors as the DBP, e.g. CAP from E. coli, the repressor from phage lambda, or the Cro67 (BUSH88) mutant of lambda Cro.

The selections described in the Detailed Examples employ commercially available cloned genes on plasmids in strains that can be obtained from the ATCC (Rockville, Md.). Alternatively, the genes can be produced synthetically from published sequences or isolated from a suitable genomic or cDNA library.

Numerous types of selections are possible for selection of DBP expression in E. coli. The toxic and inhibitory agents listed in Table 4 are used with appropriately engineered host strains and vectors to select loss of gene function listed above. Repression of transcription of these genes allows growth in the presence of the agents. Other outcomes such as deletions or point mutations in these genes may also be selected with these agents, hence two functionally unrelated selections are used in combination. These agents share the property that cell metabolism is stopped, and unlike the nutritional selections, the inhibitory agents are not overcome by components of the growth medium or turnover of macromolecules in the cells. Selections using antibiotics, metabolite analogs, or inhibitors are preferred. Another class of selections includes those for repression of phage or colicin receptors, or for repression of phage promoters. These agents kill by single-hit kinetics, and in the case of phage, are self-replicating, making the multiplicity of agent to putative repressed cell much more difficult to control. Colicin titers are determined indirectly from survival of treated cells, and vary with the other conditions of the assay. Phage and colicin selections can be applied to the processes claimed here, but are not preferred.

Any selection system relevant to the cell line or strain may be substituted for those in the examples given here, with appropriate changes in the engineering of the cloning vectors. One example is the dominant pheS$^+$ gene carried on plasmid pHE3 (ATCC #37,161) in a pheS12 background. Turn-off of pheS$^+$ is selected with p-fluorophenylalanine (Sigma Corp., St. Louis, Mo.). A second example is the use of lambda phage for the selection of E. coli cells containing functional DNA-binding proteins (REID88, BENS86). Cells containing potential-DBPs are challenged with cI$^-$ derivatives of lambda phage which have been further modified to include the specific appropriate target DNA sequences as replacements for the wild-type $O_R$ and $O_L$. The selection requires that cells express active DBPs to repress lytic development of the challenge phage. In mammalian cell lines selections can be employed using the neomycin acetyl transferase gene (HOUS86), the hygromycin phosphotransferase gene (BLOC84), or ouabain resistance (KENT87).

In addition, a variety of mutant cell lines and cloned mammalian genes are useful in combination to enable selection of the DBP$^+$ phenotype. The thymidine kinase gene is introduced into TK$^-$ cells and selected with aminopterin and thymidine (RUDD86). Lack of expression of the cloned TK gene in an established cell line is selected with bromouridine. Similarly, HGPRT$^-$ (hypoxanthine-guanine phosphoribosyltransferase) cells are transformed with the cloned normal gene for this enzyme, and selected with aminopterin and hypoxanthine. Lack of expression of the cloned HGPRT gene in an established clone is selected with thioguanine or azaguanine. Thus systems are available for DBP production in mammalian systems.

Extending this principle to another system, we choose the Streptomyces coelicolor cloned glucose kinase gene for selection of the DBP$^+$ phenotype, using the metabolite analog deoxyglucose.

A major class of selective agents comprises antibiotics and metabolite analogs. Antibiotic preparations can differ in potency, hence each batch is checked for MIC (minimum inhibitory concentration) under the condition of use. Potency further declines with age of the batch, age of the stock solution, nature of the solvent, and age of the medium in Petri plates. These factors are controlled for each new antibiotic employed and for each fresh batch. Stringency of the selection is low with selection at a concentration of antibiotic at or just above the MIC. In the progressive process embodied here by which rounds of mutagenesis and selection are employed to improve the affinity of each successive DBP for the target DNA compared to the parent obtained from the previous round, increased concentration of antibiotic may be used to increase the stringency of the selection.

Control cultures of antibiotic-sensitive cells are applied to media containing antibiotic concentrations close to the MIC to determine the frequency of resistant mutants. Cairns et al. (CAIR88) have described increased frequency of site-specific mutation at the locus being selected. This phenomenon is observed with nutritional selections, but not with lethal selections, however, thus it is not relevant to the processes described here.

For a selection employing turn-on of a gene for metabolite utilization carried by a minority of a population, stringency of the selection is increased by centrifugation of a cell sample and resuspension in a non-nutritive buffer prior to application of cells to the medium. A similar effect is obtained by reducing the inoculum size (vide infra). Similarly, stringency is decreased by addition of a very small quantity of the limiting nutrient (e.g. the permissive metabolite). This procedure allows limited growth of the non-selected population, and increased growth rate of colony formation by the selected members of the population.

The formulation of the growth medium can affect success of the selection by affecting the differential growth rate of the background and the selected colonies. Thus Maloy and Nunn (MAL081) describe a medium yielding improved selection of $Fus^R$ *E. coli* colonies from a $Tet^R$ background, compared to the medium employed by Bochner (BOCH81) for this purpose using *S. typhimurium*. Media formulations differ in pH, cation concentrations, buffering agent, etc. Increased agar content selects against strains of *E. coli* with the tonB mutation (GUTE73), and in general the genetic background affects the growth rate of a strain on each of several media. The user therefore varies the medium formulation for a particular selection if the results are not optimal with the strain at hand.

Stringency of selection can be modulated by controlling copy number of plasmids bearing the selectable genes; increasing copy number of selectable genes increases the stringency of the selection. For example, it has been reported that copy number of plasmids containing the ColE1 origin is determined by the relative abundance of two plasmid-encoded species of RNA (LINC87, BREM86), denoted RNAI and RNAII. Increasing RNAI lowers copy number while increasing RNAII raises copy number. By engineering a Trp operator into the promoter that regulates transcription of RNAI, we could cause RNAI to be negatively regulated by 5-methyltryptophan, a tryptophan analogue. This in turn would cause the copy number of plasmids bearing the ColE1 origin to be positively regulated by 5-methyltryptophan. Similarly, we could introduce a CRP operator upstream of the promoter that regulates transcription of RNAII in such a way that binding of cAMP-CRP will enhance transcription of RNAII. Such a CRP operator would cause cAMP build-up or glucose starvation to positively regulate plasmid copy number. Preferably, the pdbp genes are placed on a plasmid that has an origin, such as that derived from R1, that is unaffected by RNAI or RNAII.

Transcriptional regulation of the idbp gene or the pdbp gene by an exogenously added inducer, e.g. IPTG, enables modulation of selectable phenotypes, as described above. Thus in a lacI+ or $lacI^q$ strain with the idbp gene placed downstream of the lacUV5 promoter, increasing IPTG concentration yields increasing cellular DBP protein. During the initial phases of the progressive development of DBP molecules, it is desirable to produce a high intracellular concentration of DBP to shift the equilibrium in the direction of DBP-target complexes. The stringency of the selection is increased at subsequent phases of successful DBP development by allowing fewer molecules of DBP per cell, so that cell survival under selective pressure is due to development of successful DBP proteins with increased target affinity.

Inoculum size considerations include: 1) total cell input; 2) number of successful transformants; 3) number of cells that survive selection for the functions of the successful DBP; and 4) volume of the inoculum, especially if the cells are selected directly from a culture grown in the permissive growth medium. High total cell input often decreases stringency of selections, by providing metabolites that are specifically omitted, by mass action with respect to an inhibitory agent, or by generating a large number of artificial satellite colonies that follow the appearance of genetically resistant colonies. The number of cells that are successfully transformed is a function of efficiency of ligation and transformation processes, both of which are optimized in the embodiment of this invention. Procedures for maximal transformation and ligation efficiency are from Hanahan (HANA85) and Legerski and Robberson (LEGE85) respectively. Increasing stringency is imposed under the conditions of high efficiency of these processes by inoculation of plates with small volumes or dilutions of cell samples. Pilot experiments are performed to determine optimum dilution and volume.

The protocol following transformation is designed to obtain simultaneous selection for transformation and successful DBP function. This possibility is determined by the compatibility of the selections. In Detailed Example 1, the transformation event is followed by dilution and growth of cells in permissive medium following transformation. Exogenous inducer of DBP expression is included at this step, and a set of selections are then imposed in liquid medium. Surviving cells are concentrated by centrifugation, and selected for these and additional traits using solid medium in Petri plates. This protocol offers the advantage that fewer identical siblings are obtained and a larger population is easily screened. In Detailed Example 1, repression of the $Gal^S$ phenotype is selected by exposing transformants to galactose in liquid medium, which produces visible lysis of galactose sensitive cells. The second selection employed in Detailed Example 1 is for the $Fus^R$ phenotype due to repression of $Tet^R$, which requires limitation of total inoculum size to $10^6$ cells/plate. Similar protocol variations are introduced to combine selections for transformation and successful DBP function.

Tests of selective agents that kill or inhibit sensitive cells are performed with pure cultures of sensitive cells. These include strains carrying the selective marker genes (the products of which render the cell sensitive to the selective media) but no IDBP, or carrying the IDBP but grown without the inducer of expression of this gene. Resistant strains carry the vector with the idbo gene, and are grown under selective conditions. Thus, the selective genes are repressed by the IDBP.

Cultures of sensitive cells are applied to selective media as inocula appropriate to the selection (usually $10^6$ to $10^8$ per plate). Sufficient numbers of replicates ($10^7$ to $10^9$ total sensitive cells for each medium) are tested by each selection. The rate at which the cultures produce revertants and phenotypic suppressors (considered together as revertants) is determined. A rate greater than $10^{-6}$ per cell indicates that stringency must be increased. If reversion rates are below this level, as we have shown for the selections described in Example 1, mixing experiments are performed to determine the sensitivity of recovery of a small fraction of resistant cells from a vast excess of sensitive cells.

Cultures are mixed in the following proportions: 10 resistant cells to $10^8$ sensitive cells, 10 resistant cells to 10⁷ sensitive cells, 10 resistant cells to 10⁶ sensitive cells, 50 resistant cells to 10⁶ sensitive cells, etc., up to 2,000 resistant cells to 10⁶ sensitive cells. Mixtures are applied to plates so that total cell inoculum is controlled, initially at $10^6$, $10^7$, or $10^8$ cells per plate. Plates are incubated overnight and examined for ability to distinguish discrete colonies from background, and for yield of resistant colonies (at levels of 200 or fewer colonies per plate). Further, a number of resistant colonies are picked and streaked or patched to the same selective medium, and scored for growth. Appearance of these plates allows the user to formulate expectations for the reliability of the phenotypes that can be obtained over a range of total inoculum size and total resistant colony-forming units under the selective conditions.

The size of the variegated population from which we can select a single desirable mutant is limited by the efficiency of the selection, as well as by other factors such as efficiency of the ligation and transformation processes.

Normally, the deleterious gene product of a binding marker gene is a protein. However, it may also be an RNA, e.g., an mRNA which is antisense to the mRNA of an essential gene and therefore blocks translation of the latter mRNA into protein. Selectively deleterious genes suitable for use in the present invention include those shown in Table 4.

These two selectably deleterious genes are preferably not functionally related. Choice of two selectable binding markers that are not related by function is guided by several considerations. For example, the chosen genes should not code for proteins localized to or affecting the same macromolecular assembly in the cell or which alter the same or intersecting anabolic or catabolic pathways. Thus, use of two inhibitors that select for mutations affecting RNA synthesis, aromatic amino acid synthesis, or each of histidine and purine synthesis are not preferred. Similarly, two inhibitors that are transported into the cell by shared membrane components are thus functionally related, and are not preferred. In this manner the user reduces the frequency of isolation of single host mutations that yield the apparent desired phenotype, because of suppression of the shared functionality, interacting component, or precursor relationship. Host mutations of this type are conveniently distinguished by a screen of the selectable phenotypes in the absence of the inducer of the DBP, e.g. IPTG. A strain producing a true novel DBP displays the DBP+ phenotype only in the presence of the inducer of DBP expression, while a spontaneous suppressing mutation is constitutive for the DBP+ phenotype.

Examples of pairs of deleterious genes which are recommended for use in the present invention are given in Table 5A. In each case, one of the paired genes codes for a product that acts intracellularly while the other codes for a product that acts either in transport into or out of the cell or acts in an unrelated biological pathway. Table 5B gives some pairs that are not recommended. These pairs have not been shown to malfunction, but they are not recommended, given the large number of choices that are clearly functionally unrelated.

Each plasmid contains at least one beneficial or conditionally essential gene, e.g., an antibiotic resistance gene, to allow selection for uptake and maintenance of the plasmid. Table 2 lists various beneficial or conditionally essential genes suitable for this purpose.

A preferred novel feature is the use of a copy of the promoter of one of these beneficial or conditionally essential genes, operably linked to the target DNA subsequence, to direct transcription of the selectably deleterious or conditionally lethal binding marker genes of the plasmid. If the potential-DBP should repress the selectable gene by binding to this promoter, it would also repress this beneficial activity. Thus, if the beneficial gene was an antibiotic resistance gene, repression would render an appropriate cell antibiotic-sensitive.

In order to assure that selection for DBP binding is specific to the target and not the promoter, we place one of the two selectable binding marker genes under the same transcription initiation signal as the gene we use for selection of vector uptake and maintenance. In Detailed Example 1, transcription of the galT and galK genes is initiated by the $P_{amp}$ promoter, as is the amp gene. Similarly, the pheS gene, if chosen for selection of DBP binding with fluorophenylalanine, could be under transcription regulation of whatever promoter initiates transcription of the gene used for selection of plasmid uptake.

It is possible that the potential-DBP will bind specifically to the boundary between the target DNA sequence and the promoter, or within the structural gene. In the preferred embodiment, we discriminate against this mechanism by choosing a different promoter, operably linked to another copy of the same target DNA sequence, for the second selectable gene. The second promoter may be chosen from known promoters that are active in *E. coli*. Preferably, the two promoters that initiate transcription of the selectable genes should be strong enough to give a sensitive selection, but not too strong to be repressed by binding of a novel DBP. Hawley and McClure (HAWL83) have reviewed the similarities of *E. coli* promoters and Mulligan et al. (MULL84) have related the strength of the promoter to a homology score. Some well studied promoters and their scores are shown in Table 6. Promoters that score between 50. and 70. on the Mulligan formula are good candidates for use in binding marker genes. Preferably, the two promoters have significant sequence differences, particularly in the region of the junction to the target DNA sequence. Specifically, the region between the −10 region and the target sequence, which comprises five to seven bases, should have no more than two identical bases in the two promoters. Although the −10 regions of promoters show high homology, promoters are known (e.g. $P_{amp}$ having GACAAT and $P_{neo}$ having TAAGGT) that have as few as two out of six bases identical in this region, and such difference is preferred. Furthermore, $P_{amp}$ and $P_{neo}$ differ even more in the regions between the −10 region and the initiation of transcription: $P_{amp}$ has TGGGAAG while $P_{neo}$ has AACCCTG so that only the final G is common.

The target DNA sequence for the potential DNA-binding protein must be associated with the two deleterious or conditionally lethal binding marker genes and their promoters so that expression of the binding marker genes is blocked if one of the generated mutant proteins in fact binds to the target sequence. The target DNA sequence conceivably could appear upstream of the gene, downstream of the gene, or, in certain hosts, in the noncoding region (viz. an "intron") within the gene. Preferably, it is placed upstream of the coding region of the gene, that is, in or near the RNA polymerase binding site for the gene, i.e. the promoter. Placement of the test DNA sequence relative to the promoter is influenced by two main considerations: a) protein binding should have a strong effect on transcription so that the selection is sensitive, b) the activity of the promoter in the absence of a binding protein should be relatively unaffected by the presence of the test DNA sequence compared to any other target subsequence.

DNA binding sites found in bacteria and phage range from a few base pairs for restriction enzymes, to twenty or more for repressors and activators, to forty or more for RNA polymerase. In the present invention, we will deal primarily with DNA target subsequences of 10 to 25 bases. Hawley and McClure have compiled 168 *E. coli* promoters (HAWL83) and Mulligan et al. (MULL84) have published an algorithm for evaluation of the similarity of any DNA sequence to known *E. coli* promoters. These authors and others have noted that the highly conserved −35 region and the highly conserved −10 region are separated by between 15 and 21 base pairs with a mode of 17 base pairs. Some of the bases between −35 and −10 are statistically non-random; thus placement of target DNA sequences longer than 10 bases between the −10 and −35 regions would likely affect the promoter activity independent of binding by potential-DBPs. Because quantitative relationships between promoter sequence and promoter strength are not well understood; it is preferable, at present, to use known promoters and to position the target at the edge of the RNA polymerase binding site.

Protein binding to DNA has maximum effect on transcription if the binding site is in or just downstream from the promoter of a gene. Hoopes and McClure (HOOP87) have reviewed the regulation of transcription initiation and report that the LexA binding site can produce effective repression in a variety of locations in the promoter region. In a preferred embodiment, we place the target DNA sequences that begin with A or G so that the first 5' base of the target sequence is the +1 base of the mRNA, as the LexA binding site is located in the uvrD gene (see HOOP87, p1235). If the target sequence begins with C or T, we preferably place the target so that the first 5' base of the target is the +2 base of the mRNA and we place an A or G at the +1 position. An alternative is to place the target DNA sequences upstream of the +35 region as the LexA binding site is located in the ssb gene (see HOOP87, p1235).

It may be useful in early stages of the development of a DBP to have more than one copy of the target DNA sequence positioned so that binding of a DBP reduces transcription of the selectable gene. Multiple copies of the target DNA sequence enhances the sensitivity of phenotypic characteristics to binding of DBPs to the target DNA sequence. Multiple copies of the target DNA sequence are, preferably, placed in tandem downstream of the promoter. Alternatively, one could place one copy upstream of the promoter and one or more copies downstream.

We arrange the genes on the plasmid or plasmids in such a way that no single deletion event eliminates both deleterious genes without also eliminating a gene essential either to plasmid replication or cell survival. Thus, resistant colonies are unlikely to arise through deletions because two independent deletion events are required. Similarly, simultaneous occurrence of one point mutation and one deletion is as unlikely as two point mutations or two deletions.

A typical arrangement of genes on the operative cloning vector, similar to that used in Detailed Example 1, is:

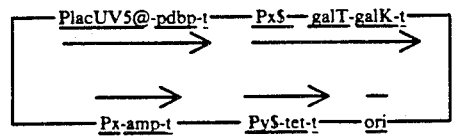

Px represents the promoter that initiates transcription of the amo gene. A second copy of Px initiates transcription of galT,K. Py is a promoter driving tet, t is a transcriptional terminator (different terminators may be used for different genes), and $ is the target subsequence. PlacUV5 is the lacUV5 promoter, @ represents the lacO operator, and pdbp is a variegated gene encoding potential DBPs. Placement of the pdbp relative to other genes is not important because mutations or deletions in odbo cannot cause false positive colony isolates. Indeed, it is not strictly necessary that the pdbp gene be on the selection vector at all. The purpose of the selection vector is to ensure that the host cell survives only if the one of the PDBPs binds to the target sequence (forward selection) or fails to so bind (reverse selection). The pdbp gene may be introduced into the host cell by another vector, if desired.

The tet gene and galT,K operon are both examples of binding marker genes for which two-way selections are available. In a medium containing tetracycline, cells expressing the tet gene product survive. In a medium containing fusaric acid, the same product allows fusaric acid to enter and poison cells expressing the tet gene. Similarly, galT,K expression is essential in a galE+, galT− host or a galE+, galK− host in medium in which galactose is the only carbon source. Expression of galT,K is lethal when the host is galE− and the medium contains galactose, as the transferase and kinase enzymes, in a cell lacking the epimerase activity, lead to an accumulation of phosphorylated galactose and lysis of the host cell due to lack of UDPGal (a cell wall precursor).

The orientation of each gene in the selection vector is unimportant because strong terminators (e.g. rrnBt1, rrnBt2, phage fd terminator, or troa terminator) are preferably placed at the ends of each transcription unit. That galT,K and tet are separated by essential genes, however, is of fundamental importance. The sequence ori is essential for plasmid replication, and the amo gene, the transcription of which is initiated by Px, is essential in the presence of ampicillin. Successful repression of galT+,K+ and tet is selected with galactose and fusaric acid. No single deletion event can remove both the latter genes and allow plasmid maintenance or cell survival under selection. In addition, binding by a novel DBP to the Px promoter would render the cell ampicillin sensitive. These arrangements make appearance of a novel DBP that binds the target DNA more probable than any of the other modes by which the cells can escape the designed selections.

Overview: Choice of Target DNA Binding Sequence for Development of Successful Novel DBPs Our goal is the development, in part by conscious design and in part by in vivo selection, of a protein which binds to a DNA sequence of significance, e.g., a structural gene or a regulatory element, and through such binding inhibits or enhances its biological activity. In the preferred embodiment, the protein represses expression of a structural gene.

When the DNA sequence of interest is long enough (viz. several times 20 bases), there may be many possible target subsequences from which to choose DBP binding sites. A sufficiently long sequence could be the target of several independently acting DBPs.

Another goal of this invention is to derive one or more DBPs that bind sequence-specifically to any predetermined target DNA subsequence. It is not yet possible to design the DBP-domain amino-acid sequence from a set of rules appropriate to the target DNA subsequence. Rather, it is possible to pick sets of residues that can affect the DNA recognition of a parental DBP. Then, variegation of residues that affect DNA recognition coupled with selection for binding to the target DNA subsequence can produce a novel DBP specific for the target DNA subsequence. Such a method is limited by the number of amino acids that can be varied at one time. To develop a novel DBP that recognizes 15 bases could require changing 15 or more residues in the initial DBP. Variegation of 15 residues through all 20 amino acids would produce $20^{15} = 3.3 \times 10^{19}$ sequences and is beyond current technology. (Current technology can produce up to $10^9$ independent transformants in one transformation; the above level of variegation would require $10^{10}$ transformations.) Thus we start with the recognition sequence of the initial DBP, change two to five bases and select, in one or more rounds of variegation and selection, a novel DBP that recognizes this new target DNA subsequence. This new DBP becomes the parent to the next step in which the target DNA subsequence is changed by an additional two to five bases so that a stepwise series of changes in binding protein and changes in target is used. It is emphasized here that, although we initially select DBPs that recognize sequences similar to that recognized by the IDBP, the ultimate target sequence recognized by the desired final DBP can be completely unrelated to the recognition sequence of the IDBP.

The process of finding a DBP that recognizes a sequence within a genome is shortened if we pick sequences that have some similarity to the cognate sequence of the initial DBP. Any sequence in any genome can be examined for possible target DNA binding sites provided DNA sequence information is available. Sequences coding for unspliced mRNA molecules or transcriptional regulatory regions are preferred. The intent is to locate several unique sites in the gene which can be bound specifically by DBPs such that transcription through those sites is reduced.

The sequences of some regions of eukaryotic genes vary among individuals or strains. This phenomenon is also observed among pathogens of eukaryotes (SAAG88). To optimize the search for target sites in the gene selected for repression such that repression will be effective in all or the majority of the individuals within a species, or among strains of a pathogen, regions of conserved DNA sequence within the gene should be identified if possible.

The methods of the present invention may be used to obtain DBPs specific to almost any DNA sequence. There may be a very small number of sequences that occur in the genome of the host cells for which binding of a DBP will be lethal. For this reason, the regulatory sequences, such as promoters, of the host organism are not preferred targets for DBP development. The usefulness of a DBP is determined, in part, by its ability to bind to the target DNA sequence, the expression of which is to be affected, without affecting the expression of other genes. Preferably, the target sequence occurs only in the gene of interest. For some applications, target sequences that occur in vivo at locations other than the site of intended action may be used if binding of a protein to the extra sites is acceptable.

To ensure uniqueness, preliminary elimination of non-unique sequences is done by searching DNA sequence data banks of host genomic sequences and bacterial strain sequences, and by searching the plasmid sequences for matches to the potential target subsequences. Remaining potential target subsequences are then used as oligonucleotide probes in Southern analyses of host genomic DNA and bacterial DNA. Sequences which do not anneal to host or bacterial DNA under stringent conditions are retained as target subsequences. These target subsequences are cloned into the operative vector at the promoters of the selection genes for DBP function, as described for the test DNA binding sequence.

Choice of target subsequences is based also on the optimal location of target sites within a gene such that transcription will be maximally affected. Studies of monkey L-cells show that lac repressor can bind to lac operator, or to two lac operators in tandem, in the L-cell nucleus (HUMC87). Further, this binding results in repression of a downstream chloramphenicol acetyl transferase gene in this system, and repression is relieved by IPTG. Two tandem operators repress CAT enzyme production to a greater extent than a single operator. Whether the effect is additive or multiplicative cannot be discerned, since the CAT enzyme level found with repression by tandem operators is within the background level. The user preferably locates two to four target sites relatively close to each other within the transcriptional unit.

Overview: Strategies for Obtaining Protein Recognition of Non-Symmetric Target DNA Sequences For proteins which recognize and distinguish between a number of closely related operator sites having imperfect symmetry (e.g. E. coli lac and trp repressors, CAP, lambda, 434, P22 repressors and Cros), the argument has been proposed that the tightest binding will be observed between the protein and a perfectly symmetric consensus sequence palindrome (BERG88b, BASS87, SADL83, SIMO84, BENS88). The reasoning is as follows. Repressor proteins bind two identical sites, each composed of two operator half-sites. The consensus sequence for an operator half-site represents the DNA sequence which permits the optimal interaction between protein and DNA. Thus, the maximum binding energy will be obtained when the operator presents two identical consensus sequence half-sites to the binding protein, optimizing DNA-protein interactions at each half-site.

Sadler et al. (SADL83) have described the construction of a synthetic lac operator which omits the central base pair of the natural operator and is a perfect consensus palindrome. In vitro lac repressor binds to the synthetic operator 10 times more tightly than does the wild-type repressor. In vivo, the synthetic operator represses beta-galactosidase activity to a 4-fold lower level than does the wild-type repressor. Simons et al. (SIMO84) describe the isolation of five lac operator-like subsequences from eukaryotic DNA that titrate lac repressor in vivo. All five subsequences share a 14 bp consensus subsequence that lacks the central base pair of the natural lac operator and is a perfect palindrome of the left seven base pairs of the natural lac operator. A synthetic 11-base pair inverted repeat of the left half of the *E. coli* lac operator binds lac repressor 8-fold more tightly than does the natural operator. One may conclude that natural repressors have not evolved to have maximal affinity for their operators, rather they have evolved to produce optimal regulation.

*E. coli* tro repressor (BASS87) and lambda repressor (BENS88) symmetrized operator subsequences bind their respective repressors more tightly than do the natural operators. For lambda repressor, unlike lac repressor, the optimal binding subsequence both includes a base pair at the center of symmetry and contains a non-consensus base pair (BENS88).

It is important to note that the focus of all of the above experiments has been on symmetry: symmetric operators, symmetric changes in protein binding residues, etc. In the natural systems discussed above, increasing operator subsequence symmetry towards the consensus palindrome does indeed increase the strengths of the binding interactions. This result arises, however, not from symmetry per se, but from optimizations of the protein-DNA interactions at both operator half-sites. If the DNA-binding protein presents a different binding domain to the operator at each half-site, symmetric DNA operator subsequences are not only not optimal but are unfavorable. The implications of this distinction have not been considered in the literature.

Starting from natural, dyad symmetric or de novo designed DBPs we can generate specific DBPs with non-symmetric target recognition using a variety of strategies. Seven examples of strategies are listed; however, this invention is not limited to these particular strategies.

1) Produce two dimeric DBPs. One DBP is produced by the means described here to recognize a symmetrized version of the left half of the target and is called $DBP_L$. The other DBP is similarly produced to recognize a symmetrized version of the right half of the target and is called $DBP_R$. Cells producing equimolar mixtures of $DBP_R$ and $DBP_L$ contain approximately 1 part $DBP_L$ dimer, 2 parts $DBP_L:DBP_R$ heterodimer, and 1 part $DBP_R$ dimer. Thus one half of the DBP molecules bind to the non-symmetric target subsequence. These heterodimers may be isolated by affinity separation techniques, or the 50% active mixture may be used directly.

2) Produce a mixture of $DBP_R$ and $DBP_L$ as described in (1) and crosslink proteins with an agent such as glutaraldehyde. Use a column that contains the DNA target subsequence to purify $DBP_L:DBP_R$ heterodimer from the homodimers.

3) Produce (by variegation of the dimerization interface of a known DBP, as described more fully hereafter) a heterodimer comprised of complementing mutant sequences DBP1 and DBP2 such that the heterodimer DBP1:DBP2 is exclusively formed. Next, alter the recognition domains of DBP1 and DBP2 by the methods described here to produce heterodimers having asymmetric recognition, e.g. $DBP1_L:DBP2_R$.

4) Produce a heterodimer DBP1:DBP2 as in (3) and crosslink the proteins in vitro with an agent such as glutaraldehyde as in (2).

5) Produce two dimeric DBPs with left and right target recognition elements as in (1); produce complementing heterodimer mutations as in (3) such that the non-symmetric recognition heterodimer $DBP1_L:DBP2_R$ is constructed.

6) Produce a pseudo-dimer composed of a single polypeptide chain such that recognition elements that contact different bases are encoded by different codons; each DNA-contacting residue and every domain is independently variable and so asymmetric recognition can be established.

7.) Produce $DBP_L$ and $DBP_R$ in separate steps where heterodimers of $DBP:DBP_R$ is developed to recognize a hybrid target consisting of the wild type left half-site fused to the right half of the target and $DBP_L:DBP$ is developed to recognize a hybrid target consisting of the wild type right half-site fused to the left half of the target. Once produced, $DBP_L$ and $DBP_R$ are co-expressed intracellularly as described in (1) above, crosslinked as described in (2) above, or are modified to produce the obligately complementing non-symmetric recognition heterodimer $DBP_L:DBP_R$ as described in (5) above.

Any of the above strategies employ the processes claimed in this patent application. Detailed Example 1 employs strategy 5; Detailed Example 2 employs strategy 6. Section 6 of Detailed Example 1 also describes strategy 3.

For each target DNA sequence chosen, a left arm $T_L$, a center core $T_C$ and a right arm $T_R$ are defined. Two symmetrized derivatives of this target subsequence, the left symmetrized target $T_L$->-$T_C$-$T_L$<- and the right symmetrized target $T_R$<-·-$T_C$-$T_R$-> are designed and synthesized.

We divide the target DNA sequence into $T_L$, $T_C$, and $T_R$ based on knowledge of the interaction of the parental DBP with DNA sequences to which it binds, i.e. the operator. This knowledge may come from X-ray structures of parental DBP-operator complexes, models based on 3D structures of the DBP, genetics, or chemical modification of parental DBP-operator complexes.

Our strategy is to pick a target by finding a sequence that contains a close approximation to the central core of the operator. The rationale is that bases in the center of the target may not be contacted directly by the DBP but affect the specificity of binding by influencing the position or flexibility of the bases that are contacted directly by the DBP. Accommodating changes (operator vs. target) in uncontacted bases may require subtle changes in the tertiary or quaternary structure of the DBP, such as might be effected by alterations in the dimerization interface of a dimeric DBP. We can accommodate most changes in bases directly contacted by the DBP by altering the residues that contact those bases. Therefore, it is easier to accommodate changes in those bases that are directly contacted by the DBP and we endeavor to avoid changes in the central core by seeking a target the central core of which is highly similar to the central core of the operator of the parental DBP.

We must balance two tendencies: a) if we assign too many bases to $T_C$, we are unlikely to find a close approximation of $T_C$ in the genome of interest; and b) if we assign too few bases to $T_C$, we may thereby assign uncontacted bases to the arms. Differences between the target and the DNA sequence that binds the initial DBP at uncontacted bases in the arms may be difficult to accommodate through variegation of residues that contact the DNA directly; such a situation could cause variegation and selection to yield a functional DBP very slowly. Preferably, the length of $T_C$ is at least 6 but not greater than 10.

We search the target genome, first with the entire operator binding sequence, and then with progressively shorter central fragments of the operator, until an acceptable match is found. A match is acceptable if all or almost all the bases (e.g. six out of seven) match and other criteria are met.

Consider matching 6 of 7 bases as the criterion for choosing a target. The original sequence is acceptable, as are the 21 ($=7 \times 3$) sequences that differ by one base. There are $4^7 = 2^{14} = 16384$ possible heptamers. Thus we should expect to find an acceptable match every $16384/22 = 745$ bases. Similarly, matching 7 of 8 bases should occur every $65536/25 = 2622$ bases; matching 8 of 9 bases should occur every $262144/28 = 9362$ bases. These expected frequencies are such the viruses, which have genome sizes ranging from $5 \times 10^3$ bases up to $10^6$ bases or more, should have one or more matches of 6 of 7 bases. Larger viruses should contain matches of 7 of 8 or even 8 of 9 bases.

Other criteria may include restricting the search to parts of the genome not known to vary among different isolates of the organism.

If the longest matching search sequence is such that bases known to have no direct contact with the DBP are assigned to the arms, then we increase the size of $T_C$ to at least seven and then use a progression of core sequences to move in a stepwise fashion from a sequence that closely resembles the operator of the parental DBP to that of the target. We obtain an acceptable DBP for each target by variegation and selection. The best DBP from one target becomes the parental DBP for the next target in the progression. Accommodating changes in uncontacted bases in the central core may require variegation of residues in the protein:protein interface to produce subtle changes in the tertiary and quaternary structure of the DBP.

To illustrate this process, we consider the target chosen for Detailed Example 1. The HIV 353-369 target subsequence ACTTTCCGCTGGGGACT is nucleotides 353 to 369 of the HIV-1 genome (RATN85), chosen because of the close match of the Kim Consensus sequence (CCGCGGG) for lambda Cro binding (KIMJ87) to the underscored bases. No non-variable HIV sequence matched the nine central bases of any $O_R3$-like sequence. Highly conserved bases of lambda $O_R3$ are written bold with stars above.

```
          123456789
          *  *  *     *  *  *
O_R3 5' TATCACCGCAAGGGATA 3'
     3' ATAGTGGCGTTCCCTAT 5'

HIV-1 5' ACTTTCCGCTGGGGACT 3'
      3' TGAAAGGCGACCCCTGA 5'
  353 ↑
```

$T_L$, $T_C$, and $T_R$ are defined, in this case, as the first 5 bases, the center 7 bases (underlined), and the last 5 bases, respectively, of the target subsequence. $T_L$-> differs from the corresponding bases of $O_R3$ at four of five bases, including the strongly conserved A2 and C4. $T_L$<- is complementary to $T_L$->:

```
T_L --> = 5' ACTTT 3'
T_L <-- = 3' TGAAA 5'
```

We create the symmetrized target by rotating $T_L$<- about the center of the 17 bp sequence into the same strand as $T_L$->:

```
T_L --> = 5' ACTTT        AAAGT 3' = T_L <--
T_L <-- = 3' TGAAA_________↑      5'
```

$T_R$<- differs from the corresponding bases of $O_R3$ at three of five positions, including the highly conserved A2. We rotate $T_R$<- into the same strand as $T_R$->:

```
T_R <-- = 5' AGTCC        GGACT 3' = T_R -->
          3'  ↑_________CCTGA 5' = T_R <--
```

Symmetrized operators derived from HIV 353-369 are:

Left Symmetrized Target:

```
5' A C T T T C C G C T G G A A A G T 3'
3' T G A A A G G C G A C C T T T C A 5'
  | T_L --> |     T_C     | T_L <-- |
``` and

Right Symmetrized Target:

```
5' A G T C C C C G C T G G G G A C T 3'
3' T C A G G G G C G A C C C C T G A 5'
  | T_R <-- |     T_C     | T_R --> |
```

The two symmetrized derivatives are engineered into the appropriate vectors so that each of these sequences regulates the expression of the designed selectable genes of each of the respective vectors.

Had the best match in HIV to the CCGCGGG core been, for example, CTGCTGG, then we would use the symmetrized targets shown above until we found acceptable DBPs for the right and left targets. At that point, we would change the symmetrized targets to:

Second Left Symmetrized Target:

```
               ↓
5' A C T T T C T G C T G G A A A G T 3'
3' T G A A A G A C G A C C T T T C A 5'
  | T_L --> |     T_C     | T_L <-- |
``` and

Second Right Symmetrized Target:

```
               ↓
5' A G T C C C T G C T G G G G A C T 3'
3' T C A G G G A C G A C C C C T G A 5'
  | T_R <-- |     T_C     | T_R --> |
```

Using these targets and the selected right and left DBPs as new parental DBPs, we would initiate a new round of variegation and selection.

As another example, consider the 14 bp 434 operator. We could take each arm as 4 bp and the central core as 6 bp. We are likely to find good matches to the 6 bp core in any genome larger than 4096 bases. Thus, this division of the operator is preferred over that which assigns 5 bp to each arm and 4 bp to the core.

In order to obtain proteins that bind to these symmetrized targets, we generate a population of potential dbp genes by synthesizing DNA inserts that code on expression for part or all of a potential DBP and having variegated bases in the codons that encode residues of the parental DBP that are thought to contact the DNA or that influence the detailed position or dynamics of residues that contact the DNA.

The synthetic DNA insert containing vgDNA is ligated into both of the two vectors, each carrying the Right Symmetrized or Left Symmetrized Targets, and each ligation mixture is used to transform competent cells. The two sets of transformed cells are selected for vector uptake and successful repression at low stringency of selection. In the case described in Detailed Example 1, cells containing DBPs will be $Tet^S$, $Fus^R$, and $Gal^R$.

After one or more variegation steps, DBPs that bind tightly and specifically to each of the Left Symmetrized and Right Symmetrized Targets are obtained. These DBPs are designated, in general terms, $DBP_L$ and $DBP_R$, respectively. If these proteins are produced in equal amounts in the same cell, then approximately 50% of DBP protein dimers consist of the $DBP_L:DBP_R$ heterodimer. This may be sufficient for repression of the target. In the preferred embodiment, further mutations are introduced into the $DBP_L$ and $DBP_R$ proteins, as described below, to enable 100% of the molecules to form heterodimers.

In an especially preferred embodiment, variegation of the gene to alter its DNA-specificity is combined with variegation of its gene to alter its dimerization (protein-protein binding) characteristics, so that the formation of the heterodimer $DBP_L:DBP_R$ is favored. The variegation of the dimerization interface may precede (strategy 3) or follow (strategy 5) the alteration of the DNA specificity. Simultaneous variegation at both sites is also possible.

The DNA-binding proteins considered here interact with specific DNA sequences as multimers (usually dimers or tetramers) (PABO84). Monomers usually associate independently and the resulting multimer interacts with DNA. Coupling between oligomerization and DNA-binding equilibria results in explicit inclusion of oligomerization effects in the apparent affinity of DNA-binding proteins for their operators (JOHN80, RIGG70, and CHAD71).

Lambda repressor binds to operator DNA as a dimer (CHAD71, PTAS80) and consists of two domains (N- and C-terminal) connected by a short protease-sensitive region (PABO79). The C-terminal domain of lambda repressor contains both a strong dimerization site (PABO79, PTAS80) and the site for cooperative, pairwise binding among repressor dimers bound to operator DNA (JOHN79, PTAS80). The N-terminal domain of lambda repressor contains a weak dimerization site along with the operator binding and regulatory functions of the repressor (SAUE79, PTAS80). When separated from the C-terminal domain, the N-terminal domain binds to the operator as a dimer (JOHN79, SAUE86, and SAUE79); however, the apparent affinity of the N-terminal fragment for operator DNA is reduced by a factor of about 800 relative to the apparent operator affinity of the intact protein (JOHN79). The N-terminal domain dimer actually shows a slight increase in operator affinity (2- to 3-fold, JOHN79, SAUE86) but this is masked by the enormous loss of dimerization energy which accompanies the loss of the C-terminal dimerization site. $K_1$, the dimer dissociation equilibrium constant, increases from 20 nM for intact lambda repressor to 0.1 mM for the isolated N-terminal domain, a factor of 5000 (JOHN79, SAUE86).

The weak dimerization of the lambda repressor N-terminal domain has been deduced from X-ray crystal structure (PABO82b), model building (LEWI83, OHLE83), solution NMR studies (WEIS87a,b,c), and mutational analysis (SAUE86, REID88, and WEIS87b) to result from hydrophobic interactions between alpha helix 5 of one monomer with alpha helix 5' of the other monomer. Dimer interaction in the N-terminal DNA-binding domain of the closely related 434 repressor also involves hydrophobic packing interactions in a nonhelical region (ANDE87).

The precise geometry of the protein in the complex with DNA strongly influences the strength of the interaction with DNA. For example, Sauer et al. generated a 92 amino-acid fragment of lambda repressor carrying the YC88 mutation. This N-terminal domain dimerizes through a covalent S-S bond. Although the dissociation into monomers is unmeasurable, the binding to DNA is diminished about 10-fold relative to intact lambda repressor (SAUE86).

The results presented by Reidhaar-Olson and Sauer (REID88), summarized in Table 7, show which residues in the dimerization region, when varied, will produce functional homodimers of N-terminal domains with little alteration of structure. Wide variation is tolerated at solvent exposed positions 85, 86, and 89. In contrast, almost no substitutions are tolerated at the buried positions 84 and 87. Most hydrophobic residues are functional at position 91 (except P) although aromatic residues are excluded. The hydrophobic interactions among I84, M87, and V91' had previously been shown to be major components of dimerization free energy (NELS83, WEIS87b). In general, mutations that destabilize lambda repressor N-terminal dimerization are similar to those that destabilize global protein structure.

The P22 Mnt repressor, like lambda Cro, is a small protein containing both DNA-binding and oligomerization sites. Unlike Cro, P22 Mnt is a tetramer in solution (VERS85b, VERS87a). The amino acid sequence of Mnt has been determined (VERS87a) but the three dimensional structure of the protein is not known. Knight and Sauer (KNIG88) have shown, by sequential deletion of C-terminal residues, that Y78 is essential for tetramer formation.

A preferred embodiment of this process utilizes information available on protein structure obtained from crystallographic, modeling, and genetic sources to predict the residues at which mutation results in stable protein monomers that retain substantially the same 3D structure as the wild-type DBP, but that fail to form dimers. Dimerization mutants are constructed using site-directed mutagenesis to isolate one or more user specified substitutions at chosen residues. The process starts using one of the genes selected for binding to a symmetrized target, denoted $dbp_1$ ($dbp_1$ could be either the dbp$_L$ gene or the dbp$_R$ gene), as the parental sequence, so that each of several specific mutations is engineered into the gene for a protein binding specifically to the symmetrized target used in the selection (the Left Symmetrized Target in the case of the dbp$_L$ gene).

Reverse selection isolates cells not expressing a protein that binds to the target DNA sequence. This phenotype could arise in several ways, including: a) a mutation or deletion in the dbp$_1$ gene so that no protein is produced, b) a mutation that renders the descendant of the parental DBP$_1$ unstable, c) a mutation that allows the descendant of the parental DBP$_1$ to persist and to fold into nearly the same 3D structure as the parental DBP, but which prevents oligomerization. It is anticipated that reverse selection will isolate many genes for non-functional proteins and that these proteins must be analyzed until a suitable oligomerization-mutant is found. Therefore, we choose sites carefully so that we maximize the chance of disrupting oligomerization without destroying tertiary structure. We also use lower levels of variegation in reverse selection so that the number of mutants to be analyzed is not too large. For forward selection, the number of different mutants is preferably $10^4$ to $10^9$, and more preferably greater than $10^6$. For reverse selection, it is $10^3$ to $10^6$. (Under certain circumstances, the number of reverse selection mutants could be as low as 10–20).

Cassettes bearing the site-specific changes are synthesized and each is ligated into the vector at the appropriate site in the dbp$_1$ gene. Transformants are obtained by the antibiotic-resistance selection for vector maintenance (e.g. ampicillin in the case of Detailed Example 1), and screened for loss of repression of the selective systems under control of Dbp$_1$ binding. Defective dimerization results in substantially decreased DNA affinity, hence the altered derivatives are recognized by screening isolates obtained using the selectable gene systems. In Detailed Example 1 (where dbp$_1$ is dbp$_L$), dimerization-defective derivatives are Tet$^R$, Fus$^S$ and Gal$^S$ in $E.$ $coli$ delta4 cells (Gal+ in cells of $E.$ $coli$ strain HB101). Restriction digestion and sequencing is used to verify that loss of repression is not due to deletion in the dbp$_L$ gene. The putative dbp$_L^-$ gene is backcrossed to determine that the Dbp$_L^-$ phenotype is due to a mutation specifically in that gene. Small-zone gel filtration (WEIS87b) is used to verify the dimer$^-$ phenotype. Genes from plasmids that satisfy these criteria are designated dbp$^-$.

In the specific case shown in Detailed Example 1 (using an engineered synthetic lambda cro gene designated rav), the mutant Rav protein with specific binding to the Left Symmetrized Target (designated Rav$_L$; gene, rav$_L$) is used to produce a derivative defective in dimerization. Crystallographic and computer modeling studies of lambda Cro suggest that the dimer is stabilized by interactions in an anti-parallel beta sheet between residues E54, V55 and K56 from each monomer (ANDE81, PAB084). In addition, F58 appears to stabilize the Cro dimer through hydrophobic interactions between F58 of one monomer and residues in the hydrophobic core of the other monomer (TAKE85). Further, mutational studies (PAKU86) show that some substitutions at E54 and at F58 result in decreased intracellular specific protein levels and that these mutant proteins lack repressor activity. Mutants are constructed by using site specific mutagenesis to isolate VF55 and FW58 mutants of Rav$_L$. The cassettes bearing mutations that confer the VF55 and FW58 substitutions are synthesized, and each is ligated into the operative vector at the appropriate site within the rav$_L$ gene. Selections and characterizations are as described above. These alleles are designated rav$_L$-55 and rav$_L$-58.

Alternative methods of obtaining dimerization-defective DBP derivatives are not excluded. Thus the rav+ gene (Detailed Example 1) or a potential-dbp+ gene coding for any globular dimerizing protein, may be subjected to Structure-directed Mutagenesis of residues involved in the protein-protein dimer interface. In the case of the rav+ allele, residues 7, 23, 25, 30, 33, 40, 42, 52, 54, 55 and 58 are candidates for mutagenesis.

For example, mutagenesis of rav+ residues 52, 54, 55 and 58, using a cassette carrying vgDNA at codons specifying these residues, is followed by ligation and transformation of cells. Selection is applied for plasmid maintenance (ampicillin-resistance) and loss of repression (Tet$^R$, and galactose utilization in HB101 cells). Variegated plasmid DNA is purified from a population of Amp$^R$ Tet$^R$ Gal+ cells, digested with restriction endonucleases that span the rav+ gene, and analyzed by Southern blots to probe the population for the size of DNA that hybridizes to full-length rav+ probe. Plasmid preparations containing the vg-rav fragment of predominantly rav+ molecular weight are retained, and are designated vg-ravA.

To isolate a second dimer-specific rav mutant protein, designated RavB, such that the mutation in ravB is complementary to a mutation contained in the vg-ravA population, Structure-directed Mutagenesis is performed on a second copy of the rav gene, designated ravB, carried on a plasmid conferring a different antibiotic resistance (e.g. kanamycin resistance). Residues affecting the same dimer interface are varied. Competent vg-ravA cells are transformed with the vg ravB plasmid preparation. Transformants are obtained as Amp$^R$ Kan$^R$, and further selected for Rav+ phenotype using the selection systems (Tet$^S$, Fus$^R$, Gal$^R$ in an $E.$ $coli$ delta4 cell genetic background).

The surviving colonies are analyzed by restriction analysis of plasmids, and are backcrossed to obtain pure plasmid lines that confer each of the Amp$^R$ and Kan$^R$ phenotypes. In this manner, mutants bearing obligate complementing dimerization alleles of ravA and ravB are isolated. These rav mutations may be tested pairwise to confirm complementation, and are sequenced. The information obtained from these mutants is used to introduce these dimerization mutations into rav$_L$ and ravR genes previously altered by Structure-directed Mutagenesis in DNA-binding specificity domains as described above.

In the preferred embodiment of this invention (strategy 3), isolation of dbp$_L$ and dbp$_R$ mutations that confer specific and tight binding to target DNA sequences $T_L\text{-}>\text{-}T_C\text{-}T_L\text{<-}$ and $T_R\text{<-}\text{-}T_C\text{-}T_R\text{-}>$ is followed by engineering of second site mutations causing a dimerization defect, for example dbp$_L$-1 as described herein. Complementing mutations are introduced into each of the dbp$_R$ and dbp$_L$ genes, such that obligate heterodimers are co-synthesized and folded together in the same cell and bind specifically to the non-palindromic targets. Successful complementing mutations confer the phenotypes of repression of the operative selection systems.

A primary set of residues is identified. These residues are predicted, on the basis of crystallographic, modeling, and genetic information, to make contacts in the dimer with the residue altered to produce DBP$_L$-1. A secondary set of residues is chosen, whose members are believed to touch or influence the residues of the primary set. An initial set of residues for Focused Mutagenesis in the first variegation step is selected from residues in the primary set. A variegation scheme, consistent with the constraints described herein, is picked for these residues so that the chemical properties of residues produced at each variegated codon are similar to those of the wild-type residue; e.g. hydrophobic residues go to hydrophobic or neutral, charged residues go to charged or hydrophilic. A cassette containing the vgDNA at the specified codons is synthesized and ligated into the $dbp_R$ gene carried in a vector with a different antibiotic selection than that on the vector carrying the $dbp_L$-1 gene. For example, in Detailed Example 1, $rav_L$-55 or $rav_L$-58 are encoded on plasmids that carry the gene for ampicillin resistance. Variegated $rav_R$ genes are cloned into plasmids bearing the gene for kanamycin resistance.

The protein produced by the $dbp_L$-1 allele carrying the dimerization mutation fails to bind to the $dbp_L$ target $T_L$->-$T_C$-$T_L$<-. Cells bearing this target as a regulatory site upstream of selection genes display the DBP− phenotype. This phenotype is employed to select complementary mutations in a $dbp_R$ gene. Following ligation of the mutagenized cassette into the appropriate (e.g. $Kan^R$) plasmid, cells bearing $dbp_L$-1 on a differently marked (e.g. $Amp^R$) plasmid are made competent and transformed. Transformants that have maintained the resident plasmid (e.g. $Amp^R$ $Kan^R$) are further selected for DBP+ phenotype in which binding of the non-palindromic target subsequence $T_L$->-$T_C$-$T_R$-> is required for repression. Only heterodimers consisting of a 1:1 complex of the $dbp_L$-1 gene product and the complementing $dbp_R$-1 gene product bind to the target, and produce $Tet^S$ $Fus^R$ $Gal^R$ colonies in the appropriate cell host.

Each resident plasmid is obtained from candidate colonies by plasmid preparation and transformation at low plasmid concentration. Strains carrying plasmids encoding either mutant $dbp_L$-1 or mutant $dbp_R$-1 genes are selected by the appropriate antibiotic resistance (e.g. in Detailed Example 1, $Amp^R$ or $Kan^R$ selection, respectively). Plasmids are independently screened for the DBP− phenotype, characterized by restriction digestion and agarose gel electrophoresis, and plasmid pairs are co-tested for complementation by restoration of the DBP+ phenotype when both dbp alleles are present intracellularly. Successfully complementing pairs of dbp genes are sequenced. Subsequent variegation steps may be required to optimize dimer interactions or DNA binding by the heterodimer.

In Detailed Example 1, the VF55 change in $Rav_L$-55 introduces a bulky hydrophobic side group in place of a smaller hydrophobic residue. A complementary mutation inserts a very small side chain, such as G55 or A55, in a second copy of the protein. In this case, the primary set for mutagenesis is V55. A secondary set of residues includes nearby components of the beta strand E54, K56, P57, and E53 as well as other residues. In the initial variegation step, residues 53–57 are subjected to Focused Mutagenesis, such that all amino acids are tested at this location. Cells containing complementing mutant proteins are selected by requiring repression of the nonpalindromic HIV 353-369 target subsequence $T_L$->-$T_C$-$T_R$->.

In another embodiment, the $rav_L$-58 allele carrying the substitution FW58 and conferring the Rav− phenotype, is used for selection of complementing mutations following Structure-directed Mutagenesis of the $rav_R$ gene. Residues L7, L23, V25, A33, I40, L42, A52, and G54 are identified as the principal set. Residues in the secondary set include F58, P57, P59, and buried residues in alpha helix 1. In the initial variegation step residues 23, 25, 33, 40, and 42 are varied through all twenty amino acids. Subsequent iterations, if needed, include other residues of the primary or secondary set. In this manner, $rav_R$-1, -2, -3, etc. are isolated, each of which yields a protein that is an obligate complement of the $rav_L$-58 mutation. Selection for Rav+ phenotype using the HIV 353-369 target $T_L$->-$T_C$-$T_R$-> sequence is used as described in the preferred embodiment.

In either the preferred or alternative embodiments, this process teaches a method of constructing obligate complementing mutations at an oligomer interface. These pairs of mutations may be used in further embodiments to engineer novel DBPs specific for HIV 681-697 and HIV 760-776 targets; for targets in other pathogenic retroviruses such as HTLV-II; for other viral DNA-containing pathogens such as HSVI and HSVII; as well as for non-viral targets such as deleterious human genes. Similar methodology is claimed for engineering DBPs for use in animal and plant systems.

Overview: Selection of the Initial DNA-Binding Protein for Variegation

The choice of an initial DBP is determined by the degree of specificity required in the intended use of the successful DBP and by the availability of known DBPs. The present invention describes three broad alternatives for producing DBPs having high specificity and tight binding to target DNA sequences. The present invention is not limited to these classes of initial potential DBPs.

The first alternative disclosed is to use a polypeptide that will conform to the DNA and can wind around the DNA and contact the edges of the base pairs. The second alternative is to use a globular protein (such as a dimeric H-T-H protein) that can contact one face of DNA in one or more places to achieve the desired affinity and specificity. The third alternative is to use a series of flexibly linked small globular domains that can make contact with several successive patches on the DNA. The following considerations allow a choice among these alternatives and combinations of them.

DNA Features Influencing Choice of an Initial DBP

A number of features of DNA influence the choice of an initial DBP. These include sequence-specific DNA structure and the size of the genome within which the DBP is expected to recognize and affect gene expression.

Sequence-specific aspects of DNA structure that can influence protein binding include: a) the edges of the bases exposed in the major groove, b) the edges of the bases exposed in the minor groove, c) the equilibrium positions of the phosphate and deoxyribose groups, d) the flexibility of the DNA toward deformation, and e) the ability of the DNA to accept intercalated molecules. Note that the sequence-specific aspects of DNA are carried mostly inside a highly charged molecular framework that is nearly independent of sequence.

The strongest signals of sequence are found in the edges of the base pairs in the major groove, followed by the edges in the minor groove. The groove dimensions depend on local DNA sequence. The minor groove of "average" B-DNA is approximately 5.7 Å wide and 7.5 Å deep, while the major groove is approximately 11.7 Å wide and 8.5 Å deep (NEID87b). In AT-rich regions, the minor groove is narrower than average and the major groove is wider. In GC-rich regions, conversely, the minor groove is wider than average and the major groove is narrower. These differences in minor groove width and the differences in groups on the base edges allow sequence-specific binding in the minor groove. In principle, each base pair of the DNA influences the position of all the other atoms in the DNA, but the effects are actually localized. The effects of nearby sequence are degenerate; often permutations of local sequences have little or no effect on segments more than two or three base pairs away (KOUD87). However, see also Ulanovsky and Trifonov (ULAN87) who have pointed out that inversion of a non-palindromic subsequence leaves the twist and tilt unchanged, but changes the sign of the roll. The number of base pairs required to define a unique site depends on the size and non-randomness of the genome. Consider a genome of length $Z_g$ bases and consider a specific subsequence of length Q. If the genome is random, the subsequence is expected to occur N(Q) times, where $$N(Q) = \frac{2 Z_g}{4^Q} = \frac{2 Z_g}{2^{2Q}}.$$

From this equation, we derive the expression $Q_u$, which is the lower limit of the length of subsequences that are expected to occur once or be absent:

$$Q_u = \log_2(2 Z_g)/2.$$

| $Z_g$ | $\log_2 (2 Z_g)/2$ | $Q_u$ |
|---|---|---|
| $10^6$ | 10.5 | 11 |
| $10^7$ | 12.1 | 13 |
| $10^8$ | 13.8 | 14 |
| $10^9$ | 15.5 | 16 |
| $10^{10}$ | 17.1 | 18 |

Thus, a DNA subsequence comprising 12 base pairs may be unique in the E. coli genome ($5 \times 10^6$ bp), but is likely to occur about 180 times in a random sequence the size of the human genome ($3 \times 10^9$ bp).

Many DBPs form complexes with operator DNA in which some base pairs internal to the operator are not directly contacted by the protein. In such a case, the effective length of uniquely recognized sequence is different from either the length of the operator sequence or the number of bases directly contacted by the protein. Consider a protein, similar to 434 repressor, that binds a 14 base pair operator and makes direct contacts with 8 base pairs in two segments of 4 at either end of the operator. Changing any of these 8 base pairs greatly reduces binding. There are $4^6 = 4096$ possible intervening sequences. If, for example, only 20 of these possible sequences allow strong binding, then we say that the protein in effect recognizes R additional bases, where $$R = \log_4 \left( \frac{\text{possible subseq's}}{\text{recognized seq's}} \right) = \log_4 (204.8) = 3.84.$$

$$20/4096 = 204.8$$

Although the hypothetical protein directly contacts only 8 of the 14 base pairs of the operator, it shows a sequence selectivity greater than that of a protein that contacts a string of 11 specific base pairs, but slightly less than that of a protein that directly contacts 12 base pairs.

The non-random nature of DNA sequences in genomes has been shown to result in the over- and underrepresentation of specific sequences. Lathe (LATH85) has shown that for sequences coding for amino-terminal protein regions, the random-genome model can underestimate the probe length needed to define a unique sequence. Smith et al. (SMIT87) have found that recognition sites for certain restriction enzymes (choosen for study because their recognition sites were predicted to be rare) occur in clusters and are found much more often than expected. In contrast, Simons et al. (SIMO84) found that lac repressor binding sites in eukaryotic genomes were almost two orders of magnitude less frequent than expected on the basis of random sequence. We use the calculations shown above to estimate the degree of recognition that a given number of bases provides. For example, based on the above calculations, a single DBP could uniquely recognize a subsequence of 17 base pairs. Since $4^{17}$ approximately equals $10^{10}$, such a subsequence is unlikely to occur in the human genome by chance and so is worth testing via an oligonucleotide probe. A subsequence of twelve base pairs is likely to occur 64 times in a random genome of $10^9$ bp and so is not a good candidate for unique recognition. In the preferred embodiment of this invention, candidate sequences are used as probes to measure the number of times the sequence occurs in a genome of interest.

Disclosure of how we choose initial polypeptides or DBPs to achieve chosen levels of specificity is deferred until we discuss the structural features of proteins and polypeptides that are available to form sequence-specific DNA-polypeptide or DNA-protein complexes.

Protein Features Influencing Choice of Initial DBP

Neidle et al. (NEID87b) have recently reviewed current knowledge of the structure of DNA and how the structure is perturbed by binding of several small-molecule drugs. The drugs reviewed fall into two general classes: those that intercalate and those that bind in one of the grooves. Drugs such as netropsin and Hoechst 33258 bind in the minor groove and displace structural waters or cations; these drugs contain many of the same chemical groups as proteins, but are more planar than genetically encoded polypeptides. Drugs that intercalate have large hydrophobic surfaces with polar atoms, if any, limited to the periphery; it may be possible for the side groups of two tryptophans or of a tryptophan and another aromatic side group (H, F, or Y) to intercalate into DNA.

Although large protein complexes, such as RNA polymerase, can disrupt base pairs and gain access to the primary base-pairing edges of the bases, sequence-specific binding to DN by DBPs does not require unpairing of the bases. Indeed, RNA polymerase initially binds to fully base-paired DNA and then undergoes an isomerization to form the "open" complex that contains unpaired bases. Most sequence-specific binding by proteins to DNA is thought to involve contacts in the DNA major groove.

Figure 9:
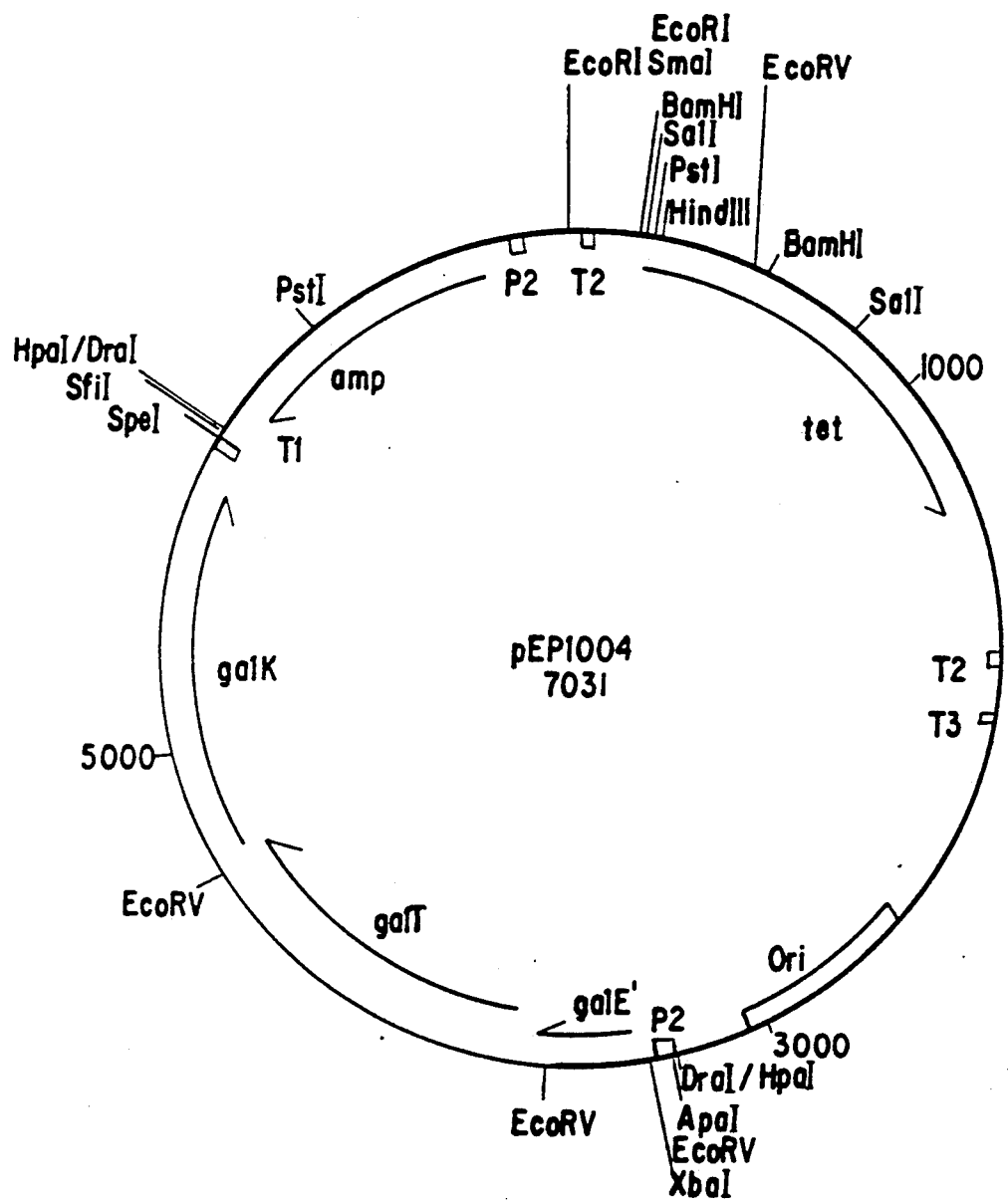
FIG. 9 Plasmid pEP1004.

To be certain of unique recognition in the human genome, it is best to design a protein that recognizes 19 to 21 base pairs. To contact 20 base pairs directly, a protein would need to: a) wind two full turns around the DNA making major groove contacts, b) make a combination of major groove and minor groove contacts, or c) contact the major groove at four or five places. A path along the major groove of an ideal B-DNA helix and 4.0 Å from the axis covers about 4.2 Å per base pair; at 6.0 Å from the axis the path covers 5.0 Å per base pair. In ideal B-DNA, a polypeptide could come no closer than 5.0 Å from the axis; see SAEN83, FIG. 9-5, p238. Thus the polypeptide chain covers about 5.0 Å per base pair, which represents about 1.5 amino acids in an extended conformation.

A nine residue alpha helix, such as the recognition helices of H-T-H repressors, extends about 13.5 Å along the major groove. If residues with long side chains are located at each terminus of the helix, the helix can make contacts over a 20.0 Å stretch of the major groove allowing six base pairs to be contacted (OHLE82). Parts of the DBP other than the second helix of the H-T-H motif can make additional protein-DNA contacts, adding to specificity and affinity. The rigidity of the alpha helix prevents a long helix from following the major groove around the DNA. A series of small domains, appropriately linked, could wind around DNA, as has been suggested for the zinc-finger proteins (BERG88a,- GIBS88). In an extended configuration a polypeptide chain progresses roughly 3.2 to 3.5 Å between consecutive residues. Thus, a 10 residue extended protein structure could contact 5 to 8 bases of DNA.

Stable complexes of proteins with other macromolecules involve burial of 1000 Å$^2$ to 3000 Å$^2$ of surface area on each molecule. For a globular protein to make a stable complex with DNA, the protein must have substantial surface that is already complementary to the DNA surface or can be deformed to fit the surface without loss of much free energy. Considering these modalities we assign each genetically encoded polypeptide to one of three classes:

1) a polypeptide that can easily deform to complement the shape of DNA,
2) a globular protein, the internal structure of which supports recognition elements to create a surface complementary to a particular DNA sub-sequence, and
3) a sequential chain of globular domains, each domain being more or less rigid and complementary to a portion of the surface of a DNA subsequence and the domains being linked by amino acid subsequences that allow the domains to wind around the DNA.

Complementary charges can accelerate association of molecules, but they usually do not provide much of the free energy of binding. Major components of binding energy arise from highly complementary surfaces and the liberation of ordered water on the macromolecular surfaces.

Properties of Sequence-Specific DNA-Binding by Polypeptides:

An extended polypeptide of 24 amino acids lying in the major groove of B-DNA could make sequence-specific interactions with as many as 15 base pairs, which is about the least recognition that would be useful in eukaryotic systems. Peptides longer than 24 amino acids can contact more base pairs and thus provide greater specificity.

Extended polypeptide segments of proteins bind to DNA in natural systems (e.g. lambda repressor and Cro, P22 Arc and Mnt repressors). The DNA major groove can accommodate polypeptides in either helical or extended conformation. Side groups of polypeptides that lie in the major groove can make sequence-specific or sequence-independent contacts.

Since the polypeptide can lie entirely within the major groove, contacts with the phosphates are allowed but not mandatory. Thus a polypeptide need not be highly positively charged. A neutral or slightly positively charged polypeptide might have very low non-specific binding.

Polypeptides composed of the 20 standard amino acids are not flat enough to lie in the minor groove unless the sequence contains an extraordinary number of glycines, however, residue side-groups could extend into the minor groove to make sequence-specific contacts. Polypeptides of more than 50 amino acids may fold into stable 3D structures. Unless part of the surface of the structure is complementary to the surface of the target DNA subsequence, formation of the 3D structure competes with DNA binding. Thus polypeptides generated for selection of specific binding are preferably 25 to 50 amino acids in length.

Polypeptides present the following potential advantages:

a) low molecular weight: an extended polypeptide offers the maximum recognition per amino acid,
b) polypeptides have no inherent dyad symmetry and so are not biased toward recognition of palindromic sequences, and
c) polypeptides may have greater specificity than globular proteins.

Thus, one would choose a polypeptide as initial DNA-binding molecule if high specificity and low molecular weight are desired.

No sequence-specific DNA-binding by small polypeptides has been reported to date. Possible reasons that such polypeptides have not been found include: a) no one has sought them, b) cells degrade polypeptides that are free in the cytoplasm, and c) they are too flexible and are not specific enough.

In a preferred embodiment, a DNA-binding polypeptide is associated with a custodial domain to protect it from degradation, as discussed more fully in Examples 3 and 4.

Properties of Globular Proteins Influencing Choice of Initial DBP

The majority of the well-characterized DBPs are small globular proteins containing one or more DNA-binding domains. No single-domain globular protein comprising 200 or fewer amino acids is likely to fold into a stable structure that follows either groove of DNA continuously for 10 bases. The structure of a small globular protein can be arranged to hold more than one set of recognition elements in appropriate positions to contact several sites along the DNA thereby achieving high specificity, however, the bases contacted are not necessarily sequential on the DNA. For example, each monomer of lambda repressor contains two sequence-specific DNA recognition regions: the recognition helix of the H-T-H region contacts the front face of the DNA binding site and the N-terminal arm contacts the back face. To obtain tight binding, a globular protein must contact not only the base-pair edges, but also the DNA backbone making sequence-independent contacts. These sequence-independent contacts give rise to a certain sequence-independent affinity of the protein for DNA. The bases that intervene between segments that are directly contacted influence the position and flexibility of the contacted bases. If the DNA-protein complex involves twisting or bending the DNA (e.g. 434 repressor-DNA complex), non-contacted bases can influence binding through their effects on the rigidity of the target DNA sequence.

DNA-binding motifs are shared among the globular DNA-binding proteins. H-T-H DBPs recognize DNA at least partly via an alpha helix. In this motif, nine residues in alpha helical conformation lie along the major groove. Side groups of some of these residues make sequence-specific contacts with the edges of base pairs. Main-chain protein atoms and side groups make sequence-independent contacts with atoms in the DNA backbone. X-ray structures have been determined for several proteins of this class together with a few protein-DNA complexes.

The phage repressors Arc, Mnt, lambda repressor and Cro are proposed to bind to DNA at least partly via binding of extended segments of polypeptide chain. The N-terminal arm of lambda repressor makes sequence-specific contacts with bases in the major groove on the back side of the binding site. The C-terminal "tail" of lambda Cro is proposed to make sequence-independent contacts in the minor groove of the DNA. The structure of neither Arc nor Mnt has been determined; however, the sequence specificity of the N-terminal arm of Arc can be transferred to Mnt; viz. when Arc residues 1-9 are fused to Mnt residues 7 through the C-terminal, the fusion protein recognized the arc operator but not the mnt operator. Residues 2, 3, 4, 5, 8, and 10 of Arc have been proposed to contact operator DNA and residue 6 of Mnt has been shown to be involved in sequence-specific operator contacts.

Many types of globular proteins occur naturally as DNA-binding proteins. Alteration of DNA-binding specificity has been demonstrated for globular proteins. In six studies the sequence-specificity of globular DBPs has been changed. Further, DNA-recognition regions have been interchanged among similar proteins.

Dyad-symmetric globular proteins bind well to palindromic sequences. Binding to non-palindromic sequences requires alteration of dyad-symmetric proteins. Even non-palindromic DNA has approximate dyad symmetry in the deoxyribophosphate backbone; proteins that are heterodimers or pseudo-dimers engineered from known globular DBPs are good candidates for the mutation process described here to obtain globular proteins that bind non-palindromic DNA. It has been observed that the DNA restriction enzymes having palindromic recognition are composed of dyad symmetric multimers (MCCL86), while restriction enzymes and other DNA-modifying enzymes (e.g. Xis of phage lambda) having asymmetric recognition are comprised of a single polypeptide chain or an asymmetric aggregate (RICH88). Such proteins may also provide reasonable starting points to generate DBPs recognizing non-palindromic sequences.

Globular proteins are capable of complex functions. For example, a globular protein can bind sequence-specifically to DNA through one set of residues and activate transcription from an adjacent gene through a different set of residues (for example, lambda or P22 repressors). The internal structure of the protein, defined by the amino acid sequence, establishes the appropriate geometric relationship between these two sets of residues. Globular proteins may also bind particular small molecules, effectors, in such a way that the affinity of the protein for its specific DNA recognition subsequence is a function of the concentration of the particular small molecules (e.g. CRP and trp repressor). Conditional DNA-binding and gene activation are most easily obtained by engineering changes into known globular DBPs.

Some DBPs from bacteria and bacteriophage have been shown to have sufficient specificity to operate in mammalian cells. The lac operator-repressor system functions in oocytes of *Xenopus laevis* (HUMC88), in mouse L-cells (HUMC87), in NIH-3T3 cells (BROW87), and in monkey cells (FIGG88). The lac repressor is thus found to be stably synthesized in mammalian systems, to be translocated into the nucleus in sufficient quantity to be active, and to be responsive to inactivation by the inducer IPTG, leading to release of repressor from the lacO operator (BROW87). These studies indicate that prokaryotic transcriptional negative regulatory elements can function in the eukaryotic nucleus.

An initial DBP may be chosen from natural globular DBPs of any cell type. The natural DBP is preferably small so that genetic engineering is facile. Preferably, the 3D structure of the natural DBP is known; this can be determined from X-ray diffraction, NMR, genetic and biochemical studies. Preferably, the residues in the natural DBP that contact DNA are known. Preferably the residues that are involved in multimer contacts are known. Preferably the natural operator of the natural DBP is known. More preferably, mutants of the natural operator are known and the effects of these mutants on binding by natural DBP and mutant DBPs are known. Preferably, mutations of the DBP are known and the effects on protein folding, multimer formation, and in vivo half life-time are known. Most of the above data are available for lambda Cro, lambda repressor and fragments of lambda repressor, 434 repressor and Cro proteins, *E. coli* CRP and trp repressor, P22 Arc, and P22 Mnt.

Globular DBPs are the best understood DBPs. In many cases, globular DBPs are capable of sufficient specificity and affinity for the target DNA sequence. Thus globular DBPs are the most preferred candidates for initial DBP.

Table 8 contains a list of some preferred globular DBPs for use as initial DBPs.

Each of *Escherichia coli* bacteriophage lambda repressor (236 amino acid residues) and phage 434 repressor (209 residues long) has two structural and functional domains: amino terminal (N-terminal) for DNA binding and carboxy terminal (C-terminal) for dimerization (SAUE79, PTAS86). Models of these proteins based on X-ray crystallographic studies have been developed to describe the DNA-binding activities of their N-terminal domains (PAB082b, PAB084, ANDE87). The N-terminal 92 amino acids of lambda repressor form five alpha helices separated by small surface turns with an eight residue flexible arm at the N terminus; the N-terminal 69 amino acids of 434 repressor form four separate alpha helices homologous in structure to the first four of the lambda repressor helices. In phage repressor-operator binding models, alpha helix 3 (alpha 3) from the N-terminal domain is the recognition helix which lies along the major groove of the B-form DNA operator sequence which is 17 base pairs long in lambda and 14 base pairs in phage 434. Residues in the N-terminal and central portion of alpha 3 that are exposed to solvent in the free protein dimer become buried in the protein-DNA complex forming contacts with the edges of nucleotide bases in the DNA major groove. Additional contacts to operator bases proposed exclusively in the model of lambda repressor binding are those made to major groove nucleotides by a residue in the region between alpha 3 and alpha 4 that is solvent exposed in the free protein dimer (NELS86). Lambda repressor makes contacts on the back face of the operator helix using the N-terminal arm (PABO82a, ELIA85). Alpha helix 2 of both lambda and 434 repressors acts as an alignment helix as it lies across the major groove with its N-terminal residue contacting a DNA backbone phosphate at the outer end of the half-operator sequence. In the lambda repressor model (PABO84) the C-terminal residue of alpha 3 contacts a backbone phosphate at the inner end of the half-operator, while in the 434 repressor model comparable contact is made by the N-terminal residue of alpha 4 and more weakly by a residue in the region between alpha 2 and alpha 3. Residues in the region between alpha 3 and alpha 4 of both repressors also make contacts to operator backbone phosphates.

Analysis of crystals of the 92 residue lambda repressor N-terminal domain has revealed that monomers contact each other at residues in alpha 5 (PABO82b). Study of co-crystals of the 69 residue N-terminal 434 repressor domain and a 14 base pair consensus operator oligonucleotide has shown that monomers contact at residues in the C-terminal region adjacent to helix alpha 4 (ANDE87). The N-terminal fragments of lambda repressor, though capable of dimeric interaction when bound as described above to operator DNA, do not form dimers in solution as readily as the intact repressor protein (PTAS86, p79). The C-terminal domain of intact lambda repressor mediates formation of dimers which bind operator DNA with higher affinity than the N-terminal domain fragment (PABO82b).

The DNA sequences of operator sites to which lambda and 434 repressors bind have approximate palindromic sequence symmetry. Two-fold rotational symmetry is evident for repressor dimer-operator DNA complexes from crystal structure and model building. The operator DNA bends symmetrically in the 434 repressor-consensus operator co-crystal (ANDE87). The center of the 14 base pair DNA helix is over-wound and bends slightly along its axis such that it curls around the alpha 3 helix of each repressor monomer; the ends of the operator DNA helix are underwound. Bending of operator DNA has also been proposed in models of Cro protein and CAP protein operator binding (OHLE83, GART88). Consistent with the results of Gartenberg and Crothers, bending of the 434 operator toward Cro is toward the minor groove and occurs most readily when the central bases consist exclusively of A and T (KOUD87); in this case, substitution of CG base pairs greatly reduces binding.

Crystal studies of lambda Cro describe this 66 amino acid dimeric protein as a structure containing in each monomer three alpha helices separated by short turns, a beta sheet comprising one strand N-terminal to the alpha helices and two strands C-terminal to the helices, and a C-terminal flexible region. The three beta strands are arranged antiparallel to each other. The C-terminal residues of beta strand 3 contact the same residues of the other Cro monomer in antiparallel fashion to form a dimer, the active DNA-binding form of Cro (ANDE81). As described for lambda and 434 repressors, the model of Cro-operator binding specifies that the alpha helix 3 of each monomer lies along the DNA major groove of the half-operator with N-terminal and center residues of the helix contacting nucleotide bases in the operator. Alpha helix 2 lies across the operator major groove and may make contacts to operator backbone phosphates at its N-terminal and C-terminal ends. In addition, backbone phosphates may be contacted by residues at the C terminus of alpha 3, N terminus of beta 2, and C terminus of beta 3 (PABO84). In computer model building of lambda Cro-operator DNA interactions, bending of operator DNA or bending at the monomer-monomer interface of the Cro dimer have been proposed to make the best fit between operator and dimer (PABO84). Lack of operator-dimer co-crystal data for Cro leaves this question open; however many DNA-binding proteins are assumed to induce DNA bending (GART88).

Wolberger et al. recently published a crystal structure of a complex of 434 Cro and a palindromic synthetic 14 bp DNA operator (WOLB88). Cro from 434 affects 434 gene expression in a manner analogous to lambda Cro affecting lambda gene expression. Key amino acids within the H-T-H region of 434 Cro and lambda Cro are highly conserved (PABO84), and 434 Cro binds operator DNA as a dimer (WHAR85a). Because the crystals of 434 Cro and DNA do not diffract to high resolution, atomic details of the protein-DNA interactions are not revealed. Nevertheless, Wolberger et al. report very significant similarities and differences between the DNA binding patterns of 434 repressor and 434 Cro. In both complexes, the H-T-H motif fits into the major groove in the same general manner, but the conformation of the DNA is significantly different. Both complexes do, however, involve B-form DNA. These observations on DBPs from 434, together with recent results on Trp repressor (vide infra), support the view that a) structural elements that fit into the major groove of DNA can function in a variety of closely related ways, b) bending of DNA complexed to proteins is an important determinant of specificity, and c) that mechanisms of recognition may be quite subtle.

Crystal structures have been determined for two bacterial DBPs, CRP (also known as CAP, cAMP receptor protein)(WEBE87a) and Trp repressor, TrpR (OTWI88) from E. coli. Both these proteins contain H-T-H motifs and bind their cognate operators only when particular effector molecules are bound to the protein, cAMP for CRP and L-tryptophan for TrpR. Binding of each effector molecule causes a conformational change in the protein that brings the DNA-recognizing elements into correct orientation for strong, sequence-specific binding to DNA. The DNA-binding function of Lac repressor is also modulated through protein binding of an effector molecule (e.g. lactose); unlike CRP and TrpR, Lac repressor binds DNA only in the absence of the effector.

Two structures of CRP (MCKA81, MCKA82) and one structure of a CRP mutant (WEBE87a) are available. Although no structure of CRP bound to DNA is available, Otwinowski et al. (OTWI88) have published an X-ray crystal structure of TrpR bound to the Trp operator. This structure shows that, although TrpR contains a canonical H-T-H motif, the positioning of the recognition helix with respect to the DNA is quite different from the positioning of the corresponding helix in other H-T-H DBPs (viz. 434 Cro, 434 repressor, lambda Cro, and lambda repressor, cited in MATT88) for which X-ray structures of protein-DNA complexes are available. The TrpR-DNA structure confirms the general notion that the globular protein holds recognition elements in position to form a surface complementary to the DNA and that substantial surface is buried in the complex. Unlike previously determined structures, most of the interactions between atoms of the protein and bases are mediated by localized water molecules. It is not possible to distinguish between localized water and atomic ions, such as Na+ or Mg++, by X-ray diffraction alone. We shall follow Otwinowski et al. and refer to these peaks in electron density as water, although ions cannot be ruled out.

Using a genetic approach, Bass et al. (BASS88) studied the binding of wild type TrpR and single amino acid missense mutants of TrpR to a consensus palindromic Trp operator and to palindromic operators that differ from the consensus by a symmetric substitution at one base in each half operator. Bass et al. conclude that the contact between the H-T-H motif of TrpR and the operators must be substantially different from the model that had been built based on the 434 Cro-DNA structure.

Thus the binding of globular DBPs that are modulated by effector molecules is fundamentally the same as the binding of unmodulated globular DBPs, but the details of each protein's interactions with DNA are quite different. Prediction of which amino acids will produce strong specific binding is beyond the capabilities of current theory. Given the important role of localized waters or ions in the TrpR-DNA interface (OTWI88) and in the 434R-DNA interface (AGGA88), such predictions are likely to remain beyond reach for some time.

The Mnt repressor of P22 is an 82 residue protein that binds as a tetramer to an approximately palindromic 17 base pair operator presumably in a manner that is twofold rotationally symmetric. Although the Mnt protein is 40% alpha helical and has some homology to lambda Cro protein, Mnt is known to contact operator DNA by N-terminal residues (VERS87a) and possibly by a residue (K79) close to the C terminus (KNIG88). It is unlikely, therefore, that an H-T-H structure in Mnt mediates DNA binding (VERS87a). Another residue (Y78) close to the C-terminal end has been found to stabilize tetramer formation (KNIG88). Though the three dimensional structure of Mnt is not known, DNA-binding experiments have indicated that the Mnt operator, in B-form conformation, is contacted at major groove nucleotides on both front and back sides of the operator helix (VERS87a).

The Arc repressor of P22 is a 53 residue protein that binds as a dimer to a partially palindromic 21 base pair operator adjacent to the mnt operator in P22 and protects a region of the operator that is only partially symmetric relative to the symmetric sequences in the operator (VERS87b). Arc is 40% homologous to the N-terminal portion of Mnt, and the N-terminal residues of the Arc protein contact operator DNA such that an H-T-H binding motif is unlikely, as in Mnt binding (VERS86b). The three dimensional structure of Arc, like Mnt, is not known, but a crystallgraphic study is in progress (JORD85). DNA-binding experiments have shown that Arc probably binds along one face of B-form operator DNA. These experiments indicate that Arc contacts operator phosphates farther out from the center of operator symmetry than do the repressors or Cro proteins of lambda or 434, or P22 Mnt protein. Thus the researchers state that the operator DNA may be bent around Arc in binding or Arc dimer may have an extended structure to allow such contacts to occur (VERS87b). These alternatives are not mutually exclusive.

DNA-Binding Proteins Other Than Repressor Proteins

Any protein (or polypeptide) which binds DNA may be used as an initial DNA-binding protein; the present method is not limited to repressor proteins, but rather includes other regulatory proteins as well as DNA-binding enzymes such as polymerases and nucleases.

Derivatives of restriction enzymes may be used as initial DBPs. All known restriction enzymes recognize eight or fewer base pairs and cut genomic DNA at many places. Expression of a functional restriction enzyme at high levels is lethal unless the corresponding sequence-specific DNA-modifying enzyme is also expressed. Barnes and Rine (BARN85) showed that the ecoRI gene could be tolerated in yeast cells if fully repressed. Jen-Jacobson et al. (JENJ86) report that EcoRI that lacks residues 1-29, denoted EcoRI-delN29, has no nuclease activity; Becker et al. (BECK88) report that EcoRI-delN29 binds sequence-specifically to DNA that includes the EcoRI recognition sequence, CTTAAG.

Wolfes et al. (WOLF86) report that the EcoRI point mutants EQ111, EQ144, and RK145 have values of $K_M$ approximately two-fold higher that wild-type EcoRI, but that the specific activity is approximately 100-fold lower. Wolfes et al. did not report culture of cells expressing these mutants, and such expression may be lethal, even though nuclease activity is greatly reduced.

Yanofsky et al. (YANO87) report a number of mutants of EcoRI obtained by mutagenesis of a plasmid-borne gene with hydroxylamine and expression in cells lacking the EcoRI methylase activity. The initial gene comprises the lacUV5 promoter and a coding region that codes on expression for the EcoRI endonuclease. Three of the mutants could be expressed at high levels and were shown to be dimeric, viz. AT139, GS140, and RQ203; these mutations prevent protein-DNA binding. Other mutants (viz. LF46, RQ56, GE129, AT142, GE210, and SL259) of the ecoRI gene were obtained that were "leaky", i.e. they were lethal if induced with 1.0 mM IPTG. (This level of IPTG induces lacUV5 to the maximum extent.) The authors do not report whether these leaky mutants retain endonucleolytic activity; strong binding, without cleavage, to all EcoRI sites in the *E. coli* genome is likely to be toxic. It is likely that leaky mutants can be expressed in cells that also express the EcoRI methylase activity so that the proteins can be characterized. Leaky mutants that lack nuclease activity or EcoRI-delN29 could be used as an initial DBP for DNA targets related to the EcoRI sequence. The non-binding mutants, AT139, GS140, and RQ203, could also be used as initial DBPs; alterations or extension of the protein in such a way that additional base pairs are contacted will supply the free-energy lost through these mutations. Yanofsky et al. state that most null mutants of EcoRI accessible through hydroxylamine have probably been identified. Other mutants are likely to be revealed by other mutagens. Null mutants are, however, selected not only for lack of nuclease activity, but also for non-binding, and therefore are not so useful as leaky mutants.

Rosenberg and colleagues (MCCL86) have determined the 3D structure of a complex of EcoRI with an oligonucleotide that contains the EcoRI recognition sequence to 3 Å resolution. From this structure, we can see that extension of the polypeptide chain at either the amino or carboxy terminus would allow contacts with base pairs outside of the canonical hexanucleotide.

Specifically, extending EcoRI(AT139), EcoRI-(GS140), or EcoRI(RQ203) by, for example, ten highly variegated residues at the amino terminus and selecting for binding to a target such as, TGAATTCA or GGAATTCC, allows isolation of a protein having novel DNA-recognition properties. Alternatively, EcoRI may be extended at the amino terminus by addition of a zinc-finger domain. It may be useful to have two or more tandem repeats of the octanucleotide target placed in or near the promoter region of the selectable gene. Fox (FOXK88) has used DNase-I to footprint EcoRI bound to DNA and reports that 15 bp are protected. Thus, repeated octanucleotide targets for proteins derived from EcoRI should be separated by eight or more base pairs; one could place one copy of the target upstream of the −35 region and one copy downstream of the −10 region. There are many residues in EcoRI that contact the DNA as the enzyme wraps around it. These residues could be varied to alter the binding of the protein. To obtain acceptable specificity, we may need to pick as initial DBP a mutant of EcoRI that folds and dimerizes, but that binds DNA weakly. The mutations in regions of the protein that contact DNA outside of the original GAATTC will confer the desired affinity and specificity on the novel protein.

One may wish to obtain a protein that binds to one target DNA sequence, but not to other sequences that contain a subsequence of the target. For example, we may seek a protein that recognizes TGAATTCA, but not any of the sequences vGAATTCb. To achieve this distinction, we place the target sequence in the promoter region of the selectable gene and one or more instances of the related sequences, to which we intend that the protein not bind, in the promoter region of an essential gene, such as an antibiotic-resistance gene.

Other stable proteins may also be used as initial DBPs, even if they show no DNA-binding properties. Parraga et al. (Reference 8 in PARR88) report that Eisen et al. have fused 229 residues of yeast ADRI to beta-galactosidase and that the fusion protein binds sequence-specifically to DNA in vitro.

Eukaryotic proteins function in the regulation of transcriptional selectivity of the eukaryotic genome at greater levels of complexity than bacterial regulatory proteins. Eukaryotic transcription involves multiple RNA polymerases with larger number and sizes of subunits; one or more required cis-acting sites upstream of the site of initiation of synthesis; and one or more regulatory proteins acting positively or negatively at the upstream sites (reviewed by Struhl, STRU87; Maniatis et al., MANI87). RNA polymerases recognize TATA boxes that designate initiation of synthesis, and also recognize upstream promoter elements that function to regulate the rate of initiation. Eukaryotic regulatory proteins interact with each other and with general transcription initiation factors at the upstream promoter elements or at enhancer sites distal to the promoter.

Enhancer sites may be common to a number of genes at different loci, or even among distantly related organisms. Recently elucidated enhancer subsequences of several human genes reveal shared regulation with genes in pathogenic viruses. Adenovirus EIA protein turns on early viral genes as well as the human heat shock protein hsp70 (SIM088). Further, a normal inducible nuclear DNA-binding protein regulates the IL-2alpha interleukin-2 receptor-R(alpha) gene and also promotes activation of transcription from the HIV-1 virus LTR (BOHN88). These studies indicate one of the many difficulties of designing antiviral chemotherapy by using the transcriptional regulatory apparatus of the virus as a target. This invention uses unique target sequences, not represented elsewhere in the host genome, as targets for suppression of gene expression.

Some DNA-binding protein functions involved in regulation of transcription appear to be common among different eukaryotes, and between eukaryotes and prokaryotes. Tissue-specific regulation is in general modulated by dominant negative regulation. Catabolic genes of bacteria are similarly regulated. The E. coli repressor protein LexA functions in yeast at the lexA operator placed between the upstream activating subsequence and the TATA region of the GALI gene to shut off transcription of this gene (BREN84). The LexA DNA binding helix has also been shown to function in the context of monkey CV-1 cells to allow binding of a chimeric glucocorticoid receptor protein into which this helix has been substituted for the putative zinc finger DNA binding domain (GOD088). Thus bacterial and eukaryotic binding proteins appear to have some interchangeable DNA-binding components.

The proteins that regulate determination of mating type in yeast have been analyzed in great detail. The DNA sequences of these genes (ASTE81) have been used to obtain XhoI-linker insertion mutations (TATC81) of both the MATal and MATalpha2 genes, and have allowed physical and functional characterization. The MATalpha2 gene product represses transcription of a-factor and a-factor receptor genes.

The DNA sequences of operators that interact with proteins that control mating-type and cell-type specific transcription in yeast (MILL85) reveal that the consensus site for action of the alpha2 protein dimer is symmetric, while a heterodimeric complex of alpha2 and al subunits acts on an asymmetric site. The alpha2al-responsive site consists of a half-site that is identical to the alpha2 half-site, and another half-site that is a consensus for al protein binding. The spacings between the symmetric and asymmetric sites are not the same.

The 68 amino acid alpha2 DNA-binding domain shares considerable homology with domains of homeo proteins from Drosophila (HALL87), which are responsible for development in this organism. Thus mechanisms of great complexity have evolved to regulate development and gene expression at the level of transcription in eukaryotes.

Anderson et al. (ANDE88) have reviewed the use of murine monoclonal antibodies in the study of DNA-protein interactions. Antibodies that bind DNA and other nucleic acids have been obtained from human patients suffering from Systemic Lupus Erythematosus. Murine monoclonal antibodies have been obtained that specifically recognize Z-DNA, B-DNA, ssDNA, triplex DNA, and certain repeating sequences. Crystals of some of these antibodies, of Fab fragments of these antibodies, or complexes of DNA and fragments of these antibodies have been obtained and used for X-ray diffraction studies. The authors report that: 1) the antibodies studied contact six base pairs and four phosphates, 2) antibodies are unlikely to provide some of the well known motifs for DNA-binding, e.g. helix-turn-helix, 3) study of DNA-antibody complexes may yield insights into mechanisms of recognition, and 4) a DNA-recognizing antibody might be converted into a sequence or structure specific nuclease.

Properties of Serially-linked Globular Domains

A protein motif for DNA binding, present in some eukaryotic transcription factors, is the zinc finger in which zinc coordinately binds cysteine and histidine residues to form a conserved structure that is able to bind DNA. *Xenopus laevis* transcription factor TFIIIA is the first protein demonstrated to use this motif for DNA binding, but other proteins such as human transcription factor SP1, yeast transcription activation factor GAL4, and estrogen receptor protein have been shown to require zinc for DNA binding in vitro (EVAN88). Other mammalian and avian steroid hormone receptors and the adenovirus E1A protein, that bind DNA at specific sites, contain cysteine-rich regions which may form metal chelating loops; however, the existence of such structures has not been demonstrated. Such metal binding domains may mediate protein binding interactions rather than DNA-binding interactions in some cases (FRAN88).

Landschulz et al. (LAND88) have identified a new class of eukaryotic DNA-binding proteins that includes C/EBP, c-Myc, Fos, Jun, and GCN4. The sequences of members of the class contain a periodic repetition of leucine residues such that, according to the authors' model, alpha helix formation results in an array of leucines down one side of the helix. Interaction of this array with such an array on another protein molecule forms a "leucine zipper" (LAND88) which, though not directly implicated in the binding of these proteins to DNA, may influence the ability of these proteins to bind DNA by changing protein structure through protein-protein interactions. Landschulz et al. suggest that heterologous aggregates may form by association of two different proteins that share the leucine zipper motif. They do not suggest how one might generate or select such heterologous aggregates in vivo.

Zinc-finger regions have been observed in the sequences of a number of eukaryotic DBPs, but no high-resolution 3D structure of a Zn-finger protein is yet available. A variety of models have been proposed for the binding of zinc-finger proteins to DNA (FAIR86, PARR88, BERG88, GIBS88). Model building suggests which residues in the Zn-fingers contact the DNA and these would provide the primary set of residues for variation. Berg (BERG88) and Gibson et al. (GIBS88) have presented models having many similarities but also some significant differences. Both models suggest that the motif comprises an antiparallel beta structure followed by an alpha helix and that the front side of the helix contacts the major groove of the DNA. By assuming that conserved basic residues of the Zn-finger make contact with phosphate groups in each copy of the motif, Gibson et al. deduce that the amino terminal part of the helix makes direct contact to the DNA. The Gibson model does not, however, account well for the number of bases contacted by Zn-finger proteins. The observations on H-T-H proteins suggest that a DNA-recognizing element can interact in a variety of ways with DNA and we assert that a similar situation is likely in Zn-finger proteins. Thus, until a 3D model of a Zn-finger protein bound to DNA is available, all of the residues modeled as occurring on the alpha helix away from the beta structure should be considered as primary candidates for variegation when one wishes to alter the DNA-binding properties of a Zn-finger protein. In addition, residues in the beta segment may control interactions with the sugar-phosphate backbone which can effect both specific and non-specific binding.

Parraga et al. (PARR88) have reported a low-resolution structure of a single zinc-finger from NMR data. They confirm the alpha helix proposed by Berg and by Gibson et al., but not the antiparallel beta sheet. The models proposed by Klug and colleagues (FAIR86) have a common feature that is at variance with the models of Berg and of Gibson et al., viz. that the protein chain exits each finger domain at the same end that it entered. The structure published by Parraga et al. does not settle this point, but suggests that the exit strand tends toward the end opposite from the entrance strand, thereby supporting the overall models of Berg and of Gibson et al. Parraga et al. also report that a) a chimeric molecule consisting of zinc-finger domains linked to beta-galactosidase binds sequence-specifically to DNA and b) a protein comprising only two finger motifs can bind sequence-specifically to DNA. They do not suggest that the residues could be mutagenized to achieve novel recognition.

A protein composed of a series of zinc fingers offers the greatest potential of uniquely recognizing a single site in a large genome. A series of zinc fingers is not so well suited to development of a DBP that is sensitive to an effector molecule as is a more compact globular protein such as *E. coli* CRP. Positive control of genes adjacent to the target DNA subsequence can be achieved as in the case of TF-IIIA.

Overview: Variegation Strategy

Choice of Residues in Parental Potential-DBP to Vary

We choose residues in the initial potential-DBP to vary through consideration of several factors, including: a) the 3D structure of the initial DBP, b) sequences homologous to the initial DBP, c) modeling of the initial DBP and mutants of the initial DBP, d) models of the 3D structure of the target DNA, and e) models of the complex of the initial DBP with DNA. Residues may be varied for several reasons, including: a) to establish novel recognition by changing the residues involved directly in DNA contacts while keeping the protein structure approximately constant, b) to adjust the positions of the residues that contact DNA by altering the protein structure while keeping the DNA-contacting residues constant, c) to produce heterodimeric DBPs by altering residues in the dimerization interface while keeping DNA-contacting residues constant, and d) to produce pseudo-dimeric DBPs (see below) by varying the residues that join segments of dimeric DBPs while keeping the DNA-contacting residues and other residues fixed.

If a dimeric protein comprises two identical polypeptide chains related by a two-fold axis of rotation, we speak of a homodimer with two-fold dyad symmetry. When two very similar polypeptides fold into similar domains and associate, we may observe that there is an approximate two-fold rotational axis that relates homologous residues, such as the alpha1-beta1 dimer of haemoglobin. We refer to such a protein as a heterodimer and to the symmetry axis as a quasi-dyad. When we produce a single-chain DBP by fusing gene fragments that encode two DNA-binding domains joined by a linker amino acid subsequence, we call the molecule a pseudo-dimer and the axis that relates pairs of residues a pseudo-dyad.

The number of residues that could strongly influence binding is always greater than the number that can be varied simultaneously. Therefore, we pick a subset of those residues to vary at one time. We pick trial levels of variegation and calculate the abundances of various sequences. We adjust the subset of varied residues and the level of variegation at each varied residue until the composite variegation is commensurate with the number of independent transformants that can be examined as determined by the sensitivity of the selection and the laboratory limitation of the user.

Principles that Guide Choice of Residues to Vary

As discussed in this section, residues are chosen to vary in light of: a) the need to retain the underlying structure of the initial potential-DBP, b) the fit of the protein surfaces to the surfaces of the macromolecule with which it interacts, c) the types of amino acids and types of chemical bonds that can be formed, and d) the objective of maximizing the variation of protein surfaces. Also considered in this section is choice of a mutagenesis method appropriate to the type and extent of variation desired.

A key concept is that only structured proteins exhibit specific binding, i.e. can bind to a particular chemical entity to the exclusion of most others. In the case of polypeptides, the structure may require stabilization in a complex with DNA. The residues to be varied are chosen to preserve the underlying initial DBP structure or to enhance the likelihood of favorable polypeptide-DNA interactions. The selection process eliminates cells carrying genes with mutations that prevent the DBP from folding. Genes that code for proteins or polypeptides that bind indiscriminately are eliminated since cells carrying such proteins are not viable. Although preservation of the basic underlying initial DBP structure is intended, small changes in the geometry of the structure can be tolerated. For example, the spatial relationship between the alpha 3 helix in one monomer of lambda Cro and the alpha 3 helix in the dyad-related monomer (denoted alpha 3') is a candidate for variation. Small changes in the dimerization interface can lead to changes of up to several Å in the relative positions of residues in alpha 3 and alpha 3'.

Burial of hydrophobic surfaces so that bulk water is excluded is one of the strongest forces driving the folding of macromolecules and the binding of proteins to other molecules. Bulk water can be excluded from the region between two molecules or between two portions of a single molecule only if the surfaces are complementary. The double helix of B-DNA allows most of the hydrophobic surface nucleotides to be buried. The edges of the bases have several hydrogen-bonding groups; the methyl group of thymine is an important hydrophobic group in DNA (HARR88). To achieve tight binding, the shape of the protein must be highly complementary to the DNA, all or almost all hydrogen-bonding groups on both the DNA and the protein must make hydrogen bonds, and charged groups must contact either groups of opposite charge or groups of suitable polarity or polarizability.

There are two complementary interfaces of major interest: a) the DNA-protein interface and b) the interface between protein monomers of dimers or between domains of pseudo-dimers. The DNA-protein interface is more polar than most protein-protein interfaces, but hydrophobic amino acids (e.g. F, L, M, V, I, W, Y) occur in sequence-specific DNA-protein interfaces. The protein-protein interfaces of natural DBPs are typical protein-protein interfaces. An important feature of such interfaces is contact between hydrophobic groups.

Amino acids are classified as hydrophilic or hydrophobic (ROSE85, EISE86a,b), and although this classification is helpful in analyzing primary protein structures, it ignores the fact that the side groups may contain both hydrophobic and hydrophilic portions, e.g., lysine. Hydrogen bonds and other ionic interactions have strong directional behavior, while hydrophobic interactions are not directional. Thus substitution of one hydrophobic side group for another hydrophobic side group of similar size in an interface is frequently tolerated and causes subtle changes in the interface. For example, V, I, M, and L often can be interchanged; Y and F are also often interchangeable. For the purposes of the present invention, such hydrophobic-interchange substitutions are made in the protein-protein interface of DBPs so that a) the geometry of the two monomers in the dimer will change, and b) compensating interactions produce exclusively heterodimers.

The process claimed here tests as many surfaces as possible to select one as efficiently as possible that binds to the target. The selection isolates cells producing those proteins that are more nearly complementary to the target DNA, or proteins in which intermolecular or intramolecular interfaces are more nearly complementary to each other so that the protein can fold into a structure that can bind DNA. The effective diversity of a variegated population is measured by the number of different surfaces, rather than the number of protein sequences. Thus we should maximize the number of surfaces generated in our population, rather than the number of protein sequences.

The example shown in FIG. 1 considers a hypothetical DBP binding to a hypothetical target DNA sequence. FIG. 1 is a 2D schematic of 3D objects; by hypothesis, residues 1, 2, 4, 6, 7, 13, 14, 15, 20, 21, 22, 27, 29, 31, 33, 34, 36, 37, 38, and 39 of the DBP are on the 3D surface of the DBP, even though shown well inside the circle. Proteins do not have discrete, countable faces. Therefore we define an "interaction set" to be a set of residues such that all members of the set can simultaneously touch one copy of the target DNA sequence without any main chain atom of the DBP coming closer than van der Waals distance to any atom of the target DNA. One hypothetical interaction set, Set A, in FIG. 1 comprises residues 6, 7, 20, 21, 22, 33, and 34, represented by squares. Another hypothetical interaction set, Set B, comprises residues 1,2, 4, 6, 31, 37, and 39, represented by circles.

If we vary one residue, number 21 for example, through all twenty amino acids, we obtain 20 protein sequences and 20 different surfaces for interaction set A. Note that residue 6 is in two interaction sets and variation of residue 6 through all 20 amino acids yields 20 versions of interaction set A and 20 versions of interaction set B.

Now consider varying two residues, each through all twenty amino acids, generating 400 protein sequences. If the two residues varied were, for example, number 1 and number 21, then there would be only 40 different surfaces because interaction set A is independent of residue 1 and interaction set B is independent of residue 21. If the two residues varied, however, were number 7 and number 21, then 400 different surfaces of potential interaction are generated.

If N spatially separated residues are varied, 20 x N surfaces are generated. Variation of N residues in the same interaction set yields $20^N$ surfaces. For example, if N 6. variation of spatially separated residues yields 120 surfaces while variation of interacting residues yields $20^6$ $6.4 \times 10^7$ surfaces. Variation of several residues in one interaction set generates an exponential number of surfaces while variation of separated surface residues generates only a linear number. Thus, to maximize the number of surfaces generated when N residues are varied, all residues should be in the same interaction set. The process of varying residues in an interaction set to maximize the number of surfaces obtained is referred to as Structure-directed Mutagenesis.

The amount of surface area buried in strong protein-protein interactions ranges from 1000 $Å^2$ to 3000 $Å^2$, as summarized by Schulz and Schirmer (SCHU79, p103ff). This also applies to DNA-protein interactions (OTWI88). Individual amino acids have total surface areas that depend mostly on type of amino acid and weakly on conformation. These areas range from about 180 $Å^2$ for glycine to about 360 $Å^2$ for tryptophan. In globular proteins, most of the area of each residue is not accessible to solvent. Averages of total surface area by amino acid type and maximum exposed surface area of each amino acid type for two typical proteins, hen egg white lysozyme and T4 lysozyme, are shown in Table 10. From these exposures, one can calculate that 1000 $Å^2$ on a protein surface comprises between 4 and 30 amino acids, depending on the amino acid types and the protein 3D structure. Studies of natural proteins indicate 10 to 25 residues comprise 1000 $Å^2$ of protein surface. Schulz and Schirmer estimate that 100 $Å^2$ of protein surface can exhibit as many as 1000 different specific patterns (SCHU79, p105). The number of surface patterns rises exponentially with the area that can be varied independently. One of the BPTI structures recorded in the Brookhaven Protein Data Bank (6PTI), for example, has a total exposed surface area of 3997 $Å^2$ (using the method of Lee and Richards (LEEB71) and a solvent radius of 1.4 Å and atomic radii as shown in Table 11). If this surface is varied freely and if 100 $Å^2$ produces 1000 patterns, $10^{120}$ different patterns are constructed from the surface of BPTI! This calculation is intended only to suggest the huge number of possible surface patterns based on a common protein backbone.

One protein framework cannot, however, display all possible patterns over any one particular 100 $Å^2$ of surface merely by replacement of the side groups of surface residues. The protein backbone holds the varied side groups in approximately constant locations so that the variations are not independent. We can, nevertheless, generate a vast collection of different protein surfaces by varying those protein residues that face the outside of the protein.

If the protein residues to be varied are close enough together in sequence that the variegated DNA (vgDNA) encoding all of them can be made in one piece, then cassette mutagenesis is picked. The present invention is not limited to a particular length of vgDNA that can be synthesized. With current technology, a stretch of 60 amino acids (180 DNA bases) can be spanned.

Mutation of residues further than sixty residues apart can be achieved using other methods, such as single-stranded-oligonucleotide-directed mutagenesis (BOTS85) and two or more mutating primers.

Alternatively, to vary residues separated by more than sixty residues, two cassettes may be mutated as follows:
1) vgDNA having a low level of variegation (for example, 20- to 400-fold variegation) is introduced into one site in the vector,
2) cells are transformed and cultured,
3) vgDNA plasmid population is prepared,
4) a second segment of vgDNA is inserted into a second site of the vg plasmid DNA, and
5) cells are transformed and subjected to appropriate selection.

The composite level of variation preferably does not exceed the prevailing capabilities to a) produce very large numbers of independently transformed cells or b) select small components in a highly varied population. The limits on the level of variegation are discussed below.

Assembly of Relevant Data

Here we assemble the data about the initial DBP and the target that are useful in deciding which residues to vary in the variegation cycle:
1) 3D structure, or at least a list of residues that contact DNA and that are involved in the dimer contact of the initial DBP,
2) list of sequences homologous to the initial DBP, and
3) model of the target DNA sequence.

These data and an understanding of the function and structure of different amino acids in proteins will be used to answer three questions:
1) which residues of the initial DBP are on the outside and close enough together in space to touch the target DNA simultaneously?
2) which residues of the initial DBP can be varied with high probability of retaining the underlying initial DBP structure?
3) which residues of the initial DBP can affect the dimerization or folding of the initial DBP?

Although an atomic model of the target material (obtained through X-ray crystallography, NMR, or other means) is preferred in such examination, it is not necessary. X-ray structures of short segments of DNA have shown the tendency of DNA from nature to depart from the theoretical B-DNA model. Harrison and coworkers point out that theoretical B-DNA is a poor approximation to the DNA structure observed in 434 Cro-operator DNA (ANDE87), however, no structure of operator DNA alone has been published. Sequence-specific models of DNA can be constructed that make allowance for the over- and under-winding of AT and GC base pairs (CALL82).

Graphical and Computational Tools

The most appropriate method of picking the residues of the protein chain at which the amino acids should be varied is by viewing with interactive computer graphics a model of the initial DBP complexed with operator DNA. This model need not come from an X-ray ray structure of the complex, but could instead be obtained by docking a 3D structure of the initial DBP to an appropriate model of the DNA operator sequence. A model based on X-ray data from the DNA-protein complex is preferred. A stick-figure representation of molecules is preferred. A suitable set of hardware is an Evans & Sutherland PS390 graphics terminal (Evans & Sutherland Corporation, Salt Lake City, Utah) and a MicroVAX II supermicro computer (Digital Equipment Corp., Maynard, Mass.). The computer should, preferably, have at least 150 megabytes of disk storage, so that the Brookhaven Protein Data Bank can be kept on line. A FORTRAN compiler, or some equally good higher-level language processor is preferred for program development. Suitable programs for viewing and manipulating protein and nucleic acid models include: a) PS-FRODO written by T. A. Jones (JONE85) and distributed by the Biochemistry Department of Rice University, Houston, Tex.; and b) PROTEUS, developed by Dayringer, Tramantano, and Fletterick (DAYR86). Important features of PS-FRODO and PROTEUS that are advantages to view and manipulate protein models for the purposes of the present invention are the abilities to: 1) display molecular stick figures of proteins and other molecules, 2) zoom and clip images in real time, 3) prepare various abstract representations of the molecules, such as a line joining $C_{alpha}$s and side group atoms, 4) compute and display solvent-accessible surfaces reasonably quickly, 5) point to and identify atoms, and 6) measure distance between atoms.

In addition, one could use theoretical calculations, such as dynamic simulations of proteins, DNA, or protein-DNA complexes to estimate whether a substitution at a particular residue of a particular amino acid type might produce a protein of approximately the same 3D structure as the parent protein. Such calculations might also indicate whether a particular substitution will greatly affect the flexibility of the protein; calculations of this sort may be useful but are not required.

Use of Knowledge of Mutations Affecting Protein Stability

In choosing the residues to vary, and the substitutions to be made for such residues, one may make use not only of modelling as described above but also of experimental data concerning the effects of mutation in the initial DNA-binding protein. Plainly, mutations which will markedly reduce protein stability are to be avoided in most cases.

Missense and suppressed nonsense mutations (considered together as missense) affect specific residues in proteins and so are particularly informative about structure-function relationships. Missense mutations that decrease DNA-binding protein function non-specifically by affecting protein folding are distinguished from binding-specific mutations primarily on the basis of protein stability (NELS83, PAKU86, and VERS86b). Proteins with folding mutations are more thermolabile and more sensitive to proteolysis both in vivo and in vitro than either the wild-type proteins or their binding-specific mutants (HECH84, HECH85a, HECH85b, PAKU86, and VERS86b).

Tables 1, 12, and 13 summarize the results of a number of studies on single missense mutations in the three bacteriophage repression proteins: lambda repressor (Table 12) (NELS83, GUAR82, HECH85a, and NELS85), lambda Cro (Table 1) (PAKU86, EISE85), and P22 Arc repressor (Table 13) (VERS86a, VERS86b). The majority of the mutant sequences shown in Tables 1, 12, and 13 were obtained in experiments designed to detect loss of function in vivo. The second-site pseudo-reversion mutations (HECH85a), and suppressed nonsense mutations (NELS83), restore function, and some of the site specific changes (EISE85) produce functional proteins.

Roughly 50-70% of the single missense mutations of the DNA-binding proteins selected for loss of function (Tables 1, 12, and 13) produce protein folding defects. The majority of these mutations involve inappropriate substitutions in residues that form the densely-packed, hydrophobic protein cores. Substitutions in these residues often remove favorable hydrophobic interactions (e.g. lambda Cro FL14 and lambda repressor YH22) or introduce unfavorable interactions due to size, charge or polarity (e.g. lambda Cro AV33, LR23, and lambda repressor LF18, LR65). (Point mutations are denoted by the wild-type amino acid, followed by the mutant amino acid, followed by the residue number. Thus the change FL14 denotes the change of F to L at position 14.) Some substitutions destabilize structure by disrupting hydrogen bonds among various protein surfaces. Lambda Cro DY47 and SN49 mutations each remove one hydrogen bond linking the side groups at these positions (PAKU86). In lambda repressor, substitutions at S77 (SN77, SR77, SI77) disrupt a hydrogen bonding network, which the pseudo-revertant ST77 apparently restores (HECH85a, HECH83). Finally, there are mutations that are incompatible with secondary structure: e.g. insertion of proline residues at sites in helices (QP16, TP19 in lambda Cro; LP12, Sp35 in lambda repressor); and replacement of a glycine residue in a sharp turn with an incompatible residue (lambda Cro GA48).

Use of Knowledge of Mutations Affecting the DNA-Protein Interface

Similar use may be made of data regarding mutations in DNA-protein interaction sites.

Missense mutations in residues thought to be involved in specific interactions with DNA have been reported for several prokaryotic repressor proteins. Table 14 shows an alignment of the H-T-H DNA-binding domains of four prokaryotic repressor proteins (from top to bottom: lambda repressor, lambda Cro, 434 repressor and trp repressor) and indicates the positions of missense mutations in residues that are solvent-exposed in the free protein but become buried in the protein-DNA complex, and that affect DNA binding.

As shown in Table 14, randomly obtained missense mutations in solvent-exposed residues of lambda repressor, lambda Cro, and trp repressor, yield sets of mutants that reduce DNA binding. These sets correlate well to the sets of residues that, on the basis of crystallographic studies and model building, are proposed to interact directly with DNA. Some mutations in lambda Cro (EISE85) and all those shown for 434 repressor (WHAR85a) were obtained through site-directed mutagenesis. Most of the mutations shown in the lambda and trp repressor sequences are trans-dominant when the mutant gene is present on an overproducing plasmid (NELS83, KELL85). The exceptions to transdominance are the lambda repressor SP35 and the trp repressor AT80 mutations. This latter change produces a repressor that has only slightly reduced binding (KELL85). The trans-dominance observed for these mutations is proposed by the authors to result from the wild-type repressor and the mutant repressor forming mixed oligomers which are inactive in binding to operator sites. The overproduction of plasmid-encoded mutant repressor prevents formation of wild-type homo-oligomers.

Three types of missense mutation result in loss of DNA binding activity in these proteins. A substitution may remove favorable interactions (e.g. lambda repressor QS45, QS33; lambda Cro KT32, QC27, KT39; 434 repressor QA28, QS28; trp repressor RC84). Secondly, a substitution may introduce an unfavorable interaction or structure (e.g. lambda repressor GE43; lambda Cro YD26; 434 repressor QP28; trp repressor GD78). Thirdly, a substitution may both remove a favorable interaction and introduce an unfavorable interaction simultaneously (e.g. lambda repressor SL45, ND52, AD49, AV49; lambda Cro RL38, QP16; 434 repressor QL28; trp repressor RH84). Among mutations in these four repressor proteins, no substitutions in either of the first two residues of alpha 3 that produced functional proteins able to bind to wild-type operator sequences were isolated. Wharton (WHAR85a) has reported that extensive site-directed mutagenesis of 434 repressor positions 28 and 29 produced no functional protein sequences other than the wild-type. Apparently, in the context of 434 repressor structure and operators, only proteins with the wild-type Q28-Q29 sequence bind to the wild-type operators.

Table 14 also shows missense mutations that result in near normal repressor activity. Substitution of 434 repressor Q33 with H, L, V, T, or A produces repressors that function if expressed from overproducing plasmids (WHAR85a). However, repressor specificity is reduced. Mutations in lambda repressor, QY33 (NELS83, HECH83), and in lambda Cro, YF26 (EISE85), produce altered proteins which make one less H-bond to the DNA and which bind to the operator DNA with reduced affinity. Thus, loss of a single H-bond is insufficient to completely abolish binding of DNA. Lastly, the lambda Cro YK26 and HR35 substitutions produce functional proteins having different contacts with the operator (EISE85). The functional YK26 alteration is suggested to result from the replacement of a sequence-specific major groove contact (H-bond between Y26 and O4 of a thymidine) with an interaction between the substituting K26 and the phosphate backbone. The HR35 substitution is proposed to involve the exchange of a sequence-independent interaction at one phosphate for a similar interaction at an adjacent phosphate.

A third group of missense mutations in DNA-binding residues which alter DNA binding without changing specificity are those in which the affinity of the mutant protein for DNA is greater than that of the wild-type protein. Nelson and Sauer (NELS85) and Hecht et al. (HECH85a,b) have described four such replacements in lambda repressor (Table 12): EK34, GN48, GS48, and EK83. The four altered protein dimers all bind more tightly than wild-type dimers both in the sequence-specific ORI operator complex and in sequence-independent complexes with pBR322 DNA. In vivo measurements (NELS85), show that GN48, GS48, and EK83 mutant repressors are roughly 8-fold more active in vivo than the wild-type protein while EK34 repressor activity is roughly the same as wild-type.

The EK34, GN48, and GS48 changes result in polypeptides that can make more contacts with DNA than does the wild-type protein. Molecular modeling suggests (NELS85) that N48 and S48 could make sequence-independent H-bonds with backbone phosphate oxygens in the sequence-specific operator-protein complex. N48 may also make a sequence-specific contact with C4 of $O_R1$. Since H-bonds are relatively short-range interactions, these mutations are not expected to contribute substantially to the rate of protein binding to DNA at non-operator sites. In contrast, model building suggests that the EK34 substitution results in the formation of a new salt bridge between repressor and DNA (NELS85). The relatively low in vivo activity of the EK34 repressor (relative to the GS48, GN48, and EK83 proteins) may reflect the effect in vivo of the sequence-independent binding properties of the molecule.

EK83 is the only change that increases repressor affinity for operator DNA and does not involve residues in direct contact with the DNA. Residue 8 is located too far from the DNA to interact directly and binding of the K83 protein to DNA shows no more salt dependence than wild-type repressor binding (NELS85). Nelson and Sauer (NELS85) have argued that since residue 83 is located on the solvent-exposed surface of the dimerization helix 5 and does not affect dimerization directly, the EK83 substitution alters the conformation of the repressor dimer to confer tighter binding of the sequence-specific complex.

Extended amino acid arms at N- and C-terminal locations are important DNA-binding structures in at least four prokaryotic repressors: lambda repressor and Cro, and P22 Arc and Mnt. In these proteins, arm residues make sequence-specific and sequence-independent contacts with DNA components in major and minor grooves. These contacts contribute substantially to binding energies in both sequence-specific and sequence-independent DNA-repressor complexes.

Sequence-specific and sequence-independent contacts are made by the first 6 amino acid residues (STKKKP) of the lambda repressor N-terminal region which form an "arm" that model building suggests can wrap around the DNA (ELIA85, PAB082a). Missense mutations KE4 and LP12 (Table 12) both greatly reduce repressor activity in vivo (NELS83). The KE4 change may replace a favorable interaction with an unfavorable interaction while the LP12 change in alpha helix 1 may prevent the correct orientation of the arm. Deletion of the first six residues results in a protein which is non-functional in vivo, even when present at 150 times the level found in a lysogen (ELIA85). Deletion of the first three residues from either repressor dimers or N-terminal domain dimers results in decrease of affinity for ORI, loss of protection of back side guanines, altered specificity between $O_R1$ and $O_R3$, and decreased binding sensitivity to changes in temperature or salt concentration (ELIA85, PAB082a).

Missense mutations of P22 Arc that produce non-functional proteins with high intracellular specific proteinlevels (Table 13) are found only in the N-terminal 10 residues of the protein (VERS86b). A single residue change at position 6 (HP6) in P22 Mnt changes operator recognition in the altered protein (YOUD83, VERS8-6a,b, vide infra). Knight and Sauer (as reported in VERS86a,b) replaced the first 6 residues of Mnt repressor with the first 9 residues of Arc repressor to produce a repressor that binds to the arc operator but not to the mnt operator. Thus P22 Mnt and Arc use a recognition region located in the first 6-10 amino-terminal residues for DNA recognition and binding. The N-terminal DNA-binding of these proteins can not be the recognition helix of a typical H-T-H region because there are no residues to form the preceding alignment helix and turn (PAB084, VERS86b). Other regions of Arc and Mnt could provide the functions of the alignment helix and turn, but the presence of proline residues in the DNA-binding regions argues against helical structure.

In lambda Cro, a C-terminal sequence (K62-K63-T64-T65-A66) has been suggested on the basis of model building (TAKE85) and NMR measurements (LEIG87) to form a flexible arm that interacts with minor groove phosphates. Eisenbeis and Caruthers (cited in Knight and Sauer (KNIG88)) have found that T64, T65, and A66 have minor effects on protein-operator affinity, while K63 is extremely important. The C-terminal sequence of P22 Mnt (K79-K80-T81-T82) is almost identical to that of lambda Cro. Knight and Sauer (KNIG88) have shown that deletion of the three residues after K7 has little effect on protein structure or DNA binding. Subsequent deletion of K79 and the distal residues, however, reduces operator binding by three orders of magnitude with little apparent change in protein structure.

Use of Knowledge of Mutations Affecting the Protein-Protein Interface

It is also possible to modulate DNA-binding specificity by altering the protein-protein interface. Because the oligomerization equilibrium is coupled to DNA binding, mutations that damage oligomerization (see discussion, supra) reduce operator site affinity. Since oligomerization involves the matching of protein surfaces, many interactions are hydrophobic in nature and mutations which specifically destabilize oligomerization are similar to mutations which destabilize global protein structure. Interactions at the site of oligomerization can influence the strength of interactions at the DNA-binding site by subtle alterations in protein structure.

Use of Mutations That Affect Activation

When lambda, 434, and P22 repressors bind to their operator sites in OR they repress transcription from $P_R$ and so prevent lytic development (POTE80, POTE82, PTAS80, WHAR85a, and CHAD71). In addition, these repressors, when bound to their respective $O_R2$ sites, activate transcription from the divergent promoter $P_{RM}$ which maintains lysogeny. The site on lambda repressor which activates RNA polymerase has been shown to be located on the N-terminal domain of the molecule (BUSH88, HOCH83, and SAUE79). The mechanism of activation requires contact between the N-terminal domain of repressor bound to $O_R2$ and RNA polymerase at $P_{RM}$ (HOCH83, SAUE79) and this contact stimulates isomerization of the closed form of the polymerase complex to the open form (McClure and Hawley, cited in GUAR82).

Missense mutations in lambda, P22, or 434 repressors which specifically reduce PRM activation while having no effect on repressor operator binding have been shown to alter residues in the solvent-exposed protein surface closest to RNA polymerase bound at $P_{RM}$ (GUAR82, PAB079, BUSH88, and WHAR85a). For lambda and 434 repressor this surface includes residues in alpha helix 2 and in the turn between alpha helices 2 and 3. In P22 repressor, the surface is formed at the carboxyl terminus of alpha helix 3 (PAB079, TAKE83). In each repressor, the changes which reduce transcriptional activation at $P_{RM}$ involve the substitution of a basic residue for a neutral or acid residue. Further, missense mutations in lambda and 434 repressors which increase transcription at $P_{RM}$ involve the substitution of an acidic residue for a neutral or basic residue (GUAR82, BUSH88).

Bushman and Ptashne (BUSH88) report that when the alpha helix 2 and turn region of lambda Cro (which binds to lambda $O_R$ but does not stimulate transcription at $P_{RM}$) is modified to resemble that of lambda repressor, the modified Cro protein (Cro67) binds to an appropriately modified lambda $O_R$ in vitro and stimulates transcription at $P_{RM}$. (Cro67 binding to unaltered lambda operator sequences was too low to demonstrate activity in vivo.) Thus, transcriptional activation at $P_{RM}$ involves the apposition of a negatively charged surface on the N-terminal domain of lambda, 434, or P22 repressor to a unique site on RNA polymerase bound to $P_{RM}$. Mutations that a) alter the negatively-charged surface of repressor by removing acidic residues or by replacing them with basic residues, or b) that position the negative surface incorrectly with respect to RNA polymerase, decrease transcriptional activation at $P_{RM}$. Alterations that produce a more negatively charged surface act to increase transcription at $P_{RM}$.

Pick Principal Set of Residues to Vary

Here we pick residues to vary and the range of variation. A huge number of variant DNA sequences can be generated by synthesis with mixed reagents a chosen bases. In most cases, it is necessary that the number of variants not exceed the number of independently transformed cells generated from the synthetic DNA. On the other hand, it is efficient to make the number of variants as close as practical to this limit. The total number of variants is the product of the number of variants at each varied codon over all the variable codons. Thus, we first consider which residues could be varied with an expectation that alteration could affect DNA binding. We then pick a range of amino acids at each variable residue. By multiplying these numbers together, we obtain a total number of variants. If the product is too large or too small, we alter the list of residues and range of variation at each variable residue until an acceptable number is found.

In this section we pick a principal set of residues of the initial DBP to vary. Using the knowledge of which residues are on the surface of the initial DBP, we pick residues that are close enough together on the surface of the initial DBP to touch a molecule of the target simultaneously without having any initial DBP main-chain atom come closer than van der Waals distance (viz. 4.0 to 5.0 Å center to center) to any target atom. For the purposes of the present invention, a residue of the initial DBP "touches" the target if: a) a main-chain atom is within van der Waals distance, viz. 4.0 to 5.0 Å center to center, of any atom of the target molecule, b) the $C_{beta}$ is within a specific distance of any atom of the target molecule so that a side-group atom could make contact with that atom, or c) there is evidence that altering the residue alters the DNA-binding of the initial DBP. Because side groups differ in size (cf. Table 15), some judgement is required in picking the maximum specific distance required between $C_{beta}$ and any atom of the target molecule. In the preferred embodiment, we use a maximum specific distance of 8.0 Å, but other values, preferably in the range 6.0 Å to 10.0 Å, could be used. If a residue of the initial DBP is a G, we construct a pseudo-$C_{beta}$ with the correct bond distance and angles and judge the ability of the residue to touch the target from this pseudo-$C_{beta}$.

The residues in the principal set need not be contiguous in the protein sequence. The exposed surfaces of the residues to be varied do not need to be connected. We prefer only that the amino acids in the residues to be varied all be capable of touching a single copy of the target DNA sequence simultaneously without having atoms overlap.

In addition to the geometrical criteria, we prefer that there be indications that the underlying initial DBP structure will tolerate substitutions at each residue in the principal set of residues. Indications could come from various sources, including: a) homologous sequences, including mutant proteins, b) static computer modeling, or c) dynamic computer simulations.

Pick a Secondary Set of Residues to Vary

The secondary set comprises those residues not in the primary set that touch residues in the primary set. These residues might be excluded from the primary set because: a) the residue is internal, b) the residue is highly conserved, or c) the residue is on the surface, but the curvature of the initial DBP surface prevents the residue from being in contact with the target at the same time as one or more residues in the primary set.

Internal residues are frequently conserved and the amino acid type can not be changed to a significantly different type without substantial risk that the protein structure will be disrupted. Nevertheless, some conservative changes of internal residues, such as I to L or F to Y, are tolerated. Such conservative changes affect the detailed placement and dynamics of adjacent protein residues and such variation may be useful to improve the characteristics of DBP binding in downstream iterations of the process.

Surface residues in the secondary set are most often located on the periphery of the principal set. Such peripheral residues can not make direct contact with the target simultaneously with all the other residues of the principal set. The charge on the amino acid in one of these residues could, however, have a strong effect on binding. It is appropriate to vary the charge of some or all of these residues for DBP improvement. For example, the variegated codon containing equimolar A and G at base 1, equimolar C and A at base 2, and A at base 3 yields amino acids T, A, K, and E with equal probability.

Choice of Residues to Vary Simultaneously

In this section we pick a subset of the residues in the primary and secondary sets to vary simultaneously, based on geometry and on the maximum allowed level of variegation that assures progressivity. The allowed level of variegation determines how many residues can be varied at once; geometry determines which ones.

The user may pick residues to vary in many ways; the following is a preferred manner. The user decides what the objective of the variegation is; possible goals include: a) to change specific DNA recognition, vary the DNA-contacting residues, b) to change the dimerization pattern, vary residues in the dimerization interface, c) to improve the DNA binding of a selected successful DBP, vary 1) the DNA-contacting residues, 2) the dimerization interface, or 3) a combination of the two, d) to create a pseudo-dimer, vary the residues forming the linkage.

The number of residues picked is coupled to the range through which each can be varied. In the first round, we do not assume any binding between initial DBP and the target and so progressivity is not an issue. At the first round, the user may elect to produce a level of variegation such that each molecule of vgDNA is potentially different through, for example, unlimited variegation of 10 codons ($20^{10}$ approx$=10^{13}$ different protein sequences). One run of the DNA synthesizer produces approximately $10^{13}$ molecules of length 100 nucleotides. The levels of efficiency of ligation and transformation reduce the number of DNA sequences actually tested to between $10^7$ and $5\times10^8$. Multiple performances of the process with very high levels of variegation will not yield repeatable results; the user decides whether this is important.

Pick Range of Variation

Having picked which residues to vary, we must now decide the range of amino acids to allow at each variable residue. The total level of variegation is the product of the number of variants at each varied residue. Each varied residue can have a different scheme of variegation, producing 2 to 20 different possibilities. We require that the process be progressive, i.e. each variegation cycle produces a better starting point for the next variegation cycle than the previous cycle produced.

N.B.: Setting the level of variegation such that the parental pdbp and many sequences related to the parental pdbp sequence are present in detectable amounts insures that the process is progressive. If the level of variegation is so high that the frequency of the parental pdbp sequence can not be detected as a transformant, then each round of mutagenesis is independent of previous rounds and there is no assurance of progressivity. This approach can lead to valuable DNA-binding proteins, but multiple repetitions of the process at this level of variegation will not yield progressive results. Excessive variegation is not preferred in subsequent iterations of this process.

The example shown in FIG. 2 considers the effects of the level of variegation on the progressivity of the process of the present invention. FIG. 2 is a schematic view of a hypothetical eight-residue binding surface of a DBP comprising residues 11, 24, 25, 30, 34, 42, 44, and 47 of a hypothetical protein. These residues are implicated in sequence-specific DNA-binding by the initial DBP to the test DNA sequence. Each polygon represents the exposed portion of one residue. By hypothesis, there exists at least one protein, shown in FIG. 2e, having a specific amino acid in each of the eight residues that will bind to the target subsequence, but we do not, at first, know what that sequence is.

The initial DBP, shown in FIG. 2a, may have none of the optimal amino acids on its DNA-contacting surface. In the absence of target information, all amino acids theoretically have equal likelihood of being the best at each of the eight residues. Although DNA is highly charged and contains many solvent-exposed ionic groups and few solvent-exposed hydrophobic groups, numerous hydrophobic residues (F, L, V, etc.) occur in the DNA-contacting face of alpha 3 in H-T-H DBPs.

The genetic engineering system of the example shown in FIG. 2 can produce 107 independent transformants and the selection system can select one cell in $10^7$. Assume that the variegation method can produce all amino acids at a given residue with equal probability. (The effects that the degeneracy of the genetic code has on amino acid abundances are explicitly considered below). In the first variegation, we vary residues 11, 24, 25, 34, and 44 through all twenty amino acids, producing $20^5 3.2\times10^6$ different protein sequences, encoded by an even greater number of DNA sequences. Assume that a cell is isolated carrying a gene that encodes the first successful DBP, shown in FIG. 2b, that has improved binding for the target DNA sequence and has the amino acid sequence W11-F24-E25-G30-D34-E42-P44-T47. This amino acid sequence becomes the parental sequence to the next cycle of variegation. After the first variegation and selection, the evidence favors W11, F24, E25, D34, and P44 as optimal amino acids at their respective residues. That residues 30, 42, add 47 were not varied has two implications:

1) we still have no information about which amino acid is optimal at these residues, and
2) the amino acids selected at the varied residues are optimal, given the identities of the amino acids in the non-varied residues; when residues 30, 42, and 47 are varied, our estimate of the optimal amino acids in other residues may change.

Now consider two versions of a variegation that use the first intermediate successful DBP as parent for subsequent cycles of the process that yields the optimal successful DBP.

In the first version of the second variegation, we vary only five residues, producing $3.2 \times 10^6$ different protein sequences, all of which are expressed and subjected to selection. We vary residues 30, 42, and 47 because they were not varied previously. We also vary two other residues so that as many surfaces as possible are tested; residues 24 and 44 are chosen. Suppose that we isolate a cell that carries a successful dbp gene encoding the amino acid sequence W11-L24-E25-I30-D34-R42-P44-K47, shown in FIG. 2c. Consider the reason that D is retained at residue 34. We know that all the sequences W11-L24-E25-I30-x34-R42-P44-K47 (where x runs through all twenty amino acids) were tested and therefore can conclude with improved confidence that D34 is optimal, given the rest of the selected sequence. Now consider the change at residue 24 from F to L. We know that all the sequences W11-x24-E25-I30-D34-R42-P44-K47 were tested and we can conclude that L24 is optimal, given the rest of the sequence. We gain information about which amino acids are optimal at each varied residue under the conditions imposed.

In an alternate hypothetical variegation, we vary residues 11, 24, 30, 34, 42, and 47, each through all twenty amino acids, producing $20^6 = 6.4 \times 10^7$ possible different sequences. Our hypothesis is that only $1.0 \times 10^7$ of these sequences are produced and subjected to selection. Because only 15.6% of the programmed sequences are actually subjected to selection, it is likely that the parental sequence, W11-F24-E25-G30-D34-E42-P44-T47, is not present in the selection step and there is, consequently, no assurance that the best successful DBP binds more tightly to target than did the parental DBP. Suppose that we isolate a cell that carries a successful dbp gene encoding the amino acid sequence V11-R24-E25-Q30-D34-R42-P44-D47, shown in FIG. 2d. Consider the reason that D is retained at residue 34. Is it that D is optimal, or is it that, by chance, the sequence encoding the optimal amino acid, x, was not present as V11-R24-E25-Q30-x34-R42-P44-D47 in the sample? The results do not discriminate between these alternatives. Furthermore, retaining an amino acid can not move us toward the optimal sequence. Now consider the change at residue 24 from F to R. Was V11-R24-E25-Q30-D34-R42-P44-D47 selected because R24 is optimal in the presence of V11-R24-E25-Q30-D34-R42-P44-D47, or was V11-R24-E25-Q30-D34-R42-P44-D47 selected because V11-F24-E25-Q30-D34-R42-P44-D47 was not present to be selected? The results yield no information, thus we can not conclude that R24 is more likely to be optimal than is F24. In both cases, no information is gained about which amino acids belong at each residue. We may have obtained a successful DBP with superior binding to the target. Another variegation cycle at this level of variegation, however, may produce a better protein or a worse protein and the process may not be progressive.

Let us contrast versions 1 and 2 of the second variegation. In version 1, we retained more information, viz. that W11 allows improved binding, and therefore our selection of K47 incorporates the information obtained in the previous rounds. In version 2 of the second variegation, we discarded the information that W11 allows stronger binding than Y11.

Progressivity is not an all-or-nothing property. So long as most of the information obtained from previous variegation cycles is retained and many different surfaces that are related to the parental DBP surface are produced, the process is progressive. If the level of variegation is so high that the parental dbp gene may not be detected, the assurance of progressivity diminishes. If the probability of recovering the parental DBP is negligible, then the probability of progressive results is also negligible.

An opposing force in our design considerations is that DBPs are useful in the population only up to the amount that can be detected; any excess above the detectable amount is wasted. Thus we produce as many surfaces related to the parental DBP as possible within the constraint that the parental DBP be present as a marker for the detection level.

We defer specification of exactly how much variegation is allowed until we have: a) specified real nucleotide distributions for a variegated codon, and b) examined the effects of discrepancies between specified nucleotide distributions and actual nucleotide distributions.

Mutagenesis of DNA

We now decide how to distribute the variegation within the codons for the residues to be varied. These decisions are influenced by the nature of the genetic code. When vgDNA is synthesized, variation at the first base of a codon creates a population coding for amino acids from the same column of the genetic code table (as shown in the Table 16); variation at the second base of the codon creates a population coding for amino acids from the same row of the genetic code table; variation at the third base of the codon creates a population coding for amino acids from the same box. If two or three bases in the same codon are varied, the pattern is more complicated. Work with 3D protein structural models may suggest definite sets of amino acids to substitute at a given residue, but the method of variation may require either more or fewer kinds of amino acids be included. For example, examination of a model might suggest substitution of N or Q at a given residue. Combinatorial variation of codons requires that mixing N and Q at one location also include K and H as possibilities at the same residue. In a single round of variegation one may choose to put: 1) N only, 2) Q only, or 3) a mixture of N, K, H, and Q. The present invention does not rely on accurate predictions of the amino acids to be placed at each residue, rather attention is focused on which residues should be varied.

There are many ways to generate diversity in a protein. (See RICH86, CARU85, and OLIP86.) An extreme case is that one or a few residues of the protein are varied as much as possible (inter alia see CARU85, CARU87, RICH86, and WHAR85a). We will call this limit "Focused Mutagenesis". Focused Mutagenesis is appropriate when the initial DBP or other parental DBP show little or no binding to the target, as at the beginning of the search for a protein to bind to a new target material. When there is no binding between the parental DBP and the target, we preferably pick a set of five to seven residues on the surface and vary each through all 20 possibilities.

An alternative plan of mutagenesis ("Diffuse Mutagenesis") that may be useful is to vary many more residues through a more limited set of choices (See VERS86a,b; Ch15 of INOU86; and PAKU86). This can be accomplished by spiking each of the pure nucleotides activated for DNA synthesis (e.g. nucleotide-phosphoramidites) with one or more of the other activated nucleotides. Contrary to general practice, the present invention sets the level of spiking so that only a small percentage (1% to .00001%, for example) of the final product will contain the parental DNA sequence. This will insure that the majority of molecules carry single, double, triple, and higher mutations and, as required for progressivity, that recovery of the parental sequence will be a possible outcome.

Let $N_b$ be the number of bases to be varied, and let Q be the fraction of all DNA sequences that should have the parental sequence, then M, the fraction of the nucleotide mixture that is the majority component, is $$M = \exp\{\log_e(Q)/N_b\} = 10^{(\log_{10}(Q)/N_b)}.$$

If, for example, thirty base pairs on the DNA chain were to be varied and 1% of the product is to have the parental sequence, then each mixed nucleotide substrate should contain 86% of the parental nucleotide and 14% of other nucleotides. Table 17 shows the fraction (fn) of DNA molecules having n non-parental bases when 30 bases are synthesized with reagents that contain fraction M of the majority component. When M=0.63096, f24 and higher are less than $10^{-8}$. The entry "most" in Table 17 is the number of changes that has the highest probability. Note that substantial probability for 8 or more substitutions occurs only if the fraction of 3 parental sequence (f0) drops to around $10^{-3}$. Mutagenesis of this sort can be applied to any part of the protein at any time, but is most appropriate when intermediate binding to the target has been established.

The $N_b$ base pairs of the DNA chain that are synthesized with mixed reagents need not be contiguous. They are picked so that between $N_b/3$ and $N_b$ codons are affected to various degrees. The residues picked for mutation are picked with reference to the 3D structure of the initial DBP, if known. For example, one might pick all or most of the residues in the principal and secondary set. We may impose restrictions on the extent of variation at each of these residues based on homologous sequences or other data. The mixture of non-parental nucleotides need not be random, rather mixtures can be biased to give particular amino acid types specific probabilities of appearance at each codon. For example, one residue may contain a hydrophobic amino acid in all known homologous sequences; in such a case, the first and third base of that codon would be varied, but the second would be set to T. Other examples of how this might be done will be given in the Detailed Examples. This Diffuse Mutagenesis will reveal the subtle changes possible in the protein backbone associated with conservative interior changes, such as V to I, as well as some not so subtle changes that require concomitant changes at two or more residues of the protein.

For Focused Mutagenesis, we now consider the distribution of nucleotides that will be inserted at each variegated codon. Each codon could be programmed differently. If we have no information indicating that a particular amino acid or class of amino acid is appropriate, we substitution of all amino acids with approximately equal probability because representation of one or a few pdbp genes above the detectable level is unproductive (as illustrated above). Equal amounts of all four nucleotides at each position in a codon yields the amino acid distribution:

| | | | | | |
|---|---|---|---|---|---|
| 4/64 A | 2/64 C | 2/64 D | 2/64 E | 2/64 F | 4/64 G |
| 2/64 H | 3/64 I | 2/64 K | 6/64 L | 1/64 M | 2/64 N |
| 4/64 P | 2/64 Q | 6/64 R | 6/64 S | 4/64 T | 4/64 V |
| 1/64 W | 2/64 Y | 3/64 stop | | | |

This distribution has the disadvantage of giving two basic residues for every acidic residue. Such predominance of basic residues is likely to promote sequence-independent DNA binding. In addition, six times as much R, S, and L as W or M occur for the random distribution.

Consider the distribution of amino acids encoded by one codon in a population of vgDNA. Let Abun(x) be the abundance of DNA sequences coding for amino acid x; Abun(x) is uniquely defined by the distribution of nucleotides at each base of the codon. For any distribution, there will be a most-favored amino acid (mfaa) with abundance Abun(mfaa) and a least-favored amino acid (lfaa) with abundance Abun(lfaa). We seek the nucleotide distribution that allows all twenty amino acids and that yields the largest ratio Abun(lfaa)/Abun(mfaa) subject to two constraints. First, the abundances of acidic and basic amino acids should be equal to avoid bias. Second, the number of stop codons should be kept as low as possible. Thus only nucleotide distributions that yield $$Abun(E) + Abun(D) = Abun(R) + Abun(K)$$

are considered, and the function maximized is:

$$\{(1 - Abun(stop))(Abun(lfaa)/Abun(mfaa))\}.$$

A constraint that simplifies the search for an optimal nucleotide distribution is to limit the third base to T or G; C or G at the third base would be equivalent. All amino acids are possible and the number of accessible stop codons is reduced because TGA and TAA codons are eliminated. Assuming equimolar T and G at the third base, the amino acids F, Y, C, H, N, I, and D require T while W, M, Q, K, and E require G. Thus we use an equimolar mixture of T and G at the third base.

A computer program, "Find Optimum vgCodon." (Table 18), varies the composition at bases 1 and 2, in steps of 0.05, and reports the composition that gives the largest value of the quantity {(Abun(lfaa)/Abun(mfaa)) (1-Abun(stop)))}. A vg codon is symbolically defined by the nucleotide distribution at each base:

| | T | C | A | G |
|---|---|---|---|---|
| base #1 = | t1 | c1 | a1 | g1 |
| base #2 = | t2 | c2 | a2 | g2 |
| base #3 = | t3 | c3 | a3 | g3 |

-continued

| | T | C | A | G |
|---|---|---|---|---|
| | t1 + c1 + a1 + g1 | | | = 1.0 |
| | t2 + c2 + a2 + g2 | | | = 1.0 |
| | t3 = g3 = 0.5, c3 = a3 = 0. | | | |

The variation of the quantities t1, c1, a1, g1, t2, c2, a2, and g2 is subject to the constraint that $$Abun(E)+Abun(D)=Abun(K)+Abun(R);$$

$$Abun(E)+Abun(D)=g1 \cdot a2$$

$$Abun(K)+Abun(R)=a1 \cdot a2/2+c1 \cdot g2+a1 \cdot g2/2$$

$$g1 \cdot a2=a1 \cdot a2/2+c1 \cdot g2+a1 \cdot g2/2$$

Solving for g2, we obtain $$g2=(g1 \cdot a2-0.5 \cdot a1 \cdot a2)/(c1+0.5 \cdot a1).$$

In addition, $$t1=1-a1-c1-g1$$

$$t2=1-a2-c2-g2$$

We vary a1, c1, g1, a2, and c2 and then calculate t1, g2, and t2. Initially, variation is in steps of 5%. Once an approximately optimum distribution of nucleotides is determined, the region is further explored with steps of 1%. The logic of this program is shown in Table 18. The optimum distribution is:

| | Optimum vgCodon | | | |
|---|---|---|---|---|
| | T | C | A | G |
| base #1 = | 0.26 | 0.18 | 0.26 | 0.30 |
| base #2 = | 0.22 | 0.16 | 0.40 | 0.22 |
| base #3 = | 0.5 | 0.0 | 0.0 | 0.5 | and yields DNA molecules encoding each type of amino acid with the abundances shown in Table 19.

The computer that controls a DNA synthesizer, such as the Milligen 7500, can be programmed to synthesize any base of an oligonucleotide with any distribution of nucleotides by taking some nucleotide substrates (e.g. nucleotide phosphoramidites) from each of two or more reservoirs. Alternatively, nucleotide substrates can be mixed in preset ratios and placed in one of the extra reservoirs for so-called "dirty bottle" synthesis. Either of these methods amounts to specifying the nucleotide distribution. The actual nucleotide distribution obtained will differ from the specified nucleotide distribution due to several causes, including: a) differential inherent reactivity of nucleotide substrates, and b) differential deterioration of reagents. It is possible to compensate partially for these effects, but some residual error will occur. We denote the average discrepancy between specified and observed nucleotide fraction as $S_{err}$, $$S_{err}=\text{square root (average } [(f_{obs}-f_{spec})/f_{spec}])$$

where $f_{obs}$ is the amount of one type of nucleotide found at a base and $f_{spec}$ is the amount of that type of nucleotide that was specified at the same base. The average is over all specified types of nucleotides and over a number (e.g. 10 or 20) of different variegated bases. By hypothesis, the actual nucleotide distribution at a variegated base will be within 5% of the specified distribution. Actual DNA synthesizers and DNA synthetic chemistry may have different error levels. It is the user's responsibility to determine $S_{err}$ for the DNA synthesizer and chemistry employed by the user.

To determine the possible effects of errors in nucleotide composition on the amino acid distribution, we modified the program "Find Optimum vgCodon" in four ways:
1) the fraction of each nucleotide in the first two bases is allowed to vary from its optimum value times $(1-S_{err})$ to the optimum value times $(1+S_{err})$ in seven equal steps ($S_{err}$ is the hypothetical fractional error level entered by the user), maintaining the sum of nucleotide fractions for one codon position at 1.0,
2) g2 is varied in the same manner as a2, i.e. we dropped the restriction that Abun(D)+Abun(E) Abun(K)+Abun(R),
3) t3 and g3 re varied from 0.5 times $(1-S_{err})$ to 0.5 times $(1+S_{err})$ in three equal steps,
4) the smallest ratio Abun(lfaa)/Abun(mfaa) is sought.

In actual experiments, we direct the synthesizer to produce the optimum DNA distribution "Optimum vgCodon" given above. Incomplete control over DNA chemistry may, however, cause us to actually obtain the following distribution that is the worst that can be obtained if all nucleotide fractions are within 5% of the amounts specified in "Optimum vgCodon". A corresponding table can be calculated for any given $S_{err}$ using the program "Find worst vgCodon within $S_{err}$ of given distribution." given in Table 20.

| | Optimum vgCodon, worst 5% errors | | | |
|---|---|---|---|---|
| | T | C | A | G |
| base #1 = | 0.251 | 0.189 | 0.273 | 0.287 |
| base #2 = | 0.209 | 0.160 | 0.400 | 0.231 |
| base #3 = | 0.475 | 0.0 | 0.0 | 0.525 |

This distribution yields DNA encoding each of the twenty amino acids at the abundances shown in Table 21.

Each codon synthesized with the distribution of bases shown above displays $4 \times 4 \times 2 = 2^5 = 32$ possible DNA sequences, though not in equal abundances. An oligonucleotide containing N such codons would display $2^5N$ possible DNA sequences and would encode $20^N$ protein sequences. Other variegation schemes produce different numbers of DNA and protein sequences. For example, if two bases in one codon are varied through two possibilities each, then there are $2 \times 2 = 4$ DNA sequences and $2 \times 2 = 4$ protein sequences.

If five codons are synthesized with reagents mixed so as to produce the nucleotide distribution "Optimum vgCodon", and if we actually obtained the nucleotide distribution "Optimum vgCodon, worst 5% errors", then DNA sequences encoding the mfaa at all of the five codons are about 277 times as likely as DNA sequences encoding the lfaa at all of the five codons. Further, about 24% of the DNA sequences will have a stop codon in one or more of the five codons.

Figure 2:
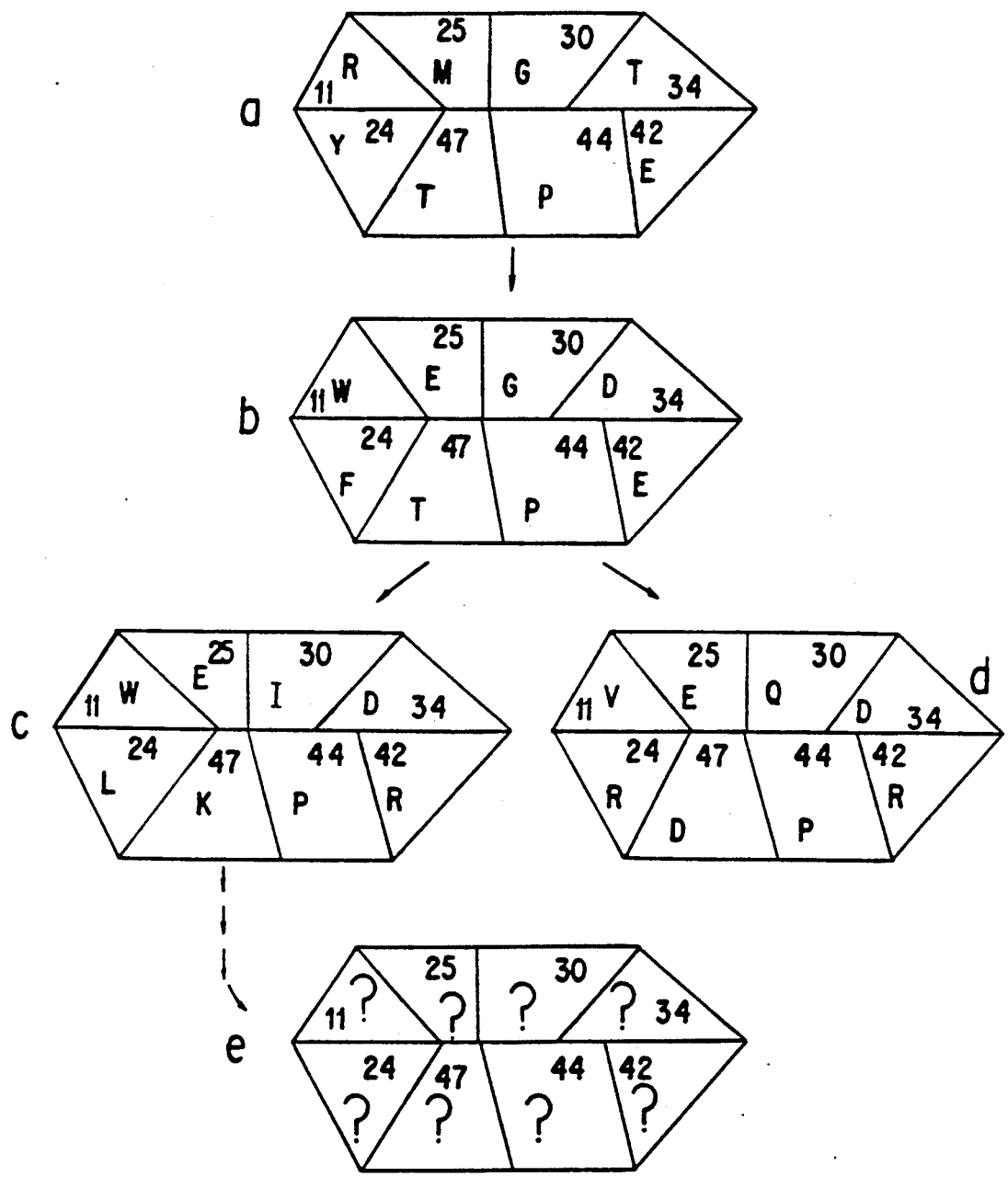
FIG. 2 Progressive variegation and selection of a protein surface.

By hypothesis, the distribution "Optimal vgCodon" is used in the second version of the second variegation of the example shown in FIG. 2. The actual abundance of the DNA encoding each type of amino acid is, however, taken from the case of $S_{err}$ 5% given in Table 21.

The abundance of DNA encoding the parental amino acid sequence is:

$$\begin{aligned}
&\text{Amount(parental seq.)}\\
&\quad F24 \quad\quad G30 \quad\quad D34 \quad\quad E42 \quad\quad T47\\
&= Abun(F) * Abun(G) * Abun(D) * Abun(E) * Abun(T)\\
&= .0249 \times .0663 \times .0545 \times .0602 \times .0437\\
&= 2.4 \times 10^{-7}
\end{aligned}$$

Therefore, if the efficiency of the entire process allows us to examine $10^7$ different DNA sequences, DNA encoding the parental DBP sequence as well as very many related sequences will be present in sufficient quantity to be detected and we are assured that the process will be progressive.

Setting Level of Variegation

We use the following procedure to determine whether a given level of variegation is practical:
1) from: a) the intended nucleotide distribution at each base of a variegated codon, and b) $S_{err}$ (the error level in mixed DNA synthesis), calculate the abundances of DNA sequences coding for each amino acid and stop,
2) calculate the abundance of DNA encoding the parental DBP sequence by multiplying the abundances of the parental amino acid at each variegated residue, The abundances used in the procedure above are calculated from the worst distribution that is within $S_{err}$ of the specified distribution. A variegation that insures that the parental DBP sequence can be recovered is practical. Such a level of variegation produces an enormous number of multiple changes related to the parental DBP available for selection of improved successful DBPs.

We adjust the subset of residues to be varied and levels of variegation at each residue until the calculated variegation is within bounds.

Reduction of Gratuitous Restriction Sites

Here we consider the interactions between the sites of variegation and the surrounding DNA. If the method of mutagenesis to be used is replacement of a cassette, we consider whether the variegation generates gratuitous restriction sites. We reduce or eliminate gratuitous restriction sites by appropriate choice of variegation pattern and silent alteration of codons neighboring the sites of variegation.

Focused mutagenesis

In the preferred embodiment of this process, the number of residues and the range of variation at each residue are chosen to maximize the number of DNA binding surfaces, to minimize gratuitous restriction sites, and to assure the recovery of the initial DBP sequence. For example, in Detailed Example 1, the initial DBP is lambda Cro. One primary set of residues includes G15, Q16, K21, Y26, Q27, S28, N31, K32, H35, A36, and R38 of the H-T-H region (see Table 14b) and C-terminal residues K56, N61, K62, K63, T64, T65, and A66. A secondary set of residues includes L23, G24, and V25 from the turn portion of the H-T-H region, buried residues T20, A21, A30, I31, A34, and I35 from alpha helices 2 and 3, and dimerization region residues E54, V55, F58, P59, and S60.

The initial set of 5 residues for Focused Mutagenesis contains residues in or near the N-terminal half of alpha helix 3: Y26, Q27, S28, N31, and K32. Varying these 5 residues through all 20 amino acids produces $3.2\times10^6$ different protein sequences encoded by $32^5$ ($=3.3\times10^7$) different DNA sequences. Since all 5 residues are in the same interaction set, this variegation scheme produces the maximum number of different surfaces. Assuming optimized nucleotide distribution described above and $S_{err}=5\%$, the probability of obtaining the parental sequence is $3.2\times10^{-7}$. This level is within bounds for synthesis, ligation, transformation, and selection capable of examining $10^8$ sequences of vgDNA. Codons for the 5 residues picked for Focused Mutagenesis are contained in the 51 bp PpuMII to BglII fragment of the rav+gene constructed in Detailed Example 1. This cassette, containing vgDNA at the appropriate codons, is synthesized as described.

We synthesize DNA inserts having the appropriate level of variegation, ligate the synthetic DNA into appropriately digested and purified plasmid DNA, transform competent cells, select for uptake of plasmid, induce the cells for production of potential DBPs, and then select for the wanted DNA-binding phenotype using the binding marker genes.

Surviving colonies are screened genetically and biochemically to verify that a novel DBP is effectively binding to the target DNA sequence. DBP characterization includes, at the genetic level, deleting and backcrossing the dbp gene; at the protein level, in vitro binding assays; and, at the DNA level, determination of the complete sequence of the dbp gene.

Repetition to Obtain Desired Degree of DNA-binding

The first variegation step can produce one or more DBPs having DNA-binding properties that are satisfactory to the user. The user opts for successive variegation steps to further modify the DBP. Parental DBPs for a second variegation step are selected from DBPs isolated in the first variegation step. The second and subsequent variegation steps may employ either Focused or Diffuse Mutagenesis procedures on residues of the primary or secondary sets. In the preferred embodiment of this process, the user chooses residues and mutagenesis procedures based on the structure of the parental DBP and specific goals. For example, consider three hypothetical cases.

In the first case, a variegation step produces a DBP with greater non-specific DNA binding than is desired. Information from sequence analysis and modeling is used to identify residues involved in sequence independent interactions of the DBP with DNA in the nonspecific complex. In the next variegation step, some or all of these residues, together with one or more additional residues from the primary set, are chosen for Focused Mutagenesis and additional residues from the primary or secondary sets are chosen for Diffuse Mutagenesis.

In a second hypothetical case, a variegation step produces a DBP with strong sequence specific binding to the target and the goal is to optimize binding. In this case, the next variegation step employs Diffuse Mutagenesis of a large number of residues chosen mostly from the secondary set.

In the third hypothetical case, a DBP has been isolated that has insufficient binding properties. A set of residues is chosen to include some primary residues that have not been subjected to variation, one or more primary residues that have been varied previously, and one or more secondary residues. Focused Mutagenesis is performed on this set in the next variegation step.

Overview: DNA Synthesis, Purification and Cloning

DNA Sequence design

The present invention is not limited to a single method of gene design. The idbp gene need not be synthesized in toto; parts of the gene may be obtained from nature. One may use any genetic engineering method to produce the correct gene fusion, so long as one can easily and accurately direct mutations to specific sites. In all of the methods of mutagenesis considered in the present invention, however, it is necessary that the DNA sequence for the idbp gene be unique compared to other DNA in the operative cloning vector. The degree and nature of difference needed is determined by the method of mutagenesis to be used. For example, if the method of mutagenesis is to be replacement of subsequences coding for the potential-DBP with vgDNA, then the subsequences to be mutagenized must be bounded by restriction sites that are unique with respect to the rest of the vector. If single-stranded oligonucleotide-directed mutagenesis is to be used, then the DNA sequence of the subsequence coding for the initial DBP must be unique with respect to the rest of the vector.

The coding portions of genes to be synthesized are designed at the protein level and then encoded in DNA. The amino acid sequences are chosen to achieve various goals, including: a) expression of initial DBP intracellularly, and b) generation of a population of potential-DBPs from which to select a successful DBP. The ambiguity in the genetic code is exploited to allow optimal placement of restriction sites and to create various distributions of amino acids at variegated codons.

An ambiguous DNA sequence coding for an amino acid sequence given by the user may be constructed preferably with the aid of a computer. That is, the DNA sequence contains codes for all possible DNA sequences that produce the stated amino acid sequence. The codes used in the ambiguous DNA are shown in Table 9.

The user supplies lists of restriction enzymes that: a) do not cut the operative vector, and b) cut the vector once or twice. For each enzyme the program reads: a) the name, b) the recognition sequence, c) the cutting pattern, and d) the names of suppliers. The ambiguous DNA sequence coding for the stated amino acid sequence is examined for places that recognition sites for any of the listed enzymes could be created without altering the amino acid sequence. A master table of enzymes could be obtained from the catalogues of enzyme suppliers or other sources, such as Roberts' annual review of restriction enzymes in Nucleic Acids Research.

The choice of elective restriction sites to be built into the gene is determined as follows. The goal is to have a series of fairly uniformly spaced unique restriction sites with no more than a preset maximum number of bases, for example 100, between sites. Unless required by other sites, sites that are not present in the vector are not introduced into the designed gene more than once. Sites that occur only once or twice in the vector are not introduced into the designed gene unless necessary.

First, each enzyme that has a unique possible site is picked; if two of these overlap, then the better enzyme is picked. An enzyme is better if it: a) generates cohesive ends, b) has unambiguous recognition, c) has higher specific activity, or d) (for work in E. coli) is not sensitive to dam or dcm methylation. Next, those sites close to other sites already picked are eliminated because many sites very close together are not useful. Finally, sites are chosen to minimize the size of the longest piece between restriction sites.

The ambiguity of the DNA between the restriction sites is resolved from the following considerations. If the given amino acid sequence occurs in the recipient organism, and if the DNA sequence of the gene in the organism is known, then, preferably, we maximize the differences between the engineered and natural genes to minimize the potential for recombination. In addition, the following codons are poorly translated in E. coli and, therefore, are avoided if possible: cta(L), cga (R), cgg (R), and agg (R). For other host species, different codon restrictions are appropriate. Finally, long repeats of any one base are prone to mutation and thus are avoided. Balancing these considerations, we design a DNA sequence.

Organization of Gene Synthesis

The present invention is not limited as to how a designed DNA sequence is divided for easy synthesis. An established method is to synthesize both strands of the entire gene in overlapping segments of 20 to 50 nucleotides (THER88). Below we provide an alternative method that is more suitable for synthesis of vgDNA. This method is similar to methods published by Oliphant et al. (OLIP86 and OLIP87) and Ausubel et al. (AUSU87). Our adaptation of this method differs from previous methods in that we: a) use two synthetic strands, and b) do not cut the extended DNA in the middle. Our goals are: a) to produce longer pieces of dsDNA than can be synthesized as ssDNA on commercial DNA synthesizers, and b) to produce strands complementary to single-stranded vgDNA. By using two synthetic strands, we remove the requirement for a palindromic sequence at the 3' end. Moreover, the overlap should not be palindromic lest single DNA molecules prime themselves.

The present invention is not limited to any particular method of DNA synthesis or construction. Preferably, DNA is synthesized on a Milligen 7500 DNA synthesizer (Milligen, a division of Millipore Corporation, Bedford, Mass.) by standard procedures. High-loading columns are used for syntheses of oligonucle-otides containing up to 60 bases. Low-loading columns are used for syntheses of oligonucleotides containing 60 bases or more.

The Milligen 7500 has seven vials from which phosphoramidites may be taken. Normally, the first four contain A, C, T, and G. The other three vials may contain unusual bases such as inosine or mixtures of bases, the so-called "dirty bottle". The standard software allows programmed mixing of two, three, or four bases in equimolar quantities. Custom programming can cause substrates to be drawn from the standard vials to produce mixtures that are not equimolar. Synthetic DNA is purified by high-pressure liquid chromatography (HPLC) or polyacrylamide gel electrophoresis (PAGE).

With low-loading supports, a 65-base-long oligonucleotide is typically obtained at 1-2% of theoretical yield, i.e. 10 ug; a 100-base-long oligonucleotide is typically obtained in 0.5% of theoretical yield, i.e. 5 ug.

With high-loading supports, 1 mg of a 20-base-long oligonucleotide is typically obtained.

The present invention is not limited to any particular method of purifying DNA for genetic engineering. HPLC is appropriate for both oligonucleotides and fragments of several kb. Alternatively, agarose gel electrophoresis and electroelution on an IBI device (International Biotechnologies, Inc., New Haven, Conn.) is used to purify large dsDNA fragments. For purification of oligonucleotides, PAGE and electroelution with an Epigene device (Epigene Corp., Baltimore, Md.) are an alternative to HPLC. One alternative for DNA purification is HPLC on a Waters (division of Millipore Corporation) HPLC system using the GenPak(™)-FAX column. A NAP5 column from Pharmacia (Sweden) is used to desalt DNA eluted from the GenPak column.

IDBP Gene Cloning

We clone the idbp gene using plasmids that are transformed into competent bacterial cells by standard methods (MANI82, p250) or slightly modified standard methods. DNA fragments derived from nature are operably linked to other fragments of DNA derived from nature or to synthetic DNA fragments.

Cells transformed with the plasmid bearing the complete idbp gene are tested to verify expression of the initial DBP. Selection for plasmid presence is maintained on all media, while selections for DBP+ phenotypes are applied only after growth in the presence of inducer appropriate to the promoter. Colonies that display the DBP+ phenotypes in the presence of inducer and DBP− phenotypes in the absence of inducer are retained for further genetic and biochemical characterization. The presence of the idbp gene is initially detected by restriction enzyme digestion patterns characteristic of that gene and is confirmed by sequencing.

The dependence of the IDBP+ and IDBP−− phenotypes on the presence of this gene is demonstrated by additional genetic constructions. These are a) excision of the idbp gene by restriction digestion and closure by ligation, and b) ligation of the excised idbp gene into a plasmid recipient carrying different markers and no dbp gene. Plasmids obtained by excising the gene confer the DBP− phenotypes (e.g. $Tet^R$, $Fus^S$, and $Gal^S$ in Detailed Example 1). Plasmids obtained from ligation of idbp to a recipient plasmid confer the DBP+ phenotypes in the presence of an inducer appropriate to the regulatable promoter (e.g. $Tet^S$, $Fus^R$, and $Gal^R$ in Detailed Example 1). Finally, a most important demonstration of the successful construction involves determination of the quantitative dependence of the selected phenotypes on the exogenous inducer concentration.

Overview: DNA-binding Protein Purification and Characterization

Isolation of IDBP

Isolation of the idbp gene product and biochemical tests to verify the DNA-binding of the initial DBP are described in the next sections.

Purified initial DBP for use in the biochemical assays described herein can be obtained from cultures of strains bearing the plasmid with the idbp gene, following maximal induction of gene expression with IPTG. If even higher levels of protein yield are required, the sequences coding for the DBP can be recombined into high expression vectors such a pTR213 or pTR214 (ROBE79). Addition of IPTG to cultures of lacI$^q$ cells harboring these plasmids allows extreme overproduction of the DBP. If a previously characterized DNA-binding protein (e.g. lambda Cro or repressor or P22 Arc or Mnt) is chosen as the initial DBP, isolation of the protein from overproducing strains can be performed following the published procedures. For example, methods for purifying lambda Cro and repressor protein are described by Johnson et al. (JOHN80), Takeda et al. (TAKE86), and Leighton and Lu (LEIG87), while P22 Arc and Mnt purifications are described by Vershon et al. (VERS85b). If no published procedure is available for initial DBP purification, the user assembles a procedure using standard protocols. DBP purification can be monitored using the filter-binding or electrophoretic mobility shift assays described below.

Quantitation and Characterization of Protein-DNA Binding

Methods that can be used to quantitate and characterize sequence-specific and sequence-independent binding of a DBP to DNA include: a) filter-binding assays, b) electrophoretic mobility shift analysis, and c) DNase protection experiments. Ionic strength, pH, and temperature are important factors influencing DBP binding to DNA. For quantitative comparisons among DBPs, values for these parameters are standardized. The standard conditions should correspond closely to the anticipated conditions of use. Thus, if a binding protein is intended for use in bacterial cells in standard culture, a reasonable range of values from which to choose standard conditions would be: pH=7.5 to 8.0, 0.1 to 0.2 M KCl, and 32° to 37° C. However, studies of DBP binding as a function of pH, ionic strength, or temperature are used to analyze the contributions of various types of binding interactions to overall DBP binding. Assay buffers preferably include cofactors, stabilizing agents, and counter ions for proper DBP function.

In the preferred embodiment, the DNA fragment preparations used in binding assays are radioactively labeled by an appropriate method, such as end labeling with $^{32}$P-gamma-dATP and T4 polynucleotide kinase (MAXA77), DNA Polymerase I Klenow fragment (KLEN70) and $^{32}$P-alpha-dNTPs, or nick translation (RIGB77). DNA fragments used for sequence-specific binding assays preferably contain no more than one target binding site per molecule to avoid potential kinetic complications (KIMJ87). DNA fragments used as controls for sequence non-specific binding studies lack the target binding site, but are otherwise identical to those used in sequence-specific binding studies. A constant fragment length should be used for comparative studies (KIMJ87)

The filter-binding assay is based on the observation that free linear duplex DNA passes through a nitrocellulose filter under certain conditions, while protein and protein-bound DNA are retained (JONE66, RIGG70). In a typical experiment, a quantity of purified or crude DBP is added to a solution containing labeled DNA. After an appropriate time interval, the solution is filtered through a nitrocellulose filter. The filter is washed, dried, and the amount of radio-activity retained on the filter is measured by liquid scintillation.

The basic experimental protocol is varied to obtain different information. To determine the equilibrium dissociation constant, $K_D$, increasing quantities of DBP are added to solutions containing a constant amount of DNA. DNA retention is followed as a function of DBP concentration. To determine the dissociation rate constant for the DBP-DNA complex, $k_d$, DBP and labeled DNA are pre-incubated long enough to achieve binding equilibrium. A large excess (>100-fold) of unlabeled DNA is then added and aliquots of the resulting mixture are removed at appropriate intervals to determine the remaining DBP bound to labeled DNA via the filter assay. To determine the DBP-DNA association constant, $k_a$, DBP and labeled DNA are mixed at time 0 and aliquots are removed at subsequent times. The amount of DBP-DNA complex is determined via the filter binding assay. Kinetic and equilibrium data can be analyzed as described by Riggs et al. (RIGG70) or Kim et al. (KIMJ87).

Electrophoretic mobility shift measurements rely on the observation that free DNA and protein-DNA complexes show different mobilities in polyacrylamide gel electrophoresis (FRIE81). For these experiments, the DNA containing the target binding site must be of an appropriate size (typically a few hundred base pairs) for good resolution of bound and unbound DNA on a polyacrylamide gel. Labeled DNA and DBP are incubated under previously chosen standardized conditions. Aliquots of the mixture are added to electrophoresis loading buffer, immediately loaded onto a polyacrylamide gel, and bound and free DNA fragments are resolved by electrophoreses. Depending on fragment size, 5% to 10% acrylamide gels are used. After electrophoresis, gels are dried and autoradiographed. Quantitation is performed by scanning densitometry. Determinations of $K_D$, $k_d$, and $k_a$ are performed as described for filter binding assays.

In the DNase protection assay (JOHN79), labeled DNA is first equilibrated with DBP. DNase I is then added and the mixture incubated for a fixed time; the DNase I concentration and incubation time are picked so that each DNA fragment is, on average, cut less than once. After stopping the reaction, the DNA is purified by precipitation and the pellet is rinsed with 70% ethanol and resuspended in electrophoresis buffer. DNA fragments are resolved by electrophoresis through 8% to 20% sequencing gels (depending on original fragment size). The electrophoresis time and gel percentage for best resolution are preferably determined from initial trials using conditions appropriate for the size of the fragments being used. The origins of the DNase I cleaved fragments are determined by comparing the gel-resolved cleaved products with those generated by chemical cleavage of the original fragment (MAXA77). After electrophoresis is complete, the gel is fixed, dried, and autoradiographed. DBP bound to the DNA prevents access of DNase I to the DBP binding site and protects the DNA at the site from attack (JOHN79). Measuring the loss of DNase I generated bands as a function of the concentration of DBP allows the calculation of $K_D$, the dissociation constant. The "footprint" so obtained identifies the actual site of specific binding by the DBP to the DNA.

TABLES OF EXAMPLES

Ex.1: Protocol for developing a new DNA-binding protein with affinity for a DNA-sequence found in HIV-1, by variegation of lambda Cro.

Ex. 2: Protocol for developing a new DNA-binding polypeptide with affinity for a DNA-sequence found in HIV-1, by variegation of a polypeptide having a segment homologous with Phage P22 Arc.

Ex. 3: Use of a custodial domain (residues 20-83 of barley chymotrypsin inhibitor) to protect a DNA-binding polypeptide from degradation.

Ex. 4: Use of a custodial domain containing a DNA-recognizing element (alpha-3 helix of Cro>) to protect a DNA-binding polypeptide from degradation.

Ex. 5: Protocol for addition of arm to Phage P22 ARc to alter its DNA-binding characteristics.

Ex. 6: Protocol for preparation of novel DNA-binding protein that recognizes an asymmetric DNA sequence and corresponds to a fusion of third zinc-finger domain of the Drosophila kr gene product and the DNA-binding domain of Phage P22 Arc.

DETAILED EXAMPLE 1

Presented below is a hypothetical example of a protocol for developing a new DNA-binding protein derived from lambda Cro with affinity for a DNA sequence found in human immunodeficiency virus type 1 (HIV-1) using *E. coli* K-12 as the cell line or strain. It will be understood that further optimization, in accordance with the teachings herein, may be necessary to obtain the desired results. Possible modifications in the preferred method are discussed following various steps of the hypothetical example.

By hypothesis, we set the following technical capabilities:

Yield from DNA synthesis 500 ng/synthesis of ssDNA 100 bases long,
10 ug/synthesis of ssDNA 60 bases long,
1 mg/synthesis of ssDNA 20 bases long.

Maximum oligonucleotide 100 bases

Yield of plasmid DNA 1 mg/l of culture medium

Efficiency of DNA Ligation 0.1 % for blunt-blunt,
4 % for sticky-blunt,
11 % for sticky-sticky.

Yield of transformants $5 \times 10^8$/ ug DNA

Error in mixed DNA synthesis ($S_{err}$)

5%

Overview

In Parts I, II, and III we are concerned with: a) choice of Cro as initial DBP, b) design and implementation of a selection system, c) cloning an engineered gene having a DNA sequence modified from the cro gene, encoding wild-type Cro protein with suitable genetic regulation, and d) demonstrating that the Cro+-phenotype is expressed.

In Part IV we optimize the genetic selection systems for Cro+cells. We use cultures of cells that express Cro, cultures of cells that lack this gene, and mixtures of these cultures.

In Part V we choose a segment of HIV-1 as the target DNA sequence. Symmetrized versions of target sequences, derived from subsequences identified as left target and right target, are introduced into the cloning vector.

Part VI is iterative. For the first pass through this part of the procedure, residues in alpha 3 of Cro are varied and a Cro derived DBP, designated $Rav_L$, that recognizes the symmetrized left target is produced by selection and further characterization. Similarly, a Cro derived DBP, designated $Rav_R$, that recognizes the symmetrized right target is also created.

Figure 3:
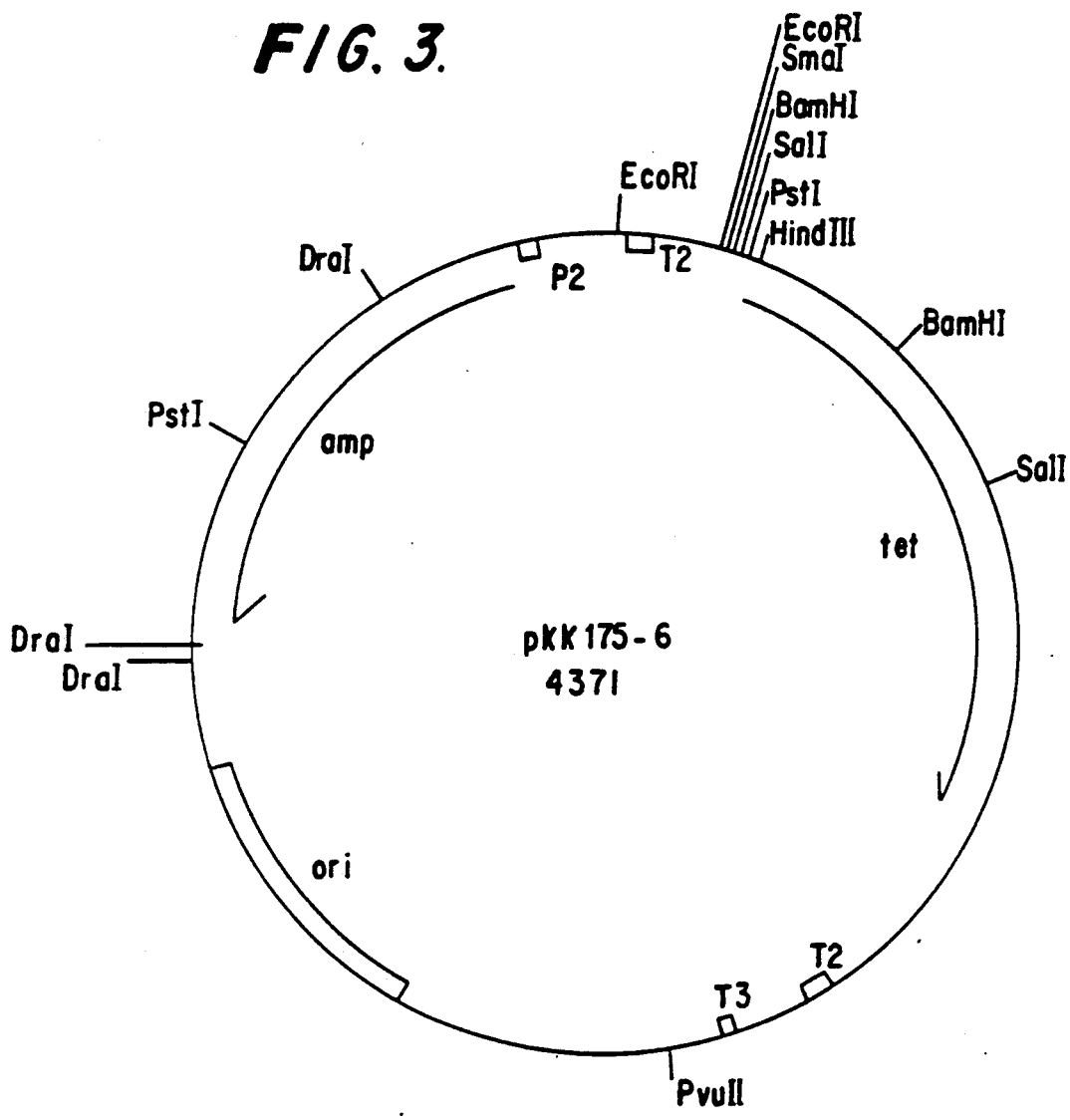
FIG. 3 Plasmid pKK175-6.

In a subsequent pass through Part VI, a mutation known to prevent dimerization is introduced into the $rav_L$ gene. A complementary mutation in $Rav_R$ is selected that allows formation of a $Rav_L$:$Rav_R$ heterodimeric protein which recognizes a unique non-palindromic target sequence, the HIV-1 target sequence chosen in Part V.

Part I

Section 1.1 Choice of Cell Line or Strain

In this example, the following *E. coli* K-12 recA strains are used: ATCC #35,882 delta4 (Genotype: W3110 trpC, recA, rpsL, sup°, delta4 (gal-chlD-pgl-$att_{lambda}$) and ATCC #33,694 HB101 (Genotype: F−, leuB, proA, recA, thi, ara, lacY, galK, xyl, mtl, rpsL, supE, hsdS, ($r_B^-$, $m_B^-$). *E. coli* K-12 strains are grown at 37° C. in LB broth (10 g Bacto-tryptone, 5 g Bacto-yeast extract, 10 g NaCl, 1 l dH20, pH adjusted to 7.0 with 1 M NaOH) and on LB agar (addition of 15 g Bacto-agar) for routine purposes. Selections for plasmid uptake and maintenance are performed with addition of ampicillin (200 ug/ml), tetracycline (12.5 ug/ml) and kanamycin (50 ug/ml).

Section 1.2 Choice of Initial DBP

The initial DBP is lambda Cro. Helix-turn-helix proteins are preferred over other known DBPs because more detail is known about the interactions of these proteins with DNA than is known for other classes of natural DBP. Lambda Cro is preferred over lambda repressor because it has lower molecular weight. Cro from 434 is smaller than lambda Cro, but more is known about the genetics and 3D structure of lambda Cro. An X-ray structure of the lambda Cro protein has been published, but no X-ray structure of a DNA-Cro complex has appeared. A mutant of lambda Cro, Cro67, confers the positive control phenotype in vitro but not in vivo. The contacts that stabilize the Cro dimer are known, and several mutations in the dimerization function have been identified (PAKU86).

By the methods disclosed herein, DBPs may be developed from Cro which recognize DNA binding sites different from the lambda $O_R3$ or lambda operator consensus binding sites, including heterodimeric DBPs which recognize non-symmetric DNA binding sites.

Part II

Section 2.1 Selective Techniques

All selections in this section are described for use with standard Petri plates of 100 mm diameter and containing 30 to 33 ml medium.

Section 2.1.1 Selections for Cells Bearing Phenotypes Conferred by DBP+Function All media generally are supplemented with IPTG and antibiotic for selection of plasmid maintenance (ampicillin, kanamycin). Cell background is generally strain delta4 (galK,T,E deletion).

a. Galactose resistance ($Gal^R$). Galactose epimerase deficient (galE−) strains of *S. typhimurium* (NIKA61) and *E. coli* (BUTT63) are sensitive to galactose, and lysis can be induced by this sugar. Selective medium, usually LB, is supplemented with 2% galactose, added after autoclaving. Additional galactose, up to 8%, somewhat reduces the background of artifactual galactose-sensitive colonies that escape the selection without affecting the yield of true GalR colonies.

b. Galactose resistance selected immediately after transformation. Inducer IPTG is added to transformed cells, to $5\times10^{-4}$ M at the start of the growth period, that allows expression of plasmid antibiotic-resistance. At 60 min after heat shock, cells are further diluted 10-fold into fresh LB broth containing IPTG, antibiotic to select for plasmid uptake (e.g. ampicillin or kanamycin), and 2% galactose. Cells are grown until lysis is complete or for 3 h, whichever occurs first, then centrifuged at 6,000 rpm for 10 min, resuspended in the initial volume of the post-transformation growth culture, and applied to medium for further selection.

c. Fusaric acid resistance ($Tet^S$, $Fus^R$). Successful repression of tet yields resistance to lipophilic chelating agents such as fusaric acid ($Fus^R$ phenotype). The following medium (MAL081) is used for selection of fusaric acid resistance in *E. coli*. Per liter: 15g Bacto-agar; 5 g tryptone; 5 g Bacto-yeast extract; 10 g NaCl; 10 g $NaH_2PO_4.H_2O$; 4 ml of a 12.5 mg/ml solution of chlortetracycline; add after autoclaving: 6 ml of a 2 mg/ml solution of fusaric acid; 5 ml of 20 mM $ZnCl_2$. Total cell inoculum is not greater than $5\times10^6$ per plate.

d. Fusaric acid resistance and galactose resistance. Galactose at a final concentration of 2% is added to the medium above (MAL081) after autoclaving. Cells that have been selected directly for galactose resistance in liquid following transformation are applied to this medium.

Selections 2.1.2 Selections for Cells Bearing Phenotypes Conferred by DBP−Function Cell background is generally strain HB101 (galK−). Media are generally supplemented with IPTG and antibiotic for plasmid maintenance.

a. Tetracycline resistance. Medium, usually LB agar, is supplemented with tetracycline after autoclaving. Tetracycline stock solution is 12.5 mg/ml in ethanol. It is stored at −20° C., wrapped in aluminum foil. Petri plates containing tetracycline are also wrapped in foil. Minimum inhibitory concentration is 3.1 ug/ml using a cell inoculum of $5\times10^7$ to $10^8$ per plate. More stringent selections employ 12.5 ug/ml to 50 ug/ml tetracycline. When used for selection of plasmid maintenance, tetracycline concentration is 12.5 ug/ml.

b. Galactose utilization. Medium A (MILL72), with galactose as carbon source, contains, per liter: 10.5 g $K_2HPO_4$; 4.5 g $KH_2PO_4$; 1 g $(NH_4)_2SO_4$; 0.5 g sodium citrate.$2H_2O$; add after autoclaving: 1 ml 1 M $MgSO_4$; 0.5 ml of 10 mg/ml thiamine HCl; 10 ml of 20% galactose; and amino acids as required, for example, leucine and proline, each 10 ml of 5 mg/ml solutions, for experiments with HB101. cell inoculum per plate is less than $5\times10^7$.

c. Tetracycline resistance and galactose utilization. Medium A with galactose (section b. above) is supplemented with tetracycline at 3.1 ug/ml.

Section 2.1.3 Selectable Systems for DBP Isolation

The plasmid pBR322 tetracycline resistance (tet) gene and the *E. coli* gal operon with a deletion of most of the galE gene are used in a gal deletion host strain for selection of DBP function. The promoter probe vector pKK175-6 (BROS84; Pharmacia, Piscataway, N.J.), is a derivative of pBR322 containing the replication origin, the amp gene for selection of plasmid maintenance, and one of the two selectable genes chosen for this Example, the tet gene. (See FIG. 3.) In pKK175-6 the tet gene is promoterless, and all DNA sequences that are part of the promoters upstream of the pBR322 tet coding region which potentially allow transcription in both directions, the P promoters of Brosius et al. (BROS82), have been deleted and replaced by the M13 mp8 polylinker. The polylinker and tet gene are flanked by strong transcription terminators from the E. coli rrnB gene running in the same direction as that of potential tet gene transcription. In this Example, the tet gene is placed under control of the Tn5 neo promoter, $P_{neo}$.

Figure 4:
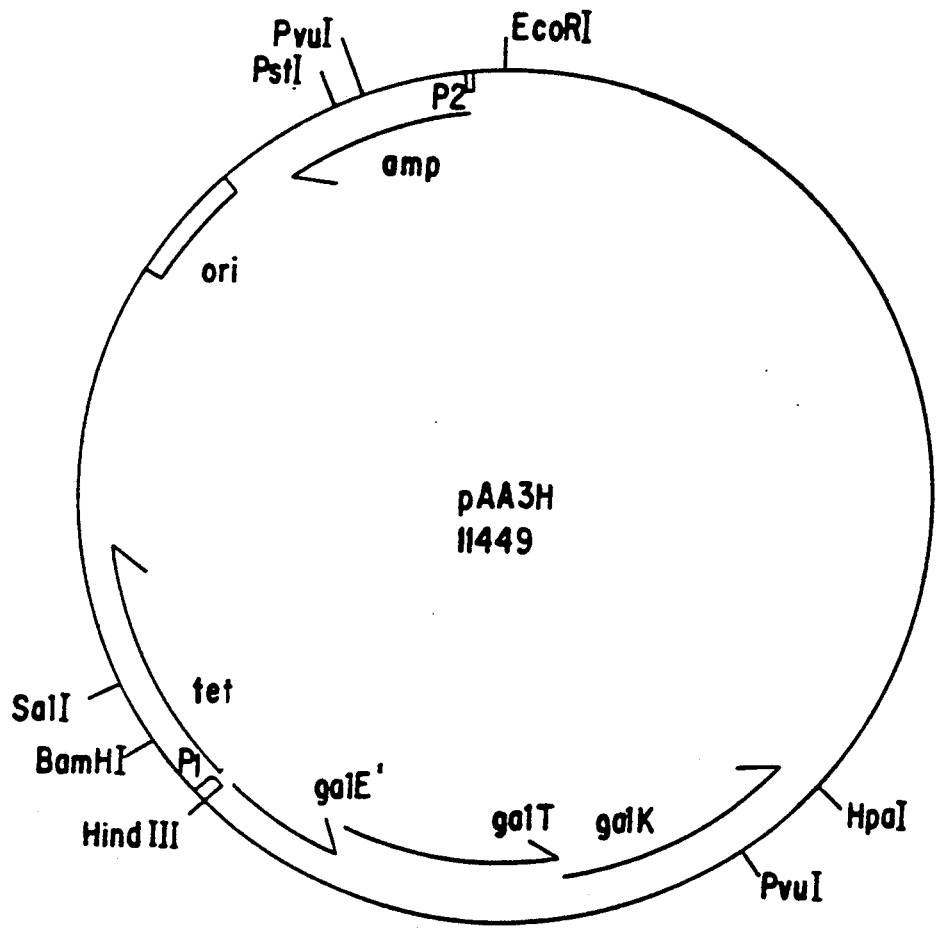
FIG. 4 Plasmid pAA3H.

Plasmid pAA3H (AHME84) is the source of the second selectable function and is available from ATCC (#37,308). This plasmid contains most of the gal operon from phage lambda gal+ inserted between the EcoRI and HindIII sites of pBR322 (FIG. 4). At the HindIII site there is a deletion of part of the galE gene and a deletion of the $-35$ RNA polymerase transcription recognition site upstream of the tet gene which destroys the tet promoter. Thus in gal deletion mutant hosts, such as strain ATCC #35,882 carrying the delta4 deletion (E. coli delta4), plasmid pAA3H confers the $Amp^R$ $Tet^S$ $Gal^S$ phenotype (AHME84). The galT and galK genes in pAA3H are transcribed from an "antitet" promoter, the $P_1$ promoter of Brosius et al. (BROS82), located in the pBR322 portion of the plasmid between the tet gene Shine-Dalgarno region, coding for translational ribosome binding, and the HindIII site. In E. coli strains carrying a galT or galK mutation, e.g. strain HB101, the Gal+ phenotype is conferred by pAA3H. In this Example, the galT+ and galK+ genes are placed under control of the pBR322 amp gene promoter.

For both tet and gal systems, positive selections, described above, are used to select cells that either express or do not express these genes from cultures containing a vast excess of cells of the opposite phenotype.

Section 2.2 Placement of Test DNA Binding Sequence

The test DNA binding sequence for the IDBP, lambda $O_R3$ (KIMJ87), is positioned so that the first 5' base is the +1 base of the mRNA transcribed in each of the tet and gal transcription units (see Table 100 and Table 101).

Section 2.3 Engineering the idbp Gene

A DNA sequence encoding the wild-type Cro protein is designed such that expression is controlled by the lacUV5 promoter, which is independent of catabolite repression and inducible using IPTG. The DNA sequence departs from the wild-type cro gene sequence due to the introduction of restriction sites for cassette mutagenesis. Because of this departure, the gene is called rav, although it encodes wild-type Cro protein. The sequence of rav flanked by the lacUV5 promoter and trpa terminator as well as the restriction sites to be used in cloning and mutating the gene are shown in Table 102.

Part III

Section 3.1 Choice of Operative Cloning Vector

The operative cloning vector is a plasmid constructed from pBR322, and from synthetic sequences and cloned E. coli chromosomal genes as described below.

Section 3.2 Vector construction

Figure 5:
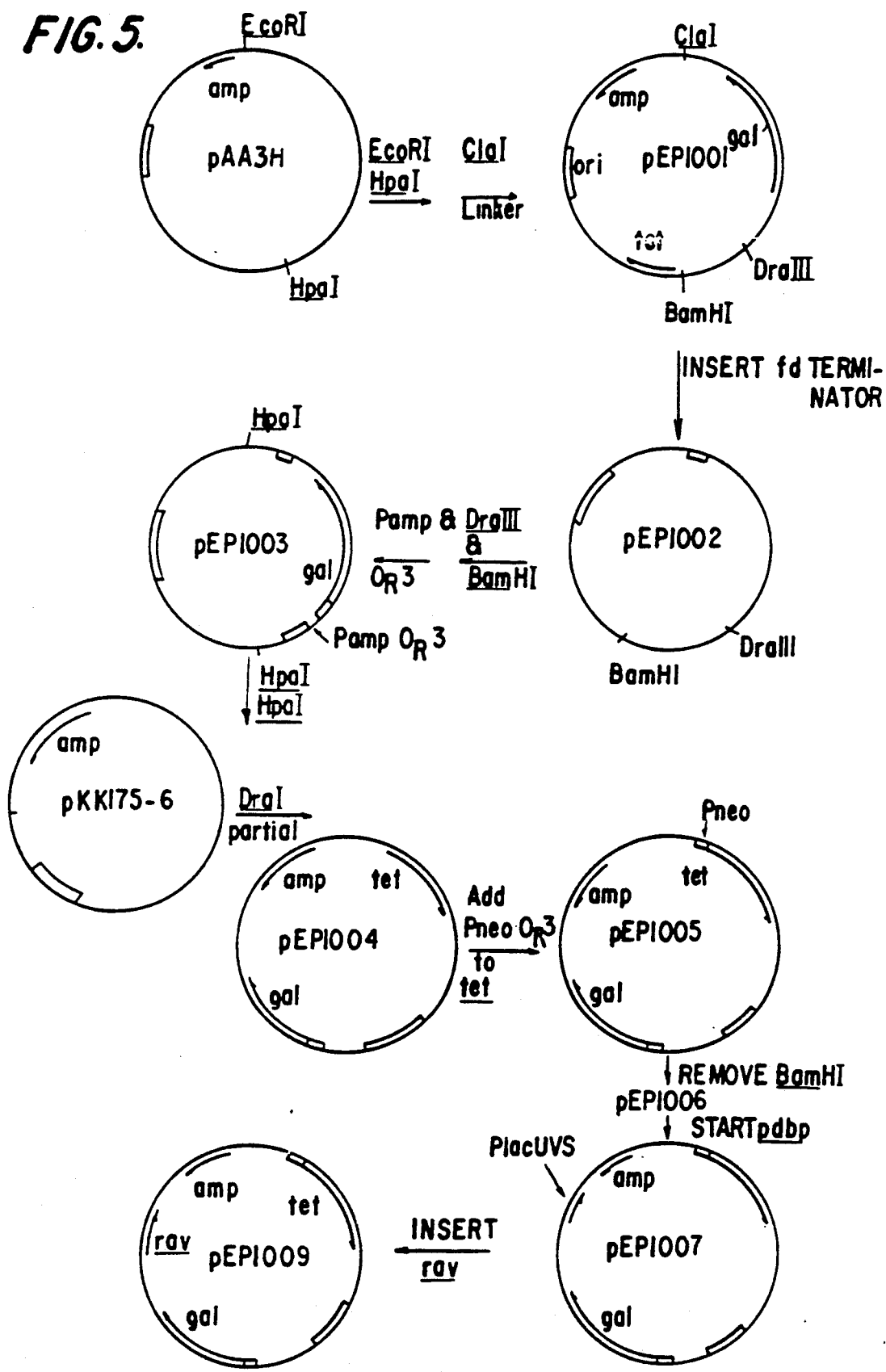
FIG. 5 Summary of construction of pEP1009.
Figure 6:
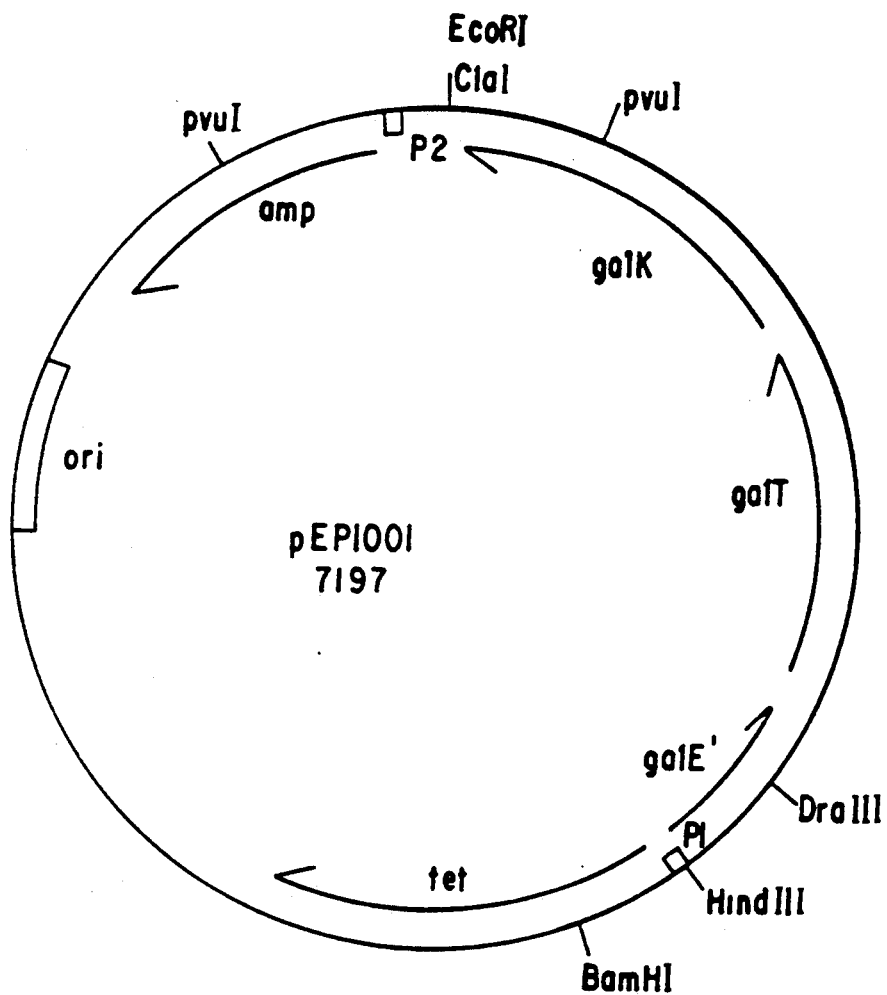
FIG. 6 Plasmid pEP1001.

The construction of an operative cloning vector described in this section is summarized in FIG. 5. The gal gene region in pAA3H requires a few manipulations prior to inserting it into pKK175-6. Phage lambda sequences (4.3 kb) are deleted and a unique ClaI site is created by restricting pAA3H DNA with EcoRI and HpaI, isolating the 7.2 kb fragment by agarose gel electrophoresis, electroelution, and chromatographic purification, blunting the EcoRI single stranded overhanging end using the Klenow enzyme reaction (KLEN70). Phosphorylated ClaI linkers (New England Biolabs #1037, Beverly, Mass.) are ligated to the fragment blunt ends, restricted with ClaI to remove concatamers from the 7.2 kb fragment and the ClaI cut ends of the 7.2 kb fragment are ligated together. The E. coli host strain delta4 is transformed and ampicillin resistant colonies are selected and tested for the $Tet^S$ $Gal^S$ phenotype. Following isolation of plasmid DNA from $Amp^R$ $Tet^S$ $Gal^S$ clones, the DNA is examined for presence of the ClaI restriction site, a regenerated EcoRI site and two PvuI sites approximately 1050 base pairs apart. The resulting 7.2 kb plasmid is designated pEP1001, as illustrated in FIG. 6. A catalogue of all plasmids referred to in the present application is given in Table 103.

Figure 7:
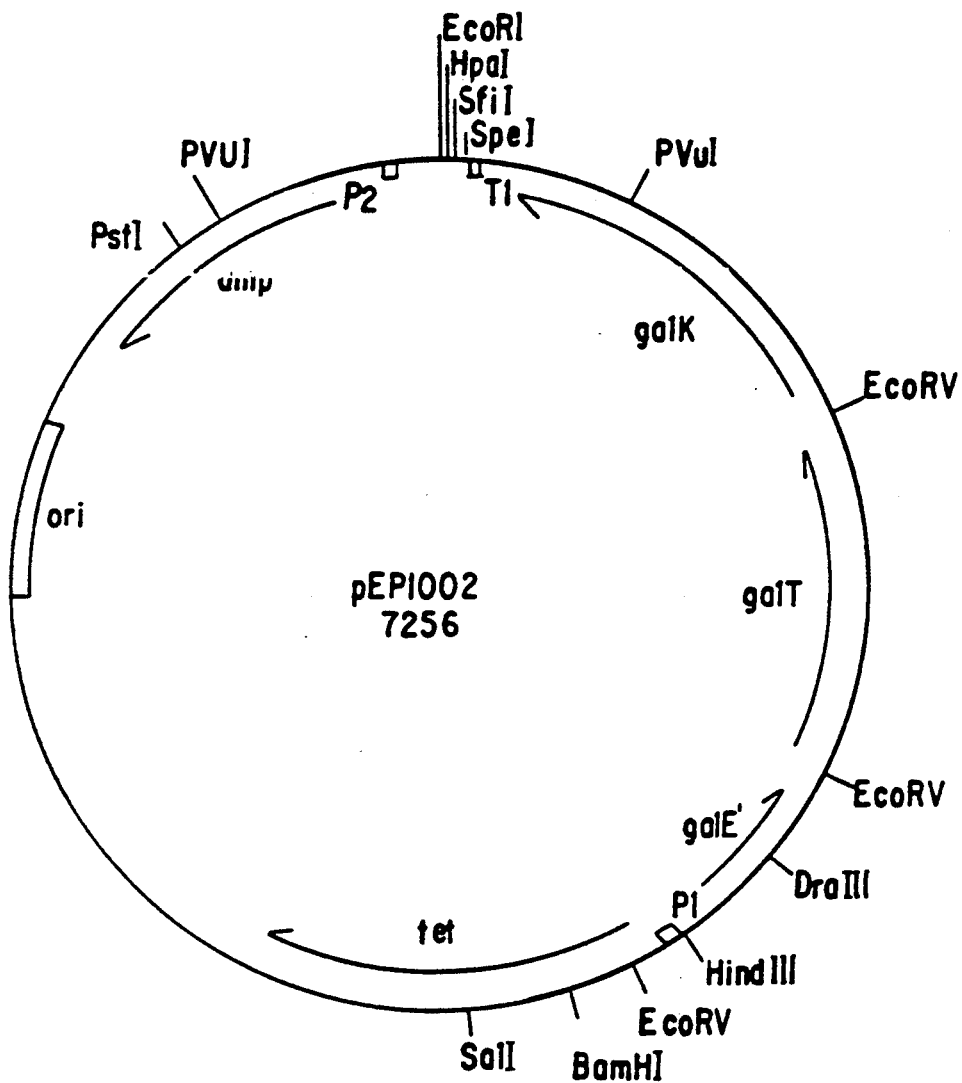
FIG. 7 Plasmid pEP1002.

A second modification of the gal gene region is insertion of a terminator and a multiple cloning site at the ClaI site distal to the gal genes. The bacteriophage fd terminator DNA (ROSE79) is synthesized (as olig#1 and olig#2) such that it is flanked upstream by a single stranded 5' overhang complementary to the ClaI restriction site overhang of pEP1001. Also included on this synthetic fragment, downstream of the 28 base pair fd terminator, are SpeI and SfiI restriction sites for later insertion of dbp genes, an HpaI site and a single stranded 5' overhang complementary to the ClaI overhang. (See Table 104.) This double stranded synthetic DNA is ligated at high molar ratio into the ClaI site of pEP1001. Competent delta4 cells are transformed with the ligated DNA and selected for ampicillin resistance. Plasmid DNAs prepared from $Amp^R$ clones are examined for the presence of SpeI, SfiI and HpaI restriction sites and for preferred orientation of the DNA insertion by HpaI-PvuI restriction analysis. The presence of the terminator is verified by DNA sequencing both strands by the Sanger dideoxy method using single stranded oligonucleotide sequencing primers complementary to pEP1001 DNA sequences on either side of the ClaI site. The 7.26 kb plasmid containing the insertion is designated pEP1002. (See FIG. 7.)

A third modification of the gal gene region is removal of the $P_1$ promoter upstream of the gal genes. A preferred promoter, the pBR322 amp gene promoter (HAWL83), and a test DNA binding sequence, phage lambda $O_R3$ (KIMJ87), are synthesized and inserted. Restriction sites that allow later promoter replacement in the development of heterodimeric DBPs are specifically included on this fragment. Plasmid pEP1002 DNA is restricted with DraIII and BamHI, and the larger 6.6 kb DNA fragment is isolated from the smaller 0.66 kb fragment by agarose gel electrophoresis, electroelution and chromatographic purification. DNA is synthesized, olig#3 and olig#4, containing the promoter sequence and test DNA binding sequence flanked by a single stranded 5' overhanging end complementary to the BamHI 5' overhang, a HpaI site, and an AoaI site at the upstream end, and at the downstream end by an XbaI restriction site and a single stranded 3' overhanging end complementary to the DraIII overhang. (See Table 100.)

Figure 8:
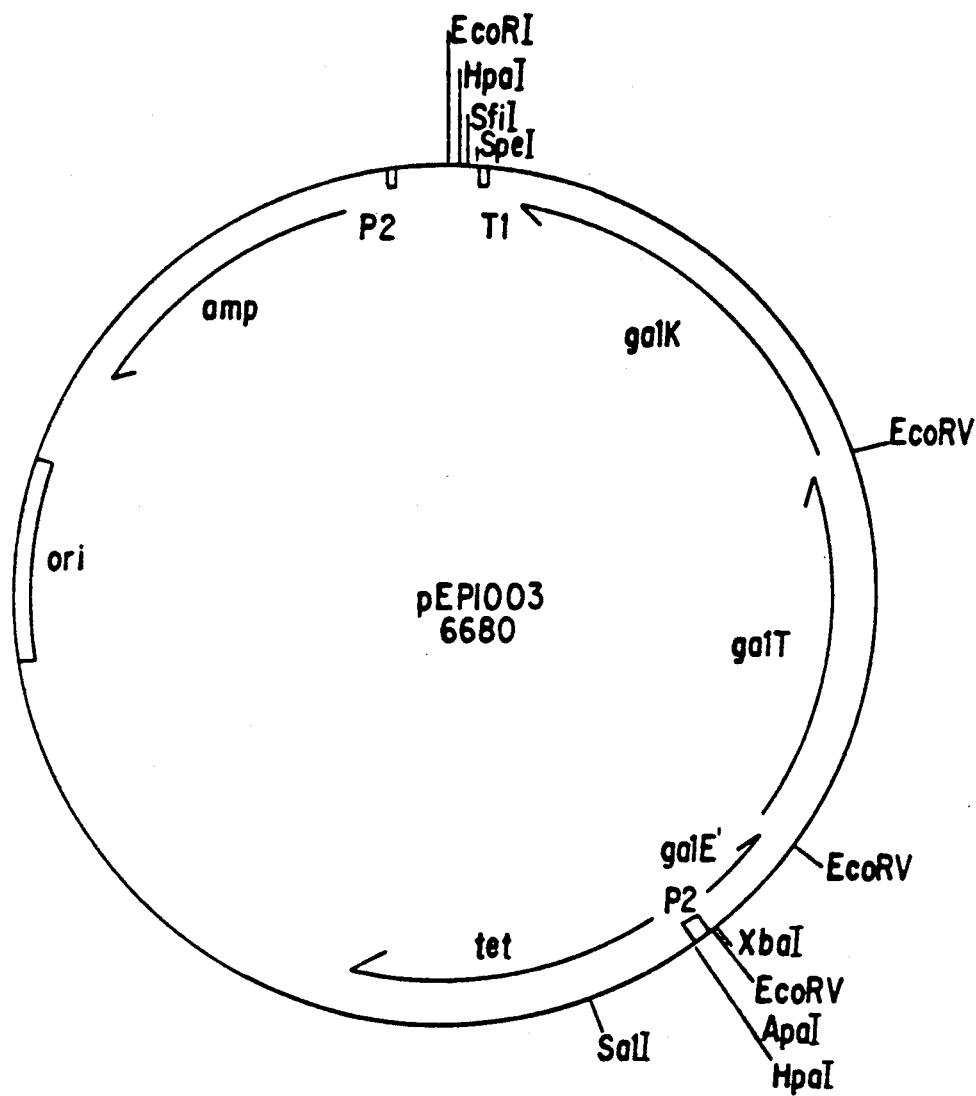
FIG. 8 Plasmid pEP1003.

This double stranded synthetic DNA is ligated, in high molar ratio, to the 6.6 kb pEP1002 fragment, competent delta4 cells are transformed, and $Amp^R$ colonies are tested for the $Gal^S$ phenotype to identify clones having functional galT and galK genes. Plasmid DNA from $Amp^R Gal^S$ clones are analyzed for insertion of the promoter DNA by EcoRV restriction digestion, and for the presence of new ApaI, HoaI, and XbaI restriction sites. The DNA sequence of both strands of the promoter insert is determined to verify that the promoter and DNA binding sites are present, using single stranded primers complementary to pEPI002 DNA sequences just outside of the DraIII and BamHI sites. The resulting 6.68 kb plasmid is designated pEP1003. (See FIG. 8.)

The gal genes with the promoter and the fd terminator are moved from pEP1003 into pKK175-6. Plasmid pEP1003 DNA is restricted with HpaI and the 2.69 kb gal gene DNA fragment is isolated from the remaining 3.99 kb fragment by agarose gel electrophoresis, electroelution and chromatographic purification. Plasmid pKK175-6 DNA is partially digested with DraI and full-length linearized plasmid is purified by agarose gel electrophoresis, electroelution, and chromatography. The blunt 2.69 kb pEPI003 DNA fragment containing the gal genes is ligated to the blunt linear pKK175-6 DNA preparation. Competent HB101 cells are transformed with the ligated DNA and selected for the $Amp^R$ Gal+ phenotype to obtain clones that have acquired a functional galK gene. Plasmid DNA from $Amp^R$ Gal+ clones are examined for the desired orientation of the gal genes (ori-galE'-galT-galK-amp), and for the presence of the cloning sites for dbp by double restriction with SpeI-PstI and SfiI-PstI. The resulting 7.05 kb plasmid is designated pEP1004. (See FIG. 9.)

Figure 10:
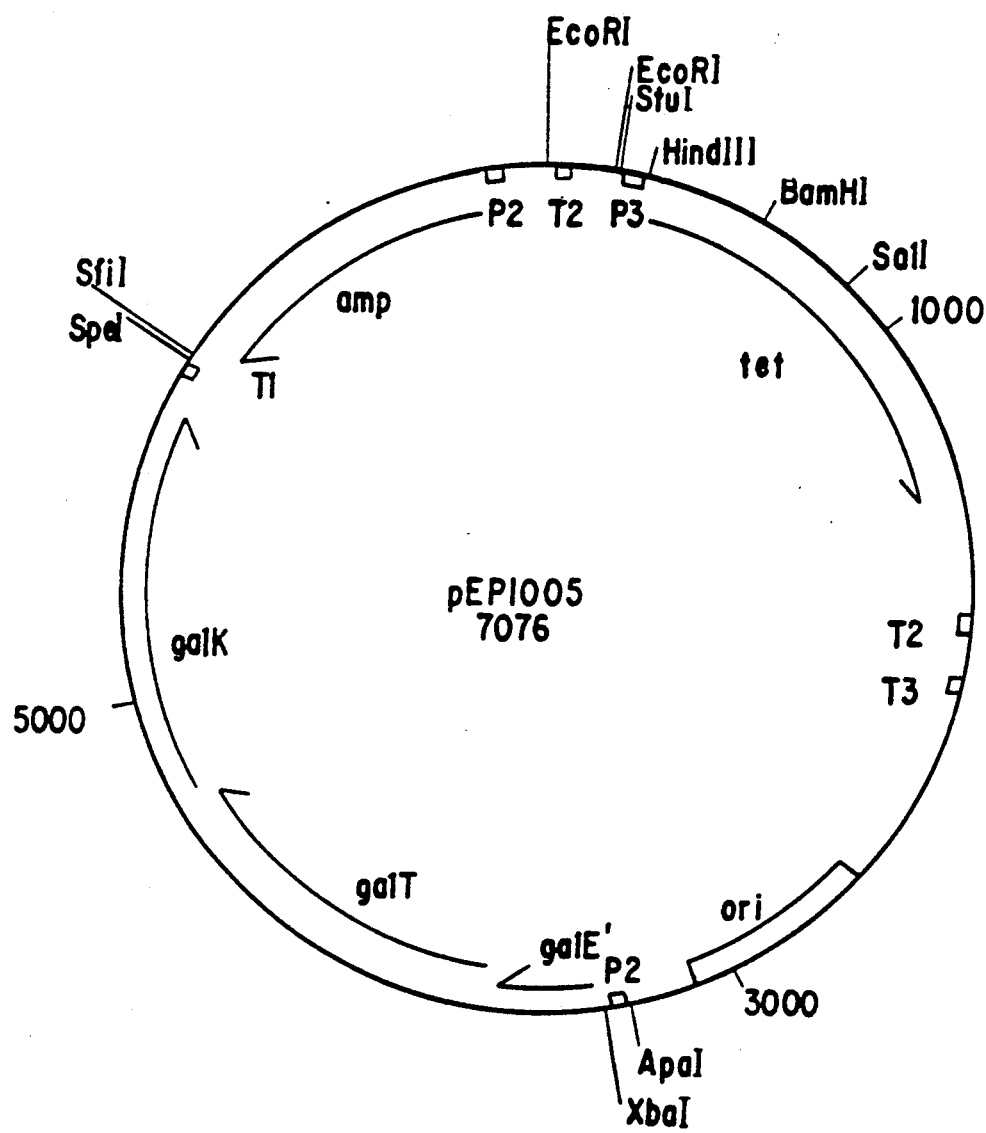
FIG. 10 Plasmid pEP1005.

The Tn5 neo gene promoter and the test DBP binding site, $O_R3$, are synthesized and inserted upstream of the tet coding region. The neo promoter-$O_R3$ DNA flanked by a StuI site upstream and a downstream HindIII site complementary 5' overhanging end is synthesized (olig#5 and olig#6 in Table 101). Plasmid pEP1004 DNA is restricted with HindIII and SmaI, the 7.03 kb large fragment is purified, and the double stranded promoter fragment is ligated to the 7.03 kb fragment at high molar ratio of insert to vector. Competent delta4 cells are transformed with the ligated DNA, and ampicillin resistant clones are tested for expression of tetracycline resistance and for sensitivity to galactose. Plasmid DNA from $Amp^R$ $Tet^R$ $Gal^S$ clones is analyzed for anserted EcoRVn the 0.62 kb EcoRI-EcoRV fragment of pEP1004 by double restriction using these two enzymes. The DNA sequence is determined for both strands at the site of the insert by the dideoxy method using synthesized oligonucleotide primers complementary to pEP1004 DNA just outside the SmaI and HindIII sites. The resulting 7.1 kb plasmid, with two separate selectable gene systems under control of two different promoters and the test DNA binding sequence, is designated pEP1005 (FIG. 10).

Section 3.3 Cloning the idbp gene

Prior to introducing the idbp gene into plasmid pEP1005, the BamHI site in the tet gene is removed from the tet gene in pEP1005 so that BamHI can be used in dbp mutagenesis. Plasmid pEP1005 DNA is restricted with EcoRV and linearized plasmid is purified. The linearized plasmid is then briefly digested with exonuclease III, sufficient to convert 10% of the plasmid to single stranded form. A 40 base oligonucleotide is synthesized as the mutagenesis primer to remove the BamHI recognition site from the tet gene and preserve the protein sequence of the tet gene product. In the middle of the 40 base primer sequence (olig#7) the ATC codon for isoleucine and the CTC codon for leucine located at the tet gene BamHI site ar changed to ATA and TTG, respectively. (See Table 105.) The remainder of the primer sequence is the same as in the tet gene. Following annealing of the primer to the partially single-stranded plasmid, Klenow polymerase fragment is used to restore the gapped DNA to double-stranded form. The double-stranded DNA is ligated and used to transform competent cells.

Following transformation and selection of $Amp^R$ $Tet^R$ colonies, plasmid DNA is prepared from clones selected for ampicillin and tetracycline resistance and tested positively for the $Gal^S$ phenotype. The DNA is analyzed for loss of the BamHI restriction site, and for presence of the HindIII, StuI, ApaI, XbaI, SpeI, and SfiI restriction sites by restriction digestion. The plasmid derivative of pEP1005 lacking the BamHI site is designated pEP1006.

Figure 11:
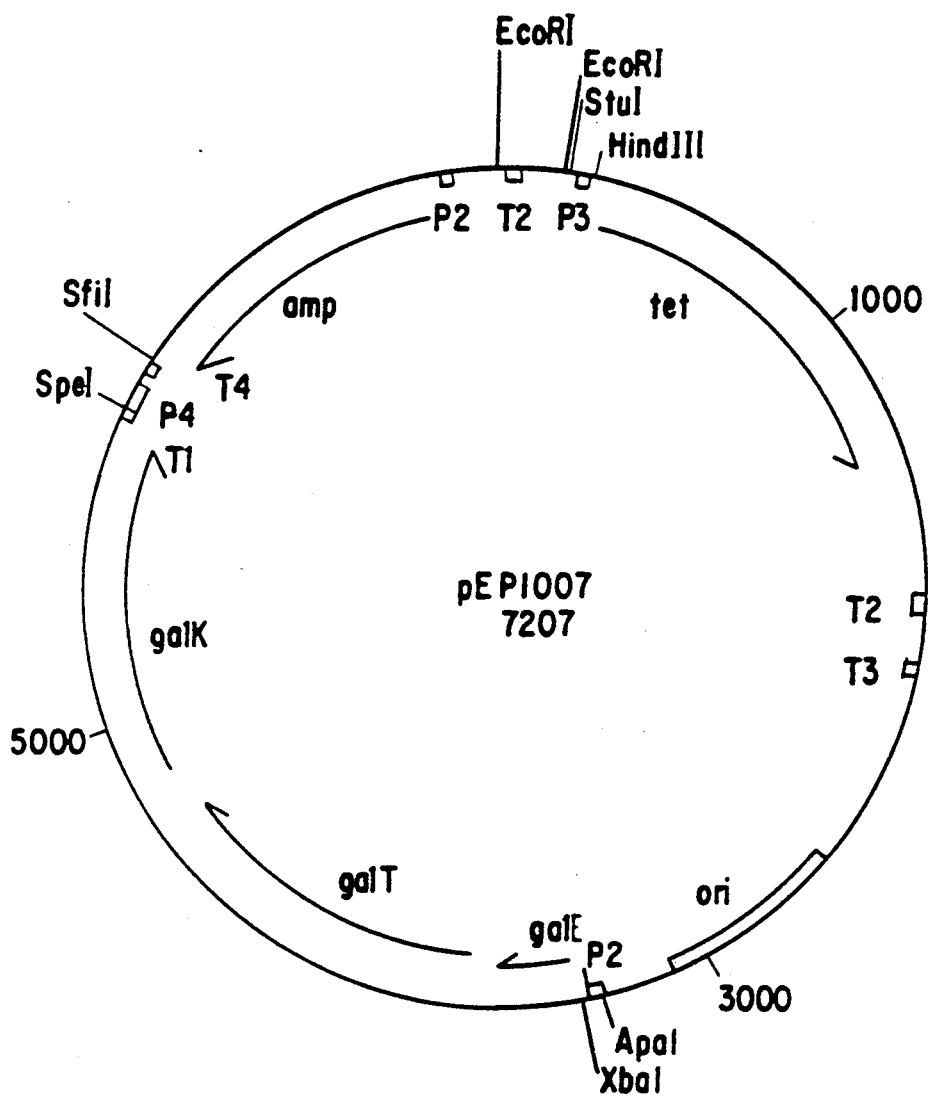
FIG. 11 Plasmid pEP1007.

Introduction of the idbp gene sequence is facilitated by synthesis and insertion of an oligonucleotide with restriction sites and transcriptional regulatory sequences for the gene into pEP1006. DNA containing the sequences of an SpeI site at one end, followed by sequences for the lacUV5 promoter (DEB083), a Shine-Dalgarno ribosome binding site, cloning sites for idbp sequence fragments, the trpa terminator sequence (ROSE79), and an SfiI restricted end complementary to the SfiI sequence of pEP1006 is synthesized as six, approximately 50 base long oligonucleotides. (See Table 106 and Table 107.) Three of the oligonucleotides comprise the non-coding strand of the composite DNA, and the other three the complementary coding strand. The sequences of four of the oligonucleotides are arranged so that the 5' end of each is complementary to a fragment different from the fragment to which its 3' end is complementary. The two oligonucleotides forming the 5' overhanging SpeI and SfiI ends of the composite DNA are each complementary to part of only one of the oligonucleotides forming the opposite strand. To assemble the composite DNA, the four oligonucleotides having 5' ends internal in the composite are phosphorylated, then mixed with the two other oligonucleotides and ligated as described by Theriault et al. (THER88). The resulting double stranded DNA fragment is ligated to SpeI-SfiI restricted pEPIO06 DNA. Competent delta4 cells are transformed with the ligated DNA and $Amp^R$ $Tet^R$ colonies are selected. Plasmid DNA is prepared from $Amp^R$ $Tet^R$ colonies displaying the $Gal^S$ phenotype, and is examined for the SpeI-SfiI insertion by restriction with SpeI, BstEII, BglII, KpnI, and SfiI. The inserted DNA is verified by DNA sequencing, and the 7.22 kb plasmid containing the proper insertion is designated pEPI007, shown in FIG. 11.

The idbp gene sequence specifying the Cro+protein and desigriated rav in this Example, is inserted in two cloning steps. The section of the rav sequence from the BstEII site to the BglII site is inserted first. (See Table 108 and Table 109.) A 74 base oligonucleotide, olig#14, is synthesized containing, from 5' to 3' end: 5 bases of spacer upstream of the BstEII site, a BstEII site and the rav gene sequence ending with the first base of codon 21. A 77 base oligonucleotide, olig#15, is also synthesized containing from 3' to 5' end: sequence complementary to the rav sequence second base of codon 17 through codon 42 which includes a BglII site spanning codons 39 through 41. The two nucleotides are annealed and the 3' termini extended using the Klenow enzyme to obtain double stranded DNA. The BglII and BstEII sites are then restricted, the resulting 123 base pair fragment is purified away from the end fragments, and is ligated to plasmid pEP1007 DNA that has been similarly restricted and purified. Competent delta4 cells are transformed with the ligated DNA, $Amp^R$ $Tet^R$ transformants are tested for the $Gal^S$ phenotype, and DNA from $Amp^R$ $Tet^R$ $Gal^S$ clones is analyzed for the BstEII-BglII insertion by restriction analysis. The DNA insert is then verified by DNA sequencing. The plasmid containing the appropriate partial rav sequence is designated pEP1008.

Figure 12:
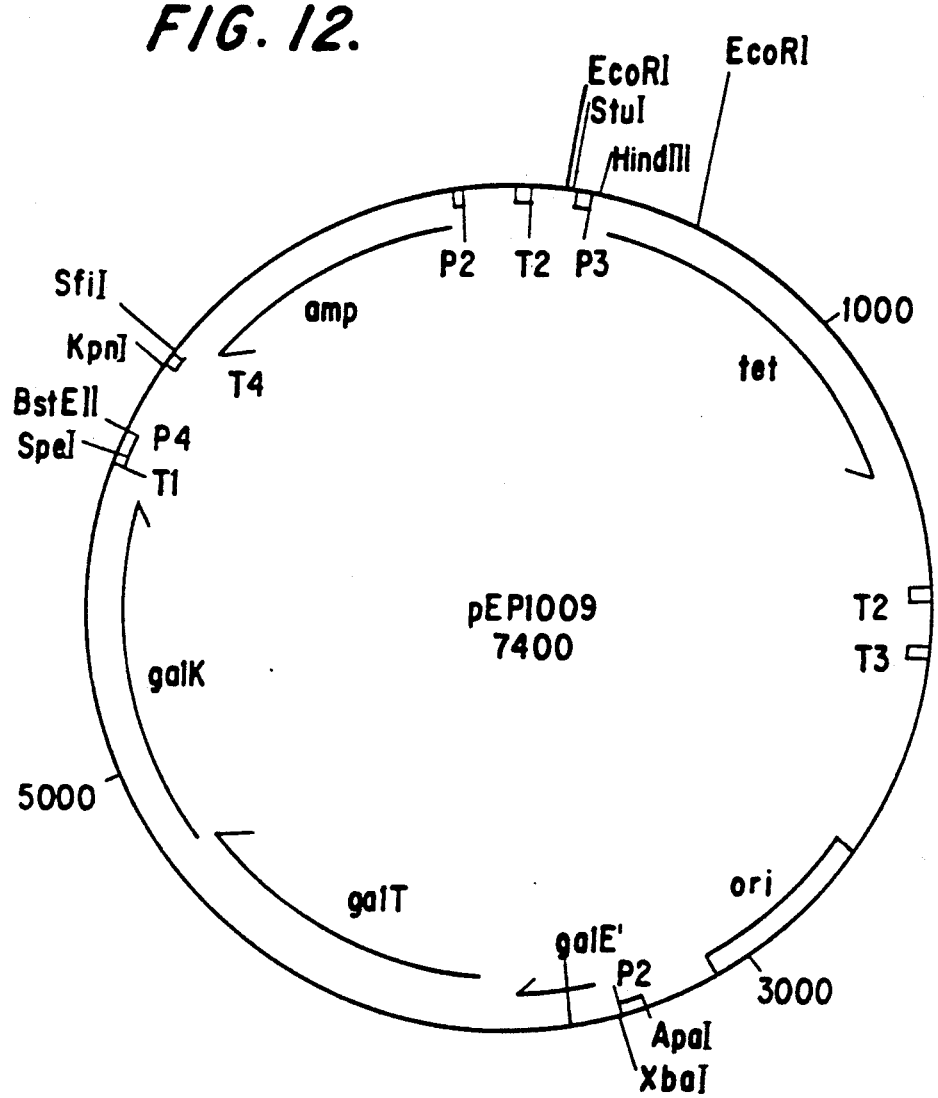
FIG. 12 Plasmid pEP1009.

The BglII-KpnI fragment of rav is synthesized and inserted in the same manner as the BstEII-BglII fragment. (See Table 110.) A 60 base oligonucleotide is synthesized containing from 5' to 3' the third base of rav codon 37 through the second base of codon 57. A 59 base oligonucleotide is also synthesized containing from 3' to 5': the third base of rav codon 53 through the three translational stop codons, a KpnI site and 5 bases of spacer. These two nucleotides are annealed and made double stranded as described above. The DNA is digested with BglII and KpnI, and the BglII-KpnI fragment is ligated to similarly digested pEP1008 DNA in the same manner as above, and competent delta4 cells are transformed. A plasmid containing the complete sequence for rav is isolated with $Amp^R$ selection, and with $Amp^R$ selection in conjunction with $Fus^R$ and $Gal^R$ selection. Plasmid DNA is characterized with BglII and KpnI, and DNA of clones carrying the predicted insert is sequenced. This plasmid carrying the complete rav gene is designated pEP1009, shown in FIG. 12. Further phenotypic tests for rav function are described in the next section.

Section 3.4 Determine Whether IDBP is Expressed

Plasmid pEP1009 carries the rav gene as demonstrated above by DNA sequence analysis. To determine whether cells carrying this plasmid display the phenotypes expected for rav expression, the delta4 strain bearing pEP1009 is tested on various ampicillin containing selective media in the presence and absence of IPTG. Cells are streaked on LB agar media containing either: a) tetracycline; b) fusaric acid; or c) galactose (see Section 2.1.1 above). Control strains are the delta4 host with no plasmid, and with pEP1005, pBR322, or pAA3H.

The results below indicate that the rav gene is expressed and the gene product is functional, and that expression is regulated by the lacUV5 promoter.

| | Growth of derivatives of strain delta4 on selective media (+ amp) | | | | | |
|---|---|---|---|---|---|---|
| | supplements: | | | | | |
| | tetracycline | | fusaric acid | | galactose | |
| | | | IPTG: | | | |
| plasmid: | + | − | + | − | + | − |
| — | − | − | − | − | − | − |
| pBR322 | + | + | − | − | + | + |
| pAA3H | − | − | + | + | − | − |

| | Growth of derivatives of strain delta4 on selective media (+ amp) | | | | | |
|---|---|---|---|---|---|---|
| | supplements: | | | | | |
| | tetracycline | | fusaric acid | | galactose | |
| | | | IPTG: | | | |
| plasmid: | + | − | + | − | + | − |
| pEP1009 | − | + | + | − | + | − |
| pEP1005 | + | + | − | − | − | − |

Additional verification is sought by cross-streaking phage lambda $cI^-$ phage with each of the above strains, on LB agar with ampicillin, and with and without IPTG. At sufficiently high intracellular levels of Cro protein, binding of the Cro repressor protein to the lambda phage operators $O_R$ and $O_L$ will prevent transcription from the early phage promoters $P_R$ and $P_L$, thus preventing phage growth. Data indicating correct expression and function of the rav gene are:

| | Growth of Lambda $cI^-$ on delta4 cells | |
|---|---|---|
| | phage growth | |
| plasmid | +IPTG | −IPTG |
| — | + | + |
| pEP1009 | − | + |
| pEP1005 | + | + |

These procedures indicate that the chosen IDBP, the product of the rav gene, is expressed and is successfully repressing both the test operators on the plasmid and the wild type operators on the challenge phage. In the next part, the genetic selections are optimized using these successfully functioning strains.

Section 3.4.2 DBP Purification

Proteins are purified as described by Leighton and Lu (LEIG87). Cell cultures in which DBP production has been induced during late log phase growth, are harvested by centrifugation. The cells are lysed using hen egg white lysozyme and sonication. Lysates are dialyzed against 20 mM potassium phosphate, 100 mM KCl, 2 mM EDTA pH 6.8. DBPs are purified from the dialyzed lysate by chromatography over a phosphocellulose column developed with a linear gradient of increasing KCl concentration (0.1 to 1.0M KCl). Gradient fractions are assayed for DBP activity by the filter binding and electrophoretic gel retardation assays described in Sections 3.5 of this Example and in the Detailed Description of the Invention.

Section 3.5 Quantitation of DBP Binding

We measure DBP binding to the target operator DNA sequence with a filter binding assay, initially using filter binding assay conditions similar to those described for lambda Cro (KIMJ87). The target DNA for the assay is the 113 base pair ApaI-RsaI fragment from plasmid pEP1009 containing the lambda $O_R3$ binding site. A control DNA fragment of the same size, used to determine non-specific DNA binding, contains a synthetic ApaI-XbaI DNA fragment specifying the amp promoter and the sequence

5' CTTATACACGAAGCGTGACAA 3'.

This sequence preserves the base content of the $O_R3$ sequence but lacks several sites of conserved sequence required for lambda Cro binding (KIMJ87) and is cloned between the ApaI-XbaI sites of the pEP1009 backbone to yield pEP1010.

Target DNA is end labeled with [gamma-$^{32}$P]ATP and T4 polynucleotide kinase (MAXA80). Initially, we use labeled DNA at 10 pM in 100 ul of assay buffer (10 mM Tris, pH=7.5, 0.2 mM EDTA, 0.1M KCl, 50 ug bovine serum albumin per ml). Further optimization is achieved by altering the pH or ionic strength the assay buffer. The assays are carried out in plastic tubes at 37° C. DBP from cell extracts is added to the assay solution at final concentrations between $10^{-13}$M and $10^{-3}$M depending on binding affinity and solubility of the protein. After a 15 min incubation, the assay solutions are filtered through Schleicher and Schuell nitrocellulose membrane filters (BA-85 0.22um, previously soaked in wash buffer, assay buffer without bovine serum albumin, for 15 min). The samples are filtered in 4 to 5 seconds with suction and are washed with three volumes (300 ul) of wash buffer. The filters are dried, counted by liquid scintillation, and the data analyzed according to RIGG70 and KIMJ87.

Part IV

Section 4.1 Media Formulations

Galactose sensitivity is demonstrable in LB agar and broth at very low concentrations (0.2% galactose), and is optimal at 2 to 8% galactose. Galactose and tetracycline selections are performed in LB medium. Fusaric acid sensitivity is best achieved in the medium described by Maloy and Nunn (MALO81, Section 2.1.1) for *E. coli* K-12 strains.

Section 4.2 Induction of DBP Expression

In this Example, the pdbp gene is regulated by the lacUV5 promoter. Optimal induction is achieved by addition of IPTG at $5 \times 10^{-4}$M (MAUR80). Subsequent experimentation for each successful DBP determines the lowest concentration that is sufficient to maintain repression of the selection system genes.

Section 4.3 Optimization of Selections

For each individual selective medium used to detect IDBP function, factors are varied to obtain a maximal number of transformants per plate and with a minimal number of false positive artifactual colonies. Of greatest importance in this optimization is the transcriptional regulation of the initial potential-DBP, such that in further mutagenesis studies, de novo binding at an intermediate affinity is compensated by high level production of DBP.

Section 4.4 Regulation of IDBP

Cells carrying pEP1009 are grown in LB broth with $10^{-6}$, $5 \times 10^{-6}$, $10^{-5}$, $5 \times 10^{-5}$, $10^{-4}$ and $5 \times 10^{-4}$M IPTG. Samples are plated on LB agar and on LB agar containing fusaric acid or galactose as described in Section 2.1.1. All media contain 200 ug/ml ampicillin, and the IPTG concentration of the broth culture media are maintained in the respective selective agar media.

The IPTG concentration at which 50% of the cells survive is a measure of affinity between IDBP and test operator, such that the lower the concentration, the greater the affinity. A requirement for low IPTG, e.g. $10^{-6}$M, for 50% survival due to Rav protein function suggests that use of a high level, e.g. $5 \times 10^{-4}$M IPTG, employed in selective media to isolate mutants displaying de novo binding of a DBP to target DNA, will enable isolation of successful DBPs even if the affinity is low.

Section 4.5. Concentration of Selective Agents and Cell Inoculum Size

The quantity of toxic agents in selective media, and the cell inoculum input per plate determines the survival of cells on the medium. Fusaric acid and galactose content of each medium is varied, to allow the largest possible cell sample to be applied per Petri plate. This objective is obtained by applying samples of large numbers of sensitive cells (e.g. $5 \times 10^7$, $10^8$, $5 \times 10^8$) to plates with elevated fusaric acid or galactose. Resistant cells are then used to determine the efficiency of plating. An acceptable efficiency is 80% viability for the resistant control strain bearing pEP1009 in a delta4 background. The total cell inoculum size is increased as is the level of inhibitory compound until viability is reduced to less than 80%.

The system is ready to be applied to a target natural DNA sequence, taken from a target gene to be repressed to fit the needs of the user of this process.

Part V

Section 5.1 Choice and Cloning of Target Sequences

In this Example, sequences of the human immunodeficiency virus type 1 (HIV-1) genome are searched for potential target sequences. The known sequences of isolates of HIV-1 are obtained from the GENBANK version 52.0 DNA sequence data base. The first step in the target sequence search is to find non-variable regions of DNA sequence. We examine the HIV-1 genome from the TATA sequence in the 5'LTR of the HIV-1 genome which is the starting control region for transcription of all HIV-1 mRNAs. We continue downstream through U3' R and U5 regions of the 5'LTR, the tRNA lysine homology and leader sequences, the gag and pol polyprotein sequences, the sor gene, to the end of the sequence coding for the tat and trs second exons. Our intent is to locate non-variable regions to be used to interfere with the production of tat and/or trs mRNA because the products of these genes are essential in production of virus (DAYT86, FEIN86).

We choose the sequence of HIV-1 isolate HXB2 (RATN85) from nucleotide number through 6100 is chosen as the reference sequence for an alignment search of the sequences of all other HIV-1 isolates. The search employs the Nucleic Acid Database Search program in the IBI/Pustell Sequence Analysis Programs software package (International Biotechnologies, Inc., New Haven, Conn.), which is based on the FASTN program, derived from the FASTP program of Lipman and Pearson (LIPM85). All stretches of at least 20 bases which have no variation in sequence among all HIV-1 isolates are retained as potential regions for locating target binding sites.

From the alignment search, segments of the HIV-1 isolate HXB2 sequence that are non-variable among all HIV-1 sequences searched are:

| | | | |
|---|---|---|---|
| 350–371, | 519–545, | 623–651, | 679–697, |
| 759–781, | 783–805, | 1016–1051, | 1323–1342, |
| 1494–1519, | 1591–1612, | 1725–1751, | 1816–1837, |
| 2067–2094, | 2139–2164, | 2387–2427, | 2567–2606, |
| 2615–2650, | 2996–3018, | 3092–3117, | 3500–3523, |
| 3866–3887, | 4149–4170, | 4172–4206, | 4280–4302, |
| 4370–4404, | 4533–4561, | 4661–4695, | 4742–4767, |

| | | | |
|---|---|---|---|
| 4808–4828, | 4838–4864, | 4882–4911, | 4952–4983, |
| 5030–5074, | 5151–5173, | 5553–5573, | 5955–5991 |

In the present Example, these potential regions are searched for subsequences matching the central seven base pairs of the lambda operators that have high affinity for lambda Cro (viz. $O_R3'$ the symmetric consensus, and the Kim et al. consensus (KIMJ87)). The consensus sequence used by Kim et al. has higher affinity for Cro than does $O_R3$ which is the natural lambda operator having highest affinity for Cro. Cro is thought to recognize seventeen base pairs, with side groups on alpha 3 directly contacting the outer four or five bases on each end of the operator. Because the composition and sequence of the inner seven base pairs affect the position and flexibility of the outer five base pairs to either side, these bases affect the affinity of Cro for the operator.

The sequences sought are shown in Table 111. The letters "A" and "S" stand for antisense and sense. "$O_R3A$/Symm. Consensus.5" is a composite that has $O_R3A$ at all locations except 5, where it has the symmetric consensus base, C. Similarly, "$O_R3A$/Symm. Consensus.6" has the symmetric consensus base at location 6 and $O_R3A$ at other locations.

A FORTRAN program written for the MicroVAX II searches the non-variable HIV-1 subsequence segments for stretches of seven nucleotides of which at least five are G or C and which are flanked on either side by five bases of non-variable HIV-1 subsequence. The 427 candidate seven-base-pair subsequences obtained using these constraints on CG content are then searched for matches to either the sense or anti-sense strand sequences of the five seven-base-pair subsequences listed above. None of the HIV-1 subsequences was identical to any of the seven-base-pair subsequences. Three HIV-1 subsequences, shown in Table 112, were found that match six of seven bases. Eight subsequences, shown in Table 113' were found that match five out of seven bases and that have five or more GC base pairs. These HIV-1 subsequences are less preferred than the HIV-1 subsequences that match six out of seven bases.

```
                          |
                           1 1 1 1 1 1 1 1
         1 2 3 4 5 6 7 8 9 0 1 2 3 4 5 6 7
     5' a Ct TTc c GCTg g GGa Ct      Bases 353-369
        a c t t t cc GCTg g a a a g t  Left symmetrized
        a g t c c cc GCTg g g g a c t  Right symmetrized
        t a t c Ac CGCAAg Gg a t a     O_R3
```

(Lower case letters are palindromic in the two halves of the targets and $O_R3$; bold bases are highly conserved.)

Among the outer five bases of each half operator, bases 1 and 3 are palindromically related to bases 17 and 15 in Target HIV 353-369.

```
                    |
        TCTCGAc GCAg GACTCG       Bases 681-697
        t c t c g Ac GCAg Gc g a g a   Left symmetrized
        c g a g t Ac GCAg Ga c t c g   Right symmetrized
        t a t c Ac CGCAAg Gg a t a     O_R3
```

None of bases 1-5 are palindromically related to bases 13-17 in Target HIV 681-697.

```
                    |
        TTTGAcTAGCGgAGGCT         Bases 760-776
        t t t g a cTAGCGg t c a a a    Left symmetrized
        a g c c t cTAGCGg a g g c t    Right symmetrized
        t a t c AcCGCAAgGg a t a       O_R3
```

None of bases 1-5 are palindromically related to bases 13-17 in Target HIV 760-776.

Consider the relative importance of each nucleotide in the lambda operators to recognition and binding by the lambda regulatory proteins. There is extensive sequence variability among the twelve phage operator half-sites. For example:

```
                    |
        tAtCaCCGCCGGt GaTa    Consensus
        tAtCaCCGCa a GgGaTa   O_R3A
```

The bases in lower case in Consensus and $O_R3$ sequences shown above are more variable among various lambdoid operators than are bases shown by upper case letters. Studies of mutant operators indicate that A2 and C4 are required for Cro binding. In Target HIV 353-369, bases T3, C6, C7, G8, C9, G14, and A15 match the symmetric consensus sequence, but the highly conserved A2 and C4 are different from lambdoid operators and Cro will not bind to these subsequences. Mutagenesis of the DNA-contacting residues of alpha 3 is the first step in producing a DBP that recognizes the left symmetrized or right symmetrized target sequences.

Target HIV 353-369 is a preferred target because the core (underlined above) is highly similar to the Kim et al. consensus. Target HIV 760-776 is preferred over Target HIV 681-697 because it is highly similar to $O_R3$.

The method of the present invention does not require any similarity between the target subsequence and the original binding site of the initial DBP. The fortuitous existence of one or more subsequences within the target genes that has similarity to the original binding site of the initial DBP reduces the number of iterative steps needed to obtain a protein having high affinity and specificity for binding to a site in the target gene.

Since the target sequence is from a pathogenic organism, we require that the chosen target subsequence be absent or rare in the genome of the host organism, e.g. the target subsequences chosen from HIV should be absent or rare in the human genome.

Candidate target binding sites are initially screened for their frequency in primate genomes by searching all DNA sequences in the GENBANK Primate directory (2,258,436 nucleotides) using the IBI/Pustell Nucleic Acid Database Search program to locate exact or close matches. A similar search is made of the E. coli sequences in the GENBANK Bacterial directory and in the sequence of the plasmid containing the idbp gene. The sequences of potential sites for which no matches are found are used to make oligonucleotide probes for Southern analysis of human genomic DNA (SOUT75). Sequences which do not specifically bind human DNA are retained as target binding sequences.

The HIV 353-369 left symmetrized and right symmetrized target subsequences are inserted upstream of the selectable genes in the plasmid pEP1009, replacing the test sequences, to produce two operative cloning vectors, pEP1011 and pEP1012, for development of Rav$_L$ and Rav$_R$ DBPs. The promoter-test sequence cassettes upstream of the tet and gal operon genes are excised using StuI-HindIII and ApaI-XbaI restrictions, respectively. Replacement promoter-target sequence cassettes are synthesized and inserted into the vector, replacing O$_R$3 with the HIV 353-369 left or right symmetrized target sequence in the sequences shown in Table 100 and Table 101.

Part VI

Section 6 1 Choice of Residues in Cro to Vary

The choice of the principal and secondary sets of residues depends on the goal of the mutagenesis. In the protocol described here we vary, in separate procedures, the residues: a) involved in DNA recognition by the protein, and b) involved in dimerization of the protein. In this section we identify principal and secondary sets of residues for DNA recognition and dimerization.

Section 6.2.1 Pick Principal Set for DNA-recognition

The principal set of residues involved in DNA-recognition is conveniently defined as those residues which contact the operator DNA in the sequence-specific DNA-protein complex. Although a crystal structure of the lambda Cro-operator DNA complex is not available, the crystal structure of the complex between the structural homolog 434 repressor N-terminal domain and a consensus operator has been described (ANDE87). The crystal structure of the Cro protein dimer has been determined (ANDE81) and modeling studies have suggested residues that can make sequence-specific or sequence-independent contacts with DNA in the sequence-specific complex (TAKE83' OHLE83' TAKE85' TAKE86). Finally, isolation and characterization of Cro mutants have identified residues which contact DNA in protein-operator complexe's (PAKU86, HOCH86a,b, EISE85).

Important contacts with DNA are made by protein residues in and around the H-T-H region and in the C-terminal region. Hochschild et al. (HOCH86a,b) have presented direct evidence that Cro alpha helix 3 residues S28, N31, and K32 make sequence-specific contacts with operator bases in the major groove. Mutagenesis experiments (EISE85' PAKU86) and modeling studies (TAKE85) have implicated these residues as well. In addition, these studies suggest that H-T-H region residues Q16, K21, Y26, Q27, H35, A36, R38, and K39 also make contacts with operator DNA. In the C-terminal region, mutagenesis experiments (PAKU86) and chemical modification studies (TAKE86) have identified K56, and K62 as making contacts to DNA. In addition, computer modeling suggests that the 5 to 6 C-terminal amino acids of lambda Cro can contact the DNA along the minor groove (TAKE85). From these considerations, we select the following set of residues as a principal set for use in variegation steps intended to modify DNA recognition by Cro or mutant derivative proteins: 16, 21, 26, 27, 31, 32, 35, 36, 38, 39, 56, 62, 63, 64, 65, 66.

Section 6.2.2 Pick Secondary Set for DNA Recognition

The residues in the secondary set contact or otherwise influence residues in the principal set. A secondary set for DNA recognition includes the buried residues of alpha helix 3: A29, I30, A33, and I34. Interactions between buried residues in alpha helix 2 and buried residues in alpha helix 3 are known to stabilize H-T-H structure and residues in the turn between alpha helix 2 and alpha helix 3 of H-T-H proteins are conserved among these proteins (PTAS86 p102). In lambda Cro these positions are T17, T19, A20, L23, G24, and V25. Changes in the dimerization region can influence binding. In lambda Cro, residues thought to be involved in dimer stabilization are E54, V55, and F58 (TAKE85, PAB084). Finally, residues influencing the position of the C-terminal arm of lambda Cro are P57, P59, and S60. Thus the secondary set of residues for use in variegation steps intended to modify DNA recognition by lambda Cro or Rav proteins is: 17, 19, 20, 23, 24, 29, 30, 33, 34, 54, 55, 57, 58, 59 and 60.

Section 6 2.3 Pick Principal Set for Dimerization

Different principal and secondary sets of residues must be picked for use in variegation steps intended to alter dimer interactions. In lambda Cro, antiparallel interactions between E54, V55, and K56 on each monomer have been proposed to stabilize the dimer (PAB084). In addition, F58 from one monomer has been suggested to contact residues in the hydrophobic core of the second monomer. Inspection of the 3D structure of lambda Cro suggests important contacts are made between F58 of one monomer and I40, A33, L23' V25, E54, and A52. In addition, residues L7, I30, and L42 of one monomer could make contact with a large side chain positioned at 58 in the other monomer. Thus, a set of principal residues includes: 7, 23, 25, 30, 33, 40, 42, 52, 54, 55, 56, and 58.

Section 6.2.4 Pick Secondary Set for Dimerization

The secondary set of residues for variegation steps used to alter dimer interactions includes residues in or near the antiparallel beta sheet that contains the dimer forming residues. Residues in this region are E53, P57, and P59. Residues in alpha helix 1 influencing the orientation of principal set residues are K8, A11, and M12. Residues in the antiparallel beta sheet formed by the beta strands 1, 2, and 3 (see Table 1) in each monomer also influence residues in the principal set. These residues include I5' T6, K39, F41, V50, and Y51. Thus the set of secondary residues includes: 5, 6, 8, 11, 12, 41, 50, 51, 53, 57, and 59.

Section 6.2.5 Pick the Range of Variation for Alteration of DNA Binding

For the initial variegation step to produce a modified Rav protein with altered DNA specificity a set of 5 residues from the principal set will be picked. Focused Mutagenesis will be used to vary all five residues through all twenty amino acids. The residues will be picked from the same interaction set so that as many as $3.2\times10^7$ different DNA binding surfaces will be produced.

A number of studies have shown that the residues in the N-terminal half of the recognition helix of an H-T-H protein strongly influence the sequence specificity and strength of protein binding to DNA (HOCH86a,b, WHAR85' PAB084). For this reason we choose residues Y26, Q27, S28, N31, and K32 from the principal set as residues to vary in the first variegation step. Using the optimized nucleotide distribution for Focused Mutagenesis described in Detailed Description of the Invention, and assuming that $S_{err}=5\%$ as defined at the start of this Example, the parental sequence is present in the variegated mixture at one part in $3.1\times10^5$ and the least favored sequence, F at each residue, is present at one part in $10^8$. Thus, this level of variegation is well within bounds for a synthesis, ligation, transformation, and selection system capable of examining $5 \times 10^8$ DNA sequences.

Section 6.2.6 Pick the Range of Variation of Residues for Alteration of Dimerization As described in Part VI of the Detailed Description and in Section 6.3 of this Example, altered lambda Cro proteins, $Rav_L$ and $Rav_R$, which bind specifically and tightly to left and right symmetrized targets derived from HIV 353-369, are first developed through one or more variegation steps. Site-specific changes are then engineered into $rav_L$ to produce dimerization defective proteins. Structure-directed Mutagenesis is performed on $rav_R$ to produce mutations in $Rav_R$ that can complement dimerization defective $Rav_L$ proteins and produce obligate heterodimers that bind to HIV 353-369.

One of the interactions in the dimerization region of lambda Cro is the hydrophobic contact between residues V55 of both monomers. The VF55 mutation substitutes a bulky hydrophobic side group in place of the smaller hydrophobic residue; other substitutions at residue 55 can be made and tested for their ability to dimerize. A small hydrophobic or neutral residue present at residue 55 in a protein encoded on expression by a second gene may result in obligate complementation of VF55. In addition, changes in nearby components of the beta strand, E53, E54, K56, and P57 may effect complementation. Thus a set of residues for the initial variegation step to alter the $Rav_R$ dimer recognition is 53, 54, 55, 56, and 57.

Another interaction in the dimerization region of lambda Cro is the hydrophobic contact between F58 of one monomer with the hydrophobic core of the other monomer. As mentioned above residues L7, L23, V25, A33, I40, L42, A52, and E54 of one monomer all could make contacts with a large residue at position 58 in the other monomer. The FW58 mutation inserts the largest aromatic amino acid at this position. Compensation for this substitution may require several changes in the hydrophobic core of the complementing monomer. Residues for Focused Mutagenesis in the initial variegation step to alter $Rav_R$ dimer recognition in this case are: 23, 25, 33, 40, and 42.

In each of the two cases described above, the initial variegation step involves Focused Mutagenesis to alter 5 residues through all twenty amino acids. As was shown in Section 6.2.5' this level of variegation is within the limits set by using optimized codon distributions and the values for $S_{err}$ and transformation yield assumed at the start of this Example.

Section 6.3 Mutagenesis of DNA

In Section 6.2.5 we selected a set of 5 residues in lambda Cro, Y26, Q27, S28, N31, and K32, for Focused Mutagenesis in the first variegation step to produce $Rav_L$ and $Rav_R$. These 5 residues are contained in a 51 base pair PpuMT to BglII fragment of the rav gene constructed in Section 3.3 of this Example. To produce the cassette containing the variegated codons we synthesize the 66 nucleotide antisense variegated strand, olig#50:

```
               d   l   g   v   X   X   X   a   i   X
               22  23  24  25  26  27  28  29  30  31
5' t cct aAG GAC CTA GGG GTG fzk fzk fzk GCG ATT fzk
          ↑  PpuM I ↑

X   a   i   h   a   g   r   k   i
32  33  34  35  36  37  38  39  40
fzk GCC ATC CAT GCC GGC CGA AAG ATC Tt 3' olig#50
                             ↑ Bgl II ↑
```

The position of the amino acid residue in lambda Cro is shown above the codon for the residue. Unaltered residues are indicated by their lower case single letter amino acid codes shown above the position number. Variegated residues are denoted with an upper case, bold X. The restriction sites for PpuMI and BglII are indicated below the sequence. Since restriction enzymes do not cut well at the ends of DNA fragments, 5 extra nucleotides have been added to the 5' end of the cassette. These extra nucleotides are shown in lower case letters and are removed prior to ligating the cassette into the operative vector. The one nucleotide 3' extension increases the palindrome at the BglII site to 8 base pairs, and this sequence is used for self-annealing. The sequence "fzk" denotes the variegated codons and indicates that nucleotide mixtures optimized for codon positions 1, 2, or 3 are to be used. "f" is a mixture of 26% T, 18% C, 26% A, and 30% G, producing four possibilities. "z" is a mixture of 22% T, 16% C, 40% A, and 22% G, producing four possibilities. "k" is an equimolar mixture of T and G, producing two possibilities. Each "fzk" codon produces $4\times4\times2=2^5=32$ possible DNA sequences, coding on expression for 20 possible amino acids and stop. The DNA segment above comprises $(2^5)^5=2^{25}=3.2\times10^7$ different DNA sequences coding on expression for $20^5=3.2\times10^6$ different protein sequences.

After synthesis and purification of the variegated DNA, the strands are self-annealed and the resulting superoverhang is filled in using Klenow fragment as described by Hill (AUSU87, Unit 8.2). The double stranded oligonucleotide is digested with the enzymes PpuMI and BglII and the mutagenic cassette is purified as described by Hill. The mutagenic cassette is cloned into the vectors pEP1011 and pEP1012 which have been digested with PpuMI and BamHI, and the ligation mixtures containing variegated DNA are used to transform competent delta4 cells. The transformed cells are selected for vector uptake and for successful repression at low stringency as described in Section 4.4 of this Example. Cells containing Rav proteins that bind to the left or right symmetrized targets display the $Tet^S$, $Fus^R$ and $Gal^R$ phenotypes.

Surviving colonies are screened for correct DBP+and DBP−phenotypes in the presence or absence of IPTG as described in Section 3.4 of this example. Relative measures of the strengths of DBP-DNA interactions in vivo are obtained by comparing phenotypes exhibited at reduced levels of IPTG. DBP genes from clones exhibiting the desirable phenotypes are sequenced. Plasmid numbers from pEP1100 to pEPI199 are reserved for plasmids yielding $rav_L$ genes encoding proteins that bind to the Left Symmetrized Targets carried on the plasmids. Similarly, plasmid numbers pEP1200 through pEP1299 plasmids containing $rav_R$ genes encoding proteins that bind to the Right Symmetrized Targets carried on these plasmids.

Based on the determinations above, one or more Rav$_L$ and Rav$_R$ proteins are chosen for further analysis in vitro. Proteins are purified as described in Section 3.4.2 of this Example. Purified DBPs are quantitated and characterized by absorption spectroscopy and polyacrylamide gel electrophoresis.

In vitro measurements of protein-DNA binding using purified DBPs are performed as described in the Overview: DNA-Binding, Protein Purification, and Characterization and in Sections 3.5 of this Example. These measurements will be used to determine equilibrium binding constants (K$_D$), and the dissociation (k$_d$) and association (k$_a$) rate constants for sequence-specific and sequence-independent DBP-DNA complexes. In addition, DNase protection assays are used to demonstrate specific DBP binding to the Target sequences.

Estimates of relative DBP stability are obtained from measurements of the thermal denaturation properties of the proteins. In vitro measures of protein thermal stability are obtained from determinations of protein circular dichroism and resistance to proteolysis by thermolysin a various temperatures (HECH84) or by differential scanning calorimetry (HECH85b). An in vivo measure of DBP thermal stability can be obtained by observing cellular resistance to lambda phage infection when cells containing DBPs are plated in the presence of the phage at temperatures between 25° C. and 45° C. (HECH84). DBPs that are resistant to thermal denaturation are preferred.

One or more iterations of variegation, involving residues thought capable of influencing DNA binding, of the rav$_L$ and rav$_R$ genes produce Rav$_L$ and Rav$_R$ proteins that bind tightly and specifically to the HIV 353-369 left and right symmetrized targets. Additional variegation steps, to optimize protein binding properties can be performed as outlined in the Overview: Variegation Strategy.

By hypothesis, we isolate pEPI127 that contains a pdbp gene that codes on expression for Rav$_L$-27, shown in Table 114, that binds the left-symmetrized target best among selected Rav$_L$ proteins. Similarly, pEP1238 contains a pdbp gene that codes on expression for Rav$_R$-38, shown in Table 115, that binds the right-symmetrized target best among selected Rav$_R$ proteins.

In the steps to follow (Sections 6.6 and 6.7), we use the genes for the Rav$_R$ and Rav$_L$ monomers as starting points for production of obligately heterodimeric proteins Rav$_L$:Rav$_R$ that recognize the HIV 353-369 target. In initial genetic engineering steps we change the target sequences in pEP1238 (containing rav$_R$-38). We replace both occurrences of the Right Symmetrized Target (in tet and galT,K promoters, see Section 5.1) with the HIV 353-369 target sequence. Delta4 cells containing plasmids carrying the HIV 353-369 targets will display the Amp$^R$, Tet$^R$, Fus$^S$ and Gal$^S$ phenotypes. Plasmids carrying HIV 353-369 targets and the rav$_R$ gene are designated by numbers pEP1400 through pEP1499 and corresponding to the number of the donor plasmid of the 1200 series; for example, replacing the target sequences in pEP1238 produces pEP1438.

Section 6.6: Engineering Dimerization Mutants of Rav$_L$

To create the site specific VF55 and FW58 mutations in rav$_L$ we synthesize the two mutagenesis primers:

```
       a   e   e   f   k   p   f
       52  53  54  55  56  57  58
5'     GGC GAA GAG TTC AAG CCC TTC    3'  VF55
primer v   k   p   w   p   s   n
       55  56  57  58  59  60  61
5'     GTA AAG CCC TGG CCC AGT AAC    3'  FW58
primer
```

Underlining indicates the varied codons and residues. The plasmid pEP1127 (containing rav$_L$-27) is chosen for mutagenesis. The gene fragment coding on expression for the carboxy-terminal region of the Rav$_L$ protein is transferred into M13mp18 as a BamHI to KpnI fragment. Oligonucleotide-directed mutagenesis is performed as described by Kunkel (AUSU87, Unit 8.1). The fragment bearing the modified region of Rav$_L$ is removed from M13 RF DNA as the BamHI to KpnI fragment and ligated into the correct location in the pEP1100 vector. Mutant-bearing plasmids are used to transform competent cells. Transformed cells are selected for plasmid uptake and screened for DBP$^-$phenotypes (Tet$^R$, Fus$^S$, and Gal$^s$ in E. coli delta4; Gal$^+$in E. coli HB101). Plasmids isolated from DBP$^-$cells are screened by restriction analysis for the presence of the rav$_L$ gene and the site-specific mutation is confirmed by sequencing. The plasmid containing the rav$_L$-27 gene with the VF55 mutation is designated pEP1301. Plasmid pEP1302 contains the rav$_L$-27 gene with the FW58 alteration.

For the production of obligate heterodimers as described in the next Section, the rav$_L$$^-$genes encoding the VF55 or FW58 mutations are excised from pEP1301 or pEP1302 and are transferred into plasmids containing the gene for kanamycin and neomycin resistance (neo, also known as npt II). These constructions are performed in three steps as outlined below. First, the neo gene from Tn5 coding for kanamycin resistance and contained on a 1.3 Kbp HindIII to SmaI DNA fragment is ligated into the plasmid pSP64 (Promega, Madison, Wis., USA) which has been digested with both HindIII and SmaI. The resulting 4.3 kbp plasmid, pEP1303, confers both ampicillin and kanamycin resistance on host cells. Next, the ampicillin resistance gene is removed from pEP1303 by digesting the plasmid with AatII and BglI. The 3.5 Kbp fragment resulting from this digest is purified, the 3' overhanging ends are blunted using T4 DNA polymerase (AUSU87, Unit 3.5), and the fragment is recircularized by ligating the resulting blunt ends. This plasmid is designated pEP1304 and transforms cells to kanamycin resistance. In the final step, the rav$_L$-gene is incorporated in to pEP1304. Plasmid pEp1301 or pEP1302 is digested with SfiI and the resulting 3' overhanging ends are blunted using T4 DNA polymerase. Next the linearized plasmid is digested with SpeI and the resulting 5' overhanging ends are blunted using the Klenow enzyme reaction (KLEN70). The ca. 340 bp blunt-ended DNA fragment containing the entire rav$_L$- gene is purified and ligated into the PvuII site in pEP1304. Transformed cells are selected for kanamycin resistance and screened by restriction digest analysis for the presence of rav$_L$- genes. The presence of rav$_L$- genes containing the site-specific VF55 or FW58 mutations is confirmed by sequencing. The plasmid containing the rav$_L$- gene with the VF55 mutation is designated pEP1305. The plasmid containing the rav$_L$- gene with the FW58 mutations is designated pEP1306.

In a manner similar to the constructions described above, we ligate the original unmodified rav$_L$ gene into pEP1304 to produce plasmid pEP1307.

Section 6.7 Engineering Heterodimer Binding of Target DNA

This round of variegation is performed to produce mutations in Rav$_R$ proteins that complement the dimerization deficient mutations in the Rav$_L$ proteins produced in Section 6.6 above. To complement the FW58 mutation, the set of five residues L23, V25, A33, I40, and L42 are chosen from the primary set of residues (Section 6.2.3 of this Example) as targets for Focused Mutagenesis.

In an initial series of procedures to test for recognition of HIV 353-369 by the heterodimer Rav$_L$:Rav$_R$, we transform cells containing pEP1438 (containing rav$_R$-38 and the HIV 353-369 targets) with pEP1307 (containing rav$_L$). Intracellular expression of rav$_L$ and rav$_R$ produces a population of dimeric repressors: Rav$_L$:Rav$_L$, Rav$_L$:Rav$_R$ and Rav$_R$:Rav$_R$. If the heterodimeric protein is formed and binds to HIV 353-369, cells expressing both rav alleles will exhibit the Kan$^R$ Amp$^R$ Gal$^R$ Fus$^R$ phenotypes (vide infra). Several pairs of rav$_L$ and rav$_R$ genes are used in parallel procedures; the best pair is picked for use and further study. Selections for binding the HIV 353-369 target by the heterodimeric protein can be optimized using this system as described in Section 4 of this Example.

Focused Mutagenesis of residues 23, 25, 33, 40, and 42 requires the synthesis and annealing of two overlapping variegated strands because in the rav gene a single cassette spanning these residues extends from the BalI site to the BamHI site and exceeds the assumed synthesis limit of 100 nucleotides. As no variegation affects the overlap, the annealing region is complementary. The 67 nucleotide antisense strand of the DNA sequence extending from the BalI site blunt end to the o end of the codon for G37 is denoted olig#52.

```
        q   t   k   t   a   k   d   X   g   X
        16  17  18  19  20  21  22  23  24  25
5' C CAA ACC AAG ACA GCG AAG GAC fzk GGG fzk
   ↑              ↑
  |BalI| y   q   s   a   i   n   k   X   i   h
        26  27  28  29  30  31  32  33  34  35
      TAT CAG AGC GCG ATT AAC AAG fzk ATC CAT a   g
                                36  37
                              GCC GGC   3' olig#52
``` f=(26% T, 18% C, 26% A, 30% G)
z=(22% T, 16% C, 40% A, 22% G)
k=equimolar T and G
Olig#52 contains variegated codons for residues 23, 25, and 33.

The second strand to be synthesized, olig#54, is the 53 nucleotide sense strand sequence extending from the first position in the codon for I34 to the BamHI site:

```
         i   h   a   g   r   k   X   f   X   t
         34  35  36  37  38  39  40  41  42  43
3'  TAG GTA CGG CCG GCA TTC jqm AAG jqm TGG i   n   a   d   n   k
         44  45  46  47  48  49
       TAA TTG CGA CTA CCT AGG cca ca   5' olig#54
                              ↑       ↑
                             |BamHI|
``` j=(26% A, 18% G, 16% T, 30% C)
q=(22% A, 16% G, 40% T, 22% C)
m=equimolar A and C Olig#54 contains variegated codons for residues 40 and 42. Since olig#54 is the complement of the antisense strand, the variegated nucleotide distributions must complement the distributions for codon positions 1, 2, and 3 that are used in the antisense strand. These sense codon distributions are designated "j", "q", and "m", and represent the base-pairing complements to the optimized codon distributions developed for codon positions 1, 2, and 3, respectively, in the antisense strand. The two strands (olig#52 and olig#54) share a 12 nucleotide overlap extending from the first position in the codon for I34 to the end of the codon for G37. The overlap region is 66% G or C.

The two strands shown above are synthesized, purified, annealed, and extended to form duplex DNA. Following restriction endonuclease digestion and purification, the mutagenic cassettes are ligated into pEP1438 (containing the asymmetric HIV 353-369 target) in the appropriate locus in the rav$_R$ gene. The ligation mixtures are used to transform competent cells that contain pEP1306 (the plasmid with the rav$_L$ gene carrying the FW58 site-specific mutation).

In Section 6.2.6 we selected a set of five residues in lambda Cro, E53, E55, V55, K56, and P57, as targets for focused mutagenesis in the first variegation step of the procedure to produce a Rav$_R$ protein that complements the dimerization-deficient VF55 Rav$_L$ mutation. These five residues are contained on a 71 bp BamHI to KpnI fragment of the rav gene constructed in Section 3.3 of this Example (see Table 100). To produce a cassette containing the variegated codons we synthesize the 78 nucleotide antisense variegated strand olig#58:

```
            g   s   v   y   a   X   X   X   X   X   f   p   s   n   k   k
            48  49  50  51  52  53  54  55  56  57  58  59  60  61  62  63
5' ct gat GGA TCC GTC TAC GCG fzk fzk fzk fzk fzk TTC CCG AGT AAC AAA AAA
          ↑       ↑
         |BamHI| t   t   a   .
      64  65  66  67
     ACA ACA GCG TAA TAGTAGGTACC ta   3' olig#58
                      ↑         ↑
                     |KpnI|
```

After synthesis and purification of the vgDNA, strands are self-annealed using the 10 nucleotide palindrome at the 3' end of the sequence. The resulting superoverhangs are filled in using the Klenow enzyme reaction as described previously and the double-stranded oligonucleotide is digested with BamHI and KpnI. Purified mutagenic cassettes are ligated into one or more operative vectors (picked from the pEP1200 series) in the appropriate locus in the $rav_R$ gene. The ligation mixtures are used to transform competent cells that contain pEP1305 (the plasmid carrying the $rav_L$-gene with the FV55 mutation).

Operative vectors carrying the VF55 or FW58 mutation in $rav_L$ confer kanamycin resistance. Operative vectors carrying mutagenized $rav_R$ genes contain the gene for ampicillin resistance as well as the selective gene systems for the DBP+phenotypes. Cells containing complementing mutant proteins are selected by requiring resistance to both ampicillin and kanamycin and repression of the complete HIV 343–369 target sequence (substituted for the Left and Right Symmetrized Targets in the selection genes). Cells possessing the desired phenotype are $Amp^R$, $Kan^R$, $Fus^R$, and $Gal^R$ (in *E. coli* delta4).

Plasmids from candidate colonies are first isolated genetically by transformation of cells at low plasmid concentration. Cells carrying plasmids coding for $Rav_L$ proteins will be kanamycin resistant, while cells carrying plasmids coding for the $Rav_R$ proteins will be ampicillin resistant. Plasmids are individually screened to ensure that they confer the $DBP^-$phenotype and are characterized by restriction digest analysis to confirm the presence of $rav_L^-$or $rav_R^-$genes. Plasmid pairs are co-tested for complementation by restoration of the DBP+phenotype when both $rav_R$ and $rav_L$ are present intracellularly. Successfully complementing plasmids are sequenced through the rav genes to identify the mutations and to suggest potential locations for optional subsequent rounds of variegation.

Plasmids containing genes for altered $Rav_R$ proteins that successfully complement the $rav_L$ VF55 mutation are designated by plasmid numbers pEP1500 to pEP1599. Similarly, plasmids containing genes for altered $Rav_R$ proteins that successfully complement the $rav_L$ FW58 mutation are designated by plasmid numbers pEP1600 to pEP1699.

Heterodimeric proteins are purified and their DNA-binding and thermal stability properties are characterized as described above. Pairwise variation of the $Rav_R$ and $Rav_L$ monomers can produce dimeric proteins having different dimerization or dimer-DNA interaction energies. In addition, further rounds of variegation of either or both monomers to optimize DNA binding by the heterodimer, dimerization strength or both may be performed.

In this manner a heterodimeric protein that recognizes any predetermined target DNA sequence is constructed.

EXAMPLE 2

Presented below is a hypothetical example of a protocol for developing new DNA-binding polypeptides, derived from the first ten residues of phage P22 Arc and a segment of variegated polypeptide with affinity for DNA subsequences found in HIV-I using *E. coli* K12 as the host cell line. It will be understood that some further optimization, in accordance with the teachings herein, may be necessary to obtain the desired results. Possible modifications in the preferred method are discussed immediately following the hypothetical example.

We set the same hypothetical technical capabilities as used in Detailed Example 1.

Overview

To obtain significant binding between a genetically encoded polypeptide and a predetermined DNA subsequence, the surfaces must be complementary over a large area, 1000 Å$^2$ to 3000 Å$^2$. For the binding to be sequence-specific, the contacts must be spread over many (12 to 20) bases. An extended polypeptide chain that touches 15 base pairs comprises at least 25 amino acids. Some of these residues will have their side groups directed away from the DNA so that many different amino acids will be allowed at such residues, while other residues will be involved in direct DNA contacts and will be strongly constrained. Unless we have 3D structural data on the binding of an initial polypeptide to a test DNA subsequence, we can not priori predict which residues will have their side groups directed toward the DNA and which will have their side groups directed outward. We also can not predict which amino acids should be used to specifically bind particular base pairs. Current technology allows production of $10^7$ to $10^8$ independent transformants per ug of DNA which allows variation of 5 or 6 residues through all twenty amino acids. Alternatively, between 23 and 30 two-way variations of DNA bases can be applied that will affect between 8 and 30 codons.

Sauer and colleagues (VERS87b) have shown that P22 Arc binds to DNA using a motif other than H-T-H. There is as yet no published X-ray structure of Arc, though the protein has been crystallized and diffraction data have been collected (JORD85). A combination of genetics and biochemistry indicates that the first 10 residues of each Arc monomer (M-K-G-M-S-K-M-P-Q-F) bind to palindromically related sets of bases on either side of the center of symmetry of the 21 bp operator shown in Table 200. Furthermore, the first ten residues of each Arc monomer assume an extended conformation (VERS87b). The hydrophobic residues may be involved in contacts to the rest of the protein, but there are several examples from H-T-H DBPs of hydrophobic side groups being in direct contact with bases in the major groove. We do know that these first ten residues of Arc can exist in a conformation that makes sequence-specific favorable contacts with the arc operator.

For this Example, we pick a target DNA subsequence from the HIV-1 genome such that a portion of the chosen sequence is similar to one half-site of the arc operator. We use part of this chosen sequence for an initial chimeric target. One half of the first target is the DNA subsequence obtained from HIV-1 and the other half of the target is one half-site of the arc operator. For this example, we will use a plasmid bearing wild-type arc operators repressed by the Arc repressor as a control. After demonstrating that Arc repressor can regulate the selectable genes, we replace the wild-type arc operator with the target DNA subsequence. We then replace the arc gene with a variegated pdbp gene and select for cells expressing DBPs that can repress the selectable genes.

Once a protein is obtained that binds to the target that has similarity to one half of the Arc operator, we can change the target so that it has less similarity to one half of the Arc operator and mutagenize those residues that correspond to residues 1–10 of Arc. In vivo selection will isolate a protein that binds to the new target. A few repetitions of this process can producer a polypeptide that binds to any predetermined DNA sequence.

Our potential DNA-binding polypeptide (DBP) will be 36 residues long and will contain the first ten residues of Arc which are thought to bind to part of the half operator. DNA encoding the first ten amino acids of Arc is linked at the 3' terminus of this gene fragment to vgDNA that encodes a further 26 amino acids. Twenty-four of the codons encode two alternative amino acids so that $2^{24}$=approx. $1.6 \times 10^7$ protein sequences result. The amino acids encoded are chosen to enhance the probability that the resulting polypeptide will adopt an extended structure and that it can make appropriate contacts with DNA. The Chou-Fasman (CHOU78a, CHOU78b) probabilities are used to pick amino acids with high probability of forming beta structures (M, V, I, C, F, Y, Q, W, R, T); the amino acids are grouped into five classes in Table 16. In addition, to discourage sequence-independent DNA binding, some acidic residues should be included. Glutamic acid is a strong alpha helix former, so in early stages we use D exclusively. Further, S and T both can make hydrogen bonds with their hydroxyl groups, but T favors extended structures while S favors helices; hence we use only T in the initial phase. Likewise, N and Q provide similar functionalities on their side groups, but Q favors beta and so is used exclusively in initial phases. Positive charge is provided by K and R, but only R is used in the variegated portion. Alanine favors helices and is excluded. P kinks the chain and is allowed only near the carboxy terminus in initial iterations.

After one selection, we design a different set of binary variegations that includes the selected sequence and perform a second mutagenesis and selection. After two or more rounds of diffuse variegation and selection, we choose a subset of residues and vary them through a larger set of amino acids. We continue until we obtain sufficient affinity and specificity for the target. None of the polypeptides discussed in this example is likely to have a defined 3D structure of its own, because they are all too short. Even if one folded into a definite structure, that structure is unlikely to be related to DNA-binding. Indeed, the polypeptide would first have to unfold before it bound to DNA. This makes DNA-binding by a peptide having a definite 3D structure less likely. A 3D structure, obtained by X-ray diffraction or NMR, of a DNA-polypeptide complex would give us useful indications of which residues to vary. Until we get fairly strong binding, obtaining crystals of such a complex will be difficult. Scattering the variegation along the chain and sampling different charges, sizes, and hydrophobicities produces a series of proteins, isolated by in vivo selection, with progressively higher affinity for the target DNA sequence.

Construction of the test plasmid

Selection systems are the same as used in Example 1, viz. fusaric acid to select against cells expressing the tet gene and galactose killing by galT,K in a galE deleted host. First, in three genetic engineering steps, we replace: a) the rav gene in pEP1009 with the arc gene, and b) the target DNA sequences (both occurrences) with the arc operator. The resulting plasmid is our wild type control.

To replace rav with arc, the synthetic arc gene, shown in Table 201 and Table 202, is synthesized and ligated into pEP1009 that has been digested with BstEII and KpnI. Cells are transformed and colonies are screened for $Tet^R$. Further, plasmid DNA is tested for the presence of a Bsu36I site characteristic of the introduced arc gene. DNA from colonies with the expected restriction digestion pattern is sequenced in the region of the insert to confirm the construction; the plasmid is named pEP2000. Delta4 cells transformed with pEP2000 are $Tet^R$ and $Gal^S$ because pEP2000 lacks the rav gene.

To insert the arc operator into the neo promoter ($P_{neo}$) for the tet gene in pEP2000, we digest pEP2000 with StuI and HindIII and ligate the purified backbone to annealed synthetic olig#430 and olig#432.

Arc operator and $P_{neo}$ that promotes tet

```
            5' |cct|gcg|aac|cgg|aat|tgc|cag|-
Olig #430 = 3'    gga cgc ttg gcc tta acg gt c-
              | Stul |                 | −35 |

|ctg|ggg|cgc|cct|ctg|gta|agg|ttg|-
   gac ccc gcg gga gac cat tcc aac-
                       | −10 |

|gga|atg|ata|gaa|gca|ctc|tac|tat|a
   cct tac tat ctt cgt gag at g at a t  tcg a
   |           Arc operator           || Hind3 |

3' = Olig#432
5'
```

Delta4 cells are transformed and selected with fusaric acid and ampicillin in the presence of IPTG as is described in Example 1. Plasmid DNA from fusaric-acid resistant cells is sequenced in the region of the insertion to confirm the construction. The plasmid is named pEP2001.

To insert the arc operator into the amp promoter ($P_{amp}$) for the galT,K genes in pEP2001, we digest pEP2001 with ApaI and XbaI and ligate the purified backbone to synthetic olig#416 and olig#417 that have been annealed in the standard way.

Arc operator and $P_{amp}$ that promotes galT,K

```
          5'        |ctt|cta|aat|aca|ttc|aaa|-
Olig#417 3' c  cgg    gaa gat tta tgt aaa ttt-
            | Apal |                 | −35 |

|tat|gta|tcc|gct|cat|gag|aca|ata|acc|-
 ata cat agg cga gta ctc tgt tat t gg-
                       | −10 |

|ctt|atg|ata|gaa|gca|ctc|tac|tat|
 gaa tac tat ctt cgt gag at g at a
 |          Arc Operator         |

CGT       3'Olig#416
gca  gat  c 5'
     | Xbal |
```

Delta4 cells are transformed and selected for galactose resistance. Plasmid DNA from $Gal^R$ colonies is sequenced to confirm the construction; the plasmid is named pEP2002. This plasmid is our wild type for work with polypeptides that are selected for binding to target DNA subsequences that are related to the arc operator.

Development of Polypeptides That Bind Chimeric Target DNA

We now replace:
a) the two occurrences of the arc operator with the first target sequence that is a hybrid of the arc operator and a subsequence picked from HIV-1, and
b) the arc gene by a variegated pdbp gene.

A hybrid non-palindromic target sequence is used in this example because selection of a polypeptide using a palindromic or nearly palindromic target DNA subsequence is likely to isolate a novel dimeric DBP. The goal of this procedure is to isolate a polypeptide that binds DNA but that does not directly exploit the dyad symmetry of DNA. The binding is most likely in the major groove, but the present invention is not limited to polypeptides that bind in the major groove. The selections are performed using a non-symmetric target to avoid isolation of novel dimers that support two symmetrically related copies of the original recognition elements.

The non-variable regions of the HIV-1 genome, as listed in Example 1, were searched using a half operator from the arc operator as search sequence.

We sought subsequences in the non-variable sequences of the HIV-I genome that match either half of the consensus P22 arc operator shown in Table 200. Subsequences that are closer to the start of transcription are preferred as targets because proteins binding to these subsequences will have greater effect on the transcription of the genes. No sequence was found that matched all six unambiguous bases; the subsequences at 1024, 1040, and 2387 (shown in Table 203) each have a single mismatch. Lower case letters in the "arcO =" sequence indicate ambiguity in the P22 arc operator sequence. Lower case, bold, underscored letters in the HIV-1 subsequences indicate mismatch with the consensus arc operator. Two other subsequences, shown in Table 203, have one mismatch at one of the conserved bases and one mismatch with one of the ambiguous bases. The HIV-1 subsequence that starts at base 1024 is chosen as a target sequence. We replace the 3' ten bases of the arc operator with the 3' ten bases of this subsequence to produce the hybrid target sequence:

ATGATAGAAG|C|GCAACCCTC.

To insert this sequence into the promotor that regulates tet in pEP2002, plasmid pEP2002 is digested with StuI and HindIII and the purified backbone is ligated to an annealed, equimolar mixture of olig#440 and olig#442. Delta4 cells are transformed and selected with tetracycline; substitution of the arc operator by the arc-HIV-1 hybrid sequence relieves the repression by Arc. Plasmid DNA from Tet$^R$ colonies is sequenced to confirm the construction; the construction is called pEP2003.

First Target and P$_{neo}$ that promotes tet

```
          5'  |CCT|GCG|AAC|CGG|AAT|TGC|CAG|-
Olig#440 = 3'   gga cgc ttg gcc tta acg gtc-
              | StuI |                | -35 |
```

```
|CTG|GGG|CGC|CCT|CTG|GTA|AGG|TTG|-
  gac ccc gcg gga gac cat tcc aac-
               | -10 |
```

```
               ATA ATA CAG TAg caa ccc t ct = HIV 1024-1044
         |GGA|ATG|ATA|GAA|GC|gc aa cc c t c t|A  3' = Olig#442
           cct tac tat ctt cgCGTTGGGAGAt tcg a 5'
         |      First Target        | | Hind3 |
```

The second instance of the target is engineered in like manner, using pEP2003 first digested with ApaI and XbaI and then ligated to annealed olig#444 and olig#446. HB101 (galK$^-$) cells are transformed and are selected for ability to grow on galactose as sole carbon source. Plasmid DNA from Gal+ colonies is sequenced in the region of the insert to confirm the construction; the plasmid is called pEP2004. The plasmid pEP2004 contains the first target sequence in both selectable genes and is ready for introduction of a variegated pdbp gene.

First Target and P$_{amp}$ that promotes galT,K

```
           5'      |CTT|CTA|AAT|ACA|TTC|AAA|
Olig#444  3'  c cgg  gaa gat tta tgt aag ttt
             | ApaI |                 | -35 |
```

```
|TAT|GTA|TCC|GCT|CAT|GAG|ACA|ATA|ACC|CT-
  at acat aggcga gt actc tgt tat tgg ga
                    | -10 |
```

```
T|ATG|ATA|GAA|GC|gc aa cc c t c t|
  a tac tat ctt cgCGTTGGGAGA
  |       First Target         |
```

```
CGT           3'Olig#446
gc a   gat c  5'
   | XbaI |
```

The variegated DNA for a 36 amino acid polypeptide is shown in Table 204. This DNA encodes the first ten amino acids of P22 Arc followed by 26 amino acids chosen to be likely to form extended structures. Residues 22 and 23 are not variegated to provide a homologous overlap region so that olig#420 and olig#421 can be annealed. After olig#420 and olig#421 are annealed and extended with Klenow fragment and all four deoxynucleotide triphosphates, the DNA is digested with both BstEII and Bsu36I and ligated into pEP2004 that has also been digested with BstEII and Bsu36I. The ligated DNA, denoted vgl-pEP2004, is used to transform Delta4 cells. After an appropriate grow out in the presence of IPTG, the cells are selected with fusaric acid and galactose.

By hypothesis, we recover ten colonies that are Gal$^R$ and Fus$^R$. We sequence the plasmid DNA from each of these colonies. A hypothetical DBP amino acid sequence from one of these colonies is shown in Table 205.

Comparison of the amino-acid sequences of different isolates may provide useful information on which residues play crucial roles in DNA binding. Should a residue contain the same amino acid in most or all isolates, we might infer that the selected amino acids is preferred for binding to the target sequence. Because we do not know that all of the isolates bind in the same manner, this inference must be considered as tentative. Residues closer to the unvaried section that have repetitive isolates containing the same amino acid are more informative than residues farther away.

In a second round of Diffuse Mutagenesis, we vary the codons shown in Table 206. Residues 1 through 10 are not varied because these provide the best match for the first ten bases of the target. Residues 19, 20, and 21 are not varied so that the synthetic oligonucleotides can be annealed. The two-way variations at residues 11 through 18 and 23 through 36 all allow the selected amino acid to be present, but also allow an as-yet-untested amino acid to appear. It is desirable to introduce as much variegation as the genetic engineering and selection methods can tolerate without risk that the parental DBP sequence will fall below detectable level. Having picked three residues for the homologous overlap, we have only 23 amino acids to vary. Thus residue 22 is varied through four possibilities instead of only two. Residue 22 was chosen for four-way variegation because it is next to the unvaried residues. We use pEP2004 as the backbone, and ligate DNA prepared with Klenow fragment from oligonucleotides #423 and #424 (Table 206) to the BstEII and Bsu36I sites. The resulting population of plasmids containing the variegated DNA is denoted vg2-pEP2004.

Table 207 shows the amino acid sequence obtained from a hypothetical isolate bearing a DBP gene specifying a polypeptide with improved affinity for the target. Changes in amino acid sequence are observed at ten positions. Comparisons of the sequences from several such isolates as well as those obtained in the first round of mutagenesis can be used to locate residues providing significant DNA-binding energy.

Having established some affinity for the target, we now seek to optimize binding via a more focused mutagenesis procedure. Table 208 shows a third variegation in which twelve residues in the variable region are varied through four amino acids in such a way that the previously selected amino acids may occur. Again, pEP2004 is used as backbone and synthetic DNA having cohesive ends is prepared from olig#325 and olig#327. The plasmid is denoted vg3-pEP2004. In subsequence variegation, we would vary other residues through four amino acids at one time. By hypothesis, we select the polypeptide shown in Table 209 that has high specific affinity for the first target; now we can:

a) replace both occurrences of the first target by a second target, i.e. the intact HIV-1 subsequence (1024–1044), and
b) use the selected polypeptide as the parental DBP to generate a variegated population of polypeptides from which we select one or more that bind to the second target.

Because the second target differs from the first in the region thought to be bound by residues 1 through 10 of the parental DBP, we concentrate our variegation within these residue for the first several rounds of variegation and selection.

To replace the target DNA sequence in the neo promoter for tet, pEP2002 is digested with StuI and HindIII and is ligated to annealed synthetic olig#450 and olig#452. Delta4 cells are transformed and selected with tetracycline; plasmid DNA from Tet$^R$ cells is sequenced in the region of the insert. The new plasmid is named pEP2010.

Second Target and P$_{neo}$ that promotes tet

Second Target and P$_{neo}$ that promotes tet

Olig#450 =

```
5' |CCT|GCG|AAC|CGG|AAC|CGG|AAT|TGC|CAG|
3'  gga cgc ttggcc ttggcc ttaacg gtc-
  | StuI |                        | −35 |
```

```
|CTG|GGG|CGC|CCT|CTG|GTA|AGG|TTG|GG-
 gac ccc gcg gga gac cat tcc aac cc-
                 | −10 |
```

```
 ATA ATA CAG TAg caa ccc tct = HIV 1024-1044
A|ATa|ATA|cAg|tag|caa|ccc|tct|A         3'Olig#452
 t taT t at Gt C AT GTT GGG AGA t tcg  a  5'
|       Second Target          |  | Hind3 |
```

To replace the target DNA subsequence in the amp promoter for galT,K, pEP2010 is digested with ApaI and XbaI and is ligated to annealed synthetic olig#454 and olig#456. HB101 cells are transformed and selected for their ability to grow on galactose as sole carbon source; plasmid DNA from Gal+ cells is sequenced in the region of the insert. The new plasmid is named pEP2011; this plasmid contains the second target in both selectable genes and is ready for introduction of a variegated pdbp gene and selection of cells expressing polypeptides that can selectively bind the target DNA subsequence.

Second Target and P$_{amp}$ that promotes galT,K

```
             5'      |CTT|CTA|AAT|ACA|TTC|AAA|
Olig#454     3' c cgg  gaa gat tta tgt aag ttt
                | ApaI |                   −35
```

```
|TAT|GTA|TCC|GCT|CAT|GAG|ACA|ATA|ACC|CT
 at a cat aggcga gt a ctc tgt tat tgg ga
                 | −10 |
```

```
 ATA ATA CAG TAg caa ccc tct = HIV 1024-1044
T|ATa|ATA|c Ag|tag|caa|ccc|tct|CGT       3'Olig#456
 a t aT t at Gt C AT GTT GGGAGAgc a  gat  c 5'
|       Second Target          |   | XbaI |
```

Variegation of the first eleven residues of the potential DNA-binding polypeptide is illustrated in Table 210. It is possible that a useful restriction site can be engineered in the residues 12–36, but the necessary operations are possible using the Bsu36I site positioned after the stop codons. Double-stranded DNA having appropriate cohesive ends is prepared from olig#460 and olig#461, Klenow fragment, BstEII, and Bsu36I. This DNA is ligated into similarly digested backbone DNA from pEP2011; the resulting plasmid is denoted vg1-pEP2011. Delta4 cells are transformed and selected with fusaric acid and galactose. Table 211 shows the sequence of a 37 amino-acid polypeptide isolated from cells exhibiting the DBP+ phenotypes by the above hypothetical selection. It is to be understood that further variegation (vg2, vg3, . . .) of this peptide and selection for binding to Target#2 will be needed to obtain a peptide of high specificity and affinity for Target#2.

We anticipate that Successful DBP production will take more than three or four cycles of variegation and selection, perhaps 10 or 15. We anticipate that initial phases will require careful adjustment of the selective agents and IPTG because the level of repression afforded by the best polypeptide may be quite low. As stated, we expect that biophysical methods, such as X-ray diffraction or NMR, applied to complexes of DNA and polypeptide will yield important indications of how to hasten the forced evolution.

The length of the polypeptide in the example may not be optimal; longer or shorter polypeptides may be needed. It may be necessary to bias the amino acid composition more toward basic amino acids in initial phases to obtain some non-specific DNA binding. Inclusion of numerous aromatic amino acids (W,F,Y,H) may be helpful or necessary.

Other strategies to obtain polypeptides that bind sequence-specifically are illustrated in examples 3, 4, and 5.

EXAMPLE 3

We present a second example of the application of our selection method applied to the generation of asymmetric DBPs. A possible problem with making and using DNA-binding polypeptides, is that the polypeptides may be degraded in the cell before they can bind to DNA. That polypeptides can bind to DNA is evident from the information on sequence-specific binding of oligopeptides such as Hoechst 33258. Polypeptides composed of the 20 common natural amino acids contain all the needed groups to bind DNA sequence-specifically. These are obtained by an efficient method to sort out the sequences that bind to the chosen target from the ones that do not. To overcome the tendency of the cells to degrade polypeptides, we will attach a domain of protein to the variegated polypeptide as a custodian. The first example of a custodial domain presented is residues 20-83 of barley chymotrypsin inhibitor.

The strategy is to fuse a polypeptide sequence to a stable protein, assuming that the polypeptide will fold up on the stable domain and be relatively more protected from proteases than the free polypeptide would be. If the domain is stable enough, then the polypeptide tail will form a make-shift structure on the surface of the stable domain, but when the DNA is present, the polypeptide tail will quickly (a few milliseconds) abandon its former protector and bind the DNA. The barley chymotrypsin inhibitor (BCI-2) is chosen because it is a very stable domain that does not depend on disulfide bonds for stability; disulfide bonds may not form in the reducing conditions found within cells. We could attach the variegated tail at either end of BCI-2. A preferred order of amino acid residues is the chimeric polypeptide is: a) methionine to initiate translation, b) BCI-2 residues 20-83, c) a two residue linker, d) the first ten residues of Arc, and e) twenty-four residues that are varied over two amino acids at each residue. The linker consists of G-K. Glycine is chosen to impart flexibility. Lysine is included to provide the potentially important free amino group formerly available at the amino terminus of the Arc protein. The first target is the same as the first target of Example 2.

Table 300 shows the sequence of a gene encoding the required sequence. The ambiguity of the genetic code has been resolved to create restriction sites for enzymes that do not cut pEP1009 outside the rav gene. This gene could be synthesized in several ways, including the method illustrated in Table 301 involving ligation of oligonucleotides 470-479. Plasmid pEP3000 is derived from pEP2004 by replacement of the arc gene with the sequence shown in Table 300 by any appropriate method.

Table 302 illustrates variegated olig#480 and olig#481 that are annealed and introduced into the CI2-arc(1-10) gene between PpuMI and KpnI to produce the plasmid population vg1-pEP3000. Cells transformed with vg1-pEP3000 are selected with fusaric acid and galactose in the presence of IPTG. It is to be understood that further variegation (vg2, vg3, . . .)will be required to obtain a polypeptide sequence having acceptably high specificity and affinity for Target#1.

EXAMPLE 4

We present a second strategy involving a polypeptide chain attached to a custodial domain. In this strategy, the custodial domain contains a DNA-recognizing element that will be exploited to obtain quicker convergence of the forced evolution.

The three alpha helices of Cro fold on each other. It has not been observed that these helices fold by themselves, but no efforts in this direction have been reported. We will attach a variegated segment of 24 residues to residue 35 of Cro (H35 is the last residue of alpha 3). The target will be picked to contain a good approximation to the half $O_R3$ site at one end but no constraint is placed on the bases corresponding to the dyad-related other half of $O_R3$. A sequence that departs widely from the $O_R3$ sequence is actually preferred, because this discourages selection of a novel dimeric molecule. We assume that alpha-3 forms and binds to the same four or five bases that it binds in $O_R3$ and that a polypeptide segment attached to the carboxy terminus of alpha-3 can continue along the major groove. We attach 24 amino acids of polypeptide immediately after the last residue of alpha-3, wherein the polypeptide is chosen: a) to have more positive charge than negative charge, b) to have beta chain predominate, c) to have some aromatic groups, and d) to have some H-bonding groups, produces a population that is then cloned and host cells are selected for expression of a polypeptide that binds preferentially to the target sequence.

We first construct a hybrid target sequence (Target #3) containing one $O_R3$ half-site fused to a portion of the final target. This hybrid target DNA subsequence is inserted into the selectable genes in the same manner as the arc operator was inserted in Example 2. We then follow the same procedure to vary the 24 residues; first we vary twenty-four residues, using two possible amino acids at each residue. We carry out two or more cycles of such diffuse variegation. Then we vary 12 residues, using 4 possible amino acids at each residue. We do two or more iterations of this process so that all residues are varied at least once.

We have now generated one or more DBPs that bind well to one half of the final target sequence. Next we generate binding to the other half of the final target. First we replace both instances of Target #3 with the final target sequence, target #4. We then vary the alpha helix 3 and the surface of the hypothesized domain formed by helices 1-3 to optimize binding to final target sequence.

A search of the non-variable regions of the HIV-1 genome reveals that bases 624-640 (aATCtCTAG-CAGTGGCG) contain a good match to one half of $O_R3$, as shown in Table 400. As first target of this example, we choose TATCCCTAGCAGTGGCG, denoted Target#3, that has one half of $O_R3$ and nine bases from HIV-1. Once a sequence is obtained that binds Target#3, we replace Target#3 by Target#4=HIV 624-640 and variegate the recognition helices taken from Cro.

To engineer Target#3 into $P_{neo}$ that regulates tet, plasmid pEP2002 is digested with StuI and HindIII and the purified backbone is ligated to an annealed, equimolar mixture of olig#490 and olig#492. Delta4 cells are transformed and selected with tetracycline; replacement of the arc operator relieves the repression by Arc. Plasmid DNA from $Tet^R$ colonies is sequenced to confirm the construction; the construction is called pEP4000.

Target #3 and $P_{neo}$ that promotes tet

```
               5' |CCT|GCG|AAC|CGG|AAT|TGC|CAG|-
Olig#490 = 3'     gga cgc ttg gcc tta acg gtc-
              | StuI |                  | -35 |

|CTG|GGG|CGC|CCT|CTG|GTA|AGG|TTG|GG-
 gac ccc gcg gga gac cat tcc aac cc-
                       | -10 | a AT Ct C TAG CAG TGG CG = HIV 624-640
A|T AT|CCC|TAG|CAG|TGG|CGA          3'Olig#492
t a t a ggg a t c g t c a c c gct  tcg  a  5'
|         Target #3           ||  Hind3  |
```

We engineer the second instance of the target, in like manner, into $P_{amp}$ for galT,K, using ApaI and XbaI to digest pEP4000 and olig#494 and olig#496. HB101 cells (galK−) are transformed and are selected for ability to grow on galactose as sole carbon source. Plasmid DNA from $Gal^+$ colonies is sequenced in the region of the insert to confirm the construction. The plasmid is called pEP4001.

Target #3 and $P_{amp}$ that promotes galT,K

```
          5'            |CTT|CTA|AAT|ACA| TTC|AAA |
Olig#494  3'  c  cgg     gaa gat tta tgt| aag ttt |
             | ApaI |                   |    -35  |
                                        |_________|

|TAT|GTA|TCC|GCT|CAT|GAG|ACA|ATA|ACC|
 ata cat agg cga gta ctc tgt tat tgg
                       | -10 |

|CTT|TAT|CCC|TAG|CAG|TGG|CG CGT        3'Olig#496
 gaa ata ggg atc gtc acc gc gca gatc 5'
 |        Target #3         |    |XbaI|
```

A gene fragment encoding the first two helices of Cro is shown in Table 401. Olig#483 and olig#484 are synthesized and extended in the standard manner and the DNA is digested with BstEII and KpnI. This DNA is ligated to backbone from pEP4001 that has been digested with BstETT and KpnI; the resulting plasmid, denoted pEP4002, contains the Target#3 subsequence in both selectable genes and is ready for introduction of a variegated pdbp gene between BglII and KpnI. Table 402 shows a piece of vgDNA prepared to be inserted into the BglII-KpnI sites of pEP4002. Table 403 shows the result of a selection of delta4 cells, transformed with vgl-pEP4002, with fusaric acid and galactose in the presence of IPTG. Additional cycles of variegation of residues 36–61 are carried out in such a way that the amino acid selected at the previous cycle is included. After several cycles in which 22–24 residues are varied through two possible amino acids, we choose 10–13 amino acids and vary them through four possibilities.

Once reasonably strong binding to Target#3 is obtained, we replace Target#3 with Target#4 and vary the residues in helix 3 (residues 26–35) and, to a lesser extent, helix 2 (residues 16–23).

EXAMPLE 5

In the present example, we disclose a method of engineering a polypeptide extension onto the amino terminus of P22 Arc, a natural DBP, so that the novel DBP develops asymmetric DNA-binding specificity for a subsequence found in the HIV-1 genome. Others have observed that loss of arms from natural DBPs may cause loss of binding specificity and affinity (PAB082a and ELIA85), but none, to our knowledge, have suggested adding arms to natural DBPs in order to enhance or alter specificity or affinity. The new construction is denoted a "polypeptide extension DBP"; the gene is denoted ped and the proteins are denoted Ped. Wild-type Arc forms dimers and binds to a partially palindromic operator. We will generate a sequence of DBPs descendent from Arc. Early members of this family will form dimers, but will have sufficient binding area such that asymmetric targets will be bound. In final stages of the development, proteins that do not dimerize will be engineered.

Table 200 shows the symmetric consensus of left and right halves of the P22 arc operator, arcO. Table 500a shows a schematic representation of the model for binding of Arc to arcO that is supported by genetic and biochemical data (VERS87b). Arc is thought to bind B-DNA in such a way that residues 1-10 are extended and the amino terminus of each monomer contacts the outer bases of the 21 bp operator (RT Sauer, public talk at MIT, 15 September 1987).

Arc is preferred because: a) one end of the polypeptide chain is thought to contact the DNA at the exterior edge of the operator, and b) Arc is quite small so that genetic engineering is facilitated. P22 Mnt is also a good candidate for this strategy because it is thought that the amino terminal six residues contact the mnt operator, mntO, in substantially the same manner as Arc contacts arcO. Mnt has significant (40%) sequence similarity to Arc (VERS87a). Mnt forms tetramers in solution and it is thought that the tetramers bind DNA while other forms do not. When the mnt gene is progressively deleted from the 3′ end to encode truncated proteins, it is observed that proteins lacking K79 and subsequent residues have lowered affinity for mntO and that proteins lacking Y78 and subsequent residues can not form tetramers and do not bind DNA sequence-specifically (KNIG88). Some truncated Mnt proteins of 77 or fewer residues form dimers, but these dimers do not present the DNA-recognizing elements in such a way that DNA can be bound. Arc is preferred over Mnt because Arc is smaller and because Arc acts as a dimer.

Other natural DBPs that have DNA-recognizing segments thought to interact with DNA in an extended conformation (referred to as arms or tails) and thought to contact the central part of the operator, such as lambda Cro or lambda cI repressor, are less useful. For these proteins to be lengthened enough to contact DNA outside the original operator, several residues would be needed to span the space between the central bases contacted by the existing terminal residues and the exterior edge of the operator.

Table 500a illustrates interaction of Arc dimers with arcO: the two "C"s of Arc represent the place, near residue F10, at which the polypeptide chain ceases to make direct contact with the DNA and folds back on itself to form a globular domain, as shown in Table 500b and Table 500c. Which of these alternative possibilities actually occurs has not been reported. Our strategy is compatible, with some alterations, with either structure. In Table 500b, each set of residues 1–10 makes contact with a domain composed of residues 11–57 of the same polypeptide chain; the dimer contacts are near the carboxy terminus. Table 500c shows an alternative interaction in which residues 1–10 of one polypeptide chains interact with residues 11–57 of the other polypeptide chain; the dimer contacts occur shortly after residue 10. The similarity of sequences of Arc and Mnt, the demonstration of function of DNA-recognizing segments transferred from Arc to Mnt (RT Sauer, public talk at MIT, 15 September 1987 and Knight and Sauer cited in VERS86b), and the behavior of Mnt on truncation suggest that Table 500b is the correct general structure for Arc, but the structure diagrammed in Table 500c is also possible.

Table 501 shows the four sites at which one of the consensus arc half operators comes within one base of matching ten bases (six unambiguous and four having two-fold ambiguity) in the non-variable segments of HIV-1 DNA sequence, as listed in Example 1. The symbol "@" marks base pairs that vary among different strains of HIV-1. Because we intend to extend Arc from its amino terminus, we seek subsequences of HIV-1 that: a) match one of the arc half operators, and b) have non-variable sequences located so that an amino-terminal extension of the Arc protein will interact with non-variable DNA. The subsequences 1024–1033 and 4676–4685 meet this requirement while the subsequences at 1040–1049 and 2387–2396 do not. In the case of 1040–1049, the amino-terminal extension would proceed in the 3+ direction of the strand shown and would reach variable DNA after two base pairs. For 2387–2396, variable sequence is reached at once. The subsequence 1024–1033 is preferred over the subsequence 4676–4685 because it is much closer to the beginning of transcription of HIV so that binding of a protein at this site will have a much greater effect on transcription. In the remainder of this example, positions within the target DNA sequence will be given the number of the corresponding base in HIV-1. Base $A_{1034}$ of HIV-1 is aligned with the central base of arcO.

HIV 1024–1044 has only three bases in each half that are palindromically related to bases in the other half by rotation about base pair 1034: $A_{1024}/T_{1044}$, $A_{1026}/T_{1042}$, and $G_{1032}/C_{1036}$. The latter two base pairs correspond to positions in arcO that are not palindromically related. Five of the six palindromically related bases of arcO correspond to non-palindromically related bases in HIV 1024–1044. Thus no dimeric protein derived from Arc is likely to bind HIV 1016–1046 if symmetric changes are made only in the residues 1–10 (or in any other set of residues originally found in Arc). Our strategy is to add, in stages, eleven variegated residues at the amino terminus and to select for specific binding to a progression of targets, the final target of the progression being bases 1016–1037 of HIV-1. Because the region of protein-DNA interaction is increased beyond that inferred for wild-type Arc-arcO complexes, unfavorable contacts in bases aligned with the right half of arcO can be compensated by favorable contacts of the polypeptide extension with bases 1016–1023. The penultimate selection isolates a dimeric protein that binds to the HIV-1 target 1016–1037; the ultimate selection isolates a protein that does not dimerize and binds to the same target.

Table 502 shows a progression of target sequences that leads from wild-type arcO to HIV 1016–1037. It is emphasized that finding a subsequence of HIV-1 that has high similarity to one half of arcO is not necessary; rather, use of this similarity reduces the number of steps needed to change a sequence that is highly similar to arcO into one that is highly similar or identical to an HIV-1 subsequence. Reducing the number of steps is useful, because, for each change in target, we must: a) construct plasmids bearing selectable genes that include the target sequence in the promoter region, b) construct a variegated population of ped genes, and c) select cells transformed with plasmids carrying the variegated population of ped genes for DBP+ phenotype.

In sections (a), (c), (e), and (g) of Table 502, bases in the targets are in upper case if they match HIV 1016–1046 and are underscored if they match the wild-type arcO sequence.

We construct a series of plasmids, each plasmid containing one of the target sequences in the promoter region of each of the selectable genes. For each target, we variegate the ped gene and select cells for phenotypes dependent on functional DBPs. For each target, several rounds of variegation and selection may be required. We anticipate that a plurality of proteins will be obtained from independent isolates by selection for binding to one target. We pick the protein that shows the strongest in vitro binding to short DNA segments containing the target as the parental Ped to the next round of variegation and selection. Genetic methods, such as generation of point mutations in the ped gene or in the target and selection for function or non-function of Ped can be used to determine associations between particular bases and particular residues (VERS86b).

Once a Ped with specific binding for the target is obtained, it may be useful to determine a 3D structure of the Ped-DNA complex by X-ray diffraction or other suitable means. Such a structure would provide great help in choosing residues to vary to improve binding to a given target or to an altered target.

We initiate development of a polypeptide extension DBP having affinity for HIV 1016–1037 by generating a variegated population of Peds and selecting for binding to the first target. Table 502a shows the first target which we designed to have identity to arcO in the left half, but to have a mismatch (arcO vs. target) at $A_{1038}$ (which is C in the corresponding position in the right half of arcO and is palindromically related to a G in the left half); the rationale is as follows. Vershon et al. (VERS87b) report that chemical modification with dimethyl sulfate of the wild-type CG at this location interferes mildly with binding of Arc and that this location is strongly protected from modification by dimethylsulfate if Arc is bound to the operator. Thus we expect a mismatch between wild-type arcO and the first target at $A_{1038}$ to make wild-type Arc bind poorly. Binding can be restored, however, by favorable contacts to bases 1021–1023 by the amino-terminal extension.

An alternative first target would have $C_{1038}$, as does arcO at the corresponding location, and $A_{1041}$, unlike arcO or HIV-1. Vershon et al. (VERS87b) report that methylation of the corresponding CG base pair strongly interferes with binding of Arc. Thus, changing the base that corresponds to HIV 1041 should have a strong effect on binding of Arc to the alternative target.

In the first variegation step, we extend Arc by five variegated residues at the amino terminal. Since five residues can contact no more than three bases in a sequence-specific manner, we limit the extent of the target to those bases that correspond to HIV 1021–1044. Inclusion of bases corresponding to HIV 1016–1020 at this initial stage might position the target too far downstream from the promoters of the selectable genes to allow strong repression of these promoters. Once a Ped displaying binding to bases corresponding to 1021–1044 has been isolated, we can introduce a greater length of the HIV-1 sequence into the left side of the target without concern that the Ped will bind too far downstream from the promoter of the selectable genes to block transcription. Furthermore, once binding by the amino terminal extension has been established, we can, in a stepwise manner, remove the right half of arcO from the target, thereby forcing more asymmetric binding to the left half of arcO and the bases upstream of 1024.

The first target is engineered into both selectable genes as in Example 2. We use olig#501 and olig#502, shown in Table 503, to introduce the first target downstream of $P_{neo}$ that promotes tet, replacing arcO in pEP2002; the resulting plasmid is called pEP5000. From pEP5000, we use olig#503 and olig#504 to construct pEP5010 in which the first target replaces arcO downstream of $P_{amp}$ that promotes galT,K.

Table 502b shows schematically how the amino terminal residues align to the first target; the five residue extension is unlikely to contact more than 3 base pairs upstream from base 1024. The alteration in the right half operator prevents tight binding unless the additional residues make favorable interactions upstream of 1024. Care is taken in designing the two instances of the target that the downstream boundaries are different, AAG in $P_{neo}$ and CGT in Pamp. Thus, for the novel DBP to bind specifically to both instances of the target, it must recognize the common sequence upstream of base 1024.

An initial variegated ped is constructed using olig#605, as shown in Table 504, and comprises: a) a methionine codon to initiate translation, b) five variegated codons that each allow all twenty possible amino acids, and c) the Arc sequence from 101 to 157. (Because we are constructing a polypeptide extension at the amino terminus, we have added 100 to the residue numbers within Arc so that Arc residue 1 is designated 101.) This variegated segment of DNA comprises $(2^5)^5 = 2^{25} = 3.2 \times 10^1$ different DNA sequences and encodes $20^5 = 3.2 \times 10^6$ different protein sequences; with the given technical capabilities, we can detect each of the possible protein sequences. The 3' terminal 20 bases of olig#605 are palindromically related so that each synthetic oligonucleotide primes itself for extension with Klenow enzyme. The DNA is then digested with Bsu36I and BstEII and is ligated to the backbone of appropriately digested pEP5010 which bears the first target in each selectable gene. Transformed delta4 cells are selected for $Fus^R$ $Gal^R$ at low, medium, and high concentrations of IPTG, the inducer of the lacUV5 promoter that regulates ped. Because the first target is quite similar to arcO, we anticipate that a functional Ped will be isolated with low-level induction of the ped gene with IPTG.

More than one round of variegation and selection may be required to obtain a Ped with sufficient affinity and specificity for the first target. Function of a Ped is judged in comparison to the protection afforded by wild-type Arc in cells bearing pEP2002. Specifically, strength of Ped binding is measured by the IPTG concentration at which 50% of cells survive selection with a constant concentration of galactose or fusaric acid, chosen as a standard for this purpose. A Ped is deemed acceptable if it can protect cells against the standard concentrations of galactose and fusaric acid, administered in separate tests, with an IPTG concentration of $5 \times 10^{-4}$ M. Preferably, a Ped can protect cells against the standard concentrations of galactose and fusaric acid, tested separately, with no more than ten times the concentration of IPTG needed by pEP2002-bearing cells. Variegation of residues 101, 102, and others may be needed. We anticipate that a plurality of independent functional Peds will be isolated; we discriminate among these by measuring in vitro binding to DNA oligonucleotides that contain the target sequence. The amino-acid sequences of different isolates are compared; residues that always contain only one or a few kinds of amino acids are likely to be involved in sequence-specific DNA binding. Table 505 shows a hypothetical isolate, Ped-6, that binds the first target.

Table 502c shows the changes between the first target and the second target. Three changes are made left of center to make the target more like HIV 1016–1042. Only the change $G_{1030} > C$ affects a base that is palindromically related in arcO. One change is made right of center that makes the target more like HIV 1016–1042, less like arcO, and less palindromically symmetric. Furthermore, the target is shortened on the right by two bases so that selection isolates proteins that bind asymmetrically to the left side of the target. Starting with pEP2002, we introduce, in two genetic engineering steps that use olig#541, olig#542, olig#543 and olig#544 (Table 506), the second target (in place of arcO) into the promoter region of each selectable gene; the resulting plasmid is denoted pEP5020.

Table 507 shows a variegated sequence that is ligated into pEP5020 between BstEII and Bsu36I. In Table 507, we indicate variegation at one base by using a letter, other than A, C, G, or T, to represent a specific mixture of deoxynucleotide substrates. The range of amino acids encoded is written above the codon number:

$$\begin{array}{c} M \vert r \\ v \vert g \\ \vert 1\ 0\ 1 \vert \\ \vert r\ k\ G \vert \end{array}$$

indicates that the first base is synthesized with a mixture of deoxynucleotide substrates denoted "r", a mixture of A nd G such that equal amounts of A and G are incorporated, that the second base is synthesized with a mixture of deoxynucleotide substrates denoted "k", a mixture of T and G such that equal amounts of T and G are incorporated, and that the resulting DNA could encode amino acids M, r, v, or g. That the parental Ped has methionine at residue 101 is indicated by writing an upper case M.

Table 502d illustrates that residues 100–110 of Ped-6 contact the bases of the second target that differ from the first target. Accordingly, residues 1 and 96–99 of Ped are not variegated in the DNA shown in Table 507;

rather, residues 100-110 are each varied through four possibilities, always including the amino acid previously present at that residue. This generates $4^{11}=2^{22}=$ approx $4\times10^6$ different DNA and protein sequences. Selection of transformed delta4 cells for $Fus^R Gal^R$ and screening by in vitro DNA binding yields, by hypothesis, a plasmid coding on expression for the protein Ped-6-2, illustrated in Table 508.

An alternative to the variegation shown in Table 507 is one in which we vary residues 101-105, 108, and 110 through eight possibilities each, yielding $2.0\times10^6$ DNA and protein sequences. These residues, except M101, are indicated to be in contact with the operator. M101 has been altered by the attachment of the polypeptide extension and thus should be altered. After variegation of the listed residues and selection, further variegation should include some variegation of residues 96-103 because changes in the listed residues may change the context within which residues 96-103 contact the DNA.

We anticipate that more than one round of variegation and selection may be required to obtain a Ped having sufficient affinity and specificity for the second target.

Table 502e shows the changes from the second target to the third, which comprise: a) inclusion of bases 1018-1020, b) one change to the left of the 21 bp arcO region, c) two changes at the center of the arcO region, d) two changes left of center, and e) removal of bases 1041 and 1042. All of these changes make the third target less symmetric and more like HIV 1016–1040. The third target is introduced into each of the selectable genes in the same manner as the second target. The resulting plasmid, obtained in two genetic engineering steps, is denoted pEP5030. Table 502f shows that residues 96–110 are all potential sites to alter the specificity and affinity of DBPs derived from Ped-6-2. Thus, in Table 510, we illustrate a segment of variegated DNA that comprises $2^{20}=10^6$ DNA sequences and encoding on expression $10^6$ protein sequences having ten residues varied through two possibilities and five residues through four possibilities. The DNA is then digested with BstEII and Bsu36I and ligated into pEP5030. Transformed delta4 cells are selected for $Fus^{R\ GalR}$. By hypothesis, we isolate a plasmid, denoted pEP5031, that codes on expression for the protein Ped-6-2-5 shown in Table 509.

Table 502g shows the changes between the third and fourth targets. The changes are: a) inclusion of bases 1016–1017, b) two changes right of center, and c) removal of bases 1038–1040. The initial variegation to be selected using the fourth target consists of an extension of six residues at the amino terminus of Ped-6-2-5, shown in Table 511. In iterative steps of forced evolution of proteins, one should not produce a number of different DNA sequences greater than the number of independent transformants that one can obtain (about $10^8$ with current technology). Because there are no residues corresponding to 90–95 in the parental DBP (Ped-6-2-5), the first variegation and selection with the fourth target is a non-iterative step and it is permissible to produce $10^{10}$ DNA sequences and $6.4\times10^7$ protein sequences. In subsequent iterative rounds of variegation, the number of variants is, preferably, limited to a fraction, e.g. 10%, of the number of independent transformants that can be generated and subjected to selection. A protein, illustrated in Table 512 and denoted Ped-6-2-5-2, is isolated, by hypothesis, through selection of a variegated population of transformed cells for $Fus^R$ $Gal^R$.

Ped-6-2-5-2 binds specifically to HIV 1016–1037 as a dimer. HIV 1016–1037 has no palindromic symmetry. Binding to an asymmetric DNA sequence by a dimeric protein is possible because the Ped-6-2-5-2 dimer has more recognition elements than wild-type P22 Arc dimer and so can bind even though nearly half of the right half of arcO has been removed from the target. Ped-6-2-5-2 is useful as is; nevertheless, obtaining a monomeric protein may have advantages, including: a) higher affinity for the target because suboptimal interactions are eliminated, and b) lower molecular weight. Obtaining a functional monomeric Ped is easiest if Arc dimers interact in the manner shown in Table 500b. We use the following steps to isolate a protein that binds specifically to HIV 1016–1037 as a monomer.

Ped-6-2-5-2 is the parental DBP from which we derive the monomeric DBP. The route taken from a palindromically symmetric arcO sequence to an asymmetric HIV sequence was designed to select for binding to the left half of the original arc operator.

Proteins that do not dimerize, but that bind specifically to the fourth target can be generated in several ways. Because the 3D structure of Arc is still unknown, we can not use Structure-Directed Mutagenesis to pick residues to vary to eliminate dimerization. One way to obtain monomeric proteins is to use diffuse mutagenesis to vary all residues from 111 to 157 and select for proteins that can bind the target sequence. Another strategy is to synthesize the ped gene in such a way that numerous stop codons are introduced. This causes a population of progressively truncated proteins to be expressed. Table 513 shows a segment of variegated DNA that spans the BglII to KpnI sites of the arc gene used throughout this example. This segment is synthesized with suitable spacer sequences on the 5′ end. The extra "t" at the 3′ end allows two such chains to prime each other for extension with Klenow enzyme. The ratios of bases in the variegated positions are picked so that each varied codon encodes about 35% of polypeptides to terminate at that position. Since we intend to determine how much the protein can be shortened and remain functional, we begin by replacing codon 153 with stop. Since 15 residues are varied, only about 0.3 % of chains will continue to stop codon 153 without one or more stop codons. All the intermediate length chains will be present in the selection in detectable amount. delta4 cells transformed with pEP5030 containing this vgDNA are selected for $Fus^R$ $Gal^R$. Because each variegated codon causes translation termination in about 35% of the genes in the variegated population, shorter coding regions are more abundant than longer ones. Thus, the shortest gene that encodes a functional repressor will be the most abundant gene selected. Plasmid DNA from a number of independent selected colonies is sequenced. The dimerization properties of several functional DBPs are tested in vitro and the sequence of the shortest monomeric protein is retained for use and further study.

In this manner, we generate a protein that binds monomerically to a DNA sequence that has no palindromic symmetry.

EXAMPLE 6

In this example we illustrate the fusion of two known DNA-binding domains to form a novel DNA-binding protein that recognizes an asymmetric target sequence.

The progression of targets is the same as shown in Table 502 (Example 5). The amino-acid sequence of the initial DBP is illustrated in Table 600 and comprises the third zinc-finger domain from the product of the Drosophila kr gene (ROSE86), a short linker, and P22 Arc. The linker consists of three residues that are picked to allow: a) some flexibility between the two domains, and b) introduction of a KpnI site. The polypeptide linker should not allow excessive flexibility because this would reduce the specificity of the DBP.

The primary set of residues to vary to alter the DNA-binding are marked with asterisks. Those in the zinc finger were picked by reference to the model of Gibson et al. (GIBS88); all residues having outward-directed side groups (except those directed upward from the beta strands) were picked. Residues 101-110 (1-10 of Arc) were also picked to be in the primary set. Other residues within the Arc sequence may be varied. For each target in the progression, we initially choose for variegation residues in the primary set that are most likely to abut that part of the target most recently changed. For example, for the first target, we begin by varying residues 21, 24, 25, 28, and 29, each through all twenty amino acids. After one or more rounds of variegation and selection, other residues in the primary and secondary set are varied.

Other zinc-finger domains, such as those tabulated by Gibson et al. (GIBS88), are potential binding domains. Other proteins with known DNA binding, such as 434 Cro, may be used in place of Arc. Multiple zinc fingers could be added, stepwise, to obtain higher levels of specificity and affinity.

TABLES

TABLE 1

MISSENSE MUTATIONS IN LAMBDA CRO

```
        5              10
       M E Q R I T L K D Y A M R F

Y
                   |
       /\/ \/ \ ┌────────┐
       beta 1   │ alpha 1│
                │   │ │  │
                I   R D (L)
                      S 15     20       25       30      35
       G Q T K T A K D L G V Y Q S A I N K A I H A G R
```

TABLE 1-continued

MISSENSE MUTATIONS IN LAMBDA CRO

```
                  (K)  R
                  (F)  C A     N
            E P       N L R    Q        (T) L
            R H       D H N    T    (R)  K  Q
            | |       | | |    |     |   |  |
           ─┌alpha 2┐────────┌ alpha 3 ┐─────
            | |       | | |    |     |   |  |
            P T       H   A    L     T   T
            V         F        S     V
                      R        T     G
                      P              K 40       45       50       55       60       65
       K I F L T I N A D G S V Y A E E V K P F P S N K K T T A G R              N    T
                Y A              A    Q   V S
       T        H (E) N    (K)   K    N   C L
       |        | | |       |    |    |   | |
       /\/\/\/ ───────── \/ \/ \ / \ /─────────
       beta 2             beta 3
       | | |              | |
       F F (A)             G T
       S                   V
       L                   S
       M
```

Notes:
Substitutions occuring at solvent exposed positions in the unbound repressor dimer are shown above the wild type sequence.
Substitutions occuring at internal positions are shown below the wild type sequence.
Subsitutions that produce repressor dimers with normal or nearly normal DNA binding affinities are shown in parentheses.

TABLE 2

Examples of selections for plasmid uptake and maintenance in *E. coli*

| gene | (alternate designation) | function |
|---|---|---|
| $Amp^R$ | $(Ap^R)$ | beta-lactamase |
| $Kan^R$ | $(Kn^R)$ | aminoglycoside P-transferase |
| $Tet^R$ | $(Tc^R)$ | membrane pump |
| $Cam^R$ | $(Cm^R)$ | acetyltransferase |
| colicin | immunity | binds to colicin in vivo |
| TrpA+ | | complementation of trpA |

TABLE 3

Examples of selections for plasmid uptake and maintenance in *S. cerevisiae*

| gene | function |
|---|---|
| Ura3+ | complements ura3 auxotroph |
| Trp1+ | complements trp1 auxotroph |
| Leu2+ | complements leu2 auxotroph |
| His3+ | complements his3 auxotroph |
| $Neo^R$ | resistance to G418 |

TABLE 4

Agents for Selection of DBP Binding in *E. coli* and Relevant Genotypes

| | Forward Selection | | Reverse Selection | |
|---|---|---|---|---|
| Plasmid Genotype | Agent | Host Genotype | Agent | Host Genotype |
| Galactose-1-phosphate uridylyltransferase and galactokinase | | | | |
| galT+ & galK+ | galactose | galE−, galT−, galK− | galactose as sole C source | galE+ & (galT− or galK−) |
| Tetracycline resistance (*E. coli* K-12 strains are $Tet^S$) | | | | |
| tetA+ | fusaric acid | $Tet^S$ | tetracycline | $Tet^S$ |
| beta galactosidase | | | | |
| lacZ+ | phenylgalactoside | lacZ− | lactose as sole C source | lacZ− |
| Phe tRNA synthetase | | | | |
| pheS+ | fluorophenylalanine | pheS12+ | growth at high temperature | pheS-amber, sup-ts |
| Transport of arginine, lysine, and ornithine | | | | |

TABLE 4-continued

Agents for Selection of DBP Binding in *E. coli* and Relevant Genotypes

| | Forward Selection | | Reverse Selection | |
|---|---|---|---|---|
| Plasmid Genotype | Agent | Host Genotype | Agent | Host Genotype |
| argP+ | canavanine | argP−<br>Arg prototroph | requirement for arginine and lysine at low conc. in medium | argP− &<br>Arg auxotroph<br>Lys auxotroph |
| thymidylate synthetase | | | | |
| thyA+ | trimethoprim + thymidylate | thyA− | thymidylate omitted from defined medium | thyA− |
| cAMP Receptor Protein (note 3) | | | | |
| crp+ | fosfomycin | crp− | lactose or other regulated sugar as sole C source | crp− |
| Orotidine-5′-phosphate decarboxylase | | | | |
| pyrF+ | 5-fluoroorotate | pyrF− | Thymine & cytosine requirement on defined medium | pyrF− |
| mannosephosphotransferase enzyme II | | | | |
| ptsM+ | deoxyglucose | ptsM− | Mannose as sole C source | ptsM− |
| Fusion protein | | | | |
| secA+ & malE signal-lacZ fusion | lactose as sole C (note 2) | secA− & lacZ− | phenylgalactoside | secA− & lacZ− |
| Outer membrane protein (note 4) | | | | |
| ompA+ | colicin E1<br>colicin E2<br>colicin E3<br>phage TuII<br>phage K3<br>phage 4-59 | ompA− | HfrH(thr+, leu+, strS) conjugation | thr−, leu−, ompA, strR |
| Vitamin B12 transport | | | | |
| btuB+ | phage BF23 | btuB−<br>B12 prototroph | requirement for B12 in defined medium | btuB− &<br>B12 auxotroph |
| Maltose transport | | | | |
| lamB+ | Phage lambda | lamB− | growth on maltose as sole C source | lamB− |
| Ferrichrome receptor | | | | |
| tonA+ | Phage phi80 | tonA− | Requirement for Fe hydroxamate as sole Fe source | tonA− |
| Colicin I receptor | | | | |
| cir+ | colicin I | cir− | screen for colicin I resistance | cir− |
| Nucleoside uptake, colicin K receptor, phage T6 receptor (note 5) | | | | |
| tsx+ | colicin K<br>Phage T6 | tsx− | requirement for nucleosides in defined medium | tsx−<br>thymine auxotroph<br>purine auxotroph |
| Aromatic amino acid transport | | | | |
| aroP+ | thienylalanine or fluorophenylalanine | aroP− | requirement for tryptophan in defined medium | Trp auxotroph<br>aroP− |
| Cysteine synthetase | | | | |
| cysK+ | selenate or azaserine in medium containing cysteine | cysK− | growth on medium lacking cysteine | cysK− |
| C4 dicarboxylic acid transport | | | | |
| dctA+ | 3-fluoromalate | dctA− | grow on C4 dicarboxylic acids as C and energy source. | dctA− |

Notes:
1) Deletions are strongly preferred over point mutations.
2) Only secA gene need be controlled by DBP.
3) Mutations in crp are highly pleotropic; some effects seen in cell wall. crp best used in connection with selections having intracellular action.
4) Resistance to colicins can arise in several ways; use of two or more E-colicins discriminates against other mechanisms. Because colicins do not replicate, they are preferred over phage for selection. Phage are useful to verify selection of cells repressing expression of ompA.
5) Because colicins do not replicate, they are preferred over phage for selection. Phage are useful to verify selection of cells repressing expression of tsx.

TABLE 5

Some Recommended Pairs of Selectable Binding Marker Genes

A) Recommended pairs:

| | |
|---|---|
| galT,K | tetA |
| argP | pheS |
| lacZ | tetA |
| dctA | cysK |
| crp | thyA |
| lamB | thyA |
| secA & malE—lacZ fusion | pyrF |
| tsx | cysK |
| dctA | thyA |
| galT,K | pheS |
| tetA | thyA |

TABLE 5-continued

Some Recommended Pairs of Selectable Binding Marker Genes

| | | | |
|---|---|---|---|
| ptsM | | thyA | |
| ompA | | pyrF | |
| btuB | | pyrF | |
| tonA | | galT,K | |
| cir | | cysK | |
| aroP | | lacZ | |

| B) Less Preferred pairs: | | Reason |
|---|---|---|
| tetA | argP | Both transport related. |
| secA & | lacZ | Both related to lacZ function. |
| malE—lacZ fusion | | |
| pyrF | thyA | Both related to thymine |
| lamB | galT,K | Both related to sugar metabolism. |
| cir | tsx | Both related to colicin |
| ptsM | tetA | Both transport related |
| tonA | ptsM | Both transport related |
| crp | lacZ | Both related to sugar metabolism |

TABLE 6

Promoters

A: Correlation between Sequence Homology and Promoter Strength (MULL84)

| Promoter | Homology score | Log $K_B k_2$ |
|---|---|---|
| T7 A1 | 74.0 | 7.40 |
| T7 A2 | 73.4 | 7.20 |
| Lambda $P_R$ | 58.6 | 7.13 |
| lac UV5 | 59.2 | 6.94 |
| | 59.2 | 6.30 |
| T7 D | 63.9 | 6.30 |
| | 63.9 | 6.00 |
| Tn10 $P_{out}$ | 56.2 | 6.71 |
| Tn10 $P_{in}$ | 52.1 | 6.18 |
| Lambda $P_{RM}$ | 49.7 | 4.71 |
| | 49.7 | 4.17 |
| $P_{amp}$ | 52.7 | |
| $P_{neo}$ | 58.0 | |

B: Sequences of some promoters

| Name | −35 | −10 | +1 |
|---|---|---|---|
| T7 A1 | GTA<u>TTGACT</u>TAAAG | TCTAACCTATAG<u>GATACT</u>TAC | AGCC<u>A</u> |
| T7 A2 | GTA<u>TTGACA</u>ACATG | AAGTAACATGCAG<u>TAAGATA</u>CA | AATC<u>G</u> |
| Lambda $P_R$ | GTG<u>TTGACT</u>ATTTT | ACCTCTGGCGGT<u>TAGAAT</u>GGT | TGC<u>A</u> |
| lac UV5 | GGC<u>TTTACA</u>CTTTA | TGCTTCCGGCTC<u>ATATAAT</u>GTG | TGG<u>A</u> |
| T7 D | GCG<u>TTGACT</u>TGATG | GGTCTTTATGT<u>GTAGGC</u>TTTA | GGT<u>G</u> |
| Tn10 $P_{out}$ | GGG<u>CAGAAT</u>TGGTA | AAGAGAGTCGT<u>GTAAAATA</u>TC | GAG<u>T</u> |
| Tn10 $P_{in}$ | AGG<u>TGGATA</u>CACAT | CTTGTCATATGA<u>TCAAAT</u>GGT | TTC<u>G</u> |
| Lambda $P_{RM}$ | TGT<u>TAGATA</u>TTTAT | CCCTTGCGGTGA<u>TAGATT</u>TAA | CAT<u>A</u> |
| $P_{amp}$ | ACA<u>TTCAAA</u>TATGT | ATCCGCTCATGA<u>GACAAT</u>AAC | CCT<u>G</u> |
| $P_{neo}$ | GAA<u>TTGCCA</u>GCTGG | GGCGCCCTCTGG<u>TAAGGT</u>TGG | GAAG |

TABLE 7

FUNCTIONAL SUBSTITUTIONS IN HELIX 5 OF LAMBDA REPRESSOR

| 84 | 85 | 86 | 87 | 88 | 89 | 90 | 91 |
|---|---|---|---|---|---|---|---|
| —I— | —Y— | —E— | —M— | —Y— | —E— | —A— | —V— |

TABLE 7-continued

FUNCTIONAL SUBSTITUTIONS IN HELIX 5 OF LAMBDA REPRESSOR

| I | I | I | M | I | I | V | I |
|---|---|---|---|---|---|---|---|
| V | F | L | F | L | L | L | V |
| L | L | | V | M | W | W | L |
| W | W | | W | A | M | M | A |
| A | M | | M | G | A | A | C |
| G | A | | A | T | G | G | S |
| C | G | | C | S | S | G | T |
| Y | Y | | Y | E | Q | H | |
| T | T | | S | Q | Q | Q | |
| S | S | | | D | | | |
| E | E | | | K | | | |
| Q | Q | | | R | | | |
| R | D | | | | | | |

TABLE 8

Some Preferred Initial DBPs

Lambda cI repressor
Lambda Cro
434 cI repressor
434 Cro
P22 Mnt
P22 Arc
P22 cII repressor
Lambda cII repressor
Lambda Xis
Lambda Int
cAMP Receptor Protein from *E. coli*
Trp Repressor from *E. coli*
Kr protein from Drosophila
Transcription Factor IIIA from *Xenopus laevis*
Lac Repressor from *E. coli*
Tet Repressor from Tn10
Mu repressor from phage mu
Yeast MAT-a1-alpha2
Polyoma Large T antigen
SV40 Large T antigen
Adenovirus E1A
Human Transcription Factor SP1 (a zinc finger protein)

TABLE 8-continued

| Some Preferred Initial DBPs |
|---|
| Human Transcription Factor AP1 (product of jun) |

TABLE 9

Single-letter codes.

Single-letter code is used for proteins:

| a = ALA | c = CYS | d = ASP | e = GLU | f = PHE |
|---|---|---|---|---|
| g = GLY | h = HIS | i = ILE | k = LYS | l = LEU |
| m = MET | n = ASN | p = PRO | q = GLN | r = ARG |
| s = SER | t = THR | v = VAL | w = TRP | y = TYR |
| . = STOP | * = any amino acid | | | |
| b = n or d | | | | |
| z = e or q | | | | |
| x = any amino acid | | | | |

Single-letter IUB codes for DNA:

T, C, A, G stand for themselves
M for A or C
R for puRines  A or G
W for A or T  (weak H-bonders)
S for C or G  (strong H-bonders)
Y for pYrimidines  T or C
K for G or T
V for A, C, or G  (not T)
H for A, C, or T  (not G)
D for A, G, or T  (not C)
B for C, G, or T  (not A)
N for any base.

TABLE 10

Exposure of amino acid types in T4 lzm & HEWL.

HEADER  HYDROLASE (O-GLYCOSYL) 18-AUG-86 2LZM
COMPND  LYSOZYME (E.C.3.2.1.17)
AUTHOR  L. H. WEAVER, B. W. MATTHEWS
Coordinates from Brookhaven Protein Data Bank: 1LYM.
Only Molecule A was considered.
HEADER  HYDROLASE(O-GLYCOSYL) 29-JUL-82 1LYM

TABLE 10-continued

Exposure of amino acid types in T4 lzm & HEWL.

COMPND  LYSOZYME (E.C.3.2.1.17)
AUTHOR  J. HOGLE, S. T. RAO, M. SUNDARALINGAM
Solvent radius = 1.40  Atomic radii in Table 11.
Surface area measured in Angstroms$^2$.

| Type | N | Total average area | sigma | max | min | Exposed Max exposed(fraction) |
|---|---|---|---|---|---|---|
| ALA | 27 | 211.0 | 1.47 | 214.3 | 207.1 | 85.1(0.40) |
| CYS | 10 | 239.8 | 3.56 | 245.5 | 234.4 | 38.3(0.16) |
| ASP | 17 | 271.1 | 5.36 | 281.4 | 262.5 | 127.1(0.47) |
| GLU | 10 | 297.2 | 5.78 | 304.9 | 285.4 | 100.7(0.34) |
| PHE | 8 | 316.6 | 5.92 | 325.4 | 307.5 | 99.8(0.32) |
| GLY | 23 | 185.5 | 1.31 | 188.3 | 183.3 | 91.9(0.50) |
| HIS | 2 | 297.7 | 3.23 | 301.0 | 294.5 | 32.9(0.11) |
| ILE | 16 | 278.1 | 3.61 | 285.6 | 269.6 | 57.5(0.21) |
| LYS | 19 | 309.2 | 5.38 | 321.9 | 300.1 | 147.1(0.48) |
| LEU | 24 | 282.6 | 6.75 | 304.0 | 269.8 | 109.9(0.39) |
| MET | 7 | 293.0 | 5.70 | 299.5 | 283.1 | 88.2(0.30) |
| ASN | 26 | 273.0 | 5.75 | 285.1 | 262.6 | 143.4(0.53) |
| PRO | 5 | 239.9 | 2.75 | 242.1 | 234.6 | 128.7(0.54) |
| GLN | 8 | 299.5 | 4.75 | 305.8 | 291.5 | 145.9(0.49) |
| ARG | 24 | 344.7 | 8.66 | 355.8 | 326.7 | 240.7(0.70) |
| SER | 16 | 228.6 | 3.59 | 236.6 | 223.3 | 98.2(0.43) |
| THR | 18 | 250.3 | 3.89 | 257.2 | 244.2 | 139.9(0.56) |
| VAL | 15 | 254.3 | 4.05 | 261.8 | 245.7 | 111.1(0.44) |
| TRP | 9 | 359.4 | 3.38 | 366.4 | 355.1 | 102.0(0.28) |
| TYR | 9 | 335.8 | 4.97 | 342.0 | 325.0 | 72.6(0.22) |

TABLE 11

Atomic Radii used in calculation of molecular surfaces Angstroms

| $C_{alpha}$ | 1.70 |
| $O_{carbonyl}$ | 1.52 |
| $N_{amide}$ | 1.55 |
| Other atoms | 1.80 |

TABLE 12

MISSENSE MUTATIONS IN LAMBDA REPRESSOR AMINO-TERMINAL DOMAIN

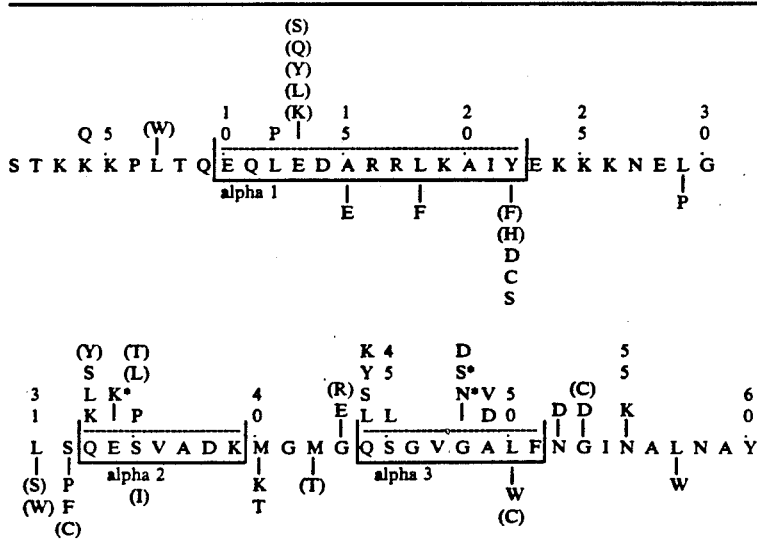

TABLE 12-continued
MISSENSE MUTATIONS IN LAMBDA REPRESSOR AMINO-TERMINAL DOMAIN

```
                                                  (K)
                                                8 (L)
                                                5 (Y)
       65        70       75      80    K*   (Q)      90
                                     (W)| (H)(S)
    N A A L L A K I L K V S V E E F S P S I A R E I Y E M Y E A V S
      |   alpha 4    |               |                |   alpha 5
          R                          N                S
         (C)                         R
                                     I
                                    (T)
                                    (C)
```

Substitutions occuring at solvent exposed positions in the unbound repressor dimer are shown above the wild type sequence.
Substitutions occuring at internal positions are shown below the wild type sequence.
Substitutions that produce repressor dimers with normal or nearly normal DNA binding affinities are shown in paren theses.
Substitutions that produce repressor dimers with increased DNA binding affinities are designated by *.

TABLE 13
MISSENSE MUTATIONS IN P22 ARC REPRESSOR THAT PRODUCE AN ARC− PHENOTYPE

```
         5         10         15         20        25        30
    M K G M S K M P Q F N L R W P R E V L D L V R K V A E E N G
high yield
      Q R I C         L     C
      T K             V
medium yield
        R                            A G     A F        G        A
                                       E
low yield
        R         L S K W Q R S         N     H    I T   K K
                        F W   L         Y     C      V   T
                                                           Y
undetermined
        L                               G     S V 35        40        45        50       55
    R S V N S E I Y Q R V M E S F K K E G R I G A − −
high yield
                                      Y+S
medium yield
      A                   A   T
low yield
    W F G H A M S P Q A   G   S       K     P
    L     K K D           C
            G C
```

TABLE 14
MISSENSE MUTATIONS AT SOLVENT EXPOSED POSITIONS OF THE H—T—H REGIONS OF REPRESSOR PROTEINS

Table 14a
Lambda Repressor

```
                            (S)
                            (N)
        L                              C
      Y(K)T         R
        35      40      45     50      55
      HELIX 2     TURN       HELIX 3
      Q E S V A D K M G M G Q S G V G A L F N G I N A
      •             • •     •   • •      •
        S P               E Y L    D D        D D K
        K                   L      V
        L                   S
                            K
```

TABLE 14-continued
MISSENSE MUTATIONS AT SOLVENT EXPOSED POSITIONS OF THE H—T—H REGIONS OF REPRESSOR PROTEINS Table 14b
Lambda Cro

```
                            F                 K
                            K                 R T
        15      20       25      30      35
                HELIX 2   TURN    HELIX 3
      G Q T K T A K D L G V Y Q S A I N K A I H A G R K
        •         •       • • •    • •   •       • •
      R H                     D H N     N         Q T
      E P                     N L R     T         L
                              C A       Q
                              R
```

Table 14c

TABLE 14-continued

MISSENSE MUTATIONS AT SOLVENT EXPOSED POSITIONS OF THE H—T—H REGIONS OF REPRESSOR PROTEINS

434 Repressor

```
                          H
                          L
                          V
                          T
                          A
      20      25      30      35
    HELIX 2  TURN     HELIX 3
    Q A E L A Q K V G T T Q Q S I E Q L E N
    •                     • •       •
                          A
                          H
                          L
                          S
                          M
                          R
                          P
                          K
```

Table 14d
Trp Repressor

```
                  T
      70      75      80      85
    HELIX 2  TURN     HELIX 3
    Q R E L K N E L G A G I A T I T R G S N
              •   •         •   •
                          S         M C
                          D         H
```

Positions in wild type repressors believed to contact DNA are indicated by a * below the wild type residue.
Substitutions that greatly decrease repressor binding to DNA are shown below the wild type sequence.
Substitutions that produce repressors with normal or nearly normal DNA binding affinities are shown above the wild type sequence.
Substitutions that increase repressor affinity for DNA are shown in parentheses above the wild type sequence.

TABLE 15

Distance from $C_{beta}$ to Tip of Extended Side Group Angstroms

| Amino acid type | Distance |
|---|---|
| A | 0.0 |
| C (reduced) | 1.8 |
| D | 2.4 |
| E | 3.5 |
| F | 4.3 |
| G | — |

TABLE 15-continued

Distance from $C_{beta}$ to Tip of Extended Side Group Angstroms

| Amino acid type | Distance |
|---|---|
| H | 4.0 |
| I | 2.5 |
| K | 5.1 |
| L | 2.6 |
| M | 3.8 |
| N | 2.4 |
| P | 2.4 |
| Q | 3.5 |
| R | 6.0 |
| S | 1.5 |
| T | 1.5 |
| V | 1.5 |
| W | 5.3 |
| Y | 5.7 |

TABLE 16

Genetic Code Table With Secondary-Structure Preferences

| First Base | Second Base T | | C | | A | | G | | Third base |
|---|---|---|---|---|---|---|---|---|---|
| T | F | b/a | S | a/b | Y | b | C | b | T |
|   | F | b/a | S | a/b | Y | b | C | b | C |
|   | L | a/b | S | a/b | stop | | stop | | A |
|   | L | a/b | S | a/b | stop | | W | b/a | G |
| C | L | a/b | P | — | H | a/b | R | b/a | T |
|   | L | a/b | P | — | H | a/b | R | b/a | C |
|   | L | a/b | P | — | Q | b/a | R | b/a | A |
|   | L | a/b | P | — | Q | b/a | R | b/a | G |
| A | I | b | T | b | N | a/b | S | a/b | T |
|   | I | b | T | b | N | a/b | S | a/b | C |
|   | I | b | T | b | K | a/b | R | b/a | A |
|   | M | b | T | b | K | a/b | R | b/a | G |
| G | V | b | A | a | D | a/b | G | b/a | T |
|   | V | b | A | a | D | a/b | G | b/a | C |
|   | V | b | A | a | E | a | G | b/a | A |
|   | V | b | A | a | E | a | G | b/a | G |

Amino acids denoted "b" strongly favor extended structures.
Amino acids denoted "b/a" favor extended structures.
Amino acids denoted "a/b" strongly favor helical structures.
Amino acids denoted "a" very strongly favor helices.
Proline is denoted "—" and favors neither beta sheets nor helices.
b: I, M, V, T, Y, C
b/a: F, Q, R, G, W
a/b: L, S, H, N, K, D
a: A, E
—: P

TABLE 17

Fraction of DNA molecules having n non-parental bases when reagents that have fraction M of parental nucleotide.
Number of bases using mixed reagents is 30.

| M | .9965 | .97716 | .92612 | .8577 | .79433 | .63096 |
|---|---|---|---|---|---|---|
| f0 | .9000 | .5000 | .1000 | .0100 | .0010 | .000001 |
| f1 | .09499 | .35061 | .2393 | .04977 | .00777 | .0000175 |
| f2 | .00485 | .1188 | .2768 | .1197 | .0292 | .000149 |
| f3 | .00016 | .0259 | .2061 | .1854 | .0705 | .000812 |
| f4 | .000004 | .00409 | .1110 | .2077 | .1232 | .003207 |
| f8 | 0. | $2 \times 10^{-7}$ | .00096 | .0336 | .1182 | .080165 |
| f16 | 0. | 0. | 0. | $5 \times 10^{-7}$ | .00006 | .027281 |
| f23 | 0. | 0. | 0. | 0. | 0. | .0000089 |
| most | 0 | 0 | 2 | 5 | 7 | 12 | fn is the fraction of all synthetic DNA molecules having n non-parental bases.
"most" is the value of n having the highest probability.

TABLE 18 best vgCodon

Program "Find Optimum vgCodon."

TABLE 18-continued best vgCodon

INITIALIZE-MEMORY-OF-ABUNDANCES
DO ( t1 = 0.21 to 0.31 in steps of 0.01 )
. DO ( c1 = 0.13 to 0.23 in steps of 0.01 )
. . DO ( a1 = 0.23 to 0.33 in steps of 0.01 )
Comment  calculate g1 from other concentrations
. . . g1 = 1.0 − t1 − c1 − a1
. . . IF( g1 .ge. 0.15 )
. . . . DO ( a2 = 0.37 to 0.50 in steps of 0.01 )
. . . . . DO ( c2 = 0.12 to 0.20 in steps of 0.01 )
Comment Force D+E = R + K
. . . . . . g2 = (g1*a2 −.5*a1*a2)/(c1+0.5*a1)
Comment Calc t2 from other concentrations.
. . . . . . t2 = 1. − a2 − c2 − g2
. . . . . . IF(g2.gt. 0.1.and. t2.gt.0.1)
. . . . . . . CALCULATE-ABUNDANCES
. . . . . . . COMPARE-ABUNDANCES-TO-PREVIOUS-ONES
. . . . . . ..end_IF_block
. . . . . ..end_DO_loop ! c2
. . . . ..end_DO_loop ! a2
. . . . ..end_IF_block ! if g1 big enough
. . . ..end_DO_loop ! a1
. . ..end_DO_loop ! c1
..end_DO_loop ! t1
WRITE the best distribution and the abundances.

TABLE 19

Abundances obtained from optimum vgCodon

| Amino acid | Abundance | Amino acid | Abundance |
|---|---|---|---|
| A | 4.80% | C | 2.86% |
| D | 6.00% | E | 6.00% |
| F | 2.86% | G | 6.60% |
| H | 3.60% | I | 2.86% |
| K | 5.20% | L | 6.82% |
| M | 2.86% | N | 5.20% |
| P | 2.88% | Q | 3.60% |
| R | 6.82% | S | 7.02% mfaa |
| T | 4.16% | V | 6.60% |
| W | 2.86% lfaa | Y | 5.20% |
| stop | 5.20% | | |

| j | (1/ratio)$^j$ | (ratio)$^j$ | stop-free |
|---|---|---|---|
| 1 | 2.454 | .4074 | .9480 |
| 2 | 6.025 | .1660 | .8987 |
| 3 | 14.788 | .0676 | .8520 |
| 4 | 36.298 | .0275 | .8077 |
| 5 | 89.095 | .0112 | .7657 |
| 6 | 218.7 | 4.57 × 10$^{-3}$ | .7258 |
| 7 | 536.8 | 1.86 × 10$^{-3}$ | .6881 | lfaa = least-favored amino acid
mfaa = most-favored amino acid
ratio = Abun(W)/Abun(S) = 0.4074

TABLE 20

Calculate worst codon.

Program "Find worst vgCodon within Serr of given distribution."
INITIALIZE-MEMORY-OF-ABUNDANCES
Comment Serr is % error level.
READ Serr
Comment T1i,C1i,A1i,G1i, T2i,C2i,A2i,G2i, T3i,G3i
Comment are the intended nt-distribution.
READ T1i, C1i, A1i, G1i
READ T2i, C2i, A2i, G2i
READ T3i, G3i
Fdwn = 1.−Serr
Fup = 1.+Serr
DO ( t1 = T1i*Fdwn to T1i*Fup in 7 steps)
. DO ( c1 = C1i*Fdwn to C1i*Fup in 7 steps)
. . DO ( a1 = A1i*Fdwn to A1i*Fup in 7 steps)
. . . g1 = 1. − t1 − c1 − a1
. . . IF( (g1−G1i )/G1i .lt. −Serr)
Comment g1 too far below G1i, push it back
. . . . g1 = G1i*Fdwn

TABLE 20-continued

Calculate worst codon.

. . . . factor = (1.−g1)/(t1 + c1 + a1)
. . . . t1 = t1*factor
. . . . c1 = c1*factor
. . . . a1 = a1*factor
. . . ..end_IF_block
. . . IF( (g1−G1i)/G1i .gt. Serr)
Comment g1 too far above G1i, push it back
. . . . g1 = G1i*Fup
. . . . factor = (1.−g1)/(t1 + c1 + a1)
. . . . t1 = t1*factor
. . . . c1 = c1*factor
. . . . a1 = a1*factor
. . . ..end_IF_block
. . . DO ( a2 = A2i*Fdwn to A2i*Fup in 7 steps)
. . . . DO ( c2 = C2i*Fdwn to C2i*Fup in 7 steps)
. . . . . DO (g2 = G2i*Fdwn to G2i*Fup in 7 steps)
Comment Calc t2 from other concentrations.
. . . . . . t2 = 1. − a2 − c2 − g2
. . . . . . IF( (t2−T2i)/T2i .lt. −Serr)
Comment t2 too far below T2i, push it back
. . . . . . . t2 = T2i*Fdwn
. . . . . . . factor = (1.−t2)/(a2 + c2 + g2)
. . . . . . . a2 = a2*factor
. . . . . . . c2 = c2*factor
. . . . . . . g2 = g2*factor
. . . . . . ..end_IF_block
. . . . . . IF( (t2−T2i)/T2i .gt. Serr)
Comment t2 too far above T2i, push it back
. . . . . . . t2 = T2i*Fup
. . . . . . . factor = (1.−t2)/(a2 + c2 + g2)
. . . . . . . a2 = a2*factor
. . . . . . . c2 = c2*factor
. . . . . . . g2 = g2*factor
. . . . . . ..end_IF_block
. . . . . . IF(g2.gt. 0.0 .and. t2.gt.0.0)
. . . . . . . t3 = 0.5*(1.−Serr)
. . . . . . . g3 = 1. − t3
. . . . . . . CALCULATE-ABUNDANCES
. . . . . . . COMPARE-ABUNDANCES-TO-PREVIOUS-ONES
. . . . . . . t3 = 0.5
. . . . . . . g3 = 1. − t3
. . . . . . . CALCULATE-ABUNDANCES
. . . . . . . COMPARE-ABUNDANCES-TO-PREVIOUS-ONES
. . . . . . . t3 = 0.5*(1.+Serr)
. . . . . . . g3 = 1. − t3
. . . . . . . CALCULATE-ABUNDANCES
. . . . . . . COMPARE-ABUNDANCES-TO-PREVIOUS-ONES
. . . . . . ..end_IF_block
. . . . . ..end_DO_loop ! g2
. . . . ..end_DO_loop ! c2
. . . ..end_DO_loop ! a2
. . ..end_DO_loop ! a1
. ..end_DO_loop ! c1
..end_DO_loop ! t1
WRITE the WORST distribution and the abundances.

TABLE 21

Abundances obtained using optimum vgCodon assuming 5% errors

| Amino acid | Abundance | Amino acid | Abundance |
|---|---|---|---|
| A | 4.59% | C | 2.76% |
| D | 5.45% | E | 6.02% |
| F | 2.49% lfaa | G | 6.63% |
| H | 3.59% | I | 2.71% |
| K | 5.73% | L | 6.71% |
| M | 3.00% | N | 5.19% |
| P | 3.02% | Q | 3.97% |
| R | 7.68% mfaa | S | 7.01% |
| T | 4.37% | V | 6.00% |
| W | 3.05% | Y | 4.77% |
| stop | 5.27% | | |

| j | (1/ratio)$^j$ | (ratio)$^j$ | stop-free |
|---|---|---|---|
| 1 | 3.079 | .3248 | .9473 |
| 2 | 9.481 | .1055 | .8973 |

TABLE 21-continued

Abundances obtained
using optimum vgCodon assuming
5% errors

| | | | |
|---|---|---|---|
| 3 | 29.193 | .03425 | .8500 |
| 4 | 89.888 | .01112 | .8052 |
| 5 | 276.78 | $3.61 \times 10^{-3}$ | .7627 |
| 6 | 852.22 | $1.17 \times 10^{-3}$ | .7225 |
| 7 | 2624.1 | $3.81 \times 10^{-4}$ | .6844 | ratio = Abun(F)/Abun(R) = 0.3248

[Table 22, deleted]

TABLES FOR EXAMPLE 1

TABLE 100

Lambda $O_R3$ Downstream
of $P_{amp}$ that promotes galT,K

```
         5' |GAT |CGT |TAA |CGG |GCC |CTT |CTA |AAT |ACA |TTC |AAA|-
Olig#4 3'       ca   att  gcc  cgg  gaa  gat  tta  tgt  aag  ttt
                    | Hpal |   | Apal |                    |  -35  |

|TAT |GTA |TCC |GCT |CAT |GAG |ACA |ATA |ACC |-
 ata  cat  agg  cga  gta  ctc  tgt  tat  tgg-
                              |  -10  |

|CTT |ATC |ACC |GCA |AGG |GAT |ATC |TAG |AGT |C  3' = Olig#3
 gaa  tag  tgg  cgt  tcc  cta  tag  atc  t     5'
      |    lambda O_R3    |        | Xbal |
```

"Top" strand 88
"Bottom" strand 81

TABLE 101

Lambda $O_R3$ Downstream
of $P_{neo}$ that promotes tet

```
Olig5' |AGG |CCT |GCG |AAC |CGG |AAT |TGC |CAG|-
 #6 3'  tcc  ggc  cgc  ttg  gcc  tta  acg  gtc-
            | StuI |                |   -35  |

|CTG |GGG |CGC |CCT |CTG |GTA |AGG |TTG |-
 gac  ccc  gcg  gga  gac  cat  tcc  aac-
                              |  -10  |

|GGA |TAT |CAC |CCT |AAG |GGA |TA     3' = Olig
 ggg  ata  gtg  gcg  ttc  cct  att cg a 5'  #5
      |    lambda O_R3    |  | HindIII |
```

"Top" strand 68
"Bottom" strand 72

TABLE 102 rav gene
using lacUV5 as promotor

SpeI—BstEII—(BalI—PpuMI—BglII—BamHI—AvaI)
—KpnI—(Trp terminator)—SfiI; !

5'-ACTAGT CCAGG C TTTACA CTT TATGC TTCCG GCTCG TATAAT GTGT GG
   | SpeI |

AAT TGTGA GCGGA TAACA ATTTC ACAC ! lacUV5

A GGA GGTAACC A    ! Shine-Dalgarno seq. & BstEII
   |  BstE2  |

```
 m   e   q   r   i   t   l   k   d   y   a   m   r
 1   2   3   4   5   6   7   8   9  10  11  12  13
ATG GAA CAA CGC ATA ACC CTA AAG GAC TAC GCG ATG CGC f   g   q   t   k   t   a   k   d   l
14  15  16  17  18  19  20  21  22  23
TTT GGC CAA ACC AAG ACA GCG AAG GAC CTA
        | Bal I |                | PpuM I | g   v   y   q   s   a   i   n   k   a   i
24  25  26  27  28  29  30  31  32  33  34
GGG GTG TAT CAG AGC GCG ATT AAC AAG GCC ATC h   a   g   r   k   i   f   l   t   i   n   a   d
35  36  37  38  39  40  41  42  43  44  45  46  47
CAT GCC GGC CGA AAG ATC TTC CTA ACC ATT AAC GCT GAT
                | Bgl II |
```

TABLE 102-continued rav gene
using lacUV5 as promotor

| g | s | v | y | a | e | e | v | k | p | f | p | s |
|---|---|---|---|---|---|---|---|---|---|---|---|---|
| 48 | 49 | 50 | 51 | 52 | 53 | 54 | 55 | 56 | 57 | 58 | 59 | 60 |
| GGA | TCC | GTC | TAC | GCG | GAA | GAG | GTA | AAG | CCC | TTC | CCG | AGT |
| |BamHI| | | | | | | | | |Ava I| |

| n | k | k | t | t | a | . | . | . |
|---|---|---|---|---|---|---|---|---|
| 61 | 62 | 63 | 64 | 65 | 66 | 67 | 67 | 68 |
| AAC | AAA | AAA | ACA | ACA | GCG | TAA | TAG | TA GGTACC |
| | | | | | | | | |KpnI| | agtcta agcccgc ctaatga gcgggct tttttttt ! terminator

GGCCcgactGGCC        -3' ! Sfi I
|    Sfi I    |

TABLE 103

Catalogue of plasmids

| | |
|---|---|
| pEP1001 | pAA3H with 4.3 kbp deletion of lambda, Cla I site introduced. |
| pEP1002 | pEP1001 with fd terminator and Spe I, Sfi I, Hpa I cloning site distal to galT,K. |
| pEP1003 | pEP1002 with P1 promoter replaced by pBR322 amp promoter (Pamp) and $O_R3$ up- stream of galT,K ; Pamp and $O_R3$ bounded by Hpa I and Xba I and containing Apa I cloning site between Hpa I and Pamp. |
| pEP1004 | pKK175-6 with (Pamp , galT,K , fd terminator, Spe I, Sfi I cloning site) from pEP1003 |
| pEP1005 | pEP1004 with Tn5 neo promoter (Pneo) and $O_R3$ bounded by Stu I and Hind III. |
| pEP1006 | pEP1005 with BamH I site removed by site-specific mutation. |
| pEP1007 | pEP1006 with (lacUV5 , S.D., rav cloning site, trpa terminator). |
| pEP1008 | pEP1007 with N-terminal part of rav gene. |
| pEP1009 | pEP1008 with complete rav gene. |
| pEP1010 | pEP1009 with $O_R3$ replaced by scrambled $O_R3$ sequence. |
| pEP1011 | pEP1009 with $O_R3$ sequences replaced with the HIV 353-369 Left Symmetrized Target. |
| pEP1012 | pEP1009 With $O_R3$ sequences replaced with the HIV 353-369 Right Symmetrized Target. |
| pEP1100 to pEP1199 | pEP1011 with $rav_L$. |
| pEP1200 to pEP1299 | pEP1012 with $rav_R$. |
| pEP1301 | pEP1100 with $rav_L^-$ VF55. |
| pEP1302 | pEP1100 with $rav_L^-$ FW58. |
| pEP1303 | pSP64 with Tn5 neo |
| pEP1304 | pEP1303 with deletion of ampicillin resistance gene. |
| pEP1305 | pEP1304 with $rav_L^-$ VF55. |
| pEP1306 | pEP1304 with $rav_L^-$ FW58. |
| pEP1307 | pEP1304 with rav. |
| pEP1400 to pEP1499 | pEP1200 series plasmids with HIV 353-369 substituted for Right Symmetrized Targets. |
| pEP1500 to pEP1599 | pEP1400 series plasmids containg modified $rav_R$ genes producing $Rav_R$ proteins that complement the $rav_L^-$ VF55 mutation. |
| pEP1600 to pEP1699 | pEP1400 series plasmids containg modified $rav_R$ genes producing $Rav_R$ proteins that complement the $rav_L^-$ FW58 mutation. |
| pEP2000 | pEP1009 with rav replaced by arc. |
| pEP2001 | pEP2000 with arc operator in Pneo , tet. |
| pEP2002 | pEP2001 with arc operator in Pamp, galT,K. |
| pEP2003 | pEP2002 with Target#1 in Pneo, tet. |
| pEP2004 | pEP2003 with Target#1 in Pamp, galT,K. |
| vg1-pEP2005 | pEP2004 with vgDNA (variegation #1 of polypeptide). |
| vg2-pEP2006 | pEP2004 with vgDNA (variegation #2 of polypeptide). |
| vg3-pEP2007 | pEP2004 with vgDNA (variegation #3 of polypeptide). |
| pEP2010 | pEP2002 with Target#2 in Pneo, tet. |
| pEP2011 | pEP2010 with Target#2 in Pamp, galT,K. |
| vg1-pEP2012 | pEP2011 with vgDNA (variegation #1 of residues 1-10). |
| pEP3000 | pEP2004 with Cl2-arc(1-10) in place of arc. |
| pEP4000 | pEP2002 with Target#3 in Pneo , tet. |
| pEP4001 | pEP4000 with Target#3 in Pamp, galT,K. |
| pEP4002 | pEP4001 with cro-h12 in place of arc. |
| vg1-pEP1233 | pEP4002 with vgDNA (variegation #1 of polypeptide segment). |

TABLE 104 fd terminator and multiple cloning site to insert after galT,K

```
             5' |CGA |AAG |GCT |CCT |TTT |GCA |GCC |TTT |TTT |TTT |-
Olig#2 = 3'     t ttc   cga  gga  aaa  cgt  cgg  aaa  aaa  aaa  -
                                    fd terminator
```

```
|ACT |AGT |CAG |TGG |CCC |GAC |TGG |CCG |TTA |AC    3' = Olig#1
 tga   tca  gtc  acc  ggg  ctg  acc  ggc  aat  tgg c  5'
|    SpeI    |           Sfil          |   HpaI  |
```

"Top" strand    59
"Bottom" strand 59

TABLE 105

Mutagenic Primer to Remove BamHI site from pEP1005

```
            | t   | p   | v   | l   | w   | i   |
            | 93  | 94  | 95  | 96  | 97  | 98  |
5'   CC     | ACA | CCC | GTC | CTG | TGG | ATC |-
3'   gg     | tgt | ggg | cag | gac | acc | taT-
```

TABLE 105-continued

Mutagenic Primer to Remove BamHI site from pEP1005

```
     | l   | y   | a   | g   | r   | i   |
     | 99  | 100 | 101 | 102 | 103 | 104 |
     | CTG | TAC | GCC | GGA | CGC | ATC | GT  3' pEP1005
       Aac   atg   cgg   cct   gcg   tag   ca  5' Olig#7
```

Bold, upper case bases indicate sites of mutation.

TABLE 106 lacUV5—BstEII—BglII—KpnI—trpa terminator

```
5' | CTA | GTC | CAG | GCT | TTA | CAC | TTT | ATG | CTT | CCG | GCT | CGT | ATA | ATG |
                          |___ −35 ___|                                    |___ −10 ___|

| TGT | GGA | ATT | GTG | AGC | GGA | TAA | CAA | TTT | CAC | ACA | GGA | GGT | AAC | CAG | TCA | GAT | CTA |
               |_____ lac operator _____|                                |___ BstEII ___|   |__ BglII __|

| TGC | GGT | ACC | AGT | CTA | AGC | CCG | CCT | AAT | GAG | CGG | GCT | TTT | TTT | TTG | GCC | CGA | C 3'
        |_ KpnI _|   |_ spacer _|          |_____ trp a terminator _____|
```

TABLE 107

Synthesis of lacUV5—BstEII—BglII—KpnI—trpa terminator

```
         5' |CTA  |GTC  |CAG  |GCT  |TTA  |CAC  |TTT  |ATG  |CTT  |CCG  |GCT  |-
Olig#9 = 3'   ag    gtc   cga   aat   gtg   aaa   tac   gaa   ggc   cga /3' = Olig#8
|CGT  |ATA  |ATG  |TGT  |GGA  |  ATT  |GTG  |AGC  |GGA  |TAA  |CAA  |TTT  |-
 gta   tgt   tac   aca   cct     taa   cac   tcg   cct   att   gtt   aaa
                            Olig #11 = 3'/

/3' = Olig #10
|CAC  |ACA  |GGA  |GGT  |AAC  |CAG  |TCA  |GAT  |CTA  |  TGC  |GGT  |ACC  |-
 gtg   tgt   cct   cca   ttg   gtc   agt   cta   gat     acg   cca   tgg
                                                     Olig #13 = 3'/

|AGT  |CTA  |AGC  |CCG  |CCT  |AAT  |GAG  |CGG  |GCT  |TTT  |TTT  |TTG  |GCC  |CGA  |C 3' = Olig #12
 tca   gat   tcg   ggc   gga   tta   ctc   gcc   cga   aaa   aaa   aac   cgg   g   5'
```

"Top" strand    48 + 48 + 52 = 148
"Bottom" strand 50 + 48 + 43 = 141

TABLE 108

First segment of rav gene

```
5' c |agg |agg |taa |cca |
        |__ BstEII __|

| m   | e   | q   | r   | i   | t   | l   | k   | d   | y   | a   | m   | r   | f   | g   | q   |
| 1   | 2   | 3   | 4   | 5   | 6   | 7   | 8   | 9   | 10  | 11  | 12  | 13  | 14  | 15  | 16  |
|ATG  |GAA  |CAA  |CGC  |ATA  |ACC  |CTA  |AAG  |GAC  |TAC  |GCG  |ATG  |CGC  |TTT  |GGC  |CAA  |
                                                                              |__ BalI __|

| t   | k   | t   | a   | k   | d   | l   | g   | v   | y   | q   | s   | a   | i   | n   | k   |
| 17  | 18  | 19  | 20  | 21  | 22  | 23  | 24  | 25  | 26  | 27  | 28  | 29  | 30  | 31  | 32  |
|ACC  |AAG  |ACA  |GCG  |AAG  |GAC  |CTA  |GGG  |GTG  |TAT  |CAG  |AGC  |GCG  |ATT  |AAC  |AAG  |
   |__ strand overlap __|     |__ PpuMI __|

| a   | i   | h   | a   | g   | r   | k   | i   | f   | l   |
| 33  | 34  | 35  | 36  | 37  | 38  | 39  | 40  | 41  | 42  |
|GCC  |ATC  |CAT  |GCC  |GGC  |CGA  |AAG  |ATC  |TTC  |CTG  | 3'
                                        |__ BglII __|
```

TABLE 109

Synthesis of First segment of rav gene

5' | C | AGG | AGG | TAA | CCA |-

| ATG | GAA | CAA | CGC | ATA | ACC | CTA | AAG |-

| GAC | TAC | GCG | ATG | CGC | TTT |-

| GGC | CAA | ACC | AAG | ACA | GCG | AAG  /3' = Olig#14
Olig#15 = 3'     gg    ttc    tgt    cgc   ttc-

| GAC | CTA | GGG | GTG | TAT | CAG | AGC | GCG |
  ctg   gat    ccc    cac    ata    gtc    tcg    cgc-

| ATT | AAC | AAG | GCC | ATC |
  taa    ttg    ttc    cgg    tag-

| CAT | GCC | GGC | CGA | AAG | ATC | TTC | CTG |
  gta    cgg    ccg    gct    ttc    tag    aag    gac   5'

"Top" strand         74
"Bottom" strand      77
Overlap              12      (7 c/g and 5 a/t)
Net length          139

TABLE 110

Second segment of rav gene

```
       r    k    i    f    l    t    i    n    a    d
       38   39   40   41   42   43   44   45   46   47
5' C | CGA | AAG | ATC | TTC | CTA | ACC | ATT | AAC | GCT | GAT |
            |_____BglII_____|
```

```
   g    s    v    y    a    e    e    v    k    p    f    p    s
   48   49   50   51   52   53   54   55   56   57   58   59   60
 | GGA | TCC | GTC | TAC | GCG | GAA | GAG | GTA | AAG | CCC | TTC | CCG | AGT |
   |_BamHI_|                    |_____strand overlap_____|   |_AvaI_|
```

```
   n    k    k    t    t    a    .    .    .
   61   62   63   64   65   66   67   67   68
 | AAC | AAA | AAA | ACA | ACA | GCG | TAA | TAG | TAG | gta | cca | gtc | t 3'
                                            |___KpnI___|
```

"Top" strand         60
"Bottom" strand      59
Overlap              12      (6 c/g and 6 a/t)
Net length          107

TABLE 111

Lambda $O_R$ core sequences Used to search HIV-1

|                          | 1 2 3 4 5 6 7                         |
|--------------------------|---------------------------------------|
| Kim et al. Consensus-A   | 5' CCGCGGG 3'                         |
|                          | 3' GGCGCCC 5' Kim Consensus-S         |
| Symmetric Consensus-A    | 5' CCGCCGG 3'                         |
|                          | 3' GGCGGCC 5' Symm. Consensus-S       |
| $O_R$3A                  | 5' CCGCAAG 3'                         |
|                          | 3' GGCGTTC 5' $O_R$3S                 |
| $O_R$3A/Symm. Consensus.6| 5' CCGCAGG 3'                         |
|                          | 3' GGCGTCC 5' $O_R$3S/Symm. Cons.2    |

TABLE 111-continued

Lambda $O_R$ core sequences Used to search HIV-1

$O_R$3A/Symm. Consensus.5   5' CCGCCAG 3'
                             3' GGCGGTC 5' $O_R$3S/Symm. Cons.3
                                7 6 5 4 3 2 1

TABLE 112

Potential target binding sequences
having subsequences matching six of seven bases

```
                            |
                            CCGCGGG  Kim consensus-A
HIV-1 subsequence  = ACTTTCCGCt GGGGACT
                 353       ↑
```

```
                            |
                            CCGCAGG  $O_R$3A/consensus.6
HIV-1 subsequence  = TCTCGa CGCAGGACTCG
                 681       ↑
```

```
                            |
                            CTTGCGG  $O_R$3S
HIV-1 subsequence  = TTTGACTa GCGGAGGCT
                 760       ↑
```

TABLE 113

Potential target binding sequences
having subsequences matching five of seven bases Symmetric consensus-S          CCGGCGG
HIV-1 subsequence     GACTTTCCGct GGGGAC
                    352   ↑

OR3S/consensus.2               CCTGCGG
HIV-1 subsequence     TTTCCg CTGg GGACTTT
                    355   ↑

OR3S/symm. consensus.3         CTGGCGG
HIV-1 subsequence     TAGCAg TGGCGc CCGAA
                    630   ↑

TABLE 113-continued

Potential target binding sequences
having subsequences matching five of seven bases

| | |
|---|---|
| Symmetric consensus-A | CCGCCGG |
| HIV-1 subsequence | CAGTGg CGCCc GAACAG |
| | 633 ↑ |
| Or3A/symm consensus.5 | CCGCCAG |
| HIV-1 subsequence | CAGTGg CGCCc GAACAG |
| | 633 ↑ |
| OR3A/consensus.6 | CCGCAGG |
| HIV-1 subsequence | GACTAg CGg AGGCTAGA |
| | 763 ↑ |
| symm consensus-S | CCGGCGG |
| HIV-1 subsequence | GACTAg CGGa GGCTAGA |
| | 763 ↑ |
| Or3A/symm consensus.5 | CCGCCAG |
| HIV-1 subsequence | GAAGAtg GCCAGTAAAA |
| | 4545 ↑ |
| OR3A/consensus.6 | CCGCAGG |
| HIV-1 subsequence | ACAGAtg GCAGGTGATG |
| | 5047 ↑ |
| OR3A/consensus.6 | CCGCAGG |
| HIV-1 subsequence | TCCTAtg GCAGGAAGAA |
| | 5965 ↑ |

TABLE 114 rav<sub>L</sub>-27 gene

SpeI—BstEII—(BalI—PpuMI—BglII—BamHI—AvaI)—
KpnI—(Trp terminator)—SfiI; !

5'-ACTAGT CCAGG C TTTACA CTT TATGC TTCCG
   |_SpeI_|

GCTCG TATAAT GTGT GG AAT TGTGA GCGGA

TAACA ATTTC ACAC ! lacUV5 A GGA GGTAACC A !
                                |_BstE2_|

Shine-Dalgarno seq. & BstEII

```
  m   e   q   r   i   t   l   k   d
  1   2   3   4   5   6   7   8   9
 ATG GAA CAA CGC ATA ACC CTA AAG GAC y   a   m   r   f   g   R   t   k
 10  11  12  13  14  15  16  17  18
 TAC GCG ATG CGC TTT GGC CGT ACC AAG t   a   k   d   l   g   v   H   I
 19  20  21  22  23  24  25  26  27
 ACA GCG AAG GAC CTA GGG GTG CAT ATT
                              |_PpuM 1_|

T   a   i   Q   N   a   i   h   a
 28  29  30  31  32  33  34  35  36
 ACG GCG ATT CAG AAT GCC ATC CAT GCC g   K   Q   i   f   l   t   i   n
 37  38  39  40  41  42  43  44  45
 GGC AAG CAG ATC TTC CTA ACC ATT AAC
```

TABLE 114-continued rav<sub>L</sub>-27 gene

SpeI—BstEII—(BalI—PpuMI—BglII—BamHI—AvaI)—
KpnI—(Trp terminator)—SfiI; !

```
  a   d   g   s   v   y   a   e   e
 46  47  48  49  50  51  52  53  54
 GCT GAT GGA TCC GTC TAC GCG GAA GAG
             |_BamHI_| v   k   p   f   p   s   n   k   k
 55  56  57  58  59  60  61  62  63
 GTA AAG CCC TTC CCG AGT AAC AAA AAA
                     |_Ava I_| t   t   a   .   .   .
 64  65  66  67  67  68
 ACA ACA GCG TAA TAG TA GGTACC
                          |_KpnI_|
``` agtcta agcccgc ctaatga gcgggct tttttttt ! terminator
GGCCcgactGGCC        -3'  ! Sfi I
|_Sfi I_|

TABLE 115 rav<sub>R</sub>-38 gene

SpeI—BstII—BalI—PpuMI—BglII—BamHI—AvaI)—
KpNI—(Trp terminator)—SfiI; !

5'-ACTAGT CCAGG C TTTACA CTT TATGC TTCCG
   |_SpeI_|

GCTCG TATAAT GTGT GG AAT TGTGA GCGGA

TAACA ATTTC ACAC ! lacUV5 A GGA GGTAACC A !
                                |_BstE2_|

Shine-Dalgarno seq. & BstEII

```
  m   g   q   r   i   t   l   k   d
  1   2   3   4   5   6   7   8   9
 ATG GAA CAA CGC ATA ACC CTA AAG GAC y   a   m   r   f   g   E   t   k
 10  11  12  13  14  15  16  17  18
 TAC GCG ATG CGC TTT GGC GAG ACC AAG t   a   k   d   l   g   v   R   T
 19  20  21  22  23  24  25  26  27
 ACA GCG AAG GAC CTA GGG GTG CGT ACT
                              |_PpuM I_|

L   a   i   R   D   a   i   K   a
 28  29  30  31  32  33  34  35  36
 CTT GCG ATT CGT GAT GCC ATC AAG GCC g   N   H   i   f   l   t   i   n
 37  38  39  40  41  42  43  44  45
 GGC AAT CAT ATC TTC CTA ACC ATT AAC a   d   g   s   v   y   a   e   e
 46  47  48  49  50  51  52  53  54
 GCT GAT GGA TCC GTC TAC GCG GAA GAG
             |_BamHI_| v   k   p   f   p   s   n   k   k
 55  56  57  58  59  60  61  62  63
 GTA AAG CCC TTC CCG AGT AAC AAA AAA
                     |_Ava I_|
```

TABLE 115-continued rav_R-38 gene

SpeI—BstII—BalI—PpuMI—BglII—BamHI—AvaI)—

KpnI—(Trp terminator)—SfiI; !

```
  t    t    a   .    .    .
  64   65   66  67   67   68
 ACA  ACA  GCG TAA  TAG   TA GGTACC
                              └ KpnI ┘
``` agtcta agcccgc ctaatga gcgggct tttttttt ! terminator
GGCCcgactGGCC        -3'   ! SfiI
└   SfiI   ┘

TABLES FOR EXAMPLE 2

TABLE 200

P22 arc operator

```
P22 arc    5' ATGATAGAAG |C| ACTCTACTAT 3'
Operator   3' TACTATCTTC |G| TGAGATGATA 5'
```

```
consensus  5' ATrrTAGArk |s| myTCTAyyAT 3'
of half-   3' TAyyATCTym |s| krAGATrrTA 5'
sites
```

P22 arc left half operator = ATrrTAGArk
P22 arc right half operator = myTCTAyyAT

TABLE 201

P22 Arc gene

|       |     | m   | k   | g   | m   | s   |
|       |     | 1   | 2   | 3   | 4   | 5   |
| GG    |TAA |CCT |ATG |AAG |GGT |ATG |TCT |-
| └ BstE II ┘ |

| k   | m   | p   | h   | f   | n   | l   | r   |
| 6   | 7   | 8   | 9   | 10  | 11  | 12  | 13  |
|AAA |ATG |CCT |CAC |TTT |AAC |CTC |AGG |-
                              └ Bsu36I ┘

| w   | p   | r   | e   | v   | l   | d   | l   |
| 14  | 15  | 16  | 17  | 18  | 19  | 20  | 21  |
|TGG |CCC |CGG |GAG |GTC |CTT |GAT |CTT |-
       └ XmaI ┘       └ PpuMI ┘

| v   | r   | k   | v   | a   | e   | e   | n   |
| 22  | 23  | 24  | 25  | 26  | 27  | 28  | 29  |
|GTT |CGC |AAG |GTT |GCT |GAG |GAA |AAC |-

| g   | r   | s   | v   | n   | s   | e   | i   | y   |
| 30  | 31  | 32  | 33  | 34  | 35  | 36  | 37  | 38  |
|GGT |CGG |TCC |GTT |AAC |TCT |GAG |ATT |TAT |-
       └ RsrII ┘    └ HpaI ┘         └ BglII ┘

| n   | r   | v   | m   | e   | s   | f   | k   |
| 39  | 40  | 41  | 42  | 43  | 44  | 45  | 46  |
|AAT |CGC |GTT |ATG |GAG |TCG |TTC |AAG |-

TABLE 201-continued

P22 Arc gene

| k   | e   | g   | r   | i   | g   | a   |
| 47  | 48  | 49  | 50  | 51  | 52  | 53  |
|AAA |GAG |GGT |CGT |ATC |GGC |GCA |-

| . | . | . |
|TAA|TAG|TGA|

|GGT|ACC|
└ KpnI ┘

Amino acid sequence encoded is identical to wild type P22 Arc.
DNA sequence designed for optimal placement of restriction sites.

TABLE 202

Synthesis of P22 Arc gene

5'-G|TAA |CCT |ATG |AAG |GGT |ATG |TCT |AAA |-
   3'- ga  tac  ttc  cca  tac  aga  ttt  -
   └ BstE II ┘

/=olig#400
|ATG |CCT |CAC |TTT |AAC |CTC |AGG |TGG |-
 tac  gga  gtg  aaa  ttg  gag  tcc  acc  -
                         └ Bsu36I ┘

|CCC |CGG |GAG |GTC |CTT |GAT |CTT |GTT |-
 ggg  gcc  ctc  cag  gaa  cta  gaa  caa  -
                       3' = olig#405

/=olig#401
|CGC |AAG |GTT |GCT |GAG |GAA |AAC |GGT |-
 gcg  ttc  caa  cga  ctc  ctt  ttg  cca  -

|CGG |TCC |GTT |AAC |TCT |GAG |ATC |TAT |-
 gcc  agg  caa  ttg  aga  ctc  tag  ata  -
                        \\ = olig#406

/=olig#402
|AAT |CGC |GTT |ATG |GAG |TCG |-
 tta  gcg  caa  tac  ctc  agc  -

|TTC |AAG |AAA |GAG |GGT |CGT |-
 aag  ttc  ttt  ctc  cca  gca  -
                  \\ = olig#407

|ATC |GGC |GCA |TAA |TAG |TGA |-
 tag  ccg  cgt  att  atc  act  -

|GGT |AC     3' = olig#403
  c       5' = olig#408
└ KpnI ┘

Number of bases in each oligonucleotide.

| 400 = 43 | 401 = 48 | 402 = 42 |
| 403 = 47 | 405 = 50 | 406 = 49 |
| 407 = 38 | 408 = 34 |          |

TABLE 203

HIV-1 Subsequences that are similar to one half of the Arc Operator

|  | Number of mismatches |
|---|---|
| ```
                1 2 3 4 5 6 7 8 9 0 | 0 9 8 7 6 5 4 3 2 1
     arcO     = ATrr TAGAr k
HIV-1 subsequence = ATtATAt AATACAGTAGCAAC
            1019 ↑
``` | 2 |
| ```
                1 2 3 4 5 6 7 8 9 0 | 0 9 8 7 6 5 4 3 2 1
     arcO     = ATr r TAGAr k
HIV-1 subsequence = ATAATAc AGTAGCAACCCTCT
            1024 ↑
``` | 1 |
| ```
                1 2 3 4 5 6 7 8 9 0 | 0 9 8 7 6 5 4 3 2 1
     arcO     =                      my TCTAyyAT
HIV-1 subsequence = ACAGTAGCAACCCTCTATTg T
               1040 ↑
``` | 1 |
| ```
                1 2 3 4 5 6 7 8 9 0 | 0 9 8 7 6 5 4 3 2 1
     arcO     = ATr r TAGAr k
HIV-1 subsequence = ATGATAGg GGGAATTGGAGGT
            2387 ↑
``` | 1 |
| ```
                1 2 3 4 5 6 7 8 9 0 | 0 9 8 7 6 5 4 3 2 1
     arcO     = ATr r TAGAr k
HIV-1 subsequence = t TGAc AGAAGAAAAAATAAAA
           2624 ↑
``` | 2 |

TABLE 204

Synthesis of Potential DBP-1 vg1 for pEP2004

```
                    M     K     G     M     S     K     M     P
                    1     2     3     4     5     6     7     8
5'- GCCGTACGG |TAA |CCT |ATG |AAG |GGT |ATG |TCT |AAA |ATG |CCT |-
        | BstE II |
```

| | | 2 | 2 | 2 | 2 | 2 | 2 | 2 | 2 | 2 | 2 |
|---|---|---|---|---|---|---|---|---|---|---|---|
| Q | F | I/M | Q/R | D/V | R/I | W/G | D/G | Q/L | R/T | F/Y | R/C |
| 9 | 10 | 11 | 12 | 13 | 14 | 15 | 16 | 17 | 18 | 19 | 20 |
| CAC | TTT | ATs | CrG | GwT | AkA | kGG | GrT | CwG | AsA | TwT | yGT |-
| | | | | | | | | | | | 3' |

```
                 ↓-3' = olig#420
   2           ↓ 2    2     2     2     2     2     2     2     2
| W/G | V | Q | I/M | T/I | R/Q | V/I | R/I | F/Y | D/V | T/I | R/Q |
|  21 | 22| 23|  24 |  25 |  26 |  27 |  28 |  29 |  30 |  31 |  32 |
| kGG |GTG|CAG| ATs | AyC | CrG | rTT | AkA | TwT | GwT | AyC | CrG |-
|  -cc| cac|gtc| taS | tRg | gYc | Yaa | tMt | aWa | cWa | tRg | gYc |
```

TABLE 204-continued

Synthesis of Potential DBP-1 vg1 for pEP2004

| 2 V/I 33 rTT Yaa | 2 D/G 34 GrT cYa | 2 V/I 35 rTT Yaa | 2 P/Q 36 CmG gKc | TAA att | TAG atc | TGA act | AAC ttg | CTC gag | AGG tcc | CGTGATCC gcactagg | -5' = olig#421 |
|---|---|---|---|---|---|---|---|---|---|---|---|
| | | | | | | | | Bsu36I | | spacer | | s = equimolar C and G
w = equimolar A and T
y = equimolar T and C
n = equimolar A, C, G, and T
r = equimolar A and G
k = equimolar T and G
m = equimolar A and C
There are $2^{24}$ = (approx.) $1.6 \times 10^7$ DNA and protein sequences.
Number of bases in each oligonucleotide.
420 = 86
421 = 73

TABLE 205

Result of first variegation

| M 1 ATG | K 2 AAG | G 3 GGT | M 4 ATG | S 5 TCT | K 6 AAA | M 7 ATG | P 8 CCT | Q 9 CAC | F 10 TTT | M 11 ATG | R 12 CGG | D 13 GAT | I 14 ATA | W 15 TGG | G 16 GGT | Q 17 CAG | T 18 ACA |
|---|---|---|---|---|---|---|---|---|---|---|---|---|---|---|---|---|---|

| Y 19 TAT | C 20 TGT | G 21 GGG | V 22 GTG | Q 23 CAG | M 24 ATG | T 25 ACC | R 26 CGG | V 27 GTT | I 28 ATA | F 29 TTT | D 30 GAT | I 31 ATC | R 32 CGG | V 33 GTT | G 34 GGT | V 35 GTT | P 36 CCG |
|---|---|---|---|---|---|---|---|---|---|---|---|---|---|---|---|---|---|

TABLE 206

Synthesis of Potential DBP14 vg2 for pEP2004

| | | M 1 | K 2 | G 3 | M 4 | S 5 | K 6 | M 7 | P 8 |
|---|---|---|---|---|---|---|---|---|---|
| 5'-GCCGTACGG | TAA | CCT | ATG | AAG | GGT | ATG | TCT | AAA | ATG | CCT |-
| | BstE II | | | | | | | | | |

| Q 9 CAC | F 10 TTT | M\|T 11 AvG | R\|Q 12 CrA | D\|N 13 rAT | I\|T 14 AyT | W\|R 15 yGG | G\|C 16 kGT | Q\|H 17 CAw |-
|---|---|---|---|---|---|---|---|---|

|= 3' olig#424

| T\|N 18 AmC -g | Y 19 TAC atg | C 20 TGC acg | G 21 GGG ccc | V\|D N\|I 22 rwT YWa | Q\|R 23 CrG gYc | M\|T 24 AyG tRc | T\|N 25 AyC tRg | R\|C 26 yGT Rca |
|---|---|---|---|---|---|---|---|---|
| | overlap | | | | | | | |

| V\|F 27 kTT Maa | R\|Q 28 CrG gYc | F\|S 29 TyT aRa | D\|N 30 rAT Yta | I\|T 31 AyC tRg | R\|I 32 AkA tMt | V\|G 33 GkT cMa | G\|R 34 sGT Sca |-
|---|---|---|---|---|---|---|---|

| V\|D 35 GwT cWa | P\|R 36 CsG gSc | TAA att | TAG atc | TGA act | AAC ttg | CTC gag | AGG tcc | CGTGATCC gcactagg | -5' = olig#423 |
|---|---|---|---|---|---|---|---|---|---|
| | | | | | | | Bsu36I | spacer | | s = equimolar C and G
w = equimolar A and T
y = equimolar T and C
n = equimolar A, C, G, and T
r = equimolar A and G
k = equimolar T and G
m = equimolar A and C
$2^{24}$ sequences = $1.6 \times 10^7$ sequences (DNA and protein).
Number of bases in each oligonucleotide.
424 = 78
423 = 81

TABLE 207

Result of second selection

| M | K | G | M | S | K | M | P | Q | F | M | R | N | I | W | G | Q | T |
|---|---|---|---|---|---|---|---|---|---|---|---|---|---|---|---|---|---|
| 1 | 2 | 3 | 4 | 5 | 6 | 7 | 8 | 9 | 10 | 11 | 12 | 13 | 14 | 15 | 16 | 17 | 18 |
| ATG | AAG | GGT | ATG | TCT | AAA | ATG | CCT | CAC | TTT | ATG | CGA | AAT | ATT | TGG | GGT | CAT | ACC |

| Y | C | G | D | R | M | T | R | F | N | S | N | I | R | G | R | V | R |
|---|---|---|---|---|---|---|---|---|---|---|---|---|---|---|---|---|---|
| 19 | 20 | 21 | 22 | 23 | 24 | 25 | 26 | 27 | 28 | 29 | 30 | 31 | 32 | 33 | 34 | 35 | 36 |
| TAC | TGC | GGG | GAT | CGG | ATG | ACC | CGT | TTT | AAT | TCT | AAT | ATC | AGA | GGT | CGT | GTT | CGG |

| TAA | TAG | TGA |

TABLE 208

Third variegation vg3 for pEP2004

```
                                            M   K   G
                                            1   2   3
5'- CGTCGCATGG | TAA | CCT | ATG | AAG | GGT | -
        spacer     BstE II
```

|   |   |   |   |   |   | M\|K |
|---|---|---|---|---|---|---|
| M | S | K | M | P | Q | F | E\|V |
| 4 | 5 | 6 | 7 | 8 | 9 | 10 | 11 |
| ATG | TCT | AAA | ATG | CCT | CAC | TTT | rwG |

|   | N\|D |   | W\|S |   | Q\|R |   | Y\|C |
|---|---|---|---|---|---|---|---|
| R | T\|A | I | R\|P | G | G\|E | T | H\|R |
| 12 | 13 | 14 | 15 | 16 | 17 | 18 | 19 |
| CGG | rmT | ATA | ysG | GGT | srG | ACA | yrT |

|   |   | D\|I | R\|Q |   |   |   |
|---|---|---|---|---|---|---|
| C | G | N\|V | G\|E | M | T | R |
| 20 | 21 | 22 | 23 | 24 | 25 | 26 |
| TGT | GGG | rwT | srG | ATG | ACC | CGC | = olig#325 olig#327 3'-         c    tac   tgg   gcg -
                          overlap

| F\|C |   | S\|N |   | I\|T |   |
|---|---|---|---|---|---|
| V\|G | N | R\|H | N | P\|L | R |
| 27 | 28 | 29 | 30 | 31 | 32 |
| kkT | AAT | mrT | AAT | myC | CGG |
| MMa | tta | KYa | cta | KRg | gtc |

| G\|D |   |   | R\|H |
|---|---|---|---|
| R\|H | R | V | P\|L |
| 33 | 34 | 35 | 36 |
| srT | CGT | GTT | CnT | TAA | TAG | TGA |
| SYa | gca | caa | gNa | att | atc | act |

TABLE 208-continued

Third variegation vg3 for pEP2004

| AAC | CTC | AGG | CGACCTGGC |
| ttg | gag | tcc | gctggaccg   -5' |
|     |     |     | Bsu36I | s = equimolar C and G
w = equimolar A and T
y = equimolar T and C
n = equimolar A, C, G, and T
r = equimolar A and G
k = equimolar T and G
m = equimolar A and C
$4^{12} = 2^{24} = 1.6 \times 10^7$ protein and DNA sequences

TABLE 209

Polypeptide that Binds First Target

| M | K | G | M | S | K | M | P |
|---|---|---|---|---|---|---|---|
| 1 | 2 | 3 | 4 | 5 | 6 | 7 | 8 |
| ATG | AAG | GGT | ATG | TCT | AAA | ATG | CCT |

| Q | F | V | R | D | I | R | G |
|---|---|---|---|---|---|---|---|
| 9 | 10 | 11 | 12 | 13 | 14 | 15 | 16 |
| CAC | TTT | GTG | CGG | GAT | ATA | CGG | GGT |

| G | T | H | C | G | I | Q | M |
|---|---|---|---|---|---|---|---|
| 17 | 18 | 19 | 20 | 21 | 22 | 23 | 24 |
| GGG | ACA | CAT | TGT | GGG | ATT | CAG | ATG |

| T | R | V | N | R | N | P | R |
|---|---|---|---|---|---|---|---|
| 25 | 26 | 27 | 28 | 29 | 30 | 31 | 32 |
| ACC | CGC | ATT | AAT | CGT | AAT | CCC | CGG |

| H | R | V | L |
|---|---|---|---|
| 33 | 34 | 35 | 36 |
| CAT | CGT | GTT | CTT |

TABLE 210

Variegation for Second Target vg1 for pEP2011

|   |   |   |   | K\|T |   |   |
|---|---|---|---|---|---|---|
|   |   |   |   | A\|V |   |   |
|   | M\|T | G\|D | G\|D | M\|T | S\|R | K\|Q |
| M | V\|A | R\|M | A\|V | V\|A | N\|K | N\|H |
| 0 | 1 | 2 | 3 | 4 | 5 | 6 |
| 5'- CGTCGCATGG | TAA | CCT | ATG | ryG | rnG | GnT | ryG | Ars | mAs |
|     spacer       BstE II |

|   |   |   | F\|Y |   |   |   |   |   |
|---|---|---|---|---|---|---|---|---|
|   |   |   | H\|L |   |   |   |   |   |
| M\|K | P\|Q | Q\|H | I\|N | V\|I |   |   |   |   |
| Q\|L | R\|L | N\|A | V\|D | T\|A | R | D | I | R | G |
| 7 | 8 | 9 | 10 | 11 | 12 | 13 | 14 | 15 | 16 |
| mwG | CnT | mAs | nwT | ryT | CGG | GAT | ATA | CGG | GGT |

TABLE 210-continued

Variegation for Second Target vg1 for pEP2011

```
                                          / = olig#460
     G    T    H    C    G    I    | Q    M    T    R
     17   18   19   20   21   22   | 23   24   25   26
    |GGG |ACA |CAc |TGc |GGG |ATc | CAG |ATG |ACC |CGC |
olig#461 = 3'-gtg  acg  ccc  tag    gtc  tac  tgg  acg  -
                    overlap V    N    R    N    P    R    H    R    V    L
    27   28   29   30   31   32   33   34   35   36
   |ATT |AAT |CGT |AAT |CCC |CGG |CAT |CGT |GTT |CTT |
    taa  tta  gca  tta  ggg  gcc  gta  gca  caa  gaa TAA |TAG |TGA |AAC |CTC |AGG |CGACCTGGC -3'
att  atc  act  ttg  gag  tcc  gctggaccg  -5'
                         Bsu36I    spacer
``` s = equimolar C and G
w = equimolar A and T
y = equimolar T and C
n = equimolar A, C, G, and T
r = equimolar A and G
k = equimolar T and G
m = equimolar A and C
$2^{24} = 1.6 \times 10^7$ protein and DNA sequences

TABLE 211

Polypeptide Selected for Binding to Second Target

```
     M    T    R    D    M    K    Q
     0    1    2    3    4    5    6
    |ATG |ACG |AGG |GAT |ATG |AAG |CAG |-

M    Q    N    D    I    R    D    I
     7    8    9    10   11   12   13   14
    |ATG |CAT |AAC |GAT |ATT |CGG |GAT |ATA |-

R    G    G    T    H    C    G    I
     15   16   17   18   19   20   21   22
    |CGG |GGT |GGG |ACA |CAc |TGc |GGG |ATc |-
```

TABLE 211-continued

Polypeptide Selected for Binding to Second Target

```
     Q    M    T    R    V    N    R    N
     23   24   25   26   27   28   29   30
    |CAG |ATG |ACC |CGC |ATT |AAT |CGT |AAT |-

P    R    H    R    V    L
     31   32   33   34   35   36
    |CCC |CGG |CAT |CGT |GTT |CTT |
```

TABLES FOR EXAMPLE 3

TABLE 300

CI2-arc(1-10) gene

```
                    m    l    k    t    e    w    p    e    l    v    g    k    s-   v
                    1    2    3    4    5    6    7    8    9    10   11   12   13   14
GG |TAA |CCT |ATG |CTT |AAG |ACT |GAA |TGG |CCT |GAG |CTT |GTT |GGT |AAA |TCT |GTC |
   BstEII              AflI e    e    a    k    k    v    i    l    q    d    k    p    e    a    q    i
    15   16   17   18   19   20   21   22   23   24   25   26   27   28   29   30
   |GAG |GAA |GCT |AAG |AAA |GTT |ATC |CTG |CAG |GAT |AAA |CCT |GAG |GCC |CAA |ATC |
                                          PstI              Bsu36I i    v    l    p    v    g    t    i    v    t    m    e    y    r    i    d    r
    31   32   33   34   35   36   37   38   39   40   41   42   43   44   45   46   47
   |ATA |GTA |CTT |CCG |GTT |GGC |ACT |ATT |GTT |ACC |ATG |GAG |TAT |CGT |ATT |GAC |CGC |
             ScaI                              NcoI
                                               StyI v    r    l    f    v    d    k    l    d    n    i    a    e    v    p    r    v
    48   49   50   51   52   53   54   55   56   57   58   59   60   61   62   63   64
   |GTT |CGT |CTT |TTT |GTC |GAC |AAA |TTG |GAT |AAC |ATT |GCT |GAG |GTC |CCT |CGC |GTA |
                        AccI                                         DraII
                        HindII                                       PpuMI
                        SalI                                         PssI
                                                                     AvaII
```

TABLE 300-continued

CI2-arc(1-10) gene

| g 65 GGT | g 66 GGC | k 67 AAA | m 68 ATG | k 69 AAA | g 70 GGT | m 71 ATG | s 72 TCT | k 73 AAG | m 74 ATG | p 75 CCG | q 76 CAA | f 77 TTT | . 78 TAA | . 79 TGA | . 80 TAG | GGT \| ACC |
|---|---|---|---|---|---|---|---|---|---|---|---|---|---|---|---|---|

Asp718 / Kpn I

Residue M1 is inserted so that translation can initiate.
Residue L2 corresponds to residue L20 of Barley chymotrypsin inhibitor CI-2.
Residues G66 and K67 are inserted to allow flexibility between CI-2 and the DNA-binding tail.
Residues 68–77 have the same sequence as the first ten residues of P22 Arc.

TABLE 301

Synthesis of CI2-arc(1-gene

3' = olig#470

```
                m   l   k   t   e   w   p   e   l   v   g   k   s   v   e
                1   2   3   4   5   6   7   8   9  10  11  12  13  14  15
5'-G|TAA |CCT |ATG|CTT|AAG|ACT|GAA|TGG|CCT|GAG|CTT|GTT|GGT|AAA|TCT|GTC|GAG|
    3'-ga   tac  gaa  ttc  tga  ctt  acc  gga  ctc  gaa  caa  cca  ttt  aga  cag  ctc
    BstEII         Afl I
```

```
    e   a   k   k   v   i   l   q   d   k   p   e   a   q   i   i
   16  17  18  19  20  21  22  23  24  25  26  27  28  29  30  31
  GAA GCT AAG AAA GTT ATC CTG CAG GAT AAA CCT GAG GCC CAA ATC ATA
   ctt cga ttc ttt caa tag gac gtc cta ttt gga ctc cgg gtt tag tat
        ↑              Pst I           Bsu36I
       5'
     olig#475
```

```
         3' = olig#471
    v   l   p   v   g   t   i   v   t   m   e   y   r   i   d   r   v
   32  33  34  35  36  37  38  39  40  41  42  43  44  45  46  47  48
  GTA CTT CCG GTT GG  C ACT ATT GTT ACC ATG GAG TAT CGT ATT GAC CGC GTT
   cat gaa ggc caa cc   g tga taa caa tgg tac ctc ata gca taa ctg gcg caa
   Sca I              ↑            Nco I                       ↑
                  5' Olig#476      Sty I            5' olig#477
```

```
         3' olig#472
    r   l   f   v   d   k   l   d   n   i   a   e   v   p   r   v   g
   49  50  51  52  53  54  55  56  57  58  59  60  61  62  63  64  65
  CGT CTT TTT GTC GAC AAA TTG GAT AAC ATT GCT GAG GTC CCT CGC GTA GGT
   gca gaa aaa cag ctg ttt aac cta ttg taa cga ctc cag gga gcg cat cca
              Acc I                               Dra II    ↑
              Hind II                             PpuM I    ↑ 3' olig#479
              Sal I                               Pss I     = 5' olig#478
                                                  AvaII
``` olig#473 3' ↓

```
    g   k   m   k   g   m   s   k   m   p   q   f   .   .   .
   66  67  68  69  70  71  72  73  74  75  76  77  78  79  80
  GGC AAA ATG AAA GGT ATG TCT AAG ATG CCG CAA TTT TAA TGA TAG
   ccg ttt tac ttt cca tac aga ttc tac ggc gtt aaa att act atc
```

|GGT |AC - 3' = olig#474
c- 5'
Kpn I

Number of bases in each oligonucleotide.

| olig#470 ... 46 | olig#475 ... 53 |
| olig#471 ... 57 | olig#476 ... 56 |
| olig#472 ... 54 | olig#477 ... 31 |
| olig#473 ... 48 | olig#478 ... 48 |
| olig#474 ... 47 | olig#479 ... 55 |

TABLE 302

Variegation of Tail on Cl-2 vgl for pEP3000

| 5' | | | | e 60 | v 61 | p 62 | r 63 | v 64 | g 65 | g 66 | k 67 | m 68 | k 69 | g 70 | m 71 | s 72 | k 73 | m 74 |
|---|---|---|---|---|---|---|---|---|---|---|---|---|---|---|---|---|---|---|
| | cga | gtc | ggc | GAG | GTC | CCT | CGC | GTA | GGT | GGC | AAA | ATG | AAA | GGT | ATG | AGC | AAG | ATG |
| | spacer | | | PpuM I | | | | | | | | | | | | | | |

3'

| | | | | | | | | | 3' = olig#480 | | | | | | | |
|---|---|---|---|---|---|---|---|---|---|---|---|---|---|---|---|---|
| p 75 | q 76 | f 77 | I/M 78 | Q/R 79 | D/V 80 | R/G 81 | G 82 | V 83 | Q/L 84 | R/T 85 | F/Y 86 | R/C 87 | W/G 88 | V/D 89 | Q/R 90 | I/M 91 |
| CCG | CAG | TTC | ATs | CrG | GwT | sGA | GGT | GTC | C | wG | AsA | TwT | yGT | kGG | GwC | CrG | ATs |
| | olig#481 | | | 3' - | ct | cca | cag | g | Wc | tSt | aWa | Rca | mcc | cWc | gYc | taS |

| T/I 92 | R/Q 93 | V/I 94 | R/I 95 | F/Y 96 | D/V 97 | T/I 98 | R/Q 99 | V/I 100 | D/G 101 | V/I 102 | P/Q 103 | . 104 | . 105 | . 106 | | |
|---|---|---|---|---|---|---|---|---|---|---|---|---|---|---|---|---|
| AyC | CrG | rTT | AkA | TwT | GwT | AyC | CrG | rTT | GrT | rTT | CmG | TAA | TGA | TAG | GGT | AC |
| tRg | gYc | Yaa | tMt | aWa | cWa | tRg | gYc | Yaa | cYa | Yaa | gKc | att | act | atc | c - | 5' |
| | | | | | | | | | | | | | | | Kpn I | |

$2^{24}$ DNA and protein sequences = (approx) $1.6 \times 10^7$.
Number of bases in each oligonucleotide.
480 ... 82   481 ... 78

TABLES FOR EXAMPLE 4

TABLE 400

Search for Lambda Cro Half Site in HIV non-variable regions.

Gene seq id = HIVHXB2CG

Sequences sought

| | Consensus | O$_{R}$3- | O$_R$3-/consensus hybrid |
|---|---|---|---|
| forward 5' | TATCACC 3' | 5' TATCCCT 3' | 5' TATCACT 3' |
| reverse 5' | GGTGATA 3' | 5' AGGGATA 3' | 5' AGTGATA 3' |

Match with Or3- matches    = TATCCCT
HIV subsequence = a ATCt CTAGCAGTGGCG
              624 ↑

Match with Or3/consensus hybrid matches    = TATCACT
HIV subsequence = a ATCt CTAGCAGTGGCG
              624 ↑

Match with Consensus matches              = GGTGATA
HIV subsequence = ACAGATGGCAGGTGATg
                 5057 ↑

Match with Consensus matches    = TATCACC
HIV subsequence = c ATCt CCTATGGCAGGA
              5961 ↑

First target: TATCCCTAGCAGTGGCG

Second target: aATCtCTAGCAGTGGCG
              624 ↑

TABLE 401

Lambda Cro alpha 1 & 2 & slot for Polypeptide

| 5' | cga | CGG | AGG | TAA | CCT | m 1 ATG | e 2 GAA | q 3 CAA |
|---|---|---|---|---|---|---|---|---|
| | | spacer | | BstE II | | | | |

| r 4 | i 5 | t 6 | l 7 | k 8 | d 9 | y 10 | a 11 |
|---|---|---|---|---|---|---|---|
| CGC | ATA | ACC | CTA | AAG | GAC | TAC | GCG |
| | | | | | | | gc | olig#483 3'  ↓

| m 12 | r 13 | f 14 | g 15 | q 16 | t 17 | k 18 | t 19 |
|---|---|---|---|---|---|---|---|
| ATG | CGC | TTT | GGC | CAA | ACC | AAG | ACA |
| tac | gcg | aaa | ccg | gtt | tgg | ttc | tgt |
| | | | Bal I | | | | |

| a 20 | k 21 | d 22 | l 23 | g 24 | v 25 | . | . |
|---|---|---|---|---|---|---|---|
| GCC | AAA | GAT | CTC | GGG | GTG | TAG | TAG |
| cgg | ttt | cta | gag | ccc | cac | atc | atc |
| | | Bgl II | | | | | |
| | | | | Ava I | | | |

| . | | | | |
|---|---|---|---|---|
| TAG | GGT | ACC | AAG | GCG |
| atc | cca | tgg | ttc | cgc  - 5' olig#484 |
| | Kpn I | | spacer | |

Number of bases in each oligonucleotide.

483 ... 60   484 ... 65

TABLE 402

Variegated Polypeptide to attach to Cro Helices 1, 2, & 3 vgl for pEP4002

| | k 21 | d 22 | l 23 | g 24 | v 25 |
|---|---|---|---|---|---|
| ccg acg gcc | cgA | GAT | CTC | GGG | GTG |
| spacer | Bgl II | | Ava I | | |

TABLE 402-continued

Variegated Polypeptide to attach to Cro Helices 1, 2, & 3 vgl for pEP4002 y = equimolar T and C    m = equimolar A and C
n = equimolar A, C, G, and T

TABLE 403

Result of first variegation of alpha 1,2,3: vgPolyPeptide

| m 1 | e 2 | q 3 | r 4 | i 5 | t 6 | l 7 | k 8 | d 9 | y 10 | a 11 | m 12 | r 13 | f 14 | g 15 | q 16 | t 17 | k 18 |
|---|---|---|---|---|---|---|---|---|---|---|---|---|---|---|---|---|---|
| ATG | GAA | CAA | CGC | ATA | ACC | CTA | AAG | GAC | TAC | GCG | ATG | CGC | TTT | GGC | CAA | ACC | AAG |

| t 19 | a 20 | k 21 | d 22 | l 23 | g 24 | v 25 | y 26 | q 27 | s 28 | a 29 | i 30 | n 31 | k 32 | a 33 | i 34 | h 35 | M 36 |
|---|---|---|---|---|---|---|---|---|---|---|---|---|---|---|---|---|---|
| ACA | GCC | AAG | GAC | CTA | GGC | GTG | TAT | CAG | AGC | GCG | ATT | AAC | AAA | GCG | ATC | CAC | ATG |

| Q 37 | V 38 | R 39 | G 40 | D 41 | L 42 | T 43 | Y 44 | C 45 | W 46 | V 47 | Q 48 | I 49 | I 50 | R 51 | V 52 | R 53 | F 54 |
|---|---|---|---|---|---|---|---|---|---|---|---|---|---|---|---|---|---|
| CAG | GTT | AGA | GGG | GAT | CTG | ACA | TAT | TGT | TGG | GTG | CAG | ATC | ATC | CGG | GTT | AGA | TTT |

| D 55 | T 56 | R 57 | V 58 | G 59 | I 60 | Q 61 | | | |
|---|---|---|---|---|---|---|---|---|---|
| GAT | ACC | CGG | GTT | GGT | ATT | CAG | TAG | TAG | TAG |

| y 26 | q 27 | s 28 | a 29 | i 30 | n 31 | k 32 | a 33 |
|---|---|---|---|---|---|---|---|
| TAT | CAG | AGC | GCG | ATT | AAC | AAA | GCG |

| i 34 | h 35 | I 36 | M Q 37 | R D 38 | V R 39 | I W 40 | G D 41 | G |
|---|---|---|---|---|---|---|---|---|
| ATC | CAC | ATs | CrG | GwT | AkA | kGG | GrT | |

| Q L 42 | R T 43 | F Y 44 | R C 45 | W G 46 | V 47 | Q 48 | |
|---|---|---|---|---|---|---|---|
| CwG | AsA | TwT | yGT | kGG | GTG | CAG | |
| | cc | cac | gac | | | | |

↓ 3' = olig#486

| I M 49 | T I 50 | R Q 51 | V I 52 | R I 53 | F Y 54 | D V 55 | T I 56 |
|---|---|---|---|---|---|---|---|
| ATs | AyC | CrG | rTT | AkA | TwT | GwT | AyC |
| taS | yRg | gYc | Yaa | tMt | aWa | cAa | tRg |

| R Q 57 | V I 58 | D G 59 | V I 60 | P Q 61 | | | |
|---|---|---|---|---|---|---|---|
| CrG | rTT | GrT | rTT | CmG | TAG | TAG | TAG |
| gYc | Yaa | cYa | Yaa | gKc | atc | atc | atc |

| GGT | ACC | AAG | GCG |
|---|---|---|---|
| cca | tgg | ttc | cgc    5' = olig#488 |
| Kpn I | | spacer | | s = equimolar C and G         r = equimolar A and G
w = equimolar A and T         k = equimolar T and G

TABLES FOR EXAMPLE 5

TABLE 500

Proposed binding of Arc dimer to arcO.

(a) Interaction of residues 1-10 with arcO

Arc    N ———→ C   C ←——— N
arcO   5' ATrrTAGArk smyTCTAyyAT
       3' TAyyATCTymsk rAGATrrTA (b) N-terminal residues interacting with same polypeptide chain, dimer contacts near C-terminus Arc    1 N————————N 2
arcO   5' ATrrTAGArk smyTCTAyyAT
       3' TAyyATCTymsk rAGATrrTA (c) N-terminal residues interacting with opposite polypeptide chain, dimer contacts close to residue 10.

Arc    1 N————————N 2
arcO   5' ATrrTAGArk smyTCTAyyAT
       3' TAyyATCTymsk rAGATrrTA

TABLE 501

Search of HIV-1 isolate HXB2 DNA sequence for sequences related to one half of arcO In arcO sequence, upper case letters represent palindromically related bases.

In HIV-1 subsequences:

TABLE 501-continued

Search of HIV-1 isolate HXB2 DNA sequence for sequences related to one half of arcO @ represents a nucleotide found to vary among HIV-1 isolates, lower case letters represent mismatch to arcO.

HIV-1 1016-1051 is non-variable.

arcO left half      =            ATr r TAGAr k
HIV-1 subsequence = @@ATCATTATATAATAc AGTAGCAACCCTCTATTGTGT@
                      1024    ↑ arcO right half     =            my TCTAy y AT
HIV-1 subsequence = CAGTAGCAACCCTCTATTg TGT@
                      1040    ↑

2387-2427 in non-variable.

arcO left half      =   ATr r TAGAr k
HIV-1 subsequence = @ATGATAGg GGGAATTGGAGGTTTTATCAAAG
              2387    ↑

4661-4695 is non-variable.

arcO left half      =            ATr r TAGAr k
HIV-1 subsequence = AAGTCAAGGAg TAGTAGAATCTATGAATAA@
                      4676    ↑

TABLE 502

Progression of Targets Leading to HIV-1 1016-1037

(a)
```
              1016       1024      center         1047
               ↓          ↓          |             ↓
HIV-1     5'  ATCATTATATAATAcAGTAGCAACCCTCTA T T
First target  5'      TAc ATg ATAgAa gc a At a CTa T@@@

P22 sequence  5'  att gacATgaTAGAagcacTCTAct ATat t ct caat a  3'
              3'  t aact gTAct ATCTt cgt gAGATgaTAt aagagt t at  5'
                                   arcO
```

In target:  Upper case indicates that HIV-1 and arcO agree.
            Lower case indicates a change to match arcO.
            Underscore indicates identity to arcO.
            @ indicates bases that vary between instances of target.
In arcO:    underscore indicates DNase I protected.
            lower case indicates not palindromically related.

(b)
```
Novel DBP = N X X X XX ─────▷C C◁───── X X X X X N
            . . . . . | | | | | | | | | | | | | # | | | | | | S S S SS
First target = @@@TAc ATgATAgAagcaCt A taCTaT@@@
```

In the Novel DBP, X represents variegated sequence.

In the line between Novel DBP and target DNA:

. represents regions where variegated sequence will produce amino acid sequences that will bind specifically.

N & C are the amino and carboxy ends residues 1-10.

| or \ represent regions where constant amino acid sequence is known to bind DNA.

\# represents regions where constant amino acid sequence is believed not to bind DNA.

S represents regions where DNA sequence varies between different instances of the target.

TABLE 502-continued

Progression of Targets Leading to HIV-1 1016-1037

(c)
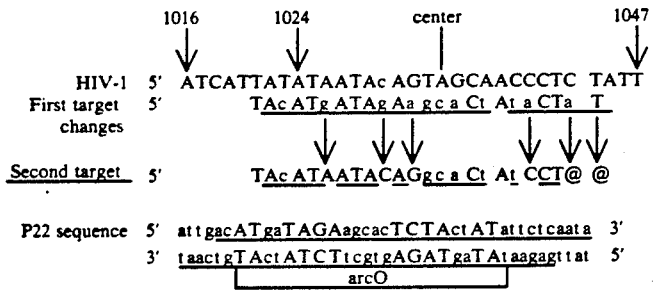

(d)
```
Novel DBP      =  N···-XXXXXXXX>C C<XXXXXXXX···N
                  \|||.........|||| ssssssssssss
Second target  =  @TAcATAATACAGgcaCt At CCT@@@@@@
```

(e)
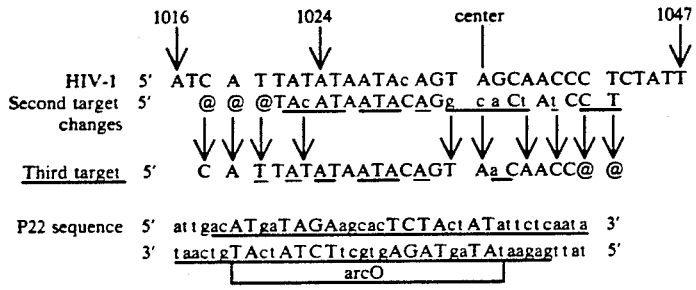

(f)
```
                 diffuse variegation
Novel DBP     =  NXXXXXXXXXXXXX>C C<XXXXXXXXXXXXXN
                 ..............||ssssssssssssssss
Third target  =  @@CATTATATAATACAGTAa CAACC@@@@@@@@@@
```

(g)
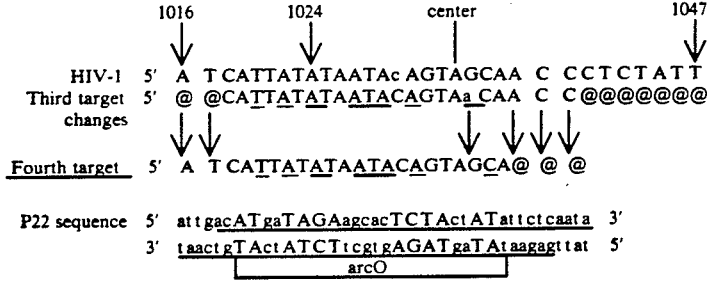

(h)
```
              diffuse variegation
Novel DBP  =  NXXXX————————>C C<————————XXXXN
              .....||||||||||||||ssssssssssssssss
Fourth target  5' ATCATTATATAATACAGTAGCA@@@@@@@@@@@@@@
```

TABLE 503

First Target Downstream of Promoters of Selectable Genes

First Target downstream of $P_{amp}$ that promotes galT,K

```
         5' |CCT |GCG |AAC |CGG |AAT |TGC |CAG |CTG |GGG |CGC |CCT |CTG |GTA |AGG |TTG |-
Olig#501 = 3' gga  cgc  ttg  gcc  tta  acg  gtc  gac  ccc  gcg  gga  gac  cat  tcc  aac-
            |StuI|              |   -35   |                   |       -10     |
```

TABLE 503-continued

First Target Downstream of Promoters of Selectable Genes

```
              1024
               ↓
| GGA | TAC | ATG | ATA | GAA | GCA | CTA | TAC | TAT | A          3' = Olig#502
   cct   atg   tac   tat   ctt   cgt   gat   atg   ata  t tcg a   5'
        |_____First Target_____|   | Hind3 |
```

First Target downstream of $P_{neo}$ that promotes tet

```
Olig#503  3'   5' | CTT | CTA | AAT | ACA | TTC | AAA | TAT | GTA | TCC | GCT | CAT | GAG | ACA | ATA |-
               c   cgg   gaa   gat   tta   tgt   aag   ttt   ata   cat   agg   cga   gta   ctc   tgt   tat-
               | ApaI |                  |_____ -35 _____|                              |___ -10 ___|
```

```
              1024
               ↓
| ACC | CT | TAC | ATG | ATA | GAA | GCA | CTA | TAC | TAT | CGT |        3' = Olig#504
   tgg   ga   atg   tac   tat   ctt   cgt   gat   atg   ata   gca   gat c  5'
        |_____First Target_____|   | XbaI |
```

TABLE 504

First variegated insert into ped gene

| 5' | cct | cag | cGG | TAA | CCT | m 1 ATG | X 96 fzk | X 97 fzk | X 98 fzk | X 99 fzk | X 100 fzk |
|---|---|---|---|---|---|---|---|---|---|---|---|
| | spacer | | BstE II | | | | | | | | |

| | m 101 ATG | k 102 AAG | g 103 GGT | m 104 ATG | s 105 TCT | k 106 AAA |
|---|---|---|---|---|---|---|

Center of symmetry for priming.
↓

| | m 107 ATG | p 108 CCT | h 109 CAC | f 110 TTT | n 111 AAC | l 112 CTC | r 113 AGG | cgt | att | aat | acg | cct | g-3' |
|---|---|---|---|---|---|---|---|---|---|---|---|---|---|
| | | | | | | Bsu36I | | | | | primer olig#605 | | |

Self priming

```
...CTC | AGG | cgt | att |
  3'-     tcc   gca   taa   >
```

3' end self primes for extension with Klenow enzyme.

f = (0.26 T, 0.18 C, 0.26 A, 0.30 G)
z = (0.22 T, 0.16 C, 0.40 A, 0.22 G)
k = equimolar T and G
There are $(2^5)^5 = 3.2 \times 10^7$ different DNA sequences encoding $20^5 = 3.2 \times 10^6$ different protein sequences.
100 has been added to residue numbers for wild-type Arc.

TABLE 505

Protein Ped-6 Selected for Binding to First Target

| m 1 ATG | k 96 AAG | d 97 GAT | i 98 ATT | w 99 TGG | r 100 CGT | m 101 ATG | k 102 AAG | g 103 GGT | m 104 ATG | s 105 TCT | k 106 AAA | m 107 ATG | p 108 CCT | h 109 CAC | f 110 TTT |
|---|---|---|---|---|---|---|---|---|---|---|---|---|---|---|---|

| n 111 AAC | l 112 CTC | r 113 AGG | w 114 TGG | p 115 CCC | r 116 CGG | e 117 GAG | v 118 GTC | l 119 CTT | d 120 GAT | l 121 CTT | v 122 GTT | r 123 CGC | k 124 AAG | v 125 GTT | a 126 GCT |
|---|---|---|---|---|---|---|---|---|---|---|---|---|---|---|---|
| | Bsu36I | | | Xma I | | PpuM I | | | | | | | | | |

| e 127 GAG | e 128 GAA | n 129 AAC | g 130 GGT | r 131 CGG | s 132 TCC | v 133 GTT | n 134 AAC | s 135 TCT | e 136 GAG | i 137 ATC | y 138 TAT | n 139 AAT | r 140 CGC | v 141 GTT | m 142 ATG |
|---|---|---|---|---|---|---|---|---|---|---|---|---|---|---|---|
| | | | | Rsr II | Hpa I | | | | | Bgl II | | | | | |

TABLE 505-continued

Protein Ped-6 Selected for Binding to First Target

| e<br>143<br>GAG | s<br>144<br>TCG | f<br>145<br>TTC | k<br>146<br>AAG | k<br>147<br>AAA | e<br>148<br>GAG | g<br>149<br>GGT | r<br>150<br>CGT | i<br>151<br>ATC | g<br>152<br>GGC | a<br>153<br>GCA | .<br>TAA | .<br>TAG | .<br>TGA | GGT \| ACC<br>Kpn I |

TABLE 506

Second Target Downstream of Promoters of Selectable Genes

Second Target downstream of P$_{amp}$ that promotes galT,K

```
         5'   | CCT | GCG | AAC | CGG | AAT | TGC | CAG | CTG | GGG | CGC | CCT | CTG | GTA | AGG | TTG |
Olig#541 = 3'    gga   cgc   ttg   gcc   tta   acg   gtc   gac   ccc   gcg   gga   gac   cat   tcc   aac-
              | StuI |                        | -35 |                                         | -10 |
```

```
          1024
           ↓
| GGA | TAC | ATA | ATA | CAG | GCA | CTA | TCC | T | A        3' = Olig#542
   cct   atg   tat   tat   gtc   cgt   gat   agg   a   t   tcga 5'
              |          Second Target           |   | Hind3 |
```

Second Target downstream of P$_{neo}$ that promotes tet

```
          5'   | CTT | CTA | AAT | ACA | TTC | AAA | TAT | GTA | TCC | GCT | CAT | GAG | ACA | ATA |
Olig#543  3'  c  cgg   gaa   gat   tta   tgt   aag   ttt   ata   cat   agg   cga   gta   ctc   tgt   tat-
              | ApaI |                        | -35 |                                         | -10 |
```

```
          1024
           ↓
| ACC | CT | TAC | ATA | ATA | CAG | GCA | CTA | TCC | T | CGT        3' = Olig#544
   tgg   ga   atg   tat   tat   gtc   cgt   gat   agg   a   gca   gat   c   5'
              |            Second Target             |   | XbaI |
```

TABLE 507

Variegation for selection with Second Target

```
                                                         R | k
                                   m    k    d    i    w  e | g
5'- cga | ctg | cGG | TAA | CCT | ATG | AAA | GAT | ATC | TGG | rrA |
         spacer    | BstE II |     1    96    97   98    99   100
```

```
                    •                    •                    •                    •
                  M | r    K | q    G | d    M | i    S | r    K | q
                  v | g    t | p    h | r    f | l    n | k    t | p
                  | 101 |  | 102 |  | 103 |  | 104 |  | 105 |  | 106 |
                  | rkG |  | mmG |  | srT |  | wTK |  | Ark |  | mmA |
```

```
         •            •
M | r    P | q    H | y    F | y
v | g    r | l    s | p    v | d    n       l        r          Center of symmetry for priming
| 107 |  | 108 |  | 109 |  | 110 |  111    112     113                      ↓
| rkG |  | CnG |  | ymT |  | kwT |  AAC    CTC     AGG     cgt | att | aat | acg | cct | g-3'
                           | Bsu36I |                                   | primer |
``` k = equimolar T and G    r = equimolar A and G
w = equimolar T and A    s = equimolar C and G
m = equimolar A and C    y = equimolar T and C
Approximately 4 × 10$^6$ DNA and protein sequences.
*indicates sites of one alternative variegation.

TABLE 508

Protein Ped-6-2 Selected for Binding to Second Target

| m<br>1<br>ATG | k<br>96<br>AAG | d<br>97<br>GAT | i<br>98<br>ATT | w<br>99<br>TGG | E<br>100<br>GAG | R<br>101<br>AGG | Q<br>102<br>CAG | G<br>103<br>GGT | M<br>104<br>ATG | R<br>105<br>AGG | T<br>106<br>ACA | M<br>107<br>ATG | P<br>108<br>CCT | Y<br>109<br>TAC | F<br>110<br>TTT |

TABLE 508-continued

Protein Ped-6-2 Selected for Binding to Second Target

| n 111 AAC | l 112 CTC | r 113 AGG | w 114 TGG | p 115 CCC | r 116 CGG | e 117 GAG | v 118 GTC | l 119 CTT | d 120 GAT | l 121 CTT | v 122 GTT | r 123 CGC | k 124 AAG | v 125 GTT | a 126 GCT |
|---|---|---|---|---|---|---|---|---|---|---|---|---|---|---|---|
| | Bsu36I | | | | Xma I | PpuM I | | | | | | | | | |

| e 127 GAG | e 128 GAA | n 129 AAC | g 130 GGT | r 131 CGG | s 132 TCC | v 133 GTT | n 134 AAC | s 135 TCT | e 136 GAG | i 137 ATC | y 138 TAT | n 139 AAT | r 140 CGC | v 141 GTT | m 142 ATG |
|---|---|---|---|---|---|---|---|---|---|---|---|---|---|---|---|
| | | | | Rsr II | | Hpa I | | | | Bgl II | | | | | |

| e 143 GAG | s 144 TCG | f 145 TTC | k 146 AAG | k 147 AAA | e 148 GAG | g 149 GGT | r 150 CGT | i 151 ATC | g 152 GGC | a 153 GCA | . TAA | . TAG | . TGA | GGT | ACC |
|---|---|---|---|---|---|---|---|---|---|---|---|---|---|---|---|
| | | | | | | | | | | | | | | | Kpn I |

TABLE 509

Protein Ped-6-2-5 Selected for Binding to Third Target

| m 1 ATG | R 96 AGG | D 97 GAT | V 98 GTT | W 99 TGG | H 100 CAT | V 101 GTG | R 102 CGG | N 103 AAT | I 104 ATT | T 105 ACG | R 106 AGA | V 107 GTG | R

TABLE 511

Variegation for Selection with Fourth Target

| | | | | | m 1 ATG | X 90 fzk | X 91 fzk | X 92 fzk | X 93 fzk | X 94 fzk | X 95 fzk | R 96 CGG | D 97 GAC | V 98 GTG | W 99 TGG | H 100 CAC |
|---|---|---|---|---|---|---|---|---|---|---|---|---|---|---|---|---|
| cct | cag | cGG | TAA | CCT | | | | | | | | | | | | |
| spacer | | BstE II | | | | | | | | | | overlap | | | | |

| V 101 GTG | R 102 CGG | N 103 AAT | I 104 ATT | T 105 ACG | R 106 CGA | V 107 GTG | R 108 CGT | H 109 CAC | L 110 CTT | n 111 AAC | l 112 CTC | r 113 AGG | cgt | cac | ggc |
|---|---|---|---|---|---|---|---|---|---|---|---|---|---|---|---|
| | | | | | | | | | | | Bsu36I | | | spacer | | f = (0.26 T, 0.18 C, 0.26 A, 0.30 G)
z = (0.22 T, 0.16 C, 0.40 A, 0.22 G)
k = equimolar T and G
There are $(2^5)^6 = 2^{30} = 10^9$ DNA sequences.
There are $20^6 = 6.4 \times 10^7$ protein sequences.

TABLE 512

Protein Ped-6-2-5-2
Selected for Binding to Fourth Target

| m 1 ATG | R 90 CGT | T 91 ACG | G 92 GGG | F 93 TTT | C 94 TGT | Q 95 CAG | R 96 CGG |
|---|---|---|---|---|---|---|---|

| D 97 GAT | V 98 GTT | W 99 TGG | H 100 CAC | V 101 GTG | R 102 CGG | N 103 AAT | I 104 ATT |
|---|---|---|---|---|---|---|---|

| T 105 ACG | R 106 CGA | V 107 GTG | R 108 CGT | H 109 CAC | L 110 CTT |
|---|---|---|---|---|---|

| n 111 AAC | l 112 CTC | r 113 AGG | w 114 TGG | p 115 CCC | r 116 CGG | G |
|---|---|---|---|---|---|---|
| Bsu36I | | | Xma I | | | |

| e 117 AG | v 118 GTC | l 119 CTT | d 120 GAT | l 121 CTT | v 122 GTT |
|---|---|---|---|---|---|
| | PpuM I | | | | |

| r 123 CGC | k 124 AAG | v 125 GTT | a 126 GCT | e 127 GAG | e 128 GAA | n 129 AAC |
|---|---|---|---|---|---|---|

| g 130 GGT | r 131 CGG | s 132 TCC | v 133 GTT | n 134 AAC | s 135 TCT | e 136 G |
|---|---|---|---|---|---|---|
| | Rsr II | | | Hpa I | | |

| | i 137 AG ATC | y 138 TAT | n 139 AAT | r 140 CGC | v 141 GTT | m 142 ATG | e 143 GAG | s 144 TCG |
|---|---|---|---|---|---|---|---|---|
| | Bgl II | | | | | | | |

| f 145 TTC | k 146 AAG | k 147 AAA | e 148 GAG | g 149 GGT | r 150 CGT | i 151 ATC | g 152 GGC |
|---|---|---|---|---|---|---|---|

TABLE 512-continued

Protein Ped-6-2-5-2
Selected for Binding to Fourth Target

| a 153 GCA | . TAA | . TAG | . TGA | GGT | ACC |
|---|---|---|---|---|---|
| | | | | | Kpn I |

TABLE 513

Variegation of Length of Ped-6-2-5-2

| | | | N\|k | | V\|g | M\|k |
|---|---|---|---|---|---|---|
| | i | y\|. | y\|. | r\|. | l\|. | l\|. |
| | 137 | 138 | 139 | 140 | 141 | 142 |
| 5'-cgacctagcAG | ATC | TAw₁ | w₃Aw₄ | y₁Ga | k₁k₂A | w₃w₄G |
| spacer | Bgl II | | | | | |

| | | F\|c | | | | |
|---|---|---|---|---|---|---|
| e\|. | s\|. | l\|. | k\|. | k\|. | e\|. | g\|. | r\|. |
| 143 | 144 | 145 | 146 | 147 | 148 | 149 | 150 |
| k₃AG | Tm₁G | Tk₂m₂ | w₂AG | w₂AA | k₃AG | k₃GA | y₁GA |

| I\|k | | | | | | |
|---|---|---|---|---|---|---|
| l\|. | g\|. | | | | | |
| 151 | 152 | 153 | . | | | |
| w₃w₄A | k₃GA | TAG | TGA | GGT | ACC | t-3' |
| | | | | | Kpn I | |

$w_1 = 0.65$ T and $0.35$ A      $y_1 = 0.65$ C and $0.35$ T
$k_1 = 0.42$ G and $0.58$ T      $k_2 = 0.42$ T and $0.58$ G
$k_3 = 0.65$ G and $0.35$ T      $m_1 = 0.65$ C and $0.35$ A
$m_2 = 0.42$ C and $0.58$ A      $w_2 = 0.65$ A and $0.35$ T
$w_3 = 0.42$ A and $0.58$ T      $w_4 = 0.42$ T and $0.58$ A Each variegated residue produces about 35% stop codons.

Because $(0.65)^{15} = 0.003$, only 0.3% of variegated genes encode a protein shortened by one residue.

TABLE FOR EXAMPLE 6

TABLE 600

Third finger domain of kr —tgs— P22 arc

| AGG | AGG | TAA | CCT | m 1 ATG | e 2 GAG | k 3 AAA | p 4 CCG | y 5 TAT | h 6 CAC | C 7 TGC | s 8 TCA | h 9 CAC | C 10 TGT | d 11 GAT | r 12 CGT | q 13 CAG | F 14 TTT |
|---|---|---|---|---|---|---|---|---|---|---|---|---|---|---|---|---|---|
| | BstE II | | | | | | | | | | | Dra III | | | | | |

TABLE 600-continued

Third finger domain of kr —tgs— P22 arc

```
     •       •    ApaL •    •              •      •        •     •    •    •     •
   | v  | q  | v  | a  | n  | l  | r  | r  | H  | l  | r  | v  | H  |
   | 15 | 16 | 17 | 18 | 19 | 20 | 21 | 22 | 23 | 24 | 25 | 26 | 27 |
   |GTC |CAA |GTG |GCC |AAC |TTA |AGA |CGT |CAT |CTA |CGC |GTG |CAC | -
         |  Bal I  |    |  Afl II |  Aat II |    |  Mlu I  |
                                                      |   Apal I   |

|← linker →|←————P22 arc
   •    •    •    •    •    •    •    •    •    •    •    •    •    •
   | t  | g  | t  | g  | s  | m  | k  | g  | m  | s  | k  | m  | p  | q  | f  |
   | 28 | 29 | 30 | 31 | 32 |101 |102 |103 |104 |105 |106 |107 |108 |109 |110 |
   |ACT |GGT |ACC |GGG |TCT |ATG |AAA |GGC |ATG |TCT |AAG |ATG |CCG |CAA |TTC |
              | Kpn I |

| n  | l  | r  | w  | p  | r  | e  | v  | l  | d  | l  | v  | r  | k  |
   |111 |112 |113 |114 |115 |116 |117 |118 |119 |120 |121 |122 |123 |124 |
   |AAC |CTT |AGG |TGG |CCC |CGG |GAG |GTC |CTT |GAT |TTG |GTT |CGC |AAA |
        | Bsu36I |         | Ava I  |     | PpuM I |
                           | Xma I  |

| v  | a  | e  | e  | n  | g  | r  | s  | v  | n  | s  |
   |125 |126 |127 |128 |129 |130 |131 |132 |133 |134 |135 |
   |GTC |GCT |GAA |GAG |AAT |GGC |CGG |TCC |GTG |AAT |TCT |
                  | Ksp 632 |          | Rsr II  |  EcoR I  |

| e  | i  | y  | n  | r  | v  | m  | e  | s  | f  | k  |
   |136 |137 |138 |139 |140 |141 |142 |143 |144 |145 |146 |
   |GAG |ATC |TAT |AAT |CGT |GTT |ATG |GAA |AGC |TTC |AAG |
        | Bgl II |

| k  | e  | g  | r  | i  | g  | a  |    |    |    |
   |147 |148 |149 |150 |151 |152 |153 |154 |155 |156 |
   |AAG |GAA |GGT |CGC |ATT |GGT |GCA |TAA |TAG |TGA |GGA |TTC |
                                                       HindIII
```

\* indicates residues of zinc finger domain thought to contact DNA in model of Gibson et al.

\* indicates residues of zinc finger domain, linker, and Arc that may influence DNA binding.

CITATIONS

AHME84
Ahmed, A; "Plasmid vectors for positive galactose-resistance selection of cloned DNA in *Escherichia coli*"; Gene (1984) 28: 37–43

AIBA86
Aiba, H, T Nakamura, H Mitani, and H Mori; "Mutations that alter the allosteric nature of cAMP receptor protein of *E. coli*"; EMBO J (1986), 4(12)3329–32

ANDE81
Anderson, WF, DH Ohlendorf, Y Takeda, BW Matthews; "Structure of the Cro Repressor from Bacteriophage Lambda and its Interaction with DNA"; Nature (1981), 290: 754–758

ANDE85
Anderson, JE, M Ptashne and SC Harrison; "A phage repressor-operator complex at 7 A resolution."; Nature (1985), 316: 596–601

ANDE87
Anderson, JE, M Ptashne and SC Harrison; "Structure of the repressor-operator complex of bacteriophage 434"; Nature (1987), 326: 846–852

ANDE88
Anderson, WF, M Cygler, RP Braun and JS Lee "Antibodies to DNA"; Bioessays (1988), 8: 69–74

ASTE81
Astell, CR, L Ahlstrom-Jonasson, M Smith, K Tatchell, KA Nasmyth, and BD Hall "The sequence of the DNAs coding for the mating-type loci of *Saccharomyces cerevisiae*"; Cell (1981) 27: 15–23

AUSU87
Ausubel, FM, R Brent, RE Kingston, DD Moore, JG Seidman, JA Smith, K Struhl; Current Protocols in Molecular Biology. 1987, John Wiley and Sons Barnes, G, and J Rine, "Regulated expression of endonuclease EcoRI in *Saccharomyces cerevisiae*: Nuclear entry and biological consequences", Proc Natl Acad Sci USA (1985), 82:1354–58.

BASH87
Bash, PA, UC Singh, R Langridge, and PA Kollman "Freee energy calculations by computer simulation."; Science (1987), 236 (4801) 564–8.

BASS87
Bass, S, P Sugiono, DN Arvidson, RP Gunsalus, and P Youderian; "DNA specificity determinants of *Escherichia coli* tryptophan repressor binding"; Genes and Development (1987) 1: 565–572

BASS88
Bass, S, V Sorrells, and P Youderian; "Mutant Trp Repressors with New DNA-Binding Specificities"; Science (1988), 242: 240–245

BECK88
Becker, MM, D Lesser, M Kurpiewski, A Baranger and L Jen-Jacobson, "'Untraviolet footprinting' accurately maps sequence-specific contacts and DNA kinking in the EcoRI endonuclease-DNA complex", Proc Natl Acad Sci USA (Sept. 1988), 85:6247–6251.

BENS86
Benson, N, Sugiono, S Bass, LV Mendleman, and P Youderian; "General Selection for Specific DNA-Binding Activities"; Genetics (1986), 114:1–14

BENS88
Benson, N, P Sugiono, and P Youderian; "DNA Sequence Determinants of Lambda Repressor Binding in Vivo"; Genetics (1988), 188: 21–29

BERG88
Berg, JM; "Proposed structure for the zinc-binding domains from transcription factor IIIA and related proteins"; Proc Natl Acad Sci USA (1988), 85: 99–102

BERG88
Berg, OG; "Selection of DNA binding sites by regulatory proteins: the LexA protein and the arginine repressor use different strategies for functional specificity"; Nucleic Acids Research (1988), 16: 5089–5105

BLOC84
Blochlinger, K and H Diggelman; "Hygromycin B phosphotransferase as a selectable marker for DNA transfer experiments with higher eucaryotic cells"; Mol Cell Biol (1984), 4: 2929–2931

BOCH80
Bochner, BR, H Huang, GL Schieven, and BN Ames; "Positive selection for loss of tetracycline resistance"; J Bacteriol (1980), 143: 926–933

BOHN88
Bohnlein, E, JW Lowenthal, M Siekevitz, DW Ballard, BR Franza and WC Greene; "The Same Inducible Nuclear Proteins Regulates Mitogen Activation of Both the Interleukin-2 Receptor-Alpha Gene and Type 1 HIV"; Cell (1988), 53: 827–836

BOTS85
Botstein, D, and D Shortle, "Strategies and Applications of in Vitro Mutagenesis.", Science (1985), 229:1193–1201.

BREM86
Bremer, H, and S Lin-Chao, "Analysis of the physiological control of replication of ColEl-type plasmids.", J Theor Biol (1986) 123(4)453–470.

BREN84
Brent, R, and M Ptashne; "A bacterial repressor protein or a yeast transcriptional terminator can block upstream activation of a yeast gene"; Nature (1984), 312: 612–615

BROS82
Brosius, J, RL Cate, and AP Perlmutter "Precise location of two promoters for the beta-lactamase gene of pBR322. S1 mapping of ribonucleic acid isolated from *Escherichia coli* or synthesized in vitro"; J Biol Chem (1982), 257: 9205–9210

BROS84
Brosius, J; "Plasmid vectors for the selection of promoters"; Gene (1984), 27: 151–160

BROW87
Brown, M, J Figge, U Hansen, C Wright, KT Jeang, G Khoury, DM Livingston, and TM Roberts; "lac Repressor Can Regulate Expression from a Hybrid SV40 Early Promoter Containing a lac Operator in Animal Cells"; Cell (1987), 49: 603–612

BRUN87:
Brunelle, A, and RF Schleif, "Missing contact probing of DNA-protein interactions", PNAS (1987), 84:6673–6676.

BUSH85
Bushman, FD, JE Anderson, SC Harrison and M Ptashne; "Ethylation interference and X-ray crystallography identify similar interactions between 434 repressor and operator"; Nature (1985), 316: 651–653

BUSH88
Bushman, FD, and M Ptashne; "Turning Lambda Cro into a Transcriptional Activator"; Cell (1988), 54: 191–197

BUTT63
Buttin, G; "Mechanismes regulateurs dan la biosynthese des enzymes du metabolisme du galactose des *Escherichia coli* K-12. I. La biosynthese induite de la galactokinase et l'induction simultanee de la sequence enzymatique"; J Mol Biol (1963), 7: 164–182

CAIR88
Cairns, J, J Overbaugh and S Miller; "The origin of mutants"; Nature (1988), 335: 142–145

CALL82
Calladine, CR; "Mechanics of sequence-dependent stacking of bases in B-DNA"; J Mol Biol (1982), 161: 343–352

CARU83
Caruthers, MH, SL Beaucage, JW Efcavitch, EF Fisher, RA Goldman, PL DeHaseth, W Mandecki, MD Matteucci, MS Rosendahl, and Y Stabinski; "Chemical Synthesis and Biological Studies on Mutated Gene-Control Regions"; Cold Spr Harb Symp Quant Biol (1983), 47:411–418

CARU85
Caruthers, MH; "Gene Synthesis Machines: DNA Chemistry and Its Uses"; Science (1985), 230:281–285

CARU87
Caruthers, MH, P Gottlieb, L Bracco and L Cummins; "The Thymine 5-Methyl Group: A Protein-DNA Contact Site Useful for Redesigning Cro Repressor to Recognize A New Operator"; Protein Structure, Folding, and Design (1987), 2: 9–24

CHAD71
Chadwick, P, V Pirrotta, R Steinberg, N Hopkins, and M Ptashne; "The Lambda and 434 Phage Repressors"; Cold Spring Harb Symp Quant Biol (1971), 35:283–294

CHEN88
Chen, W, and K Struhl; "Saturation mutagenesis of a yeast his3'TATA element': Genetic evidence for a specific TATA-binding protein"; Proc Natl Acad Sci USA (1988), 85:2691–2695

CHOT76
Chothia, C, S Wodak, and J Janin; "Role of subunit interfaces in the allosteric mechanism of hemoglobin"; Proc Natl Acad Sci USA (1976), 73:3793–7

CHOT86
Chothia, C, and AM Lesk; "The relation between the divergence of sequence and structure in proteins"; EMBO J (1986), 5:823–826

CHOU78a
Chou, PY, and GD Fasman; "Prediction of the secondary structure of proteins from their amino acid sequence"; Adv Enzymol (1978), 47:45–148

CHOU78b
Chou, PY, and GD Fasman; "Empirical predictions of protein conformation"; Annu Rev Biochem (1978), 47:251≧76

CLOR87

Clore, GM, AM Gronenborn, M Kjaer, and FM Poulsen; "The determination of the three-dimensional structure of barley serine proteinase inhibitor 2 by NMR, distance geometry, and restrained molecular dynamics"; Protein Engineering (1987), 1:305-311

COSS85
Cossart, P, and B Gicquel-Sanzey; "Regulation of expression of the crp gene of E. coli K-12: in vivo study"; J Bacteriol (1985), 161(1)454-7

CRAI85
Craik, CS, C Largman, T Flecher, S Roczniak, PJ Barr, R Fletterick, and WJ Rutter, "Redesigning trypsin: alteration of substrate specificity", Science (1985) 228:291-297.

CRAW87:
Crawford, IP, M Clarke, M van Cleemput, and C Yanofsky, "Crucial Role of the Connecting Region Joining the Two Functional Domains of Yeast Tryptophan Synthetase.", J Biol Chem (1987), 262(1)239-244.

CREI84:
Creighton, TE, *Proteins: Structures and Molecular Principles.*, W. H. Freeman & Co., New York, 1984.

DAVIS80
Davis, RW, D Botstein, and JR Roth; *Advanced Bacterial Genetics;* Cold Spring Harbor Laboratory Press, 1980

DAYR86
Dayringer, H, A Tramantano, and R Fletterick; "Proteus Software for Molecular Modeling" p.5-8 in *Computer Graphics and Molecular Modeling* Cold Spring Harbor Laboratory, Cold Spring Harbor, NY, 1986

DAYT86
Dayton, AI, JG Sodroski, CA Rosen, WC Goh, and WA Haseltine; "The Trans-Activator Gene of the Human T Cell Lymphotropic Virus Type III Is Required for Replication"; Cell (1986), 44: 941-947

DEFE86
DeFeyter, RC, BE Davidson, and J Pittard; "Nucleotide Sequence of the Transcription Unit Containing the aroL and aroM Genes from *Escherichia coli* K-12"; J Bacteriol (1986), 165: 233-239

DELO87
De Lorenzo, V, S Wee, M Herrero, and JB Neilands; "Operator Sequences of the Aerobactin Operon of Plasmid ColV-K30 Binding the Ferric Uptake Regulation (fur) Repressor"; J Bacteriol (1987) 165: 2624-2630

DICK83
Dickerson, RE; "Base Sequence and Helix Structure Variation in B and A DNA"; J Mol Biol (1983), 166: 419-441

DILL87
Dill, KA, "Protein Surgery", Protein Engineering (1987), 1:369-371.

EBRI84
Ebright, RH, P Cossart, B Gicquel-Sanzey, and J Beckwith; "Molecular basis of DNA sequence recognition by the catabolite gene activator protein: Detailed inferences from three mutations that alter DNA sequence specificity"; Proc Natl Acad Sci USA (1984), 81: 7274-7278

EISE85
Eisenbeis, SJ, MS Nasoff, SA Noble, LP Bracco, DR Dodds, and MH Caruthers; "Altered Cro repressors from engineered mutagenesis of a synthetic cro gene"; Proc Natl Acad Sci USA (1985), 82: 1084-1088

EISE86a
Eisenberg, D, W Wilcox, and AD McLachlan; "Hydrophobicity and amphiphilicity in protein structure"; J cell Biochem (1986), 31: 11-17

EISE86b
Eisenberg, D, and AD McLachlan; "Solvation energy in protein folding and binding"; Nature (1986), 319: 199-203

ELIA85
Eliason, JL, MA Weiss, and M. Ptashne; "$NH_2$-terminal arm of phage lambda repressor contributes energy and specificity to repressor binding and determines the effects of operator mutations"; Proc Natl Acad Sci USA (1985), 82: 2339-2343

EVAN88
Evans, RM, and SM Hollenberg; "Zinc Fingers: Gilt by Association"; Cell (1988), 52: 1-3

FAIR86
Fairall, L, D Rhodes, and A Klug; "Mapping of the Sites of Protection on a 5 S RNA Gene by the Xenopus Transcription Factor IIIA"; J Mol Biol (1986), 192:577-591

FEIN86
Feinberg, MB, RF Jarrett, A Aldovini, RC Gallo, and F Wong-Staal; "HTLV-III Expression and Production Involve Complex Regulation at the Levels of Splicing and Translation of Viral RNA"; Cell (1986), 46: 807-817

FIGG88
Figge, J, C Wright, CJ Collins, TM Roberts, and DM Livingston; "Stringent Regulation of Stably Integrated Chloramphenicol Acetyl Transferase Genes by E. coli lac Repressor in Monkey Cells"; Cell (1988), 52: 713-722

FILU85
Filutowicz, M, G Davis, A Greener, and DR Helinski; "Autorepressor properties of the pi-initiation protein encoded by plasmid R6K"; Nucl Acids Res (1985), 13: 103-114

FRAN88
Fankel, AD, and CO Pabo; "Fingering Too Many Proteins"; Cell (1988), 53: 675

FRIE81
Fried, MG, and DM Crothers; "Equilibria and kinetics of lac repressor-operator interactions by polyacrylamide gel electrophoresis"; Nucl Acids Res (1981), 9: 6505-6525

FOXK88
Fox, KR, "DNAase I Footprinting of Restriction Enzymes", Biochem & Biophys Res Comm (Sept 1988), 155(2)779-785.

GARG85
Garges, S, and S Adhya; "Sites of allosteric shift in the structure of the cAMP receptor protein"; Cell (1985), 41: 745-751

GARG88
Garges, S, and S Adhya; "Cyclic AMP-induced conformational change of cyclic AMP receptor protein (CRP): intragenic suppressors of cAMP-independent CRP mutations"; J Bacteriol (1988), 170: 1417-1422

GART88
Gartenberg, MR, and DM Crothers; "DNA sequence determinants of CAP-induced bending and protein binding affinity"; Nature (1988), 333: 824-829

GIBS88

Gibson, TJ, JPM Postma, RS Brown, and P Argos; "A model for the tertiary structure of the 28 residue DNA-binding motif ('zinc finger') common to many eukaryotic transcriptional regulatory proteins"; Protein Engineering (1988), 2: 209-218

GILL81:
Gilliland, GL, and FA Quiocho, "Structure of the L-arabinose-binding protein from *Escherichia coli* at 2.4 A resolution.", J Mol Biol (1981), 146(3)341-62.

GODO88
Godowski, PJ, D Picard, and KR Yamamoto; "Signal transduction and transcriptional regulation by glucocorticoid recaeptor-LexA fusion proteins"; Science (1988), 241: 812-816

GOLD87
Gold, L, and G Stormo; "Translation Initiation"; Volume 2, Chapter 78, p 1302-1307; *Escherichia coli and Salmonella typhimurium: Cellular and Molecular Biology;* Neidhardt, FC, Editor-in-Chief; Amer Soc for Microbiology, Washington, DC, 1987

GOTT87
Gottesman, S; "Regulation by Proteolysis"; Volume 2, chapter 79, p 1308-1312; *Escherichia coli and Salmonella typhimurium: Cellular and Molecular Biology;* Neidhardt, FC, Editor-in-Chief; Amer Soc for Microbiology, Washington, DC, 1987

GUAR82
Guarente, L, JS Nye, A Hochschild, and M Ptashne; "Mutant lambda phage repressor with a specific defect in its positive control function"; Proc Natl Acad Sci USA (1982), 79: 2236-2239

GUTE73
Guterman, SK; "Colicin B: Mode of Action and Inhibition by Enterochelin"; J Bacteriol (1973) 111: 1217-1224

HALL87
Hall, MN, and AD Johnson; "Homeo domain of the yeast repressor alpha 2 is a sequence-specific DNA-binding domain but is not sufficient for repression"; Science (1987), 237: 1007-1012

HANA85
Hanahan, D; "Techniques for Transformation of *E. coli*" (In: DNA Cloning Volume I. 1985 IRL Press) 109-135

HARR88
Harrison, SC, JE Anderson, GB Koudelka, A Mondragon, S Subbiah, RP Wharton, C Wolberger, and M Ptashne; "Recognition of DNA sequences by the repressor of bacteriophage 434"; Biophys Chem (1988), 29: 31-37

HAWL83
Hawley, DK, and WR McClure, "Compilation and analysis of *Escherichia coli* promoter DNA sequences", Nucl Acids Res (1983), 11(8)2237-2255.

HECH83
Hecht, MH, HCM Nelson, and RT Sauer; "Mutations in lambda repressor's amino-terminal domain: implications for protein stability and DNA binding"; Proc Natl Acad Sci USA (1983), 80: 2676-2680

HECH84
Hecht, MH, JM Sturtevant, and RT Sauer; "Effect of single amino acid replacements on the thermal stability of the $NH_2$-terminal domain of phage lambda repressor"; Proc Natl Acad Sci USA (1984), 81: 5685-5689

HECH85a
Hecht, MH, and RT Sauer; "Phage Lambda Repressor Revertants: Amino Acid Substitutions that Restore Activity to Mutant Proteins"; J Mol Biol (1985), 186: 53-63

HECH85b
Hecht, MH, KM Hehir, HCM Nelson, JM Sturtevant, and RT Sauer; "Increasing and Decreasing Protein Stability: Effects of Revertant Substitutions on the Thermal Denaturation of Phage Lambda Repressor"; J Cellular Biochem (1985), 29: 217-224

HOCH83
Hochschild, A, N Irwin, and M Ptashne; "Repressor Structure and the Mechanism of Positive Control"; Cell (1983), 32: 319-325

HOCH86a
Hochschild, A, and M Ptashne; "Homologous Interactions of Lambda Repressor and Lambda Cro with the Lambda Operator"; Cell (1986), 44: 925-933

HOCH86b
Hochschild, A, J Douhan III, and M Ptashne; "How Lambda Repressor and Lambda Cro Distinguish between $O_R1$ and $O_R3$"; Cell (1986), 47: 807-816

HOGA87
Hogan, ME, and RH Austin, "Importance of DNA stiffness in Protein-DNA binding specificity.", Nature (1987), 329:263-266.

HOLL88
Hollis, M, D Valenzuela, D Pioli, R Wharton, and M Ptashne; "A Repressor heterodimer binds to a chimeric operator"; pNAS (1988), 85:5834-5838

HOOP87
Hoopes, BC, and WR McClure; "Strategies in Regulation of Transcription Initiation" Volume 2, Chapter 75, p 1231-1240 *Escherichia coli and Salmonella typhimurium: Cellular and Molecular Biology;* Neidhardt, FC, Editor-in-Chief; Amer. Soc. for Microbiology, Washington, DC, 1987

HOUS86
Housman, DE and DL Nelson; "Use of Metaphase-Chromosome Transfer for Mammalian Gene Mapping" (In: Gene Transfer. 1986, Plenum Press): 95-115

HUMC87
Hu, MCT, and N Davidson "The Inducible lac Operator-Repressor System Is Functional in Mammalian Cells"; Cell (1987), 48: 555-566

HUMC88
Hu, MCT, and N Davidson; "The inducible lac operator-repressor system is functional for control of expression of injected DNA in Xenopus oocytes"; Gene (1988), 62: 301-313

INOU86
Inouye, M, and R Sarma, Editors; Protein Engineering: Applications in Science, Medicine, and Industry; Academic Press, New York, 1986

JENJ86
Jen-Jacobson, L, D Lesser, M Kurpiewski, "The Enfolding Arms of EcoRI Endonuclease: Role in DNA Binding and Cleavage", Cell (1986), 45:619-629.

JOHN79
Johnson, AD, BJ Meyer, and M Ptashne; "Interactions between DNA-Bound repressors govern regulation by the lambda phage repressor"; Proc Nat Acad Sci USA (1979), 10: 5061-5065

JOHN80
Johnson, AD, CO Pabo, and RT Sauer; "Bacteriophage lambda Repressor and cro Protein: interactions with Operator DNA"; Meth Enzymol (1980), 65: 839-856

JOHN86

Johnson, HL, MR Gartenberg, and DM Crothers; "The DNA Binding Domain and Bending Angle of *E. coli* CAP Protein"; Cell (1986), 47: 995–1005

JONE85
Jones, TA; "Diffraction methods for biological macromolecules. Interactive computer graphics: FRODO"; Methods Enzymol (1985), 115: 157–71

JONE87
Jones, KA, JT Kadonaga, PJ Rosenfeld, TJ Kelly, and R Tjian, "A cellular DNA-binding protein that activates eukaryotic transcription and DNA replication" Cell (1987), 48:79–89.

JORD85
Jordan, SR, CO Pabo, AK Vershon, and RT Sauer; "Crystallization of the Arc Repressor"; J. Mol. Biol. (1985), 185: 445–446

KADO86
Kadonaga, JT and R Tjian; "Affinity purification of sequence-specific DNA binding proteins"; Proc Natl Acad Sci USA (1986), 83: 5889–5893

KAIS87
Kaiser, CA, D Preuss, P Grisafi and D Botstein; "Many Random Sequences Functionally Replace the Secretion Signal Sequence of Yeast Invertase"; Science (1987), 235: 312–317

KAWA86
Kawamukai, M, J Kishimoto, R Utsumi, M Himeno, T Komano, and H Aiba; "Negative regulation of adenylate cyclase gene (cya) expression by cAMP:cAMP-receptor protein in *E. coli*: studies with cya-lac protein and operon fusion plasmids"; J Bacteriol (1986), 164: 872–877

KELL85
Kelley, RL, and C Yanofsky; "Mutational studies with the trp repressor of *Escherichia coli* support the helix-turn-helix model of repressor recognition of operator DNA"; Proc Natl Acad Sci USA 82: 483–487

KENT87
Kent, RB, JR Emanuel, Y Ben Neriah, R Levenson and DE Housman; "Ouabain Resistance Conferred by Expression of the cDNA for a Murine Na+, K+-ATPase alpha Subunit"; Science (1987), 237: 901–903

KIMJ87
Kim, JG, Y Takeda, BW Matthews, and WF Anderson "Kinetic Studies on Cro Repressor-Operator DNA Interaction"; J Mol Biol (1987), 196: 149–158

KITT87
Kitts, PA and HA Nash; "Homology-dependent interactions in phage lambda site-specific recombination"; Nature (1987), 329: 346–348

KLEN70
Klenow, H, and I Henningsen; "Selective elimination of the exonuclease activity of the deoxyribonucleic acid polymerase from *Escherichia coli* B by limited proteolysis"; Proc Natl Acad Sci USA (1970), 65: 168–175

KNIG88
Knight, KL, and RT Sauer; "The Mnt Repressor of Bacteriophage P22: Role of C-Terminal Residues in Operator Binding and tetramer Formation"; Biochem (1988), 27: 2088–2094

KOPK85
Kopka, ML, C Yoon, D Goodsell, P Pjura, and RE Dickerson; "Binding of an antitumor drug to DNA, Netropsin and C-G-C-G-A-A-T-T-BrC-G-C-G"; J Mol Biol (1985), 183(4)553–63

KOUD87
Koukelka, GB, SC Harrison, and M Ptashne; "Effect of non-contacted bases on the affinity of 434 repressor and Cro"; Nature (1987), 326: 886–888

KOUD88
Koudelka, GB, P Harbury, SC Harrison and M Ptashne; "DNA twisting and the affinity of bacteriophage 434 operator for bacteriophage 434 repressor"; Proc Natl Acad Sci USA (1988), 85: 4633–4637

KRAU86
Krause, HM, and NP Higgins; "Positive and Negative Regulation of the Mu Operator by Mu Repressor and *Escherichia coli* Integration Host Factor"; J Biol Chem (1986), 261: 3744–3752

LAND88
Landschulz, WH, PF Johnson, SL McKnight; "The Leucine Zipper: A Hypothetical Structure Common to a New Class of DNA Binding Proteins"; Science (1988), 240: 1759–1764

LATH85
Lathe, R; "Synthetic oligonucleotide probes deduced from amino acid sequence data. Theoretical and practical considerations"; J Mol Biol (1985), 183: 1–12

LEEB71
Lee, B, and FM Richards; "The interpretation of protein structures: estimation of static accessibility"; J Mol Biol (1971), 55: 379–400

LEGE85
Legerski, RJ, and DL Robberson; "Analysis and Optimization of Recombinant DNA Joining Reactions"; J Mol Biol (1985), 181: 297–312

LEIG87
Leighton, P and P Lu; "Lambda cro repressor complex with $O_R3$ DNA: $15_N$ NMR Observations"; Biochem (1987), 26: 7262–7271

LEWI83
Lewis, M, A Jeffrey, J Wang, R Ladner, M Ptashne, and CO Pabo; "Structure of the Operator-Binding Domain of Bacteriophage Lambda Repressor: Implications for DNA Recognition and Gene Regulation"; Cold Spring Harbor Symp Quant Biol (1983), 47: 435–440

LINC87
Lin-Chao, S, and H Bremer, "Activities of the RNAI and RNAII promoters of pBR322", J Bacterol (1987), 169(3)1217–22.

LINS75
Lin, S, and AD Riggs; "The General Affinity of lac Repressor for *E. coli* DNA: Implications for Gene Regulation in Procaryotes and Eucaryotes"; Cell (1975), 4: 107–111

LIPM85
Lipman, DJ, and WR Pearson; "Rapid and Sensitive Protein Similarity Searches"; Science (1985), 227: 1435–1441

MALO81
Maloy, SR, and WD Nunn; "Selection for loss of tetracycline resistance by *Escherichia coli*" J Bacteriol (1981), 145: 1110–1111

MANI82
Maniatis, T, EF Fritsch, and J Sambrook; *Molecular Cloning*; Cold Spring Harbor Laboratory, 1982

MANI87
Maniatis, T, S Goodbourn, and JA Fischer; "Regulation of Inducible and Tissue-Specific Gene Expression"; Science (1987), 236: 1237–1245

MATT88
Matthews, BW; "No code for recognition"; Nature (1988), 335: 294–295

MAUR80
Maurer, R, BJ Meyer, and M Ptashne; "Gene Regulation at the Right Operator ($O_R3$) of Bacteriophage Lambda. I. $O_R3$ and Autogenous Negative Control by Repressor"; J Mol Biol (1980), 139: 147–161

MAXA80
Maxam, A, and W Gilbert; "Sequencing end-labeled DNA with base-specific chemical cleavages"; Meth Enzymol (1980), 65: 499–599

MCCL86
McClarin, CA Frederick, B-C Wang, P Greene, HW Boyer, J Grable, and JM Rosenberg, "Structure of the DNA-EcoRI Endonuclease Recognition Complex at 3 A Resolution", Science (1986), 234:1526–41.

MCKA81:
McKay, DB, and TA Steitz, "Structure of catabolite gene activator protein at 2.9 A resolution suggests binding to left-handed B-DNA"; Nature (1981), 290: 744–749

MCKA82:
McKay, DB, IT Weber, and TA Steitz, "Structure of catabolite gene activator protein at 2.9 A resolution. Incorporation of amino acid sequence and interactions with cyclic AMP"; J Biol Chem (1982), 257: 9518–9524

MILL72
Miller, JH, *Experiments in Molecular Genetics*. Cold Spring Harbor Laboratory, Cold Spring Harbor, NY. 1972

MILL85
Miller, AM, VL Mackay, and KA Nasmyth; "Identification and comparison of two sequence elements that confer cell-type specific transcription in yeast"; Nature (1985), 314: 598–603

MILL88
Miller, J, JA Hatch, S Simonis, and SE Cullen, "Identification of the glycosaminoglycan-attachment site of mouse invariant-chain proteoglycan core protein by site-directed mutagenesis", Proc Natl Acad Sci USA (1988) 85:1359–1363.

MULL84
Mulligan, ME, DK Hawley, R Entriken, and WR McClure; "*Escherichia coli* promoter sequences predict in vitro RNA polymerase selectivity"; Nucleic Acids Research (1984), 12: 789–800

NEID87b
Neidle S, LH Pearl, and JV Skelly; "DNA structure and perturbation by drug binding"; Biochem J (1987), 243: 1–13

NELS83
Nelson, HCM, MH Hecht, and RT Sauer; "Mutations Defining the Operator-binding Sites of Bacteriophage Lambda Repressor"; Cold Spring Harbor Symp Quant Biol (1983), 47: 441–449

NELS85
Nelson, HCM, and RT Sauer; "Lambda Repressor Mutations That Increase the Affinity and Specificity of Operator Binding"; Cell (1985), 42: 549–558

NELS86
Nelson, HCM, and RT Sauer; "Interaction of Mutant Lambda Repressors with Operator and Non- operator DNA"; J Mol Biol (1986), 192: 27–38

NIKA61
Nikaido, H; "Galactose sensitive mutants of Salmonella. II. Bacteriolysis induced by galactose"; Biochem Biophys Acta (1961), 48: 460–469

OHLE83
Ohlendorf, DH, WF Anderson, M Lewis, CO Pabo, and W Matthews; "Comparison of the Structures of Cro and Lambda Repressor Proteins from Bacteriophage"; J Mol Biol (1983), 169: 757–769

OHLE85
Ohlendorf, DH, and JB Matthew; "Electrostatics and flexibility in protein-DNA interactions"; Adv Biophys (1985), 20: 137–51

OLIP86
Oiphant, AR, AL Nussbaum, and K Struhl; "Cloning of random-sequence oligodeoxynucleotides"; Gene (1986), 44: 177–183

OLIP87
Oliphant, AR, and K Struhl; "The Use of Random-Sequence Oligonucleotides for Determining Consensus Sequences"; *Methods in Enzymology* 155 (1987): 568–582; Editor Wu, R; Academic Press, New York OTWI88
Otwinoski, Z, RW Schevitz, R-G Zhang, CL Lawson, A Joachimiak, RQ Marmorstein, BF Luisi and PB Sigler; "Crystal structure of trp repressor/operator complex at atomic resolution"; Nature (1988), 335: 321–329

PABO79
Pabo, CO, RT Sauer, JM Sturtevant, and M Ptashne; "The lambda repressor contains two domains"; Proc Natl Acad Sci USA (1979), 76: 1608–1612

PABO82a
Pabo, CO, W Krovatin, A Jeffrey, and RT Sauer; "The N-terminal arms of lambda represssor wrap around the operator DNA"; Nature (1982), 298: 441–443

PABO82b
Pabo, CO, and M Lewis; "The operator-binding domain of lambda repressor: structure and DNA recognition"; Nature (1982), 298: 443–447

PABO84
Pabo, CO, and RT Sauer; "Protein-DNA Recognition"; Ann Rev Biochem (1984), 53: 293–321

PAKU86
Pakula, AA, VB Young, and RT Sauer; "Bacteriophage lambda cro mutations: Effects on activity and intracellular degradation"; Proc Natl Acad Sci USA (1986), 83: 8829–8833

PARR88
Parraga, G, SJ Horvath, A Eisen, WE Taylor, L Hood, T Young, RE Klevit; "Zinc-Dependant Structure of a Single-Finger Domain of Yeast ADR1"; Science (1988), 241: 1489–1492

POLA88
Polayes, DA, PW Rice, MM Garner, and JE Dahlberg; "Cyclic AMP-cyclic AMP receptor protein as a repressor of transcription of the spf gene of *Escherichia coli*"; J Bacteriol (1988), 170: 3110–3114

POTE80
Poteete, AR, M Ptashne, M Ballivet, and H Eisen; "Operator Sequences of Bacteriophages P22 and 21"; J Mol Biol (1980), 137: 81–91

POTE82
Poteete, AR, and M Ptashne; "Control of Transcription by the Bacteriophage P22 Repressor"; J Mol Biol (1982), 157: 21–48

PTAS80
Ptashne, M, A Jeffrrey, AD Johnson, R Maurer, BJ Meyer, CO Pabo, TM Roberts and RT Sauer; "How the Lambda Repressor and Cro Work"; Cell (1980), 19 1–11

PTAS86

Ptashne, M; A Genetic Switch: Gene Control and Phage Lambda. 1986, Cell Press and Blackwell Scientific Publications RAOS87
Rao, SN, UC Singh, PA Bash, and PA Kollman, "Free energy perturbation calculations on binding and catalysis after mutating Asn 155 in subtilisin", Nature (1987), 328(6130) 551–4.

RATN85
Ratner, L, W Haseltine, KR Patarca, KJ Livak, B Starcich, SF Josephs, ER Doran, JA Rafalski, EA Whitehorn, K Baumeister, L Ivanoff, SLR Petteway Jr, ML Pearson, JA Lautenberger, TS Papas, J Ghrayeb, NT Chang, RC Gallo, and F Wong-Staal; "Complete nucleotide sequence of the AIDS virus, HTLV-III"; Nature (1985), 313: 277–284

REID88
Reidhaar-Olson, JF, and RT Sauer; "Combinatorial Cassette Mutagenesis as a Probe of the Informational Content of Protein Sequences"; Science (1988), 241: 53–57

RENY88
Ren, YL, S Garges, S Adhya, and JS Krakow; "Cooperative DNA binding of heterologous proteins: evidence for contact between the cyclic AMP receptor protein and RNA polymerase"; Mol Microbiol (1987), 1:53–58

RICH81
Richardson, JS; "The Anatomy and Taxonomy of Protein Structure"; Adv Protein Chemistry (1981), 34:167–339

RICH86
Richards, JH; "Cassette mutagenesis shows its strength"; Nature (1986), 323:187

RICH88
Richet, E, P Abcarian and HA Nash; "Synapsis of attachment sites during lambda integrative recombination involves capture of a naked DNA by a protein-DNA complex"; Cell (1988), 52: 9–17

RIGB77
Rigby, PW, M Dieckmann, C Rhodes, and P Berg; "Labeling deoxyribonucleic acid to high specific activity in vitro by nick translation with DNA polymerase I"; J Mol Biol (1977), 113: 237–251

RIGG70
Riggs, AD, H Suzuki, and S Bourgeois; "lac Repressor-Operator interaction. I. Equilibrium studies"; J Mol Biol (1970), 48: 67–83

ROBE79
Roberts, TM, R Kacich and M Ptashne; "A general method for maximizing the expression of a cloned gene"; Proc Natl Acad Sci USA (1979), 76: 760–764

ROBE86
Roberts, S, and AR Rees, "The cloning and expression of an anti-peptide antibody: a system for rapid analysis of the binding properties of engineered antibodies", Protein Engineering (1986), 1:59–65.

ROSE79
Rosenberg, M, and D Court; "Regulatory Sequences Involved in the Promotion and Termination of RNA Transcription"; Ann Rev Genet (1979), 13: 319–353

ROSE85b
Rose, GD, AR Geselowitz, GJ Lesser, RH Lee and MH Zehfus; "Hydrophobicity of amino acid residues in globular proteins"; Science (1985), 229: 834–838

ROSE86:
Rosenberg, UB, C Schroeder, A Preiss, A Kienlin, S Cote, I Riede, and H Jaeckle, "Structural homology of the product of the Drosophila Krueppel gene with Xenopus transcription factor IIIA", Nature (1986), 319:336–339.

ROSE87
Rose, GD; "Protein hydrophobicity: is it the sum of its parts?" Proteins (1987), 2: 79–80

ROSS81
Rossman, M, and P Argos; "Protein Folding"; Ann Rev Biochem (1981), 50:497–532

RUDD86
Ruddle, FH; "Gene Transfer: A Perspective" (In: Gene Transfer. 1986, Plenum Press): 1–4

SAAG88
Saag, MS, BH Hahn, J Gibbons, Y Li, ES Parks, WP Parks, and GM Shaw; "Extensive variation of human immunodeficiency virus type-1 in vivo"; Nature (1988), 334: 440–444

SADL83
Sadler, JR, H Sasmor, and JL Betz; "A perfectly symmetric lac operator binds the lac repressor very tightly"; Proc Natl Acad Sci USA (1983), 80: 6785–6789

SAEN83
Saenger, W; Principles of Nucleic Acid Structure; Springer Verlag, New York, 1983

SAUE79
Sauer, RT, CO Pabo, BJ Meyer, M Ptashne, and KC Backman; "Regulatory functions of the lambda repressor reside in the amino-terminal domain"; Nature (1979), 279: 396–400

SAUE82
Sauer, RT, RR Yocum, RF Doolittle, M Lewis, and CO Pabo; "Homology among DNA-binding proteins suggests use of a conserved super-secondary structure"; Nature (1982), 298: 447–451

SAUE86
Sauer, RT, K Hehir, RS Stearman, MA Weiss, A Jeitler-Neilsson, EG Suchanek, and CO Pabo; "An Engineered Intersubunit Disulfide Enhances the Stability and Binding of the N-Terminal Domain of Lambda Repressor"; Biochem (1986), 25: 5992–5998

SCHE85
Schevitz, RW, Z Otwinowski, A Joachimiak, CL Lawson, and PB Sigler; "The three-dimensional structure of trp repressor"; Nature (1985), 317: 782–786

SCHL88
Schleif, R; "DNA binding by Proteins"; Science (1988), 241:1182–87

SCHU79
Schulz, GE, and RH Schirmer; Principles of Protein Structure; Springer-Verlag, New York, 1979

SHAW83
Shaw, DJ, DW Rice, and JR Guest; "Homology between CAP and FNR, a regulator of anaerobic respiration in E. coli"; J Mol Biol (1983), 166:241–247

SIMO84
Simons, A, D Tils, B von Wilcken-Bergmann, and B Muller-Hill; "Possible ideal lac operator: Escherichia coli lac operator-like sequences from eukaryotic genomes lack the central G-C pair"; Biochem. (1984) 81: 1624–1628

SIMO88
Simon, MC, TM Fisch, BJ Benecke, JR Nevins, and N Heintz; "Definition of Multiple, Functionally Distinct TATA Elements, One of Which Is a Target in the hsp70 Promoter for E1A Regulation"; Cell (1988), 52: 723–729

SMIT87

Smith, DI, W Golembieski, JD Gilbert, L Kizyma, and OJ Miller, "Overabundance of rare-cutting restriction endonuclease sites in the human genome", Nucl Acid Res (1987), 15(3)1173-84.

SOUT75
Southern, E; "Detection of specific sequences among DNA fragments separated by gel electrophoresis"; J.Mol. Biol. (1975) 98: 503

SPIR88
Spiro, S, and JR Guest; "Activation of the lac operon of *E. coli* by a mutant FNR protein"; Mol Microbiol (1987), 1:53-58

STRU87
Struhl, K; "Promoters, Activator Proteins, and the Mechanism of Transcriptional Initiation in Yeast"; Cell (1987), 49: 295-297

SVEN86
"Multiple conformations of amino acid residues in ribonuclease A"; Svensson, LA, L Sjolin, GL Gilliland, BC Finzel, and A Wlodawer; Proteins (1986), 1: 370-375

TAKE77
Takeda, Y, A Folkmanis, and H Echols; "Cro Regulatory Protein Specified by Bacteriophage Lambda. Structure, DNA-Binding, and Repression of RNA Synthesis"; J Biol Chem (1977), 252: 6177-6183

TAKE83
Takeda, Y, H Ohlendorf, WF Anderson, and BW Matthews; "DNA-Binding Proteins"; Science (1983), 221: 1020-1026

TAKE85
Takeda, Y, DH Ohlendorf, WF Anderson, and BW Matthews; "The Structure of Cro Repressor Protein"; (In: Biological Macromolecules and Assemblies: Volume 2-Nucleic Acids and Interactive Proteins. 1985, John Wiley and Sons, Inc.) 234-263

TAKE86
Takeda, Y, JG Kim, CG Caday, E Steers Jr., DH Ohlendorf, WF Anderson, and BW Matthews; "Different Interactions Used by Cro Repressor in Specific and Nonspecific DNA Binding"; J Biol Chem (1986), 261: 8608-8616

TATC81
Tatchell, K, KA Nasmyth, BD Hall, C Astell and M Smith; "In vitro mutation analysis of the mating-type locus in yeast"; Cell (1981), 27: 25-35

THER88
Theriault, NY, JB Carter, and SP Pulaski; "Optimization of Ligation Reaction Conditions in Gene Synthesis"; Biotechniques (1988), 6: 470-474

TOTH86
Toth MJ, and P Schimmel, "Internal Structural Features of *E. coli* Glycyl-tRNA Synthetase Examined by Subunit Polypeptide Chain Fusions"; J Biol Chem (1986), 261: 6643-6646

ULAN87
Ulanovsky, LE, and EN Trifonov; "Estimation of wedge compinents in curved DNA"; Nature (1987), 326: 720-722

ULME83
Ulmer, KM, "Protein Engineering", Science (1983), 219(4585)666-71.

VERS85a
Vershon, AK, P Youderian, MA Weiss, MM Susskind, and RT Sauer; "Mnt Repressor-Operator Interactions: Altered Specificity Requires N-6 Methylation of Operator DNA"; (In: Sequence Specificity in Transcription and Translation. 1985, Alan R. Liss, Inc.) 209-218

VERS85b
Vershon, AK, P Youderian, MM Susskind, and RT Sauer; "The Bacteriophage P22 Arc and Mnt Repressors. Overproduction, Purification, and Properties"; J Biol Chem (1985), 260: 12124-12129

VERS86a
Vershon, AK, K Blackmer, and RT Sauer; "Mutagenesis of the Arc Repressor Using Synthetic Primers with Random Nucleotide Substitutions" (In: Protein Engineering. Applications, in Science, Medicine, and Industry. 1986, Academic Press, Inc.) p243-256

VERS86b
Vershon, AK, JU Bowie, TM Karplus, and RT Sauer; "Isolation and Analysis of Arc Repressor Mutants: Evidence for an Unusual Mechanism of DNA Binding" (In: Proteins: Structure, Function, and Genetics. 1986, Alan R. Liss, Inc.) 302-311

VERS87a
Vershon, AK, SM Liao, WR McClure, and RT Sauer; "Bacteriophage P22 Mnt Repressor DNA Binding and Effects on Transcription in Vitro"; J Mol Biol (1987), 195: 311-322

VERS87b
Vershon, AK, SM Liao, WR McClure, and RT Sauer; "Interaction of the Bacteriophage P22 Arc Repressor with Operator DNA"; J Mol Biol (1987), 195: 323-331

VINO87
Vinopal, RT; "Selectable Phenotypes" (In: *Escherichia coli* and *Salmonella typhimurium*: Cellular and Molecular Biology. 1987, American Society for Microbiology)

VINS88
Vinson, CR, KL LaMarco, PF Johnson, WH Landschulz, and SL McKnight; "In situ detection of sequence-specific DNA binding activity specified by a recombinant bacteriophage"; Genes and Development (1988), 2: 801-806

WARD86
Ward, WH, DH Jones, and AR Fersht; "Protein Engineering of Homodimeric tyrosyl tRNA Synthetase to produce active heterodimers"; J Biol Chem (1986), 261: 9576-8

WATS87
Molecular Biology of the Gene, Fourth Edition; Watson, JD, NH Hopkins, JW Roberts, JA Steitz, and AM Weiner; Benjamin/Cummings Publishing Company, Inc., Menlo Park, CA., 1987

WEBE87a
Weber, IT, GL Gilliland, JG Harman, and A Peterkofsky; "Crystal structure of a cyclic AMP-independent mutant of catabolite gene activator protein"; J Biol Chem (1987), 262: 5630-5636

WEBE87b
Weber, IT, TA Steitz, J Bubis, and SS Taylor; "Predicted structures of cAMP binding domains of type I and II regulatory subunits of cAMP-dependent protein kinase"; Biochem (1987), 26: 343-351

WEIS87a
Weiss, MA, M Karplus, and RT Sauer; "$^1$H NMR Aromatic Spectrum of the Operator Binding Domain of the Lambda Repressor: Resonance Assignment with Application to Structure and Dynamics"; Biochem (1987), 26: 890-897

WEIS87b

Weiss, MA, CO Pabo, M Karplus, and RT Sauer; "Dimerization of the Operator Binding Domain of Phage Lambda Repressor"; Biochem (1987), 26: 897-904

WEIS87c
Weiss, MA, M Karplus, and RT Sauer; "Quarternary Structure and Function in Phage Lambda Repressor: 1H-NMR Studies of Genetically Altered Proteins"; J Biomol Struct Dynam (1987), 5: 539-556

WHAR84
Wharton, RP, EL Brown, and M Ptashne; "Substituting an Alpha Helix Switches the Sequence-Specific DNA Interactions of a Repressor"; Cell (1984), 38: 361-369

WHAR85a
Wharton, RP; "The Binding Specificity Determinants of 434 Repressor"; Ph. D. Thesis, Harvard University WHAR85b
Wharton, RP, and M Ptashne; "Changing the binding specificity of a repressor by redesigning an alpha helix"; Nature (1985), 316: 601-605

WHAR87
Wharton, RP, and M Ptashne; "A new-specificity mutant of 434 repressor that defines an amino acid-base pair contact"; Nature (1987), 325: 888-891

WOLB88
Wolberger, C, Y Dong, M Ptashne, and SC Harrison; "Structure of a phage 434 Cro/DNA complex"; Nature (1988), 335: 789-795

WOLF86
Wolfes, H, J Alves, A Fliess, R Geiger, and A Pingoud, "Site directed mutagenesis experiments suggest the Glu 111, Glu 144, and Arg 145 are essential for endonucleolytic activity of EcoRI", Nucl Acids Res (1986), 14(22)9063-9080.

YANO87
Yanofsky, SD, R Love, JA McClarin, JA Rosenberg, and HW Boyer, "Clustering of Null Mutations in the EcoRI Endonuclease", Proteins (1987), 2:273-282.

YOUD83
Youderian, P, A Vershon, S Bouvier, RT Sauer, and MM Susskind; "Changing the DNA-Binding Specificity of a Repressor"; Cell (1983), 35: 777-783

ZOLL84
Zoller, MJ, and M Smith; "Oligonucleotide-Directed Mutagenesis: A Simple Method Using Two Oligonucleotide Primers and a Single-Stranded DNA Template"; DNA (1984), 3: 479-488

We claim:

1. A cell culture comprising a plurality of cells, each cell bearing a selection vector, said selection vector comprising a first and a second operon, each comprising at least one expressible gene, the genes of said first and second operons being different, a copy of the target DNA sequence being included in each operon and positioned therein so that under forward selection conditions the transformed cells enjoy a selective advantage if they express a protein or polypeptide which binds to said copies of the target DNA sequence, said cell culture being transformed with a variegated gene encoding potential DNA-binding proteins or polypeptides, where said cells collectively can express a plurality of different but sequence-related potential DNA-binding proteins or polypeptides.

2. The cell culture of claim 1 wherein the cells are bacterial cells.

3. The cell culture of claim 2 in which the cells are *Escherichia coli* cells.

4. The cell culture of claim 1 wherein the potential DNA-binding protein encoding gene is borne by the selection vector.

5. A method of obtaining a gene coding on expression for a novel DNA-binding protein or polypeptide that preferentially binds a predetermined DNA target sequence in double stranded DNA, comprising:
    (a) providing a cell culture according to claim 1;
    (b) causing the cells of such culture to express said potential DNA-binding proteins or polypeptides;
    (c) exposing the cells to forward selection conditions to select for cells which express a protein or polypeptide which preferentially binds to said target DNA sequence; and
    (d) recovering the selected cells bearing a gene coding on expression for such protein or polypeptide.

6. A method of producing a DNA-binding protein or polypeptide which preferentially binds a predetermined double stranded DNA target, which comprises providing a gene obtained by the method of claim 5 which codes on expression for such protein or polypeptide, expressing the gene in a suitable host cells, and recovering said protein or polypeptide.

7. A method of obtaining a protein or polypeptide which may be used to specifically repress a coding or regulatory element of interest which comprises identifying an ultimate target sequence within such element and obtaining a protein or polypeptide which preferentially binds to such ultimate target sequence by the method of claim 5.

8. The method of claim 5, wherein a gene coding on expression for a polypeptide is variegated, said polypeptide having a length of 25-50 amino acids and being capable of lying in the major groove of B-DNA.

9. The method of claim 5 wherein the gene codes on expression for a molecule comprising a DNA-binding domain of 25-50 amino acids and a custodial demain that substantially inhibits the degradation of the molecule by intracellular enzymes.

10. The method of claim 5 wherein said protein is a globular protein.

11. The method of claim 10 wherein a gene coding on expression for a known DNA binding protein having a helix-turn-helix DNA binding motif is variegated.

12. The method of claim 5 wherein a gene encoding a known DNA binding protein picked from the group consisting of Cro from phage lambda, cI repressor from phage lambda, Cro from phage 434, cI repressor from phage 434, P22 repressor, *E. coli* tryptophan repressor, *E. coli* CAP, P22 Arc, P22 Mnt, *E. coli* lactose repressor, MAT-al-alpha2 from yeast, Polyoma Large T antigen, SV40 Large T antigen, Adenovirus E1A, and TFIIIA from *Xenopus laevis* is variegated to obtain genes coding on expression for a plurality of potential target DNA-binding proteins.

13. The method of claim 5 in which the cells prior to transformation are of a GalE−, GalT−, GalK−, Tet$^S$ phenotype, the binding marker genes are the tet and galT,K genes, and the forward selection condition is cultivation of the cells in a medium containing galactose, or fusaric acid, or both, or substances metabolized into or catalyzing the production of galactose or fusaric acid.

14. The method of claim 13 in which the vector further contains an origin of replication and an antibiotic resistance gene, and cells are cultured in medium that further comprises, an antibiotic for which resistance is conferred by said antibiotic resistance gene.

15. The method of claim 5 in which the forward selection conditions do not result in lytic growth of phage in unselected cells.

16. The method of claim 15 in which the forward selection conditions are selected from the group consisting of nutritional and chemical resistance selection conditions.

17. The method of claim 5 wherein at least one variegated codon encodes all twenty amino acids such that the frequency of occurrence of the least favored amino acid is about 0.4 times the frequency of occurrence of the most favored amino acid.

18. The method of claim 17 wherein for said variegated codon, the frequencies of occurrence of acidic and basic amino acid are about equal.

19. The method of claim 17 wherein said variegated codon has substantially the following base proportions:

|  | T | C | A | G |
|---|---|---|---|---|
| base #1 | 0.26 | 0.18 | 0.26 | 0.30 |
| base #2 | 0.22 | 0.16 | 0.40 | 0.22 |
| base #3 | 0.5 | 0.0 | 0.0 | 0.5. |

20. The method of claim 5 wherein for at least one variegated codon, the mixture of bases for at least one base position is non-equimolar.

21. The method of claim 5 wherein at least one operon comprises a selectable beneficial gene, an occludible promoter operably linked to said beneficial gene and directing its transcription, an occluding promoter occluding transcription of said beneficial gene, and a copy of the target DNA sequence positioned so that the binding of said protein or polypeptide to said copy represses said occluding promoter and thereby facilitates transcription of said beneficial gene.

22. The method of claim 5 in which said selection vector comprises:
(a) a first operon, which operon comprises:
(i) a first promoter directing expression of said binding marker gene(s), and
(iii) a first copy of the target DNA sequence, where said target DNA sequence interferes substantially with expression of the first gene(s) if and only if a protein expressed by the transformed cell binds to the target DNA sequence,
(b) a second operon, which operon comprises:
(i) a second binding marker gene(s),
(ii) a second promoter directing expression of said binding marker gene(s), and
(iii) a second copy of the target DNA sequence, where said target DNA sequence interferes substantially with expression of said gene(s) if and only if a protein expressed by the transformed cell binds to the target DNA sequence,
where the binding marker genes of said first and second operons are different, and where, when said cells are exposed to forward selection conditions the gene products of said first and second binding marker genes are deleterious or conditionally lethan to the cell.

23. The method of claim 22 in which at least one of the operons confers a genotype selected from the group consisting of galT,K+, tetA+, lacZ+, pheS+, argP+, thyA+, crp+, pyrF+, ptsM+, secA+/malE+/lacZ+, ompA+, btuB+, lamB+, tonA+, cir+, tsx+, aroP+, cysK+, and dctA+.

24. A method of claim 23 wherein the degree of homology between the first and second promoters is less than 50% in the region between the −10 region of the promoter and the base at which transcription is initiated.

25. The method of claim 24 in which one of said genetic elements is the origin of replication of said vector.

26. The vector of claim 22 wherein the binding marker genes are functionally unrelated.

27. The method of claim 26 wherein the first and second operons confer, respectively, a pair of genotypes selected from the group consisting of:
(a) galT,K+ and tetA+;
(b) argP+ and pheS+;
(c) lacZ+ and tetA+;
(d) dctA+ and cysK+;
(e) crp+ and thyA+;
(f) lamB+ and thyA+;
(g) SecA+/malE+/lacZ+ and pyrF+;
(h) tsx+ and cysK+;
(i) dctA+ and thyA+;
(j) galT,K+ and pheS+;
(k) tetA+ and thyA+;
(l) ptsM+ and thyA+;
(m) ompA+ and pyrF+;
(n) btuB+ and pyrF+;
(o) tonA+ and galT,K+;
(p) cir+ and cysK+; and
(q) aroP+ and lacZ+.

28. The method of claim 22 wherein the promoters of said first and second operons are different.

29. The method of claim 22, wherein at least one of said operons comprises a plurality of copies of the target DNA sequences, wherein each copy is positioned so that the target DNA sequence interferes substantially with expression if and only if a protein expressed by the recipient cell binds to the target DNA sequence.

30. The method of claim 22, further comprising a plurality of genetic elements essential to the maintenance of the vector or the survival of the transformed cells under conditions that select for presence of said vector, said operons and said genetic elements being positioned on said vector so no single deletion event can render non-functional more than one of said operons without also rendering nonfunctional one of said essential genetic elements.

31. The method of claim 30, wherein at least one of said genetic elements comprises a selectably beneficial or essential gene, and a control promoter operably linked to said beneficial or conditionally essential gene, but where no instance of said target DNA sequence is associated with said genetic element.

32. The method of claim 22 wherein the control promoter is essentially identical to the promoter of one of said selectable binding marker operons, so that proteins binding to the latter promoter will also bind to the control promoter and thereby inhibit expression of said beneficial or essential gene.

33. The method of claim 1, wherein under reverse selection conditions the gene products of said binding marker genes are beneficial or conditionally essential to the transformed cells.

34. The method of claim 33, wherein each of the first and second operons confers a phenotype selected independently but non-identically from the group consisting of: galT,K+, tetA+, lacZ+, pheS+, argP+, thyA+, crp+, pyrF+, ptsM+, secA+/malE+/lacZ+, ompA+, btuB+, lamB+, tonA+, cir+, tsx+, aroP+, cysK+, and dctA+.

35. The vector of claim 22, wherein said promoter of said gene is an inducible or repressible promoter.

36. The method of claim 22, further comprising a nondeleterious cloning site so positioned that insertion of a foreign gene at such site does not inactivate said first or second operons or any genetic element of said vector required for its maintenance within the transformed cell.

37. The method of claim 22 in which the target sequence associated with at least one of said operons is positioned within the RNA-polymerase binding site of the promoter of the operon.

38. The method of claim 22 in which the target sequence associated with at least one of said operons is positioned upstream of the −35 region of the promoter of the operon.

39. The method of claim 22 in which the target sequence associated with at least one of said operons in positioned downstream of the −10 region of the promoter of the operon.

40. A selection vector, said selection vector comprising a first and a second operon, each comprising at least one expressible gene, the genes of said first and second operons being different, a copy of the target DNA sequence being included in each operon and positioned therein so that under forward selection conditions the transformed cells enjoy a selective advantage if they express a protein or polypeptide which binds to said copies of the target DNA sequence, and further comprising a gene coding on expression for a potential DNA-binding protein or polypeptide, said gene comprising:
 (a) a coding region that codes on expression for a polypeptide, each domain of said polypeptide having at least 50% sequence identify to a known DNA-binding domain, and
 (b) a promoter operably linked to said coding region for controlling its expression.

41. A variegated population of vectors according to claim 40, the variegation occurring within the pdbp gene so that said vectors collectively can express a plurality of different but sequence-related potential DNA-binding proteins.

42. The population of claim 41, wherein the level of variegation is such that from $10^6$ to $10^9$ different potential DNA-binding proteins can be expressed.

* * * * *